(12) United States Patent
Purcell

(10) Patent No.: US 12,091,449 B2
(45) Date of Patent: Sep. 17, 2024

(54) ANTI-PfRH5 ANTIBODIES AND ANTIGEN-BINDING FRAGMENTS THEREOF

(71) Applicant: Regeneron Pharmaceuticals, Inc., Tarrytown, NY (US)

(72) Inventor: Lisa Purcell, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/139,626

(22) Filed: Apr. 26, 2023

(65) Prior Publication Data
US 2023/0365668 A1    Nov. 16, 2023

Related U.S. Application Data

(62) Division of application No. 17/041,595, filed as application No. PCT/US2019/023734 on Mar. 22, 2019, now Pat. No. 11,667,701.
(Continued)

(51) Int. Cl.
| C07K 16/20 | (2006.01) |
| A61K 9/00 | (2006.01) |
| A61K 39/015 | (2006.01) |

(52) U.S. Cl.
CPC .......... *C07K 16/205* (2013.01); *A61K 9/0019* (2013.01); *A61K 39/015* (2013.01); *C07K 2317/14* (2013.01); *C07K 2317/31* (2013.01); *C07K 2317/565* (2013.01); *C07K 2317/73* (2013.01); *C07K 2317/92* (2013.01)

(58) Field of Classification Search
CPC .............. C07K 16/205; C07K 2317/14; C07K 2317/31; C07K 2317/33; C07K 2317/565; C07K 2317/73; C07K 2317/76; C07K 2317/92; Y02A 50/30; A61K 2300/00; A61K 31/4706; A61K 39/015;
(Continued)

(56) References Cited

U.S. PATENT DOCUMENTS

| 11,667,701 B2 | 6/2023 | Purcell |
| 2002/0062010 A1 | 5/2002 | Arathoon et al. |

FOREIGN PATENT DOCUMENTS

| WO | 12/061882 A1 | 5/2012 |
| WO | 13/138712 A1 | 9/2013 |

(Continued)

OTHER PUBLICATIONS

Bustamante et al., "A full-length recombinant Plasmodium falciparum PfRH5 protein induces inhibitory antibodies that are effective across common PfRH5 genetic variants," Vaccine, vol. 31 (No. 2), pp. 373-379, DOI: 10.1016/j.vaccine.2012.10.106, (2013).
Douglas et al., "Neutralization of Plasmodium falciparum Merozoites by Antibodies against PfRH5," The Journal Of Immunology, vol. 192 (No. 1), pp. 245-258, DOI: 10.4049/jimmunol.1302045, (2013).
Ord et al., "A malaria vaccine candidate based on an epitope of the Plasmodium falciparum RH5 protein," Malaria Journal, vol. 13 (No. 1), p. 1-9, DOL: 10.1186/1475-2875-13-326, (2014).
(Continued)

*Primary Examiner* — Jana A Hines
(74) *Attorney, Agent, or Firm* — Schwabe, Williamson & Wyatt PC; Gabe Amodeo

(57) ABSTRACT

The present invention includes antibodies and antigen-binding fragments thereof that specifically bind to *Plasmodium falciparum* reticulocyte binding protein homologue 5 (PfRH5), compositions thereof and methods of making such antibodies, fragments and compositions. Method and compositions for treating, preventing or diagnosing *Plasmodium falciparum* infection and malaria are also part of the present invention.

11 Claims, 12 Drawing Sheets
Specification includes a Sequence Listing.

Related U.S. Application Data

(60) Provisional application No. 62/648,259, filed on Mar. 26, 2018.

(58) Field of Classification Search
    CPC ........ A61K 9/0019; A61P 33/02; A61P 33/06; A61P 2039/505; G01N 33/56905
    See application file for complete search history.

(56) References Cited

FOREIGN PATENT DOCUMENTS

| WO | 15/017552 A1 | 2/2015 |
| WO | 15/092393 A2 | 6/2015 |
| WO | 16/106302 A1 | 6/2016 |

OTHER PUBLICATIONS

Patel et al., "Plasmodium falciparum Merozoite Surface Antigen, PfRH5, Elicits Detectable Levels of Invasion-Inhibiting Antibodiesin Humans," The Journal of Infectious Diseases, vol. 208: 1679-1687, (2013). [DOI: 10.1093/infdis/jit385].
U.S. Appl. No. 17/041,595, Requirement for Restriction/Election mailed Apr. 18, 2022.
U.S. Appl. No. 17/041,595, Non-Final Office Action mailed Jul. 19, 2022.
U.S. Appl. No. 17/041,595, Non-Final Office Action mailed Aug. 22, 2022.
U.S. Appl. No. 17/041,595, Notice of Allowance mailed Jan. 27, 2023.
WIPO Application No. PCT/US2019/023734, PCT International Search Report mailed Jul. 8, 2019.
WIPO Application No. PCT/US2019/023734, PCT International Search Report and Written Opinion of the International Searching Authority mailed Aug. 16, 2019.

| | | (PANEL C) | Cont. From PANEL A | Cont. On PANEL D |
|---|---|---|---|---|
| H1H29089P {1} | 301 | CCTTCTCATAATTCTTTTATAAAAAAATATTCTGTATTTAATCAAATAATGCAAATTGATGATGGCATGTTATTAA |
| H1H29089P {2} | 301 | CCTTCTCATAATTCTTTTATAAAAAAATATTCTGTATTTAATCAAATAATGCAAATTGATGATGGCATGTTATTAA |
| H1H29100P {1} | 301 | CCTTCTCATAATTCTTTTATAAAAAAATATTCTGTATTTAATCAAATAATGCAAATTGATGATGGCATGTTATTAA |
| H1H29100P {2} | 301 | CCTTCTCATAATTCTTTTATAAAAAAATATTCTGTATTTAATCAAATAATGCAAATTGATGATGGCATGTTATTAA |
| H1H29147P2 {1} | 301 | CCTTCTCATAATTCTTTTATAAAAAAATATTCTGTATTTAATCAAATAATGCAAATTGATGATGGCATGTTATTAA |
| H1H29147P2 {2} | 301 | CCTTCTCATAATTCTTTTATAAAAAAATATTCTGTATTTAATCAAATAATGCAAATTGATGATGGCATGTTATTAA |
| H1H29187P2 {1} | 301 | CCTTCTCATAATTCTTTTATAAAAAAATATTCTGTATTTAATCAAATAATGCAAATTGATGATGGCATGTTATTAA |
| H1H29187P2 {2} | 301 | CCTTCTCATAATTCTTTTATAAAAAAATATTCTGTATTTAATCAAATAATGCAAATTGATGATGGCATGTTATTAA |
| REGN1932 | 301 | CCTTCTCATAATTCTTTTATAAAAAAATATTCTGTATTTAATCAAATAATGCAAATTGATGATGGCATGTTATTAA |
| e Sequence {3D7} | | CCTTCTCATAATTCTTTTATAAAAAAATATTCTGTATTTAATCAAATAATGCAAATTGATGATGGCATGTTATTAA |

| | | | Cont. On PANEL E |
|---|---|---|---|
| H1H29089P {1} | 451 | GAGTTATCAAATTATAACATTGCAAATTCTATTGATATTTTACAAGAAAAAGAAGGACATTTGGATT |
| H1H29089P {2} | 451 | GAGTTATCAAATTATAACATTGCAAATTCTATTGATATTTTACAAGAAAAAGAAGGACATTTGGATT |
| H1H29100P {1} | 451 | GAGTTATCAAATTATAACATTGCAAATTCTATTGATATTTTACAAGAAAAAGAAGGACATTTGGATT |
| H1H29100P {2} | 451 | GAGTTATCAAATTATAACATTGCAAATTCTATTGATATTTTACAAGAAAAAGAAGGACATTTGGATT |
| H1H29147P2 {1} | 451 | GAGTTATCAAATTATAACATTGCAAATTCTATTGATATTTTACAAGAAAAAGAAGGACATTTGGATT |
| H1H29147P2 {2} | 451 | GAGTTATCAAATTATAACATTGCAAATTCTATTGATATTTTACAAGAAAAAGAAGGACATTTGGATT |
| H1H29187P2 {1} | 451 | GAGTTATCAAATTATAACATTGCAAATTCTATTGATATTTTACAAGAAAAAGAAGGACATTTGGATT |
| H1H29187P2 {2} | 451 | GAGTTATCAAATTATAACATTGCAAATTCTATTGATATTTTACAAGAAAAAGAAGGACATTTGGATT |
| REGN1932 | 451 | GAGTTATCAAATTATAACATTGCAAATTCTATTGATATTTTACAAGAAAAAGAAGGACATTTGGATT |
| e Sequence {3D7} | | GAGTTATCAAATTATAACATTGCAAATTCTATTGATATTTTACAAGAAAAAGAAGGACATTTGGATT |

(PANEL G) Cont. From PANEL E

| | | | Cont. On PANEL H |
|---|---|---|---|
| H1H29089P {1} | 901 | AAAAAGATGATGATGAATATAACAAAAAAAAAAAAAAAATTAATTAAATGTATAAAAACCATGAGA |
| H1H29089P {2} | 901 | AAAAAGATGATGATGAATATAACAAAAAAAAAAAAAAAATTAATTAAATGTATAAAAACCATGAGA |
| H1H29100P {1} | 901 | AAAAAGATGATGATGAATATAACAAAAAAAAAAAAAAAATTAATTAAATGTATAAAAACCATGAGA |
| H1H29100P {2} | 901 | AAAAAGATGATGATGAATATAACAAAAAAAAAAAAAAAATTAATTAAATGTATAAAAACCATGAGA |
| H1H29147P2 {1} | 901 | AAAAAGATGATGATGAATATAACAAAAAAAAAAAAAAAATTAATTAAATGTATAAAAACCATGAGA |
| H1H29147P2 {2} | 901 | AAAAAGATGATGATGAATATAACAAAAAAAAAAAAAAAATTAATTAAATGTATAAAAACCATGAGA |
| H1H29187P2 {1} | 901 | AAAAAGATGATGATGAATATAACAAAAAAAAAAAAAAAATTAATTAAATGTATAAAAACCATGAGA |
| H1H29187P2 {2} | 901 | AAAAAGATGATGATGAATATAACAAAAAAAAAAAAAAAATTAATTAAATGTATAAAAACCATGAGA |
| REGN1932 | 901 | AAAAAGATGATGATGAATATAACAAAAAAAAAAAAAAAATTAATTAAATGTATAAAAACCATGAGA |
| e Sequence {3D7} | | AAAAAGATGATGATGAATATAACAAAAAAAAAAAAAAAATTAATTAAATGTATAAAAACCATGAGA |

Cont. On PANEL I

| | | |
|---|---|---|
| H1H29089P {1} | 1051 | TGTAATACAAACGGAATAAGATATCATTATGATGAATATCATTAATATTATCTGTTAAAT |
| H1H29089P {2} | 1051 | TGTAATACAAACGGAATAAGATATCATTATGATGAATATCATTAATATTATCTGTTAAAT |
| H1H29100P {1} | 1051 | TGTAATACAAACGGAATAAGATATCATTATGATGAATATCATTAATATTATCTGTTAAAT |
| H1H29100P {2} | 1051 | TGTAATACAAACGGAATAAGATATCATTATGATGAATATCATTAATATTATCTGTTAAAT |
| H1H29147P2 {1} | 1051 | TGTAATACAAACGGAATAAGATATCATTATGATGAATATCATTAATATTATCTGTTAAAT |
| H1H29147P2 {2} | 1051 | TGTAATACAAACGGAATAAGATATCATTATGATGAATATCATTAATATTATCTGTTAAAT |
| H1H29187P2 {1} | 1051 | TGTAATACAAACGGAATAAGATATCATTATGATGAATATCATTAATATTATCTGTTAAAT |
| H1H29187P2 {2} | 1051 | TGTAATACAAACGGAATAAGATATCATTATGATGAATATCATTAATATTATCTGTTAAAT |
| REGN1932 | 1051 | TGTAATACAAACGGAATAAGATATCATTATGATGAATATCATTAATATTATCTGTTAAAT |
| e Sequence {3D7} | | TGTAATACAAACGGAATAAGATATCATTATGATGAATATCATTAATATTATCTGTTAAAT |

FIG. 1-Cont.

| | | |
|---|---|---|
| H1H29089P {1} | 1201 | ATGGGTTCCTATATATATATTGATACAATAAATTTATACATAAGAAATGAAACATATTTTAACA |
| H1H29089P {2} | 1201 | ATGGGTTCCTATATATATATTGATACAATAAATTTATACATAAGAAATGAAACATATTTTAACA |
| H1H29100P {1} | 1201 | ATGGGTTCCTATATATATATTGATACAATAAATTTATACATAAGAAATGAAACATATTTTAACA |
| H1H29100P {2} | 1201 | ATGGGTTCCTATATATATATTGATACAATAAATTTATACATAAGAAATGAAACATATTTTAACA |
| H1H29147P2 {1} | 1201 | ATGGGTTCCTATATATATATTGATACAATAAATTTATACATAAGAAATGAAACATATTTTAACA |
| H1H29147P2 {2} | 1201 | ATGGGTTCCTATATATATATTGATACAATAAATTTATACATAAGAAATGAAACATATTTTAACA |
| H1H29187P2 {1} | 1201 | ATGGGTTCCTATATATATATTGATACAATAAATTTATACATAAGAAATGAAACATATTTTAACA |
| H1H29187P2 {2} | 1201 | ATGGGTTCCTATATATATATTGATACAATAAATTTATACATAAGAAATGAAACATATTTTAACA |
| REGN1932 | 1201 | ATGGGTTCCTATATATATATTGATACAATAAATTTATACATAAGAAATGAAACATATTTTAACA |
| e Sequence {3D7} | | |
| H1H29089P {1} | 1351 | CAAAAAGATGAATTATTAAAAAGAATTTTAGACATGTCAAATGAATATCTTTATTATTACTAGTG |
| H1H29089P {2} | 1351 | CAAAAAGATGAATTATTAAAAAGAATTTTAGACATGTCAAATGAATATCTTTATTATTACTAGTG |
| H1H29100P {1} | 1351 | CAAAAAGATGAATTATTAAAAAGAATTTTAGACATGTCAAATGAATATCTTTATTATTACTAGTG |
| H1H29100P {2} | 1351 | CAAAAAGATGAATTATTAAAAAGAATTTTAGACATGTCAAATGAATATCTTTATTATTACTAGTG |
| H1H29147P2 {1} | 1351 | CAAAAAGATGAATTATTAAAAAGAATTTTAGACATGTCAAATGAATATCTTTATTATTACTAGTG |
| H1H29147P2 {2} | 1351 | CAAAAAGATGAATTATTAAAAAGAATTTTAGACATGTCAAATGAATATCTTTATTATTACTAGTG |
| H1H29187P2 {1} | 1351 | CAAAAAGATGAATTATTAAAAAGAATTTTAGACATGTCAAATGAATATCTTTATTATTACTAGTG |
| H1H29187P2 {2} | 1351 | CAAAAAGATGAATTATTAAAAAGAATTTTAGACATGTCAAATGAATATCTTTATTATTACTAGTG |
| REGN1932 | 1351 | CAAAAAGATGAATTATTAAAAAGAATTTTAGACATGTCAAATGAATATCTTTATTATTACTAGTG |
| e Sequence {3D7} | | |

(PANEL K)

| | | |
|---|---|---|
| H1H29089P {1} | 1501 | CTACAAATGAAGTTCAATGATGTCCCAATTAAAATGGAATATTTTCAAACATATAAAAAATAAAC |
| H1H29089P {2} | 1501 | CTACAAATGAAGTTCAATGATGTCCCAATTAAAATGGAATATTTTCAAACATATAAAAAATAAAC |
| H1H29100P {1} | 1501 | CTACAAATGAAGTTCAATGATGTCCCAATTAAAATGGAATATTTTCAAACATATAAAAAATAAAC |
| H1H29100P {2} | 1501 | CTACAAATGAAGTTCAATGATGTCCCAATTAAAATGGAATATTTTCAAACATATAAAAAATAAAC |
| H1H29147P2 {1} | 1501 | CTACAAATGAAGTTCAATGATGTCCCAATTAAAATGGAATATTTTCAAACATATAAAAAATAAAC |
| H1H29147P2 {2} | 1501 | CTACAAATGAAGTTCAATGATGTCCCAATTAAAATGGAATATTTTCAAACATATAAAAAATAAAC |
| H1H29187P2 {1} | 1501 | CTACAAATGAAGTTCAATGATGTCCCAATTAAAATGGAATATTTTCAAACATATAAAAAATAAAC |
| H1H29187P2 {2} | 1501 | CTACAAATGAAGTTCAATGATGTCCCAATTAAAATGGAATATTTTCAAACATATAAAAAATAAAC |
| REGN1932 | | |
| e Sequence {3D7} | 1501 | CTACAAATGAAGTTCAATGATGTCCCAATTAAAATGGAATATTTTCAAACATATAAAAAATAAAC |

FIG. 1-Cont.

| | |
|---|---|
| CACTTACACAATGA | 1581 |
| CACTTACACAATGA | 1581 |
| CACTTACACAATGA | 1581 |
| CACTTACACAATGA | 1581 |
| CACTTACACAATGA | 1581 |
| CACTTACACAATGA | 1581 |
| CACTTACACAATGA | 1581 |
| CACTTACAC | 1576 |
| CACTTACACAATGA | 1581 |
| CACTTACACAATGA | |

(PANEL L) Cont. From PANEL J
Cont. From PANEL K

FIG. 1-Cont.

ANTI-PfRH5 ANTIBODIES AND ANTIGEN-BINDING FRAGMENTS THEREOF

CROSS-REFERENCE TO RELATED APPLICATIONS

This application is a division of US application Ser. No. 17/041,595, filed Sep. 25, 2020, now U.S. Pat. No. 11,667,701 which is a US National Stage Application under 35 USC § 371 of PCT/US2019/023734, filed Mar. 22, 2019, which claims the benefit under 35 USC § 119(e) of U.S. provisional patent application No. 62/648,259, filed Mar. 26, 2018, each of which is herein incorporated by reference in its entirety.

REFERENCE TO A SEQUENCE LISTING

This application incorporates by reference a computer readable Sequence Listing in ST.26 XML format, titled 10437US02_Substitute_Sequence, created on Aug. 4, 2023 and containing 320,252 bytes.

FIELD OF THE INVENTION

The present invention relates, in part, to antibodies and antigen-binding fragments thereof that bind specifically to PfRH5 as well as methods of use thereof for treating or preventing *Plasmodium falciparum* infections.

BACKGROUND OF THE INVENTION

Invasion of host erythrocytes is an essential step of the *Plasmodium falciparum* life cycle and of malaria pathology. Multiple antimalarial drugs target the asexual blood stages, however, their efficacy is threatened by the appearance of drug resistant strains (Arrow et al., Saving Lives, Buying Time: Economics of Malaria Drugs in an Age of Resistance. *National Academies Press (US)*. 254-266 (2004). PMID: 25009879; and Wright et al., Structure of malaria invasion protein RH5 with erythrocyte basigin and blocking antibodies, *Nature:* 515: 427-430 (2014). PMID: 25132548). Furthermore, antimalarial drugs display different pharmacokinetic properties. Some antimalarial drugs, such as artemisinin and quinine, are rapidly cleared within one parasite life cycle. On the other hand, hydrophobic and lipophilic antimalarial drugs are eliminated slowly, but they are characterized by different absorption rates depending on the amount of dietary fat consumed (Arrow et al.).

*Plasmodium falciparum* Reticulocyte Binding Protein Homologue 5 (PfRH5) is a member of the super family of erythrocyte ligands referred to as the Reticulocyte Binding Like proteins (RBLs). PfRH5 binds erythrocytes, is likely essential for blood-stage growth of the parasite and is implicated in the species tropism of erythrocyte invasion. Evidence suggests that a receptor for PfRH5 on erythrocytes is the Ok blood group antigen, basigin (BSG; CD147).

SUMMARY OF THE INVENTION

The present invention provides an antigen-binding protein (e.g., antibody or antigen-binding fragment thereof) that (i) specifically binds to the same epitope on *Plasmodium falciparum* Reticulocyte Binding Protein Homologue 5 (PfRH5) as; or (ii) competes for binding to PfRH5 polypeptide with: an antibody or antigen-binding fragment thereof that comprises (a) a heavy chain immunoglobulin that comprises CDR-H1, CDR-H2 and CDR-H3 of a heavy chain immunoglobulin that comprises the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (b) a light chain immunoglobulin that comprises CDR-L1, CDR-L2 and CDR-L3 of a light chain immunoglobulin that comprises the amino acid sequence set forth in SEQ ID NO: 10, 26, 42, 58, 74, 90, 106, 122, 138, 154, 170, 186, 202, 218 or 306. For example, in an embodiment of the invention, the anti-PfRH5 antigen-binding protein (e.g., antibody or antigen-binding fragment thereof) comprises (i) a heavy chain immunoglobulin that comprises CDR-H1, CDR-H2 and CDR-H3 of a heavy chain immunoglobulin that comprises the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (ii) a light chain immunoglobulin that comprises CDR-L1, CDR-L2 and CDR-L3 of a light chain immunoglobulin that comprises the amino acid sequence set forth in SEQ ID NO: 10, 26, 42, 58, 74, 90, 106, 122, 138, 154, 170, 186, 202, 218 or 306. For example, in an embodiment of the invention, the antigen-binding protein (e.g., antibody or antigen-binding fragment thereof) comprises: (a) a heavy chain immunoglobulin variable region comprising an amino acid sequence having at least 90% amino acid sequence identity to the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (b) a light chain immunoglobulin variable region comprising an amino acid sequence having at least 90% amino acid sequence identity to the amino acid sequence set forth in SEQ ID NO: 10, 26, 42, 58, 74, 90, 106, 122, 138, 154, 170, 186, 202, 218 or 306. In an embodiment of the invention, the antigen-binding protein (e.g., antibody or antigen-binding fragment thereof) comprises (a) a heavy chain immunoglobulin comprising the CDR-H1, CDR-H2 and CDR-H3 of a heavy chain immunoglobulin comprising an amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354 and at least 90% amino acid sequence identity to the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (b) an light chain immunoglobulin comprising the CDR-L1, CDR-L2 and CDR-L3 of a light chain immunoglobulin comprising an amino acid sequence set forth in SEQ ID NO: 10, 26, 42, 58, 74, 90, 106, 122, 138, 154, 170, 186, 202, 218 or 306 and at least 90% amino acid sequence identity to the amino acid sequence set forth in SEQ ID NO: 10, 26, 42, 58, 74, 90, 106, 122, 138, 154, 170, 186, 202, 218 or 306. The present invention also includes an antigen-binding protein (e.g., antibody or antigen-binding fragment thereof) comprising: a heavy chain immunoglobulin that comprises a CDR-H1 comprising the amino acid sequence: G Y S F T S Y W (SEQ ID NO: 4); a CDR-H2 comprising the amino acid sequence: I Y P G D S D T (SEQ ID NO: 6); and a CDR-H3 comprising the amino acid sequence: A R Q D I T G T T G F D Y (SEQ ID NO: 8); or a CDR-H1 comprising the amino acid sequence: G F T F S S Y A (SEQ ID NO: 20); a CDR-H2 comprising the amino acid sequence: I S Y D G S N K (SEQ ID NO: 22); and a CDR-H3 comprising the amino acid sequence: A K E R L F G V V S Y Y G M D V (SEQ ID NO: 24); or a CDR-H1 comprising the amino acid sequence: G G S I S S S S Y Y (SEQ ID NO: 36); a CDR-H2 comprising the amino acid sequence: I Y Y S G S T (SEQ ID NO: 38); and a CDR-H3 comprising the amino acid sequence: A R Q D R E A L F D Y (SEQ ID NO: 40); or a CDR-H1 comprising the amino acid sequence: G F R F D D Y A (SEQ ID NO: 52); a CDR-H2 comprising the amino acid sequence: I N W N S G G K (SEQ ID NO: 54); and a CDR-H3 comprising the amino acid sequence: A K D R G I A A R L L S R D A F D M (SEQ ID NO: 56); or a CDR-H1 comprising the amino acid sequence: S F T F S S Y G (SEQ ID NO: 68); a CDR-H2 comprising the amino acid sequence: I S Y D G S N K (SEQ ID NO: 70); and a CDR-H3 comprising the amino acid sequence: A R E V R R Y Y Y Y G M D V (SEQ ID NO: 72); or a CDR-H1 comprising the amino acid sequence: G F T F D D Y A (SEQ ID NO: 84); a CDR-H2 comprising the amino acid sequence: I S W N S G D I (SEQ ID NO: 86); and a CDR-H3 comprising the amino acid sequence: A K D T L S G T G T T W Y Y F D Y (SEQ ID NO: 88); or a CDR-H1 comprising the amino acid sequence: G F T F S S Y G (SEQ ID NO: 100); a CDR-H2 comprising the amino acid sequence: I S Y D G S N K (SEQ ID NO: 102); and a CDR-H3 comprising the amino acid sequence: A Q D G S S A I Y Y F Y G M D V (SEQ ID NO: 104); or a CDR-H1 comprising the amino acid sequence: G F T F S S Y G (SEQ ID NO: 116); a CDR-H2 comprising the amino acid sequence: I W Y D G S N K (SEQ ID NO: 118); and a CDR-H3 comprising the amino acid sequence: A R G E H Y Y G S G P F D P (SEQ ID NO: 120); or a CDR-H1 comprising the amino acid sequence: G G S I S S F G Y Y (SEQ ID NO: 132); a CDR-H2 comprising the amino acid sequence: I Y Y S G S I (SEQ ID NO: 134); and a CDR-H3 comprising the amino acid sequence: A R E R D Y G D Y F D Y (SEQ ID NO: 136); or a CDR-H1 comprising the amino acid sequence: G F T F S S Y G (SEQ ID NO: 148); a CDR-H2 comprising the amino acid sequence: I W Y D G S N K (SEQ ID NO: 150); and a CDR-H3 comprising the amino acid sequence: A R D Q D Y Y G S G S S Y G M D V (SEQ ID NO: 152); or a CDR-H1 comprising the amino acid sequence: G F T F S T Y G (SEQ ID NO: 164); a CDR-H2 comprising the amino acid sequence: I W Y D G T N K (SEQ ID NO: 166); and a CDR-H3 comprising the amino acid sequence: A R D P S G G D H Y Y Y Y G M D V (SEQ ID NO: 168); or a CDR-H1 comprising the amino acid sequence: G F T F S S Y G (SEQ ID NO: 180); a CDR-H2 comprising the amino acid sequence: I S F D E R N K (SEQ ID NO: 182); and a CDR-H3 comprising the amino acid sequence: A S E V G Y S F G H D A F D I (SEQ ID NO: 184); or a CDR-H1 comprising the amino acid sequence: G F T F N N Y A (SEQ ID NO: 196); a CDR-H2 comprising the amino acid sequence: I S G S G D S T (SEQ ID NO: 198); and a CDR-H3 comprising the amino acid sequence: A K D Q G L Y Y Y G S G S F D Y (SEQ ID NO: 200); or a CDR-H1 comprising the amino acid sequence: G F A F S D S A (SEQ ID NO: 212); a CDR-H2 comprising the amino acid sequence: I R N K A N R F A T (SEQ ID NO: 214); and a CDR-H3 comprising the amino acid sequence: A R H G H D T L T E G Y G M D V (SEQ ID NO: 216); or a CDR-H1 comprising the amino acid sequence: G G T F S S Y T (SEQ ID NO: 228); a CDR-H2 comprising the amino acid sequence: I I P L Y G T A (SEQ ID NO: 230); and a CDR-H3 comprising the amino acid sequence: A S T L E L R A F D A F D I (SEQ ID NO: 232); or a CDR-H1 comprising the amino acid sequence: G G S I S S G G Y Y (SEQ ID NO: 236); a CDR-H2 comprising the amino acid sequence: I Y Y S G S T (SEQ ID NO: 238); and a CDR-H3 comprising the amino acid sequence: A R A P P Y N W F D Y (SEQ ID NO: 240); or a CDR-H1 comprising the amino acid sequence: G F T F S D Y Y (SEQ ID NO: 244); a CDR-H2 comprising the amino acid sequence: I S N S G N T Q (SEQ ID NO: 246); and a CDR-H3 comprising the amino acid sequence: T R E G L E Y S S S E P F D Y (SEQ ID NO: 248); or a CDR-H1 comprising the amino acid sequence: G Y T F T A Y Y (SEQ ID NO: 252); a CDR-H2 comprising the amino acid sequence: I N P N N G D T (SEQ ID NO: 254); and a CDR-H3 comprising the amino acid sequence: A R D D L A A A G I G W F D S (SEQ ID NO: 256); or a CDR-H1 comprising the amino acid sequence: G F T F D D Y A (SEQ ID NO: 260); a CDR-H2 comprising the amino acid sequence: I S W N S E S I (SEQ ID NO: 262); and a CDR-H3 comprising the amino acid sequence: A K A P Y S G T Y F E Y F R H (SEQ ID NO: 264); or a CDR-H1 comprising the amino acid sequence: G F T F S S Y G (SEQ ID NO: 268); a CDR-H2 comprising the amino acid sequence: I S Y D G S N K (SEQ ID NO: 270); and a CDR-H3 comprising the amino acid sequence: A K D D W N Y D A F D I (SEQ ID NO: 272); or a CDR-H1 comprising the amino acid sequence: G G S I S S S G Y Y (SEQ ID NO: 276); a CDR-H2 comprising the amino acid sequence: I Y Y S G S T (SEQ ID NO: 278); and a CDR-H3 comprising the amino acid sequence: A R V D Y G S G S S F D Y (SEQ ID NO: 280); or a CDR-H1 comprising the amino acid sequence: G Y T F T S Y G (SEQ ID NO: 284); a CDR-H2 comprising the amino acid sequence: I S G F N G R T (SEQ ID NO: 286); and a CDR-H3 comprising the amino acid sequence: A R D G L E K L G D Y (SEQ ID NO: 288); or a CDR-H1 comprising the amino acid sequence: G F T F S N S G (SEQ ID NO: 292); a CDR-H2 comprising the amino acid sequence: I W H D G S Y K (SEQ ID NO: 294); and a CDR-H3 comprising the amino acid sequence: A R D D Y Y A S G T S V D V (SEQ ID NO: 296); or a CDR-H1 comprising the amino acid sequence: G Y T F T G Y Y (SEQ ID NO: 300); a CDR-H2 comprising the amino acid sequence: I N P N S G G T (SEQ ID NO: 302); and a CDR-H3 comprising the amino acid sequence: A R E E V D D F W S G Y L D Y (SEQ ID NO: 304); or a CDR-H1 comprising the amino acid sequence: G F A V N G D Y (SEQ ID NO: 316); a CDR-H2 comprising the amino acid sequence: I Y S S G N T (SEQ ID NO: 318); and a CDR-H3 comprising the amino acid sequence: A R D F P P M S G A D Y (SEQ ID NO: 320); or a CDR-H1 comprising the amino acid sequence: G Y T L T E L S (SEQ ID NO: 324); a CDR-H2 comprising the amino acid sequence: F D P E H G K I (SEQ ID NO: 326); and a CDR-H3 comprising the amino acid sequence: A T F Y N W N S Y Y F G M D V (SEQ ID NO: 328); or a CDR-H1 comprising the amino acid sequence: G F T F S S Y A (SEQ ID NO: 332); a CDR-H2 comprising the amino acid sequence: V S G S A D I T (SEQ ID NO: 334); and a CDR-H3 comprising the amino acid sequence: A K D K V Y N W N Y G I Y Y G M D V (SEQ ID NO: 336); or a CDR-H1 comprising the amino acid sequence: G G S I S S S Y Y (SEQ ID NO: 340); a CDR-H2 comprising the amino acid sequence: I Y Y S G S T (SEQ ID NO: 342); and a CDR-H3 comprising the amino acid sequence: A R Q G R W E R E N F D Y (SEQ ID NO: 344); or a CDR-H1 comprising the amino acid sequence: D E S F S D Y Y (SEQ ID NO: 348); a CDR-H2 comprising the amino acid sequence: I T H S G S T (SEQ ID NO: 350); and a CDR-H3 comprising the amino acid sequence: A R G G D Y G G L L D Y (SEQ ID NO: 352); and/or a light chain immunoglobulin variable region that comprises a CDR-L1 comprising the amino acid sequence: Q S I R N Y (SEQ ID NO: 12); a CDR-L2 comprising the amino acid sequence: A A S (SEQ ID NO: 14); and a CDR-L3 comprising the amino acid sequence: Q Q S Y S T P F T (SEQ ID NO: 16); or a CDR-L1 comprising the amino acid sequence: Q D I N R D (SEQ ID NO: 28); a CDR-L2 comprising the amino acid sequence: D A S (SEQ ID NO: 30); and a CDR-L3 comprising the amino acid sequence: Q Q Y K N L P Y T (SEQ ID NO: 32); or a CDR-L1 comprising the amino acid sequence: Q R I G S S (SEQ ID NO: 44); a CDR-L2 comprising the amino acid sequence: Y A S (SEQ ID NO: 46); and a CDR-L3 comprising the amino acid sequence: H Q S S T L P T (SEQ ID NO: 48); or a CDR-L1 comprising the amino acid sequence: Q D V S S Y (SEQ ID NO: 60); a CDR-L2 comprising the amino acid sequence: A A S (SEQ ID NO: 62); and a CDR-L3 comprising the amino acid sequence: Q H L N T Y P Y T (SEQ ID NO: 64); or a CDR-L1 comprising the amino acid sequence: Q D I S N Y (SEQ ID NO: 76); a CDR-L2 comprising the amino acid sequence: D A S (SEQ ID NO: 78); and a CDR-L3 comprising the amino acid sequence: Q Q Y N N L P L T (SEQ ID NO: 80); or a CDR-L1 comprising the amino acid sequence: Q G I S S Y (SEQ ID NO: 92); a CDR-L2 comprising the amino acid sequence: A A S (SEQ ID NO: 94); and a CDR-L3 comprising the amino acid sequence: Q Q V N S Y P L T (SEQ ID NO: 96); or a CDR-L1 comprising the amino acid sequence: Q D I N N Y (SEQ ID NO: 108); a CDR-L2 comprising the amino acid sequence: A A S (SEQ ID NO: 110); and a CDR-L3 comprising the amino acid sequence: L Q Y N S Y H P T (SEQ ID NO: 112); or a CDR-L1 comprising the amino acid sequence: Q S I S N Y (SEQ ID NO: 124); a CDR-L2 comprising the amino acid sequence: A A S (SEQ ID NO: 126); and a CDR-L3 comprising the amino acid sequence: Q Q S Y S S P L T (SEQ ID NO: 128); or a CDR-L1 comprising the amino acid sequence: Q S V S S N (SEQ ID NO: 140); a CDR-L2 comprising the amino acid sequence: G A S (SEQ ID NO: 142); and a CDR-L3 comprising the amino acid sequence: Q Q Y N N W P L T (SEQ ID NO: 144); or a CDR-L1 comprising the amino acid sequence: Q S I S S Y (SEQ ID NO: 156); a CDR-L2 comprising the amino acid sequence: A A S (SEQ ID NO: 158); and a CDR-L3 comprising the amino acid sequence: Q Q S Y S T P L T (SEQ ID NO: 160); or a CDR-L1 comprising the amino acid sequence: Q D I S N Y (SEQ ID NO: 172); a CDR-L2 comprising the amino acid sequence: D A S (SEQ ID NO: 174); and a CDR-L3 comprising the amino acid sequence: Q Q Y D N I P I T (SEQ ID NO: 176); or a CDR-L1 comprising the amino acid sequence: Q D I S N Y (SEQ ID NO: 188); a CDR-L2 comprising the amino acid sequence: D A S (SEQ ID NO: 190); and a CDR-L3 comprising the amino acid sequence: Q Q Y D N F P L T (SEQ ID NO: 192); or a CDR-L1 comprising the amino acid sequence: Q S I S S Y (SEQ ID NO: 204); a CDR-L2 comprising the amino acid sequence: A A S (SEQ ID NO: 206); and a CDR-L3 comprising the amino acid sequence: Q Q S Y S T P F T (SEQ ID NO: 208); or a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); or a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312). In an embodiment of the invention, the antigen-binding protein (e.g., antibody or antigen-binding fragment thereof) comprises (1) a heavy chain immunoglobulin variable region that comprises a CDR-H1 comprising the amino acid sequence: G Y S F T S Y W (SEQ ID NO: 4); a CDR-H2 comprising the amino acid sequence: I Y P G D S D T (SEQ ID NO: 6); and a CDR-H3 comprising the amino acid sequence: A R Q D I T G T T G F D Y (SEQ ID NO: 8); and a light chain immunoglobulin variable region that comprises a CDR-L1 comprising the amino acid sequence: Q S I R N Y (SEQ ID NO: 12); a CDR-L2 comprising the amino acid sequence: A A S (SEQ ID NO: 14); and a CDR-L3 comprising the amino acid sequence: Q Q S Y S T P F T (SEQ ID NO: 16); (2) a heavy chain immunoglobulin variable region that comprises: a CDR-H1 comprising the amino acid sequence: G F T F S S Y A (SEQ ID NO: 20); a CDR-H2 comprising the amino acid sequence: I S Y D G S N K (SEQ ID NO: 22); a CDR-H3 comprising the amino acid sequence: A K E R L F G V V S Y Y G M D V (SEQ ID NO: 24); and a light chain immunoglobulin variable region that comprises: a CDR-L1 comprising the amino acid sequence: Q D I N R D (SEQ ID NO: 28); a CDR-L2 comprising the amino acid sequence: D A S (SEQ ID NO: 30); and a CDR-L3 comprising the amino acid sequence: Q Q Y K N L P Y T (SEQ ID NO: 32); (3) a heavy chain immunoglobulin variable region that comprises: a CDR-H1 comprising the amino acid sequence: G G S I S S S S Y Y (SEQ ID NO: 36); a CDR-H2 comprising the amino acid sequence: I Y Y S G S T (SEQ ID NO: 38); and a CDR-H3 comprising the amino acid sequence: A R Q D R E A L F D Y (SEQ ID NO: 40); and a light chain immunoglobulin variable region that comprises: a CDR-L1 comprising the amino acid sequence: Q R I G S S (SEQ ID NO: 44); a CDR-L2 comprising the amino acid sequence: Y A S (SEQ ID NO: 46); and a CDR-L3 comprising the amino acid sequence: H Q S S T L P T (SEQ ID NO: 48); (4) a heavy chain immunoglobulin variable region that comprises: a CDR-H1 comprising the amino acid sequence: G F R F D D Y A (SEQ ID NO: 52); a CDR-H2 comprising the amino acid sequence: I N W N S G G K (SEQ ID NO: 54); and a CDR-H3 comprising the amino acid sequence: A K D R G I A A R L L S R D A F D M (SEQ ID NO: 56); and a light chain immunoglobulin variable region that comprises: a CDR-L1 comprising the amino acid sequence: Q D V S S Y (SEQ ID NO: 60); a CDR-L2 comprising the amino acid sequence: A A S (SEQ ID NO: 62); and a CDR-L3 comprising the amino acid sequence: Q H L N T Y P Y T (SEQ ID NO: 64); (5) a heavy chain immunoglobulin variable region that comprises: a CDR-H1 comprising the amino acid sequence: S F T F S S Y G (SEQ ID NO: 68); a CDR-H2 comprising the amino acid sequence: I S Y D G S N K (SEQ ID NO: 70); and a CDR-H3 comprising the amino acid sequence: A R E V R R Y Y Y Y G M D V (SEQ ID NO: 72); and a light chain immunoglobulin variable region that comprises: a CDR-L1 comprising the amino acid sequence: Q D I S N Y (SEQ ID NO: 76); a CDR-L2 comprising the amino acid sequence: D A S (SEQ ID NO: 78); and a CDR-L3 comprising the amino acid sequence: Q Q Y N N L P L T (SEQ ID NO: 80); (6) a heavy chain immunoglobulin variable region that comprises: a CDR-H1 comprising the amino acid sequence: G F T F D D Y A (SEQ ID NO: 84); a CDR-H2 comprising the amino acid sequence: I S W N S G D I (SEQ ID NO: 86); and a CDR-H3 comprising the amino acid sequence: A K D T L S G T G T T W Y Y F D Y (SEQ ID NO: 88); and a light chain immunoglobulin variable region that comprises: a CDR-L1 comprising the amino acid sequence: Q G I S S Y (SEQ ID NO: 92); a CDR-L2 comprising the amino acid sequence: A A S (SEQ ID NO: 94); and a CDR-L3 comprising the amino acid sequence: Q Q V N S Y P L T (SEQ ID NO: 96); (7) a heavy chain immunoglobulin variable region that comprises: a CDR-H1 comprising the amino acid sequence: G F T F S S Y G (SEQ ID NO: 100); a CDR-H2 comprising the amino acid sequence: I S Y D G S N K (SEQ ID NO: 102); and a CDR-H3 comprising the amino acid sequence: A Q D G S S A I Y Y F Y G M D V (SEQ ID NO: 104); and a light chain immunoglobulin variable region that comprises: a CDR-L1 comprising the amino acid sequence: Q D I N N Y (SEQ ID NO: 108); a CDR-L2 comprising the amino acid sequence: A A S (SEQ ID NO: 110); and a CDR-L3 comprising the amino acid sequence: L Q Y N S Y H P T (SEQ ID NO: 112); (8) a heavy chain immunoglobulin variable region that comprises: a CDR-H1 comprising the amino acid sequence: G F T F S S Y G (SEQ ID NO: 116); a CDR-H2 comprising the amino acid sequence: I W Y D G S N K (SEQ ID NO: 118); and a CDR-H3 comprising the amino acid sequence: A R G E H Y Y G S G P F D P (SEQ ID NO: 120); and a light chain immunoglobulin variable region that comprises: a CDR-L1 comprising the amino acid sequence: Q S I S N Y (SEQ ID NO: 124); a CDR-L2 comprising the amino acid sequence: A A S (SEQ ID NO: 126); and a CDR-L3 comprising the amino acid sequence: Q Q S Y S S P L T (SEQ ID NO: 128); (9) a heavy chain immunoglobulin variable region that comprises: a CDR-H1 comprising the amino acid sequence: G G S I S S F G Y Y (SEQ ID NO: 132); a CDR-H2 comprising the amino acid sequence: I Y Y S G S I (SEQ ID NO: 134); and a CDR-H3 comprising the amino acid sequence: A R E R D Y G D Y F D Y (SEQ ID NO: 136); and a light chain immunoglobulin variable region that comprises: a CDR-L1 comprising the amino acid sequence: Q S V S S N (SEQ ID NO: 140); a CDR-L2 comprising the amino acid sequence: G A S (SEQ ID NO: 142); and a CDR-L3 comprising the amino acid sequence: Q Q Y N N W P L T (SEQ ID NO: 144); (10) a heavy chain immunoglobulin variable region that comprises: a CDR-H1 comprising the amino acid sequence: G F T F S S Y G (SEQ ID NO: 148); a CDR-H2 comprising the amino acid sequence: I W Y D G S N K (SEQ ID NO: 150); and a CDR-H3 comprising the amino acid sequence: A R D Q D Y Y G S G S S Y G M D V (SEQ ID NO: 152); and a light chain immunoglobulin variable region that comprises: a CDR-L1 comprising the amino acid sequence: Q S I S S Y (SEQ ID NO: 156); a CDR-L2 comprising the amino acid sequence: A A S (SEQ ID NO: 158); and a CDR-L3 comprising the amino acid sequence: Q Q S Y S T P L T (SEQ ID NO: 160); (11) a heavy chain immunoglobulin variable region that comprises: a CDR-H1 comprising the amino acid sequence: G F T F S T Y G (SEQ ID NO: 164); a CDR-H2 comprising the amino acid sequence: I W Y D G T N K (SEQ ID NO: 166); and a CDR-H3 comprising the amino acid sequence: A R D P S G G D H Y Y Y Y G M D V (SEQ ID NO: 168); and a light chain immunoglobulin variable region that comprises: a CDR-L1 comprising the amino acid sequence: Q D I S N Y (SEQ ID NO: 172); a CDR-L2 comprising the amino acid sequence: D A S (SEQ ID NO: 174); and a CDR-L3 comprising the amino acid sequence: Q Q Y D N I P I T (SEQ ID NO: 176); (12) a heavy chain immunoglobulin variable region that comprises: a CDR-H1 comprising the amino acid sequence: G F T F S S Y G (SEQ ID NO: 180); a CDR-H2 comprising the amino acid sequence: I S F D E R N K (SEQ ID NO: 182); and a CDR-H3 comprising the amino acid sequence: A S E V G Y S F G H D A F D I (SEQ ID NO: 184); and a light chain immunoglobulin variable region that comprises: a CDR-L1 comprising the amino acid sequence: Q D I S N Y (SEQ ID NO: 188); a CDR-L2 comprising the amino acid sequence: D A S (SEQ ID NO: 190); and a CDR-L3 comprising the amino acid sequence: Q Q Y D N F P L T (SEQ ID NO: 192); (13) a heavy chain immunoglobulin variable region that comprises: a CDR-H1 comprising the amino acid sequence: G F T F N N Y A (SEQ ID NO: 196); a CDR-H2 comprising the amino acid sequence: I S G S G D S T (SEQ ID NO: 198); and a CDR-H3 comprising the amino acid sequence: A K D Q G L Y Y Y G S G S F D Y (SEQ ID NO: 200); and a light chain immunoglobulin variable region that comprises: a CDR-L1 comprising the amino acid sequence: Q S I S S Y (SEQ ID NO: 204); a CDR-L2 comprising the amino acid sequence: A A S (SEQ ID NO: 206); and a CDR-L3 comprising the amino acid sequence: Q Q S Y S T P F T (SEQ ID NO: 208); (14) a heavy chain immunoglobulin variable region that comprises: a CDR-H1 comprising the amino acid sequence: G F A F S D S A (SEQ ID NO: 212); a CDR-H2 comprising the amino acid sequence: I R N K A N R F A T (SEQ ID NO: 214); and a CDR-H3 comprising the amino acid sequence: A R H G H D T L T E G Y G M D V (SEQ ID NO: 216); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (15) a heavy chain immunoglobulin variable region that comprises: a CDR-H1 comprising the amino acid sequence: G G T F S S Y T (SEQ ID NO: 228); a CDR-H2 comprising the amino acid sequence: I I P L Y G T A (SEQ ID NO: 230); and a CDR-H3 comprising the amino acid sequence: A S T L E L R A F D A F D I (SEQ ID NO: 232); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (16) a heavy chain immunoglobulin variable region that comprises: a CDR-H1 comprising the amino acid sequence: G G S I S S G G Y Y (SEQ ID NO: 236); a CDR-H2 comprising the amino acid sequence: I Y Y S G S T (SEQ ID NO: 238); and a CDR-H3 comprising the amino acid sequence: A R A P P Y N W F D Y (SEQ ID NO: 240); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (17) a heavy chain immunoglobulin variable region that comprises: a CDR-H1 comprising the amino acid sequence: G F T F S D Y Y (SEQ ID NO: 244); a CDR-H2 comprising the amino acid sequence: I S N S G N T Q (SEQ ID NO: 246); and a CDR-H3 comprising the amino acid sequence: T R E G L E Y S S S E P F D Y (SEQ ID NO: 248); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (18) a heavy chain immunoglobulin variable region that comprises: a CDR-H1 comprising the amino acid sequence: G Y T F T A Y Y (SEQ ID NO: 252); a CDR-H2 comprising the amino acid sequence: I N P N N G D T (SEQ ID NO: 254); and a CDR-H3 comprising the amino acid sequence: A R D D L A A A G I G W F D S (SEQ ID NO: 256); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (19) a heavy chain immunoglobulin variable region that comprises: a CDR-H1 comprising the amino acid sequence: G F T F D D Y A (SEQ ID NO: 260); a CDR-H2 comprising the amino acid sequence: I S W N S E S I (SEQ ID NO: 262); and a CDR-H3 comprising the amino acid sequence: A K A P Y S G T Y F E Y F R H (SEQ ID NO: 264); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (20) a heavy chain immunoglobulin variable region that comprises: a CDR-H1 comprising the amino acid sequence: G F T F S S Y G (SEQ ID NO: 268); a CDR-H2 comprising the amino acid sequence: I S Y D G S N K (SEQ ID NO: 270); and a CDR-H3 comprising the amino acid sequence: A K D D W N Y D A F D I (SEQ ID NO: 272); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (21) a heavy chain immunoglobulin variable region that comprises: a CDR-H1 comprising the amino acid sequence: G G S I S S G Y Y (SEQ ID NO: 276); a CDR-H2 comprising the amino acid sequence: I Y Y S G S T (SEQ ID NO: 278); and a CDR-H3 comprising the amino acid sequence: A R V D Y G S G S S F D Y (SEQ ID NO: 280); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (22) a heavy chain immunoglobulin variable region that comprises: a CDR-H1 comprising the amino acid sequence: G Y T F T S Y G (SEQ ID NO: 284); a CDR-H2 comprising the amino acid sequence: I S G F N G R T (SEQ ID NO: 286); and a CDR-H3 comprising the amino acid sequence: A R D G L E K L G D Y (SEQ ID NO: 288); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (23) a heavy chain immunoglobulin variable region that comprises: a CDR-H1 comprising the amino acid sequence: G F T F S N S G (SEQ ID NO: 292); a CDR-H2 comprising the amino acid sequence: I W H D G S Y K (SEQ ID NO: 294); and a CDR-H3 comprising the amino acid sequence: A R D D Y Y A S G T S V D V (SEQ ID NO: 296); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (24) a heavy chain immunoglobulin variable region that comprises: a CDR-H1 comprising the amino acid sequence: G Y T F T G Y Y (SEQ ID NO: 300); a CDR-H2 comprising the amino acid sequence: I N P N S G G T (SEQ ID NO: 302); and a CDR-H3 comprising the amino acid sequence: A R E E V D D F W S G Y L D Y (SEQ ID NO: 304); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); (25) a heavy chain immunoglobulin variable region that comprises: a CDR-H1 comprising the amino acid sequence: G F A V N G D Y (SEQ ID NO: 316); a CDR-H2 comprising the amino acid sequence: I Y S S G N T (SEQ ID NO: 318); and a CDR-H3 comprising the amino acid sequence: A R D F P P M S G A D Y (SEQ ID NO: 320); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); (26) a heavy chain immunoglobulin variable region that comprises: a CDR-H1 comprising the amino acid sequence: G Y T L T E L S (SEQ ID NO: 324); a CDR-H2 comprising the amino acid sequence: F D P E H G K I (SEQ ID NO: 326); and a CDR-H3 comprising the amino acid sequence: A T F Y N W N S Y Y F G M D V (SEQ ID NO: 328); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); (27) a heavy chain immunoglobulin variable region that comprises: a CDR-H1 comprising the amino acid sequence: G F T F S S Y A (SEQ ID NO: 332); a CDR-H2 comprising the amino acid sequence: V S G S A D I T (SEQ ID NO: 334); and a CDR-H3 comprising the amino acid sequence: A K D K V Y N W N Y G I Y Y G M D V (SEQ ID NO: 336); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); (28) a heavy chain immunoglobulin variable region that comprises: a CDR-H1 comprising the amino acid sequence: G G S I S S S S Y Y (SEQ ID NO: 340); a CDR-H2 comprising the amino acid sequence: I Y Y S G S T (SEQ ID NO: 342); and a CDR-H3 comprising the amino acid sequence: A R Q G R W E R E N F D Y (SEQ ID NO: 344); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); and/or (29) a heavy chain immunoglobulin variable region that comprises: a CDR-H1 comprising the amino acid sequence: D E S F S D Y Y (SEQ ID NO: 348); a CDR-H2 comprising the amino acid sequence: I T H S G S T (SEQ ID NO: 350); and a CDR-H3 comprising the amino acid sequence: A R G G D Y G G L L D Y (SEQ ID NO: 352); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312). For example, in an embodiment of the invention, the antigen-binding protein (e.g., antibody or antigen-binding fragment thereof) comprises (a) a heavy chain immunoglobulin that comprises the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (b) a light chain immunoglobulin that comprises the amino acid sequence set forth in SEQ ID NO: 10, 26, 42, 58, 74, 90, 106, 122, 138, 154, 170, 186, 202, 218 or 306. In an embodiment of the invention, the antigen-binding protein is multispecific (e.g., bispecific, multiparatopic or biparatopic).

In an embodiment of the invention, the antigen-binding protein (e.g., antibody or antigen-binding fragment thereof) comprises one or more of the following properties: Inhibits growth of *Plasmodium falciparum* in human red blood cells; Inhibits growth of *Plasmodium falciparum* strain D10, Dd2, 7G8, W2-mef, 3D7, HB3, FCR-1/FVO, Cam3.II or RF7 in human red blood cells; Blocks binding of PfRH5 polypeptide to basigin polypeptide; for example, at a concentration of about 6.67 micromolar, causes maximal growth inhibition (e.g., in vitro) of *Plasmodium falciparum* (e.g., strain FCR-1/FVO) in heat-inactivated human or *Aotus* monkey serum (e.g., as measured by parasite lactate dehydrogenase (LDH) activity) that at about 1-10% (e.g., 1, 2, 3, 4, 5, 6, 7, 8, 9 or 10%) (relative to uninfected erythrocytes) higher than that of non-heat-inactivated human or *Aotus* monkey serum, respectively; when exposed to said antigen-binding protein, does not induce mutation of PfRH5 in *Plasmodium falciparum* (e.g., strain 3D7), e.g., in vitro after about 45 days of gradually increasing antibody concentration, e.g., from about $1XEC_{50}$ to about $110XEC_{50}$; and/or binds to PfRH5 lacking the amino-terminal residues M1-Y139 and including residues K140-Q526 but lacking K247-L295 and having the mutations T216A and T299A, for example, wherein the antigen-binding protein comprises an amino acid sequence as set forth herein.

The present invention also includes a complex comprising an antigen-binding protein (e.g., antibody or antigen-binding fragment thereof) bound to a *Plasmodium Falciparum* reticulocyte binding protein homologue 5 (PfRH5) polypeptide. For example, the PfRH5 is on the surface of a cell such as *Plasmodium Falciparum* (e.g., merozoites of *Plasmodium Falciparum*), e.g., in the body of a subject (e.g., a human). In an embodiment of the invention, the PfRH5 is on the surface of a *Plasmodium Falciparum*, e.g., a merozoite in a red blood cell.

The present invention also provides a method for making an anti-PfRH5 antigen-binding protein (e.g., antibody or antigen-binding fragment thereof) set forth herein or immunoglobulin chain thereof comprising: (a) introducing one or more polynucleotides encoding an immunoglobulin chain of said antigen-binding protein into a host cell (e.g., a Chinese hamster ovary cell); (b) culturing the host cell under conditions favorable to expression of the polynucleotide; and (c) optionally, isolating the antigen-binding protein or immunoglobulin chain from the host cell and/or medium in which the host cell is grown. An antigen-binding protein or immunoglobulin chain which is a product of such a method also forms part of the present invention.

A lateral flow immuno-chromatographic antigen-detection test strip comprising an anti-PfRH5 antigen-binding protein set forth herein (e.g., antibody or antigen-binding fragment thereof) is part of the present invention. Methods for detecting *Plasmodium falciparum* in a blood sample from a subject and/or the body of a subject, using the test strip, are also part of the present invention.

A polypeptide comprising: (a) CDR-H1, CDR-H2, and CDR-H3 of an immunoglobulin heavy chain variable region of an immunoglobulin chain that comprises the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; or (b) CDR-L1, CDR-L2, and CDR-L3 of immunoglobulin light chain variable region of an immunoglobulin chain that comprises the amino acid sequence set forth in SEQ ID NO: 10, 26, 42, 58, 74, 90, 106, 122, 138, 154, 170, 186, 202, 218 or 306 also forms part of the present invention. Polynucleotides (e.g., DNA or RNA) encoding such a polypeptide also form part of the present invention along with a vector that comprises the polynucleotide.

The present invention also provides a host cell (e.g., a Chinese hamster ovary cell) comprising the antigen-binding protein (e.g., antibody or antigen-binding fragment thereof) or an immunoglobulin chain or a polypeptide or polynucleotide or vector which is set forth herein.

The present invention also provides a composition or kit that comprises one or more (e.g., 1, 2, 3 or 4) of the anti-PfRH5 antigen-binding proteins (e.g., antibody or antigen-binding fragment thereof) set forth herein, optionally in association with a further therapeutic agent (e.g., an anti-parasitic drug, chloroquine, atovaquone, proguanil, artemether, lumefantrine, mefloquine, quinine, quinidine, doxycycline (optionally in combination with quinine), clindamycin, a vaccine, an anti-malarial vaccine or RTS,S/AS01). The present invention also provides a pharmaceutical composition comprising an anti-PfRH5 antigen-binding protein set forth herein and pharmaceutically acceptable carrier and, optionally, a further therapeutic agent.

The present invention also provides a vessel or injection device (e.g., an autoinjector or pre-filled syringe) comprising an anti-PfRH5 antigen-binding protein (e.g., antibody or antigen-binding fragment thereof) or composition (e.g., a pharmaceutical composition) set forth herein.

The present invention provides a method for treating or preventing *Plasmodium falciparum* infection (e.g., malaria) in a subject (e.g., a human) in need thereof, comprising administering (e.g., parenterally) a therapeutically effective amount of an anti-PfFRH5 antigen-binding protein discussed herein optionally in association with a further therapeutic agent. In an embodiment of the invention, the subject is diagnosed as suffering from a *Plasmodium falciparum* infection (e.g., malaria) prior to initiation of treatment. For example, in an embodiment of the invention, the subject is diagnosed using a lateral flow test strip as set forth herein. In an embodiment of the invention, the subject is not infected with *Plasmodium falciparum*, but is administered a therapeutically effective amount of the anti-PfRH5 antigen-binding protein prophylactically, i.e., so as to prevent such an infection.

The present invention also provides a method for diagnosing *Plasmodium falciparum* infection in a subject comprising contacting an anti-PfRH5 antigen-binding protein of the present invention with a sample (e.g., blood) from said subject and, if a complex between the antigen-binding protein and PfRH5 polypeptide in the sample is detected, determining that the subject is infected with *Plasmodium falciparum*. For example, said complex can be formed on a lateral flow test strip as set forth herein comprising an anti-PfRH5 antigen-binding protein of the present invention and the PfRH5 polypeptide (from the subject's sample).

The present invention provides a method for administering an anti-PfRH5 antigen-binding protein (e.g., antibody or antigen-binding fragment thereof) set forth herein into the body of a subject (e.g., a human) comprising injecting the antigen-binding protein into the body of the subject, optionally in association with a further therapeutic agent, e.g., subcutaneously, intravenously or intramuscularly.

The present invention also encompasses any immunoglobulin polypeptide or polynucleotide set forth herein, e.g., comprising any amino acid sequence set forth in a member selected from the group consisting of SEQ ID NO: 2, 4, 6, 8, 10, 12, 14, 18, 20, 22, 24, 26, 28, 30, 34, 36, 38, 40, 42, 44, 46, 50, 52, 54, 56, 58, 60, 62, 66, 68, 70, 72, 74, 76, 78, 82, 84, 86, 88, 90, 92, 94, 98, 100, 102, 104, 106, 108, 110, 114, 116, 118, 120, 122, 124, 126, 130, 132, 134, 136, 138, 140, 142, 146, 148, 150, 152, 154, 156, 158, 162, 164, 166, 168, 170, 172, 174, 178, 180, 182, 184, 186, 188, 190, 194, 196, 198, 200, 202, 204, 206, 210, 212, 214, 216, 218, 220, 222, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 314, 316, 318, 320, 322, 324, 326, 328, 330, 332, 334, 336, 338, 340, 342, 344, 346, 348, 350, 352, 354, 356, 358 and 360; or a polynucleotide comprising any nucleotide sequence set forth in a member selected from the group consisting of SEQ ID NO: 1, 3, 5, 7, 9, 11, 13, 17, 19, 21, 23, 25, 27, 29, 33, 35, 37, 39, 41, 43, 45, 49, 51, 53, 55, 57, 59, 61, 65, 67, 69, 71, 73, 75, 77, 81, 83, 85, 87, 89, 91, 93, 97, 99, 101, 103, 105, 107, 109, 113, 115, 117, 119, 121, 123, 125, 129, 131, 133, 135, 137, 139, 141, 145, 147, 149, 151, 153, 155, 157, 161, 163, 165, 167, 169, 171, 173, 177, 179, 181, 183, 185, 187, 189, 193, 195, 197, 199, 201, 203, 205, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 313, 315, 317, 319, 321, 323, 325, 327, 329, 331, 333, 335, 337, 339, 341, 343, 345, 347, 349, 351, 353, 355, 357 and 359.

BRIEF DESCRIPTION OF THE FIGURES

Figure 1:
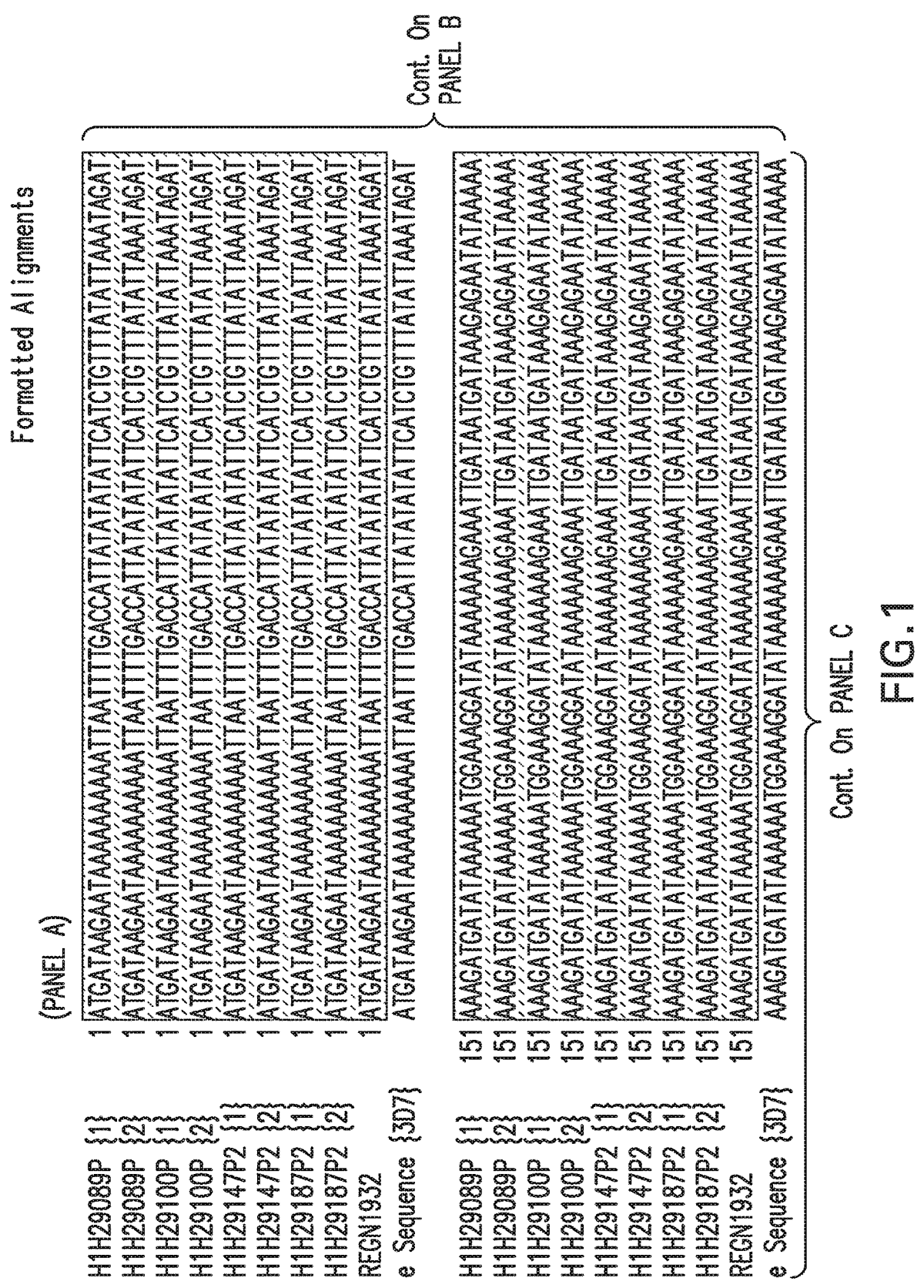
Figure 1:
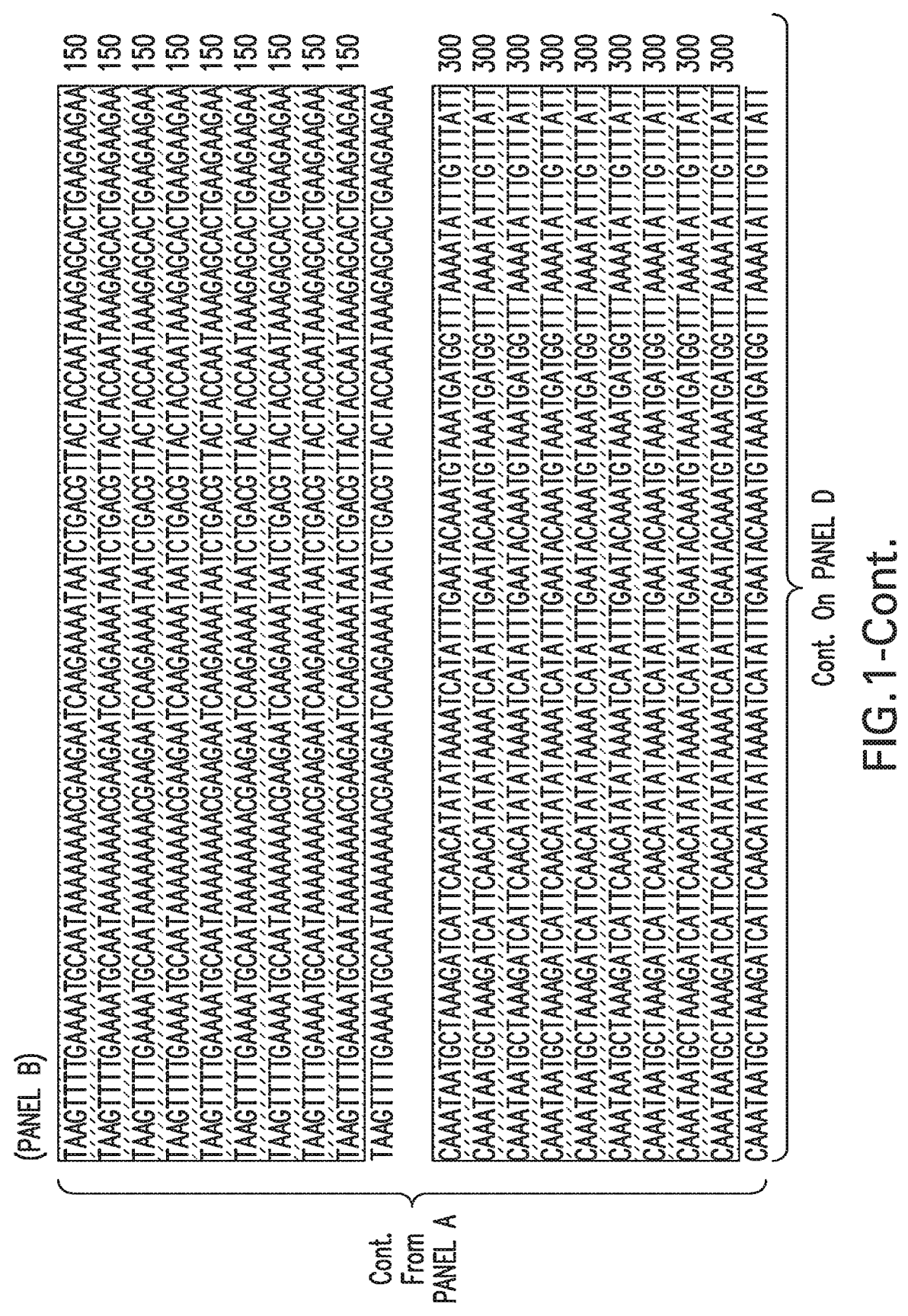
Figure 1:
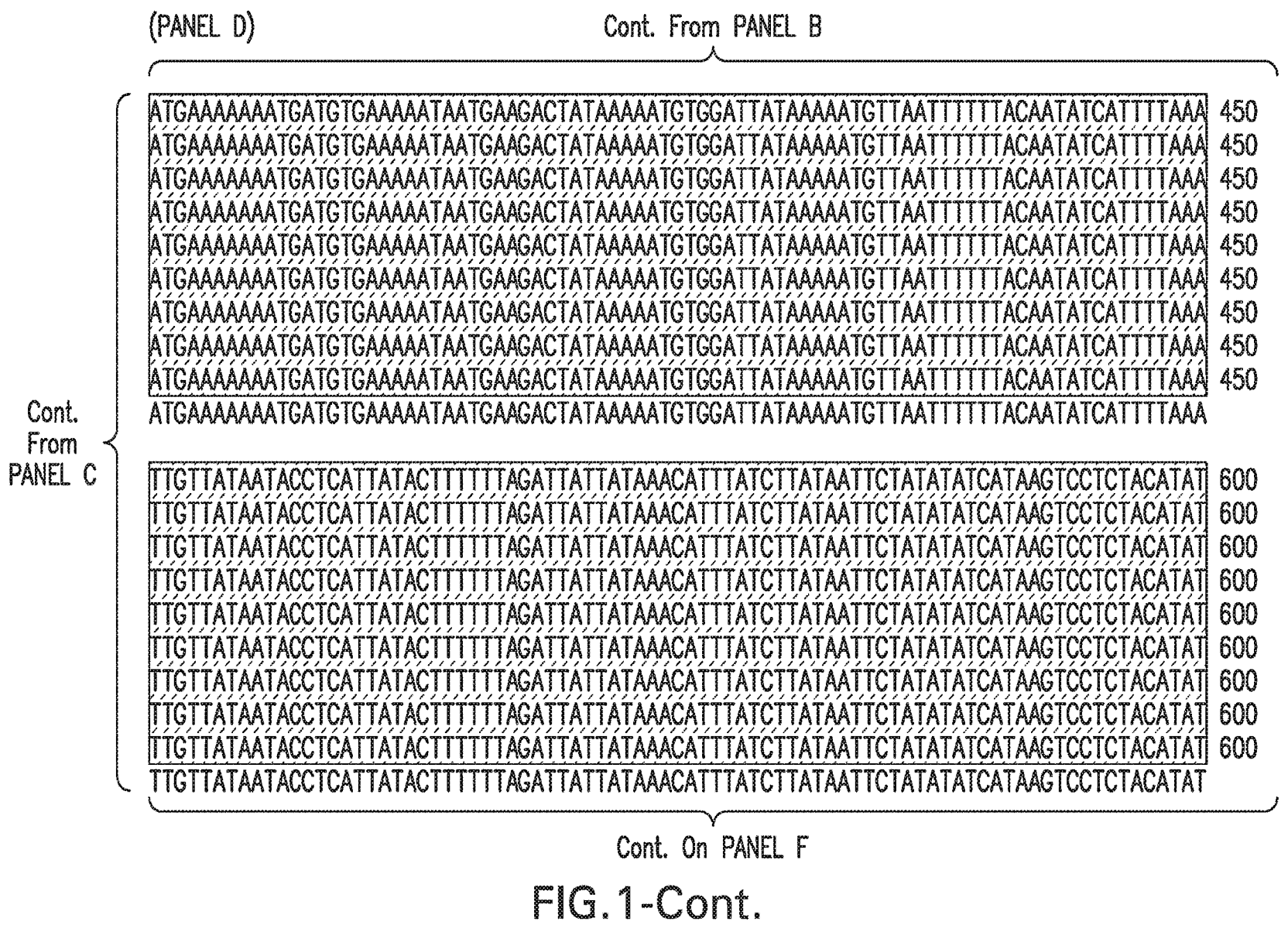
Figure 1:
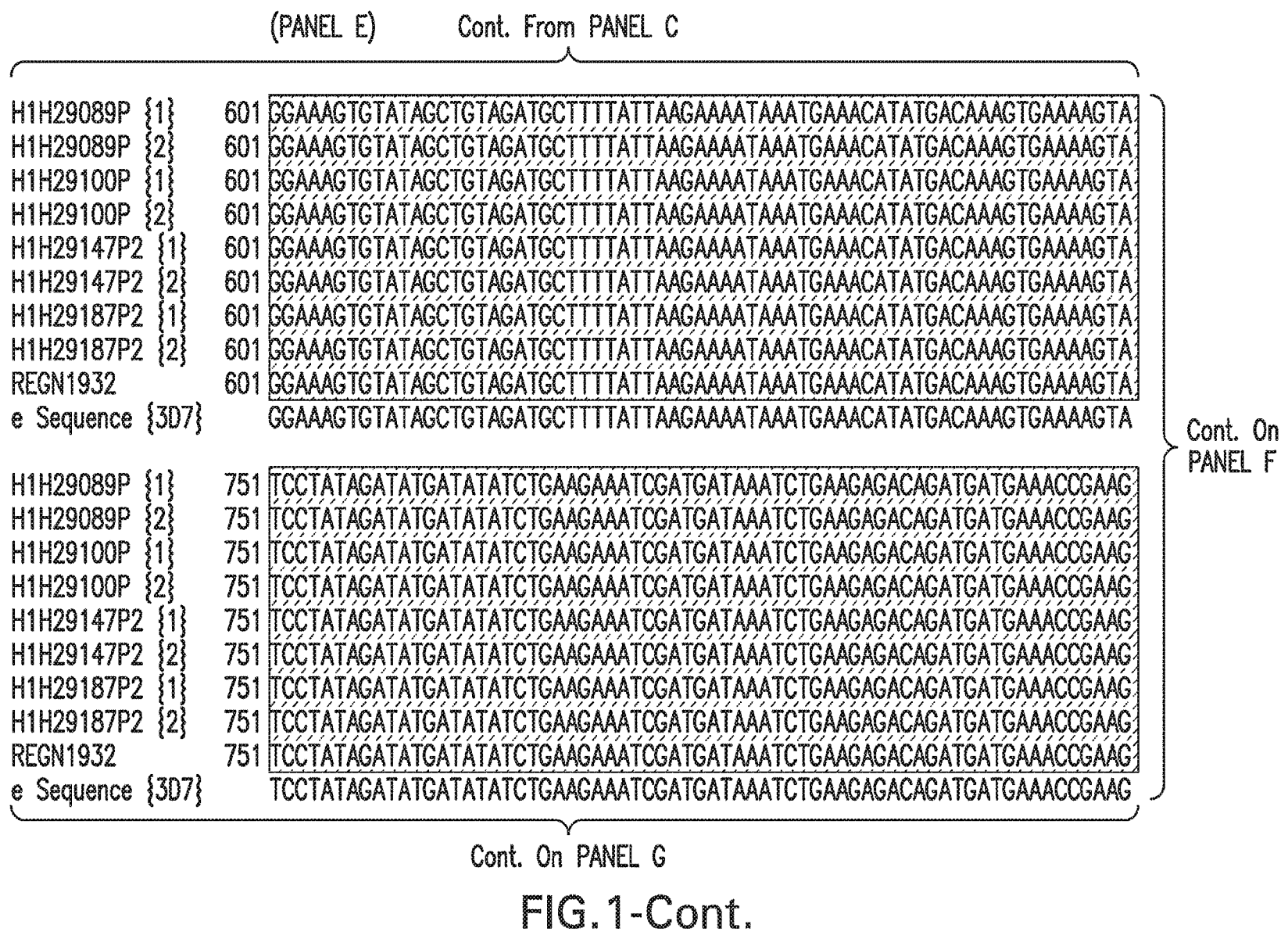
Figure 1:
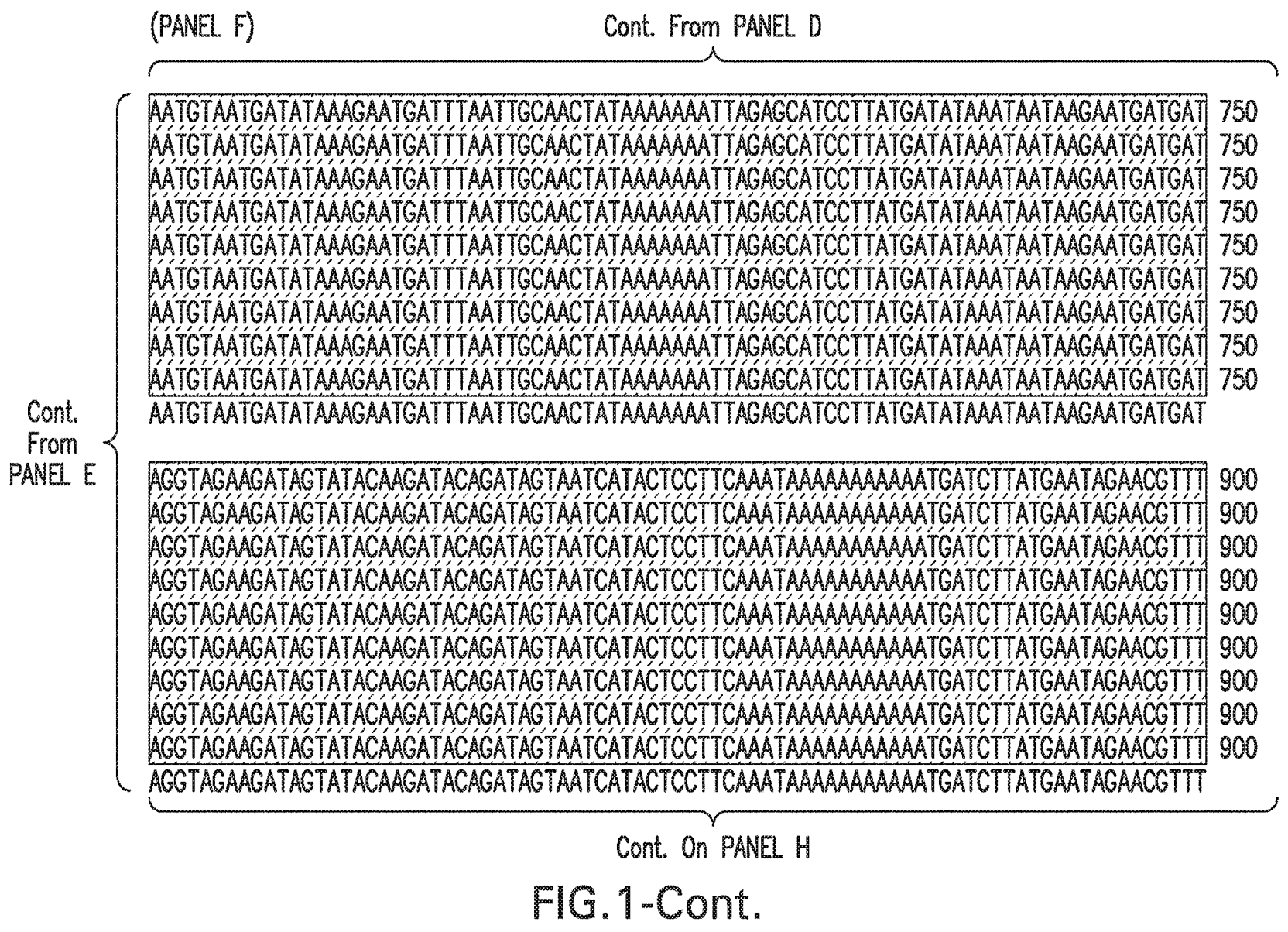
Figure 1:
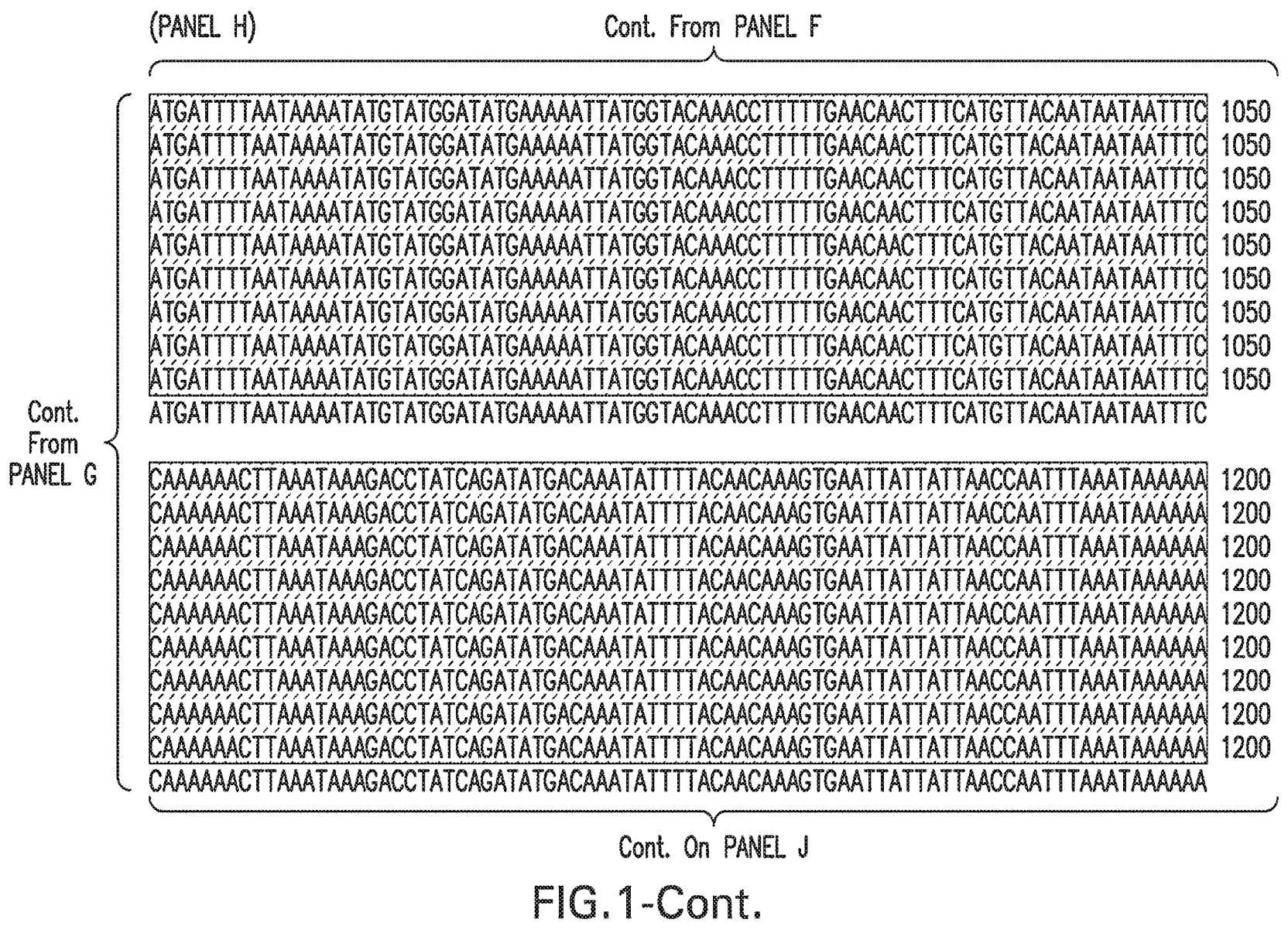
Figure 1:
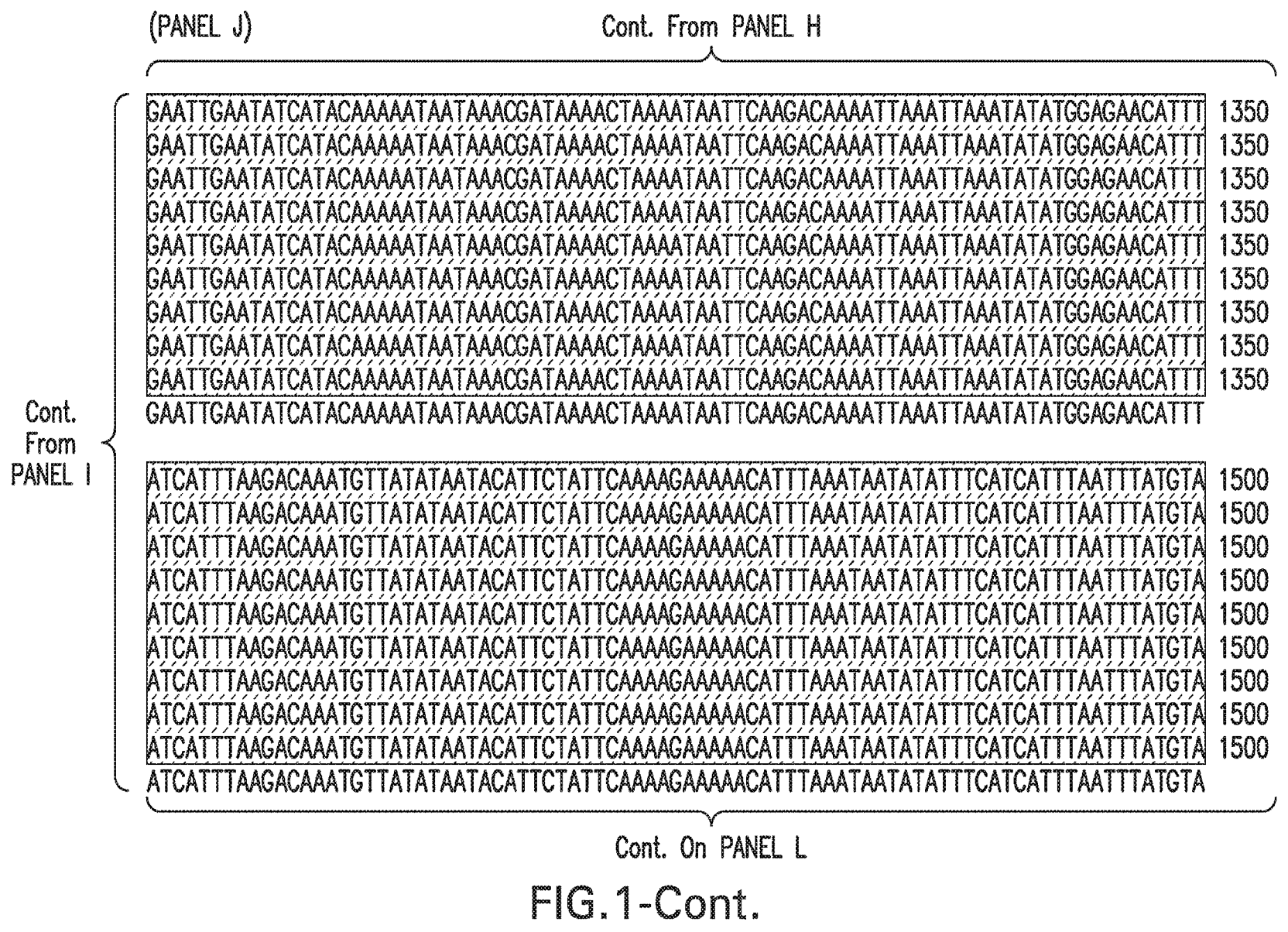

FIG. 1 shows sequence alignments of PfRH5 corresponding to each PfRH5-specific antibody after 45 days of gradual increases in antibody pressure (1×EC$_{50}$ to 110×EC$_{50}$).

DETAILED DESCRIPTION OF THE INVENTION

*Plasmodium falciparum* is a protozoan parasite, one of the species of *Plasmodium* that cause malaria in humans which can be transmitted by the female *Anopheles* mosquito. Malaria caused by this species (which may be referred to as "*falciparum* malaria") is a highly dangerous form of malaria, with a high rate of complications and mortality. See e.g., Gardner et al., Genome sequence of the human malaria parasite *Plasmodium falciparum*, Nature 419(6906): 498-511 (2002). *Plasmodium falciparum* includes any strain thereof which exhibits sensitivity to an antigen-binding protein of the present invention, e.g., D10, Dd2, 7G8, W2-mef, 3D7, HB3, FCR-1/FVO, Cam3.II or RF7. "*Plasmodium falciparum* infection" refers to the invasion and multiplication of *Plasmodium falciparum* in the body of a subject. The present invention provides various antigen-binding proteins which are effective for treatment or prophylaxis of *Plasmodium falciparum* infection.

An anti-PfRH5 "antigen-binding protein" is a single polypeptide (e.g., an ScFv (single chain variable fragment)) or complex of more than one polypeptide (e.g., a tetrameric IgG antibody) that binds specifically to PfRH5 polypeptide, for example, an anti-PfRH5 antibody or antigen-binding fragment whether monospecific or multispecific (e.g., bispecific) or monovalent or multivalent (e.g., bivalent). A monovalent antigen-binding protein has a single antigen-binding domain whereas a bivalent antigen-binding protein has two antigen-binding domains.

Basigin (BSG, extracellular matrix metalloproteinase inducer, EMMPRIN, CD147) is a polypeptide which is a target on erythrocytes to which PfRH5 binds. In an embodiment of the invention, the amino acid sequence of basigin is set forth in Uniprot accession no. Q54A51. See e.g., Crosnier et al., Basigin is a receptor essential for erythrocyte invasion by *Plasmodium falciparum*, Nature. 2011 Nov. 9; 480(7378): 534-7. In an embodiment of the invention, an antigen-binding protein of the present invention blocks binding between PfRH5 an BSG.

*Plasmodium Falciparum* Reticulocyte-Binding Protein Homologue 5 (PfRH5)

*Plasmodium falciparum* Reticulocyte Binding Protein Homologue 5 (PfRH5) is a member of the super family of erythrocyte ligands referred to as the Reticulocyte Binding-Like proteins (RBLs). Evidence suggests that PfRH5 is essential for blood-stage growth of a *Plasmodium falciparum* infection. PfRH5 binds erythrocytes and is implicated in the species tropism of erythrocyte invasion. See e.g., Bustamante et al., Vaccine. 2013 Jan. 2; 31(2): 373-379.

In an embodiment of the invention, PfRH5 comprises the amino acid sequence:

```
                                    (SEQ ID NO: 361)
MIRIKKKLIL TIIYIHLFIL NRLSFENAIK KTKNQENNLT

LLPIKSTEEE KDDIKNGKDI KKEIDNDKEN IKTNNAKDHS

TYIKSYLNTN VNDGLKYLFI PSHNSFIKKY SVFNQINDGM

LLNEKNDVKN NEDYKNVDYK NVNFLQYHFK ELSNYNIANS

IDILQEKEGH LDFVIIPHYT FLDYYKHLSY NSIYHKSSTY

GKCIAVDAFI KKINETYDKV KSKCNDIKND LIATIKKLEH

PYDINNKNDD SYRYDISEEI DDKSEETDDE TEEVEDSIQD

TDSNHTPSNK KKNDLMNRTF KKMMDEYNTK KKKLIKCIKN

HENDFNKICM DMKNYGTNLF EQLSCYNNNF CNTNGIRYHY

DEYIHKLILS VKSKNLNKDL SDMTNILQQS ELLLTNLNKK

MGSYIYIDTI KFIHKEMKHI FNRIEYHTKI INDKTKIIQD

KIKLNIWRTF QKDELLKRIL DMSNEYSLFI TSDHLRQMLY

NTFYSKEKHL NNIFHHLIYV LQMKFNDVPI KMEYFQTYKK

NKPLTQ
```

The polypeptide "PfRH5ΔNL.6his" (PfRH5 (K140-Q526; del M1-Y139; del K247-L295; T216A; T299A)) which lacks the N-terminal residues 1-139 and residues 247-295 and has mutations T216A and T299A as well as a C-terminal His$_6$ tag forms part of the present invention along with polynucleotides encoding the polypeptide. In an embodiment of the invention, the PfRH5ΔNL.6his polypeptide comprises the amino acid sequence set forth in SEQ ID NO: 362:

```
                                    (SEQ ID NO: 362)
KNVNFLQYHFKELSNYNIANSIDILQEKEGHLDFVIIPHYTFLDYYKHLS

YNSIYHKSSTYGKYIAVDAFIKKINEAYDKVKSKCNDIKNDLIATIKKLE

HPYDINNMNRAFKKMMDEYNTKKKKLIKCIKNHENDFNKICMDMKNYGTN

LFEQLSCYNNNFCNTNGIRYHYDEYIHKLILSVKSKNLNKDLSDMTNILQ

QSELLLTNLNKKMGSYIYIDTIKFIHKEMKHIFNRIEYHTKIINDKTKII

QDKIKLNIWRTFQKDELLKRILDMSNEYSLFITSDHLRQMLYNTFYSKEK

HLNNIFHHLIYVLQMKFNDVPIKMEYFQTYKKNKPLTQHHHHHH.
```

In an embodiment of the invention, the polypeptide is in a crystallized form or a non-crystallized form.

Antibodies and Antigen-Binding Fragments

The present invention provides antigen-binding proteins, such as antibodies and antigen-binding fragments thereof, that specifically bind to PfRH5 protein or an antigenic fragment thereof. Immunoglobulin chains of the present invention are described herein in Example 1 at Table 1-1.

The term "antibody", as used herein, refers to immunoglobulin molecules comprising four polypeptide chains, two heavy chains (HCs) and two light chains (LCs) inter-connected by disulfide bonds (i.e., "full antibody molecules"), as well as multimers thereof (e.g. IgM)—for example, H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2. Each heavy chain (HC) comprises a heavy chain variable region ("HCVR" or "$V_H$") (e.g., SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354) and a heavy chain constant region (comprised of domains CH1, CH2 and CH3). Each light chain (LC) is comprised of a light chain variable region ("LCVR or "$V_L$") (e.g., SEQ ID NO: 10, 26, 42, 58, 74, 90, 106, 122, 138, 154, 170, 186, 202, 218 or 306) and a light chain constant region (CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) are identical to the human germline sequences, or are naturally or artificially modified.

Typically, the variable domains of both the heavy and light immunoglobulin chains comprise three hypervariable regions, also called complementarity determining regions (CDRs), located within relatively conserved framework regions (FR). In general, from N-terminal to C-terminal, both light and heavy chains variable domains comprise FR1, CDR1, FR2, CDR2, FR3, CDR3 and FR4. In an embodiment of the invention, the assignment of amino acids to each domain is in accordance with the definitions of Sequences of Proteins of Immunological Interest, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

The present invention includes monoclonal anti-PfRH5 antigen-binding proteins, e.g., antibodies and antigen-binding fragments thereof, as well as monoclonal compositions comprising a plurality of isolated monoclonal antigen-binding proteins. The term "monoclonal antibody", as used herein, refers to a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human.

In an embodiment of the invention, an anti-PfRH5 antigen-binding protein, e.g., antibody or antigen-binding fragment comprises a heavy chain constant domain, e.g., of the type IgA (e.g., IgA1 or IgA2), IgD, IgE, IgG (e.g., IgG1, IgG2, IgG3 and IgG4) or IgM. In an embodiment of the invention, an antigen-binding protein, e.g., antibody or antigen-binding fragment, comprises a light chain constant domain, e.g., of the type kappa or lambda.

The term "human" antigen-binding protein, such as an antibody or antigen-binding fragment, as used herein, includes antibodies and fragments having variable and constant regions derived from human germline immunoglobulin sequences whether in a human cell or grafted into a non-human cell, e.g., a mouse cell. See e.g., U.S. Pat. No. 8,502,018, 6,596,541 or 5,789,215. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse) have been grafted onto human FR sequences. The term includes antibodies recombinantly produced in a non-human mammal or in cells of a non-human mammal. The term is not intended to include antibodies isolated from or generated in a human subject.

The present invention includes anti-PfRH5 chimeric antigen-binding proteins, e.g., antibodies and antigen-binding fragments thereof, and methods of use thereof. As used herein, a "chimeric antibody" is an antibody having the variable domain from a first antibody and the constant domain from a second antibody, where the first and second antibodies are from different species. (see e.g., U.S. Pat. No. 4,816,567; and Morrison et al., (1984) Proc. Natl. Acad. Sci. USA 81: 6851-6855).

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a cell (e.g., CHO cells) expression system or isolated from a recombinant combinatorial human antibody library.

Recombinant anti-PfRH5 antigen-binding proteins, e.g., antibodies and antigen-binding fragments, disclosed herein may also be produced in an *E. coli*/T7 expression system. In this embodiment, nucleic acids encoding the anti-PfRH5 antibody immunoglobulin molecules of the invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2) may be inserted into a pET-based plasmid and expressed in the *E. coli*/T7 system.

For example, the present invention includes methods for expressing an antibody or antigen-binding fragment thereof or immunoglobulin chain thereof in a host cell (e.g., bacterial host cell such as E. coli such as BL21 or BL21 DE3) comprising expressing T7 RNA polymerase in the cell which also includes a polynucleotide encoding an immunoglobulin chain that is operably linked to a T7 promoter. For example, in an embodiment of the invention, a bacterial host cell, such as an E. coli, includes a polynucleotide encoding the T7 RNA polymerase gene operably linked to a lac promoter and expression of the polymerase and the chain is induced by incubation of the host cell with IPTG (isopropyl-beta-D-thiogalactopyranoside). See U.S. Pat. Nos. 4,952,496 and 5,693,489 or Studier & Moffatt, Use of bacteriophage T7 RNA polymerase to direct selective high-level expression of cloned genes, J. Mol. Biol. 1986 May 5; 189(1): 113-30.

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Polynucleotides encoding the immunoglobulins set forth herein (e.g., comprising an nucleotide sequence set forth in SEQ ID NO: 1, 3, 5, 7, 9, 11, 13, 17, 19, 21, 23, 25, 27, 29, 33, 35, 37, 39, 41, 43, 45, 49, 51, 53, 55, 57, 59, 61, 65, 67, 69, 71, 73, 75, 77, 81, 83, 85, 87, 89, 91, 93, 97, 99, 101, 103, 105, 107, 109, 113, 115, 117,119, 121, 123, 125, 129, 131, 133, 135, 137, 139, 141, 145, 147, 149, 151,153, 155, 157, 161, 163,165, 167, 169, 171, 173, 177, 179, 181, 183, 185, 187, 189, 193, 195,197, 199, 201, 203, 205, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 313, 315, 317, 319, 321, 323, 325, 327, 329, 331, 333, 335, 337, 339, 341, 343, 345, 347, 349, 351, 353, 355, 357 and 359) which are in a vector and/or operably linked to an expression control sequence such as a promoter form part of the present invention. A promoter may be, for example, a CMV promoter (e.g., a human cytomegalovirus (CMV) major immediate-early (MIE) promoter or a mouse CMV promoter) or an SV40 promoter (e.g., SV40 early promoter). A vector may be a plasmid (e.g., a circular plasmid or a linearized plasmid) or a viral vector which may be maintained ectopically in a host cell or integrated into a host chromosome. Such host cells form part of the present invention.

A polynucleotide is "operably linked" when it is placed into a functional relationship with another nucleic acid sequence. For example, a promoter or enhancer is operably linked to a coding sequence if it affects the transcription of the sequence. Generally, but not always, "operably linked" means that the DNA sequences being linked are contiguous, and, in the case of a secretory leader, contiguous and in reading phase. However, enhancers do not have to be contiguous.

Thus, the present invention includes recombinant methods for making an anti-PfRH5 antigen-binding protein, such as an antibody or antigen-binding fragment thereof of the present invention, or an immunoglobulin chain thereof, comprising (i) introducing one or more polynucleotides (e.g., including the nucleotide sequence in any one or more of SEQ ID NOs: 1, 9, 17, 25, 33, 41, 49, 57, 65, 73, 81, 89, 97, 105, 113, 121, 129, 137, 145,153, 161, 169, 177, 185, 193, 201, 209, 217, 225, 233, 241, 249, 257, 265, 273, 281, 289, 297, 305, 313, 321, 329, 337, 345 and/or 353) encoding light and/or heavy immunoglobulin chains of the antigen-binding protein, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2, for example, wherein the polynucleotide is in a vector; and/or integrated into a host cell chromosome and/or is operably linked to a promoter; (ii) culturing the host cell (e.g., CHO or Pichia or Pichia pastoris) under conditions favorable to expression of the polynucleotide and, (iii) optionally, isolating the antigen-binding protein, (e.g., antibody or fragment) or chain from the host cell and/or medium in which the host cell is grown. When making an antigen-binding protein (e.g., antibody or antigen-binding fragment) comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antigen-binding protein (e.g., antibody or antigen-binding fragment). The methods of the present invention include those wherein only a heavy immunoglobulin chain or only a light immunoglobulin chain or both (e.g., any of those discussed herein including mature fragments and/or variable domains thereof) are expressed in a cell. Such single chains are useful, for example, as intermediates in the expression of an antibody or antigen-binding fragment that includes such a chain. For example, the present invention also includes anti-PfRH5 antigen-binding proteins, such as antibodies and antigen-binding fragments thereof, comprising a heavy chain immunoglobulin (or variable domain thereof or comprising the CDRs thereof) encoded by a polynucleotide comprising the nucleotide sequences set forth in SEQ ID NO: 1 17, 33, 49, 65, 81, 97, 113, 129, 145, 161, 177, 193, 209, 225, 233, 241, 249, 257, 265, 273, 281, 289, 297, 313, 321, 329, 337, 345 or 353 and a light chain immunoglobulin (or variable domain thereof or comprising the CDRs thereof) encoded by the nucleotide sequence set forth in SEQ ID NO: 9, 25, 41, 57, 73, 89, 105, 121, 137, 153, 169, 185, 201, 217 or 305, which are the product of such production methods, and, optionally, the purification methods set forth herein. For example, in an embodiment of the invention, the product of the method is an anti-PfRH5 antigen-binding protein which is an antibody or fragment comprising a $V_H$ comprising the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354 and a $V_L$ comprising the amino acid sequence set forth in SEQ ID NO: 10, 26, 42, 58, 74, 90, 106, 122, 138, 154, 170, 186, 202, 218 or 306.

In an embodiment of the invention, a method for making an anti-PfRH5 antigen-binding protein, e.g., antibody or antigen-binding fragment thereof, includes a method of purifying the antigen-binding protein, e.g., by column chromatography, precipitation, and/or filtration. The product of such a method also forms part of the present invention.

Eukaryotic and prokaryotic host cells, including mammalian cells, may be used as hosts for expression of an anti-PfRH5 antigen-binding protein (e.g., antibody or antigen-binding fragment thereof). Such host cells are well known in the art and many are available from the American Type Culture Collection (ATCC). These host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia, Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*. The present invention includes an isolated host cell (e.g., a CHO cell) comprising an antigen-binding protein, such as H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2; or one or more polynucleotides encoding an immunoglobulin chain or chains thereof.

The present invention also includes a *Plasmodium falciparum* cell which is expressing PfRH5 which is bound by an antigen-binding protein of the present invention e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2, e.g., wherein the cell is in the body of a subject or is in vitro.

The term "specifically binds" refers to those antigen-binding proteins (e.g., mAbs) having a binding affinity to an antigen, such as PfRH5 protein (e.g., PfRH5ΔNL.6his), expressed as $K_D$, of at least about $10^{-8}$ M (e.g., any $K_D$ set forth in Table 5-1 or 5-2 herein), as measured by real-time, label free bio-layer interferometry assay, for example, at 25° C. or 37° C., e.g., an Octet® HTX biosensor, or by surface plasmon resonance, e.g., BIACORE™, or by ELISA (enzyme linked immunosorbent assay). The present invention includes antigen-binding proteins that specifically bind to PfRH5 protein. In an embodiment of the invention, an antigen-binding protein comprises a $K_a$, $K_d$ and/or $t_{1/2}$ as set forth in Table 5-1 or 5-2 herein.

The terms "antigen-binding portion" or "antigen-binding fragment" of an antibody or antigen-binding protein, and the like, as used herein, include any naturally occurring, enzymatically obtainable, synthetic, or genetically engineered polypeptide or glycoprotein that specifically binds an antigen to form a complex. Non-limiting examples of antigen-binding fragments include: (i) Fab fragments; (ii) F(ab')₂ fragments; (iii) Fd fragments; (iv) Fv fragments; (v) single-chain Fv (scFv) molecules; (vi) dAb fragments and (vii) constrained FR3-CDR3-FR4 peptides (e.g., comprising a FR3, FR4 and CDR-H3 or CDR-L3 as set forth herein). Other engineered molecules, such as domain-specific antibodies, single domain antibodies, domain-deleted antibodies, chimeric antibodies, CDR-grafted antibodies, diabodies, triabodies, tetrabodies, minibodies and small modular immunopharmaceuticals (SMIPs) are also encompassed within the expression "antigen-binding fragment," as used herein. In an embodiment of the invention, the antigen-binding fragment comprises three or more CDRs of H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2 (e.g., CDR-H1, CDR-H2 and CDR-H3; and/or CDR-L1, CDR-L2 and CDR-L3).

An antigen-binding fragment of an antibody will, in an embodiment of the invention, comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (X) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

Antigen-binding proteins (e.g., antibodies and antigen-binding fragments) may be monospecific or multi-specific (e.g., bispecific). Multispecific antigen-binding proteins are discussed further herein.

In an embodiment of the invention, antigen-binding proteins of the present invention (e.g., an antibody or antibody fragment) may be conjugated to a moiety such as a therapeutic moiety ("immunoconjugate"), such as an anti-malarial drug, a second anti-PfRH5 antibody, or any other therapeutic moiety useful for treating a Plasmodium falciparum infection. See e.g., below.

The present invention also provides a complex comprising an anti-PfRH5 antigen-binding protein, e.g., antibody or antigen-binding fragment, discussed herein complexed with PfRH5 polypeptide or an antigenic fragment thereof and/or with a secondary antibody or antigen-binding fragment thereof (e.g., detectably labeled secondary antibody) that binds specifically to the anti-PfRH5 antibody or fragment. In an embodiment of the invention, the complex is in vitro (e.g., is immobilized to a solid substrate) or is in the body of a subject. In an embodiment of the invention, the PfRH5 is immobilized to a solid substrate (e.g., a lateral flow test strip) or is on the surface of a cell such as Plasmodium falciparum. Immobilized anti-PfRH5 antibodies and antigen-binding fragments thereof which are covalently linked to an insoluble matrix material (e.g., glass or polysaccharide such as agarose or sepharose, e.g., a bead or other particle thereof) are also part of the present invention; optionally, wherein the immobilized antibody is complexed with PfRH5 or antigenic fragment thereof or a secondary antibody or fragment thereof.

"Isolated" antigen-binding proteins (e.g., antibodies or antigen-binding fragments thereof), polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antigen-binding protein may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antigen-binding proteins (e.g., antibodies or antigen-binding fragments).

The present invention includes antigen-binding proteins, e.g., antibodies or antigen-binding fragments, that bind to the same epitope as an antigen-binding protein of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2). For example, the present invention includes antigen-binding proteins that bind to a PfRH5 variant epitope (e.g., PfRH5ΔNL.6his) lacking amino acids M1-Y139 and including residues K140-Q526 but lacking K247-L295 and having the mutations T216A and T299A (optionally, including a HisX6 tag).

The term "epitope" refers to an antigenic determinant (e.g., on PfRH5 polypeptide) that interacts with a specific antigen-binding site of an antigen-binding protein, e.g., a variable region of an antibody molecule, known as a paratope. A single antigen may have more than one epitope. Thus, different antibodies may bind to different areas on an antigen and may have different biological effects. The term "epitope" may also refer to a site on an antigen to which B and/or T cells respond and/or to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) interacts is hydrogen/deuterium exchange detected by mass spectrometry. See, e.g., Ehring (1999) Analytical Biochemistry 267: 252-259; Engen and Smith (2001) Anal. Chem. 73: 256A-265A.

The present invention includes antigen-binding proteins that compete for binding to PfRH5, e.g., a variant PfRH5 epitope as discussed herein, with an antigen-binding protein of the present invention, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2. The term "competes" as used herein, refers to an antigen-binding protein (e.g., antibody or antigen-binding fragment thereof) that binds to an antigen (e.g., PfRH5 or PfRH5ΔNL.6his) and inhibits or blocks the binding of another antigen-binding protein (e.g., antibody or antigen-binding fragment thereof) to the antigen. The term also includes competition between two antigen-binding proteins e.g., antibodies, in both orientations, i.e., a first antibody that binds and blocks binding of second antibody and vice versa. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. In an embodiment of the invention, competition between a first and second anti-PfRH5 antigen-binding protein (e.g., antibody) is determined by measuring the ability of an immobilized first anti-PfRH5 antigen-binding protein (e.g., antibody) (not initially complexed with PfRH5 protein) to bind to PfRH5 protein or a fragment thereof complexed with a second anti-PfRH5 antigen-binding protein (e.g., antibody). A reduction in the ability of the first anti-PfRH5 antigen-binding protein (e.g., antibody) to bind to the complexed PfRH5 protein, relative to uncomplexed PfRH5 protein, indicates that the first and second anti-PfRH5 antigen-binding proteins (e.g., antibodies) compete. The degree of competition can be expressed as a percentage of the reduction in binding. Such competition can be measured using a real time, label-free bio-layer interferometry assay, e.g., on an Octet RED384 biosensor (Pall ForteBio Corp.), ELISA (enzyme-linked immunosorbent assays) or SPR (surface plasmon resonance).

Binding competition between anti-PfRH5 antigen-binding proteins (e.g., monoclonal antibodies (mAbs)) can be determined using a real time, label-free bio-layer interferometry assay on an Octet RED384 biosensor (Pall ForteBio Corp.). For example, to determine competition between two anti-PfRH5 monoclonal antibodies, the anti-PfRH5 mAb can be first captured onto anti-hFc antibody coated Octet biosensor tips (Pall ForteBio Corp., #18-5060) by submerging the tips into a solution of anti-PfRH5 mAb (subsequently referred to as "mAb1"). As a positive-control for blocking, the antibody captured biosensor tips can then be saturated with a known blocking isotype control mAb (subsequently referred to as "blocking mAb") by dipping into a solution of blocking mAb. To determine if mAb2 competes with mAb1, the biosensor tips can then be subsequently dipped into a complexed solution of PfRH5 polypeptide and a second anti-PfRH5 mAb (subsequently referred to as "mAb2"), that had been pre-incubated for a period of time and binding of mAb1 to the PfRH5 polypeptide can be determined. The biosensor tips can be washed in buffer in between every step of the experiment. The real-time binding response can be monitored during the course of the experiment and the binding response at the end of every step can be recorded.

In an embodiment of the invention, the competition assay is conducted on an biosensor platform (e.g., Octet HTX), wherein one antibody is bound/complexed to PfRH5 polypeptide which has been bound to a sensor tip and binding of a second antibody to the PfRH5 is then assessed. The ability of the second antibody to bind to the pre-complexed PfRH5 polypeptide can be assessed and, if reduced binding (e.g., relative to PfRH5 not complexed with a first antibody) or an absence of binding of the second antibody is detected, then the first and second antibodies are determined to compete for PfRH5 polypeptide binding. In an embodiment of the invention, the assay is conducted at 25° C. and pH about 7, e.g., 7.4, e.g., in the presence of buffer (e.g., HEPES), salt (e.g., NaCl), EDTA, surfactant (e.g., Tween-20) and/or a non-specific protein (e.g., bovine serum albumin). In an embodiment of the invention, binding to a PfRH5 variant (e.g., PfRH5ΔNL.6his) is assessed in the competition assay, e.g., wherein the variant is PfRH5 lacking amino acids M1-Y139 and including residues K140-Q526 but lacking K247-L295 and having the mutations T216A and T299A (optionally, including a HisX6 tag). A HisX6 or $His_6$ tag is a tag that includes HHHHHH (SEQ ID NO: 365).

Typically, an antibody or antigen-binding fragment of the invention which is modified in some way retains the ability to specifically bind to PfRH5, e.g., retains at least 10% of its PfRH5 binding activity (when compared to the parental antibody) when that activity is expressed on a molar basis. Preferably, an antibody or antigen-binding fragment of the invention retains at least 20%, 50%, 70%, 80%, 90%, 95% or 100% or more of the PfRH5 binding affinity as the parental antibody. It is also intended that an antibody or antigen-binding fragment of the invention may include conservative or non-conservative amino acid substitutions (referred to as "conservative variants" or "function conserved variants" of the antibody) that do not substantially alter its biologic activity.

Anti-PfRH5 antigen-binding proteins of the present invention may comprise variants of the immunoglobulin chains whose amino acid and nucleotide sequences are specifically set forth herein.

A "variant" of a polypeptide, such as an immunoglobulin chain (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2 $V_H$, $V_L$, HC or LC), refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein (e.g., SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346, 354, 10, 26, 42, 58, 74, 90, 106, 122, 138, 154, 170, 186, 202, 218 or 306); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

A "variant" of a polynucleotide refers to a polynucleotide comprising a nucleotide sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical to a referenced nucleotide sequence that is set forth herein (e.g., SEQ ID NO: 1, 17, 33, 49, 65, 81, 97, 113, 129, 145, 161, 177, 193, 209, 225, 233, 241, 249, 257, 265, 273, 281, 289, 297, 313, 321, 329, 337, 345, 353, 9, 25, 41, 57, 73, 89, 105, 121, 137, 153, 169, 185, 201, 217 or 305); when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear).

Anti-PfRH5 antigen-binding proteins, e.g., antibodies and antigen-binding fragments thereof of the present invention, in an embodiment of the invention, include a heavy chain immunoglobulin variable region having at least 70% (e.g., 80%, 85%, 90%, 95%, 99%) amino acid sequence identity to that of an immunoglobulin heavy chain whose amino acid sequence is set forth herein, e.g., in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or a light chain immunoglobulin variable region having at least 70% (e.g., 80%, 85%, 90%, 95%, 99%) amino acid sequence identity to an immunoglobulin light chain whose amino acid sequence is set forth herein, e.g., in SEQ ID NO: 10, 26, 42, 58, 74, 90, 106, 122, 138, 154, 170, 186, 202, 218 or 306.

In addition, an anti-PfRH5 antigen-binding protein of the present invention may include a variant immunoglobulin polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), non-sense mutations, deletions, or insertions. For example, the present invention includes antigen-binding proteins which include an immunoglobulin light chain variant comprising the amino acid sequence set forth in SEQ ID NO: 10, 26, 42, 58, 74, 90, 106, 122, 138, 154, 170, 186, 202, 218 or 306 but having one or more of such mutations and/or an immunoglobulin heavy chain variant comprising the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354 but having one or more of such mutations. In an embodiment of the invention, an anti-PfRH5 antigen-binding protein includes an immunoglobulin light chain variant comprising CDR-L1, CDR-L2 and CDR-L3 wherein one or more (e.g., 1 or 2 or 3) of such CDRs has one or more of such mutations (e.g., conservative substitutions) relative to a sequence which is specifically set forth herein and/or an immunoglobulin heavy chain variant comprising CDR-H1, CDR-H2 and CDR-H3 wherein one or more (e.g., 1 or 2 or 3) of such CDRs has one or more of such mutations (e.g., conservative substitutions) relative to a sequence which is specifically set forth herein.

The invention further provides variant anti-PfRH5 antigen-binding proteins, e.g., antibodies or antigen-binding fragments thereof, comprising one or more variant CDRs (e.g., any one or more of CDR-L1, CDR-L2, CDR-L3, CDR-H1, CDR-H2 and/or CDR-H3) that are set forth herein with at least 70%, 75%, 80%, 85%, 90%, 95%, 98%, 99% or 99.9% sequence identity or similarity thereto.

Embodiments of the present invention also include anti-PfRH5 antibodies and antigen-binding fragments thereof, that comprise variant immunoglobulin $V_H$s and $V_L$s; or HCs and LCs, which comprise an amino acid sequence having 70% or more (e.g., 80%, 85%, 90%, 95%, 97% or 99%) overall amino acid sequence identity or similarity to the amino acid sequences of the corresponding $V_H$s, $V_L$s, HCs or LCs specifically set forth herein, but wherein the CDR-L1, CDR-L2, CDR-L3, CDR-H1, CDR-H2 and CDR-H3 of such immunoglobulins are not variants and comprise the amino acid sequences set forth herein. Thus, in such embodiments, the CDRs within such antigen-binding proteins are not, themselves, variants.

A "conservatively modified variant" or a "conservative substitution" refers to a variant wherein there are one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4$^{th}$ Ed.)). In addition, substitutions of structurally or functionally similar amino acids are less likely to significantly disrupt biological activity. Anti-PfRH5 antigen-binding proteins of the present invention may include immunoglobulin chains having an amino acid sequence set forth herein but having one or more conservatively modified variations.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45.

In an embodiment of the invention, an anti-PfRH5 antigen-binding protein of the present invention, e.g., comprising an immunoglobulin chain comprising a variant of an amino acid sequence set forth herein, exhibits one or more of the following functional properties:

Inhibits in vitro or in vivo growth of *Plasmodium falciparum* in human red blood cells, e.g., as measured by parasite lactate dehydrogenase (LDH) activity (e.g., at a rate of about 51 to about 69%, or up to 100% (e.g., when anti-PfRH5 antigen-binding protein is incubated with the cells for 96 hours) relative to uninfected red blood cells), for example, wherein the antigen-binding protein is H1H29100P, H1H29104P, H1H29127P, H1H29143P or any combination thereof of two of such proteins (see e.g., Table 2-1).

Inhibits growth of in vitro or in vivo *Plasmodium falciparum* strain 3D7 or 7G8 in human red blood cells, e.g., as measured by Parasite lactate dehydrogenase (LDH) activity, e.g., in the presence of chloroquine phosphate (CQ) (e.g., at a concentration of about 4.81 nM or 6.58 nM), for example, at a rate of about 34 to 61% in the absence of CQ, about 32 to 51% in the presence of 4.81 nM CQ or about 20% to 75% in the presence of 6.58 nM CQ.

Binds to PfRH5 polypeptide or an antigenic fragment thereof, e.g., PfRH5ΔNL.6his, with a $K_D$ of about 4.72 pM to about 1.67 nM at 25° C. and/or of about 1.10 pM to about 1.10 nM at 37° C., e.g., as set forth in Tables 5-1 and 5-2 herein.

Inhibits growth of in vitro or in vivo *Plasmodium falciparum* strain D10, Dd2, 7G8, W2-mef, 3D7, HB3, FCR-1/FVO, Cam3.II or RF7 in human red blood cells, e.g., as measured by Parasite lactate dehydrogenase (LDH) activity, for example, at a concentration of about 666.67 nM at a rate as set forth in Table 4-2 relative to uninfected red blood cells.

Blocks binding of PfRH5 polypeptide (e.g., PfRH5ΔNL.6his, for example, at a concentration of about 0.5 nM or 2.0 nM) to basigin polypeptide (e.g., by about 1%, 10%, 20%, 30%, 40%, 50%, 60%, 70%, 80%, 90%, 95%, 99% or 100%), for example, binding of PfRH5 to basigin that is bound to a solid matrix (e.g., an ELISA plate) wherein the anti-PfRH5 antigen-binding protein is present at about 100 nM. For example, wherein basigin was amino acids Thr25-His205 thereof, e.g., expressed with a C-terminal linker, DIEGRMD (SEQ ID NO: 363), followed by a portion of the human IgG1 (Pro100-Lys330) and a 6×histidine tag.

Binds to the same epitope as H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2, for example, binds to PfRH5 lacking the amino-terminal residues M1-Y139 and including residues K140-Q526 but lacking K247-L295 and having the mutations T216A and T299A (PfRH5ΔNL.6his), e.g., further including C-terminal hexahistidine tag, for example, as measured by surface plasmon resonance.

Competes with H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2 for binding to PfRH5 polypeptide, e.g., PfRH5ΔNL.6his.

The present invention includes a non-human primate (NHP) (e.g., monkey such as an *Aotus* monkey) whose body includes an anti-PfRH5 antigen-binding protein (e.g., antibody or antigen-binding fragment) such as H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2. For example, the non-human primate may have been injected with the antigen-binding protein or may be engineered to express the protein. In an embodiment of the invention, the non-human primate is *Aotus nancymaae*. In an embodiment of the invention, the non-human primate (e.g., monkey) is infected with *Plasmodium falciparum* (e.g., strain 3D7).

The present invention includes "neutralizing" or "antagonist" anti-PfRH5 antigen-binding proteins, e.g., antibody or antigen-binding fragment, which include molecules that inhibits an activity of PfRH5 to any detectable degree. For example, a neutralizing anti-PfRH5 antigen-binding protein may inhibit *Plasmodium falciparum* growth and/or block PfRH5/BSG binding.

"H1H29089P"; "H1H29094P"; "H1H29100P"; "H1H29104P"; "H1H29106P"; "H1H29109P"; "H1H29125P"; "H1H29127P"; "H1H29131P"; "H1H29134P"; "H1H29138P"; "H1H29141P"; "H1H29143P"; "H1H29146P2"; "H1H29147P2"; "H1H29149P2"; "H1H29151P2"; "H1H29163P2"; "H1H29166P2"; "H1H29171P2"; "H1H29179P2"; "H1H29183P2"; "H1H29187P2"; "H1H29192P2"; "H1H29196P2"; "H1H29198P2"; "H1H29207P2"; "H1H29209P2"; "H1H29214P2"; or "H1H29215P2" refer to antigen-binding proteins, e.g., antibodies and antigen-binding fragments thereof (including multispecific antigen-binding proteins), comprising an immunoglobulin heavy chain variable region ($V_H$; or a variant thereof) and an immunoglobulin light chain variable region ($V_L$; or a variant thereof) which are set forth herein in Table 1-1; or that comprise a $V_H$ that comprises the CDRs thereof (CDR-H1 (or a variant thereof), CDR-H2 (or a variant thereof) and CDR-H3 (or a variant thereof)) and/or a $V_L$ that comprises the CDRs thereof (CDR-L1 (or a variant thereof), CDR-L2 (or a variant thereof) and CDR-L3 (or a variant thereof)), e.g., wherein the immunoglobulin chains, variable regions and/or CDRs comprise the specific amino acid sequences described below. In an embodiment of the invention, the $V_H$ is linked to a constant heavy immunoglobulin chain (e.g., an IgG such as IgG1 or IgG4) and/or the $V_L$ is linked to a constant light immunoglobulin chain (e.g., kappa or lambda).

Antibodies and antigen-binding fragments of the present invention comprise immunoglobulin chains including the amino acid sequences set forth herein as well as cellular and in vitro post-translational modifications to the antibody or fragment. For example, the present invention includes antibodies and antigen-binding fragments thereof that specifically bind to PfRH5 comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more amino acid residues is glycosylated, one or more Asn residues is deamidated, one or more residues (e.g., Met, Trp and/or His) is oxidized, the N-terminal Gln is pyroglutamate (pyroE) and/or the C-terminal Lysine is missing.

The present invention provides a vessel (e.g., a plastic or glass vial, e.g., with a cap or a chromatography column, hollow bore needle or a syringe cylinder) comprising an anti-PfRH5 antigen-binding protein of the present invention, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2.

The present invention also provides an injection device comprising one or more antigen-binding proteins (e.g., antibody or antigen-binding fragment) that bind specifically to PfRH5, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2, or a pharmaceutical composition thereof. The injection device may be packaged into a kit. An injection device is a device that introduces a substance into the body of a subject via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore.

The present invention further provides methods for administering an anti-PfRH5 antigen-binding protein of the present invention, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2, to a subject, comprising introducing the antigen-binding protein into the body of the subject (e.g., a human), for example, parenterally. For example, the method comprises piercing the body of the subject with a needle of a syringe and injecting the antigen-binding protein into the body of the subject, e.g., into the vein, artery, tumor, muscular tissue or subcutis of the subject.

Preparation of Human Antibodies

Methods for generating human antibodies in transgenic mice are known in the art. Any such known methods can be used in the context of the present invention to make human antibodies that specifically bind to PfRH5. An immunogen comprising any one of the following can be used to generate antibodies that specifically bind to PfRH5. In certain embodiments of the invention, the antibodies of the invention are obtained from mice immunized with a full length, native PfRH5, or with a live attenuated or inactivated virus, or with DNA encoding the protein or fragment thereof. Alternatively, the PfRH5 protein or a fragment thereof may be produced using standard biochemical techniques and modified and used as immunogen. In one embodiment of the invention, the immunogen is a recombinantly produced PfRH5 protein or fragment thereof. In certain embodiments of the invention, the immunogen may be a PfRH5 polypeptide vaccine. In certain embodiments, one or more booster injections may be administered. In certain embodiments, the immunogen may be a recombinant PfRH5 polypeptide expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®), high affinity chimeric antibodies to PfRH5 can be initially isolated having human variable regions and mouse constant regions. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Antibodies of interest may also be isolated from mouse B-cells. Briefly, splenocytes are harvested from each mouse and B-cells are sorted (as described in US 2007/0280945A1, for example) by FACS using the antigen of interest as the sorting reagent that binds and identifies reactive antibodies (antigen-positive B cells). Various methods of identifying and sorting antigen-positive B cells, as well as constructing immunoglobulin gene expression cassettes by PCR for preparation of cells expressing recombinant antibodies, are well-known in the art. See e.g. WO20141460741, U.S. Pat. No. 7,884,054B2, and Liao, et al. June 2009. High-Throughput Isolation of Immunoglobulin Genes from Single Human B Cells and Expression as Monoclonal Antibodies. J Virol Methods 158(1-2):171-9.

Initially, high affinity chimeric antibodies are isolated having a human variable region and a mouse constant region. The antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Anti-PfRH5 Antibodies Comprising Fc Variants

According to certain embodiments of the present invention, anti-PfRH5 antigen-binding proteins, e.g., antibodies or antigen-binding fragments, are provided comprising an Fc domain comprising one or more mutations, which, for example, enhance or diminish antibody binding to the FcRn receptor, e.g., at acidic pH as compared to neutral pH. For example, the present invention includes anti-PfRH5 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-PfRH5 antigen-binding proteins, e.g., antibodies or antigen-binding fragments, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F).

Anti-PfRH5 antigen-binding proteins, e.g., antibodies and antigen-binding fragments thereof, that comprise a $V_H$ and/or $V_L$ as set forth herein comprising any possible combinations of the foregoing Fc domain mutations, are contemplated within the scope of the present invention.

The present invention also includes anti-PfRH5 antigen-binding proteins, antibodies or antigen-binding fragments, comprising a $V_H$ set forth herein and a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., WO2014/022540).

Multispecific Antigen-Binding Proteins

The present invention includes anti-PfRH5 antigen-binding proteins, e.g., antibodies and antigen-binding fragments thereof, as well as methods of use thereof and methods of making such antigen-binding proteins. The term "anti-PfRH5" antigen-binding proteins, e.g., antibodies or antigen-binding fragments, includes multispecific (e.g., bispecific or biparatopic) molecules that include at least one first antigen-binding domain that specifically binds to PfRH5 (e.g., an antigen-binding domain from H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) and at least one second antigen-binding domain that binds to a different antigen or to an epitope in PfRH5 which is different from that of the first antigen-binding domain (e.g., CD3, CD16, BSG (basigin), EXP1, MSP1, MSP2, MSPMSP3, MSP4, MSP5, MSP6, MSP7, MSP9, MSP10 GLURP, Sera, RAMA, SEA, AMA1, MTRAP, PTRAMP, ASP, RH1, RH2a, RH2b, RH4, RAP1, RAP2, RAP3, RhopH1, RhopH2, RhopH3, EMA175, EMA140 and/or EBA181). In an embodiment of the invention, the first and second epitopes overlap. In another embodiment of the invention, the first and second epitopes do not overlap.

In an embodiment of the invention, a multispecific antigen-binding protein binds to PfRH5 and to an antigen which causes activation of the immune cells such as cytotoxic T cells, NK cells, mononuclear phagocytes or neutrophils, e.g., CD3 or CD16.

"H1H29089P"; "H1H29094P"; "H1H29100P"; "H1H29104P"; "H1H29106P"; "H1H29109P"; "H1H29125P"; "H1H29127P"; "H1H29131P"; "H1H29134P"; "H1H29138P"; "H1H29141P"; "H1H29143P"; "H1H29146P2"; "H1H29147P2"; "H1H29149P2"; "H1H29151P2"; "H1H29163P2"; "H1H29166P2"; "H1H29171P2"; "H1H29179P2"; "H1H29183P2"; "H1H29187P2"; "H1H29192P2"; "H1H29196P2"; "H1H29198P2"; "H1H29207P2"; "H1H29214P2"; or "H1H29215P2" includes a multispecific molecules, e.g., antibodies or antigen-binding fragments, that include the HCDRs and LCDRs, $V_H$ and $V_L$, or HC and LC of H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2, respectively (including variants thereof as set forth herein) and one or more antigen-binding domains that bind to a different epitope.

In an embodiment of the invention, an antigen-binding domain that binds specifically to PfRH5, which may be included in a multispecific molecule, comprises:

(1)
   (i) a heavy chain variable domain sequence that comprises CDR-H1, CDR-H2 and CDR-H3 from an immunoglobulin heavy chain selected from: H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2, and
   (ii) a light chain variable domain sequence that comprises CDR-L1, CDR-L2 and CDR-L3 from an immunoglobulin heavy chain selected from: H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2, respectively;

or, (2)
   (i) a heavy chain variable domain ($V_H$) sequence selected from: H1H29089P; H1H29094P; H1H29100P; H1H29104P; H1H29106P;

H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2; and (ii) a light chain variable domain (V$_L$) sequence selected from: H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2, respectively;

and one or more antigen-binding domains that bind to a different epitope.

In an embodiment of the invention, the multispecific antibody or fragment includes more than two different binding specificities (e.g., a trispecific molecule), for example, one or more additional antigen-binding domains which are the same or different from the first and/or second antigen-binding domain.

In one embodiment of the invention, a bispecific antigen-binding fragment comprises a first scFv (e.g., comprising V$_H$ and V$_L$ of H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2) having binding specificity for a first epitope (e.g., PfRH5) and a second scFv having binding specificity for a second, different epitope. For example, in an embodiment of the invention, the first and second scFv are tethered with a linker, e.g., a peptide linker (e.g., a GS linker such as (GGGGS)$_n$ (SEQ ID NO: 364) wherein n is, for example, 1, 2, 3, 4, 5, 6, 7, 8, 9 or 10). Other bispecific antigen-binding fragments include an F(ab)$_2$ of a bispecific IgG antibody which comprises the heavy and light chain CDRs of H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2 and of another antibody that binds to a different epitope.

Immunoconjugates

The invention encompasses anti-PfRH5 antigen-binding proteins, e.g., antibodies or antigen-binding fragments, conjugated to another moiety, e.g., a therapeutic moiety (an "immunoconjugate"), such as a toxoid (e.g., diptheria toxoid or tetanus toxoid) or an anti-parasitic drug to treat *Plasmodium falciparum* infection. In an embodiment of the invention, an anti-PfRH5 antibody or fragment is conjugated to any of the further therapeutic agents set forth herein. As used herein, the term "immunoconjugate" refers to an antigen-binding protein, e.g., an antibody or antigen-binding fragment, which is chemically or biologically linked to another molecule.

Therapeutic Methods

The present invention provides methods for treating or preventing *Plasmodium falciparum* infection (e.g., malaria) by administering a therapeutically effective amount of anti-PfRH5 antigen-binding protein, e.g., antibody or antigen-binding fragment, (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) to a subject (e.g., a human) in need of such treatment or prevention. "Malaria" is a disease, frequently transmitted by the bite of an infected female mosquito (e.g., *Anopheles* mosquitos), caused by infection of a host with the parasite *Plasmodium falciparum*. The term "*Plasmodium falciparum* infection" refers to invasion of the body of a subject with *Plasmodium falciparum* and encompasses malaria.

An effective or therapeutically effective dose of anti-PfRH5 antigen-binding protein, e.g., antibody or antigen-binding fragment (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), for treating or preventing a *Plasmodium falciparum* infection refers to the amount of the antibody or fragment sufficient to alleviate one or more signs and/or symptoms of the infection in the treated subject, whether by inducing the regression or elimination of such signs and/or symptoms or by inhibiting the progression of such signs and/or symptoms. The dose amount may vary depending upon the age and the size of a subject to be administered, target disease, conditions, route of administration, and the like. In an embodiment of the invention, an effective or therapeutically effective dose of anti-PfRH5 antigen-binding protein, e.g., antibody or antigen-binding fragment thereof, of the present invention, for treating or preventing *Plasmodium falciparum* infection, e.g., in an adult human subject, is about 1 mg/kg to 150 mg/kg. Depending on the severity of the infection, the frequency and the duration of the treatment can be adjusted. In certain embodiments, the antigen-binding protein of the present invention can be administered at an initial dose, followed by one or more secondary doses. In certain embodiments, the initial dose may be followed by administration of a second or a plurality of subsequent doses of antigen-binding protein in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

As used herein, the term "subject" refers to a mammal (e.g., rat, mouse, cat, dog, cow, sheep, horse, goat, rabbit), preferably a human, for example, in need of prevention and/or treatment of a *Plasmodium falciparum* infection. A subject may have a *Plasmodium falciparum* infection or be predisposed to developing a *Plasmodium falciparum* infection or be at elevated risk of developing such an infection. Subjects predisposed to developing a *Plasmodium falciparum* infection or subjects who may be at elevated risk for contracting a *Plasmodium falciparum* infection, include those subjects with compromised immune systems, e.g., because of autoimmune disease, those persons receiving immunosuppressive therapy, those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Additionally, subjects of extreme young or old age may be predisposed. Any person who comes into contact with or close proximity to mosquitos, especially in the tropics, South America, Central America, Africa, South East Asia, and the Eastern Mediterranean Region, has an increased risk of developing *Plasmodium falciparum* infection.

"Treat" or "treating" means to administer an anti-PfRH5 antigen-binding protein, e.g., antibody or antigen-binding fragment of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), to a subject having *Plasmodium falciparum* infection, such that one or more signs or symptoms of the infection in the subject are reduced or eliminated, e.g., wherein *Plasmodium falciparum* is reduced or substantially eliminated (e.g., completely eliminated) from the body of the subject.

Signs and symptoms of *Plasmodium falciparum* infection include:
Anemia;
Bloody stools;
Chills, fever, sweating;
Coma;
Convulsions;
Headache;
Jaundice;
Muscle pain;
Nausea and vomiting;
Enlarged spleen;
Jaundice;
Enlargement of the liver;
Increased respiratory rate;
*Plasmodium falciparum* in the blood stream, liver or erythrocytes;
Anemia;
Hemolysis;
Free hemoglobin in the blood stream;
Hemoglobinuria;
Acute kidney failure;
Acute respiratory distress syndrome (ARDS);
Low blood pressure;
Metabolic acidosis; and
Hypoglycemia.

The present invention also encompasses prophylactically administering an anti-PfRH5 antigen-binding protein, e.g., antibody or antigen-binding fragment thereof of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), to a subject who is at risk (e.g., predisposed or at an elevated risk) of *Plasmodium falciparum* infection so as to prevent such infection. "Prevent" or "preventing" means to administer an anti-PfRH5 antigen-binding protein, e.g., antibody or antigen-binding fragment of the present invention, to a subject who is not infected with *Plasmodium falciparum* such that manifestation of the infection in the body of a subject is inhibited or decreased in likelihood or decreased in severity if infection does occur.

Combinations and Pharmaceutical Compositions

The present invention provides compositions that include anti-PfRH5 antigen-binding proteins and one or more ingredients; as well as methods of use thereof and methods of making such compositions.

To prepare pharmaceutical compositions of the anti-PfRH5 antigen-binding proteins, e.g., antibodies and anti-gen-binding fragments thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y. In an embodiment of the invention, the pharmaceutical composition is sterile. Such compositions are part of the present invention.

Pharmaceutical compositions of the present invention include pharmaceutically acceptable carriers, diluents, excipients and/or stabilizers, such as, for example, water, buffering agents, stabilizing agents, preservatives, isotonifiers, non-ionic detergents, antioxidants and/or other miscellaneous additives.

The scope of the present invention includes desiccated, e.g., freeze-dried, compositions comprising an anti-PfRH5 antigen-binding protein, e.g., antibody or antigen-binding fragment thereof (e.g., H1H29089P; H1H29094P; H1H29100P; H1H29104P; H1H29106P; H1H29109P; H1H29125P; H1H29127P; H1H29131P; H1H29134P;

H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), or a pharmaceutical composition thereof that includes a pharmaceutically acceptable carrier but substantially lacks water.

In a further embodiment of the invention, a further therapeutic agent that is administered to a subject in association with an anti-PfRH5 antigen-binding protein, e.g., antibody or antigen-binding fragment thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), disclosed herein is administered to the subject in accordance with the Physicians' Desk Reference 2003 (Thomson Healthcare; 57$^{th}$ edition (Nov. 1, 2002)).

The mode of administration of an antigen-binding protein or composition thereof can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal or intra-arterial.

The present invention provides methods for administering an anti-PfRH5 antigen-binding protein, e.g., antibody or antigen-binding fragment thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) to a subject, comprising introducing the protein or a pharmaceutical composition or combination thereof into the body of the subject. For example, the method comprises piercing the body of the subject with a needle of a syringe and injecting the antigen-binding protein or a pharmaceutical composition or combination thereof into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the anti-PfRH5 antigen-binding proteins, e.g., antibodies or antigen-binding fragments thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) or a pharmaceutical composition comprising a pharmaceutically acceptable carrier or combination thereof.

The present invention includes combinations including an anti-PfRH5 antigen-binding protein, e.g., antibody or antigen-binding fragment thereof of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), in association with one or more further therapeutic agents. The anti-PfRH5 antigen-binding protein and the further therapeutic agent can be in a single composition or in separate compositions. For example, in an embodiment of the invention, the further therapeutic agent is an anti-parasitic or anti-malarial therapeutic agent.

In an embodiment of the invention, the further therapeutic agent is chloroquine, atovaquone and/or proguanil, artemether and/or lumefantrine, mefloquine, quinine, quinidine, doxycycline (optionally in combination with quinine) and/or clindamycin (optionally in combination with quinine). In an embodiment of the invention, the further therapeutic agent is a vaccine such as an anti-malarial vaccine, e.g., RTS,S/AS01 (sold as Mosquirix). Methods for treating or preventing *Plasmodium falciparum* infection in a subject in need of said treatment or prevention by administering H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2 in association with a further therapeutic agent are part of the present invention.

The present invention includes a combination comprising two or more (e.g., 2, 3 or 4) of the antigen-binding proteins of the present invention (e.g., antibody or antigen-binding protein) in association with one another. For example, if H1H29089P is Ab1; if H1H29094P is Ab2; if H1H29100P is Ab3; if H1H29104P is Ab4; if H1H29106P is Ab5; if H1H29109P is Ab6; if H1H29125P is Ab7; if H1H29127P is Ab8; if H1H29131P is Ab9; if H1H29134P is Ab10; if H1H29138P is Ab11; if H1H29141P is Ab12; if H1H29143P is Ab13; if H1H29146P2 is Ab14; if H1H29147P2 is Ab15; if H1H29149P2 is Ab16; if H1H29151P2 is Ab17; if H1H29163P2 is Ab18; if H1H29166P2 is Ab19; if H1H29171P2 is Ab20; if H1H29179P2 is Ab21; if H1H29183P2 is Ab22; if H1H29187P2 is Ab23; if H1H29192P2 is Ab24; if H1H29196P2 is Ab25; if H1H29198P2 is Ab26; if H1H29207P2 is Ab27; if H1H29214P2 is Ab28; if H1H29215P2 is Ab29 and if H1H29209P is Ab30, then such compositions of the present invention include combinations including the following antigen-binding proteins of the present invention (e.g., antibodies and/or antigen-binding proteins) in association with one another:

| Ab1 & Ab2 | Ab1 & Ab18 | Ab2 & Ab7 | Ab2 & Ab23 | Ab3 & Ab13 | Ab3 & Ab29 | Ab4 & Ab20 | Ab5 & Ab12 | Ab5 & Ab28 | Ab6 & Ab21 |
|---|---|---|---|---|---|---|---|---|---|
| Ab1 & Ab3 | Ab1 & Ab19 | Ab2 & Ab8 | Ab2 & Ab24 | Ab3 & Ab14 | Ab4 & Ab5 | Ab4 & Ab21 | Ab5 & Ab13 | Ab5 & Ab29 | Ab6 & Ab22 |

-continued

| | | | | | | | | | |
|---|---|---|---|---|---|---|---|---|---|
| Ab1 & Ab4 | Ab1 & Ab20 | Ab2 & Ab9 | Ab2 & Ab25 | Ab3 & Ab15 | Ab4 & Ab6 | Ab4 & Ab22 | Ab5 & Ab14 | Ab6 & Ab7 | Ab6 & Ab23 |
| Ab1 & Ab5 | Ab1 & Ab21 | Ab2 & Ab10 | Ab2 & Ab26 | Ab3 & Ab16 | Ab4 & Ab7 | Ab4 & Ab23 | Ab5 & Ab15 | Ab6 & Ab8 | Ab6 & Ab24 |
| Ab1 & Ab6 | Ab1 & Ab22 | Ab2 & Ab11 | Ab2 & Ab27 | Ab3 & Ab17 | Ab4 & Ab8 | Ab4 & Ab24 | Ab5 & Ab16 | Ab6 & Ab9 | Ab6 & Ab25 |
| Ab1 & Ab7 | Ab1 & Ab23 | Ab2 & Ab12 | Ab2 & Ab28 | Ab3 & Ab18 | Ab4 & Ab9 | Ab4 & Ab25 | Ab5 & Ab17 | Ab6 & Ab10 | Ab6 & Ab26 |
| Ab1 & Ab8 | Ab1 & Ab24 | Ab2 & Ab13 | Ab2 & Ab29 | Ab3 & Ab19 | Ab4 & Ab10 | Ab4 & Ab26 | Ab5 & Ab18 | Ab6 & Ab11 | Ab6 & Ab27 |
| Ab1 & Ab9 | Ab1 & Ab25 | Ab2 & Ab14 | Ab3 & Ab4 | Ab3 & Ab20 | Ab4 & Ab11 | Ab4 & Ab27 | Ab5 & Ab19 | Ab6 & Ab12 | Ab6 & Ab28 |
| Ab1 & Ab10 | Ab1 & Ab26 | Ab2 & Ab15 | Ab3 & Ab5 | Ab3 & Ab21 | Ab4 & Ab12 | Ab4 & Ab28 | Ab5 & Ab20 | Ab6 & Ab13 | Ab6 & Ab29 |
| Ab1 & Ab11 | Ab1 & Ab27 | Ab2 & Ab16 | Ab3 & Ab6 | Ab3 & Ab22 | Ab4 & Ab13 | Ab4 & Ab29 | Ab5 & Ab21 | Ab6 & Ab14 | Ab7 & Ab8 |
| Ab1 & Ab12 | Ab1 & Ab28 | Ab2 & Ab17 | Ab3 & Ab7 | Ab3 & Ab23 | Ab4 & Ab14 | Ab5 & Ab6 | Ab5 & Ab22 | Ab6 & Ab15 | Ab7 & Ab9 |
| Ab1 & Ab13 | Ab1 & Ab29 | Ab2 & Ab18 | Ab3 & Ab8 | Ab3 & Ab24 | Ab4 & Ab15 | Ab5 & Ab7 | Ab5 & Ab23 | Ab6 & Ab16 | Ab7 & Ab10 |
| Ab1 & Ab14 | Ab2 & Ab3 | Ab2 & Ab19 | Ab3 & Ab9 | Ab3 & Ab25 | Ab4 & Ab16 | Ab5 & Ab8 | Ab5 & Ab24 | Ab6 & Ab17 | Ab7 & Ab11 |
| Ab1 & Ab15 | Ab2 & Ab4 | Ab2 & Ab20 | Ab3 & Ab10 | Ab3 & Ab26 | Ab4 & Ab17 | Ab5 & Ab9 | Ab5 & Ab25 | Ab6 & Ab18 | Ab7 & Ab12 |
| Ab1 & Ab16 | Ab2 & Ab5 | Ab2 & Ab21 | Ab3 & Ab11 | Ab3 & Ab27 | Ab4 & Ab18 | Ab5 & Ab10 | Ab5 & Ab26 | Ab6 & Ab19 | Ab7 & Ab13 |
| Ab1 & Ab17 | Ab2 & Ab6 A | Ab2 & Ab22 | Ab3 & Ab12 | Ab3 & Ab28 | Ab4 & Ab19 | Ab5 & Ab11 | Ab5 & Ab27 | Ab6 & Ab20 | Ab7 & Ab14 |
| Ab7 & Ab15 | Ab8 & Ab10 | Ab8 & Ab26 | Ab9 & Ab22 | Ab10 & Ab10 & | Ab11 & | Ab12 & | Ab13 & | Ab13 & |
| Ab7 & Ab16 | Ab8 & Ab11 | Ab8 & Ab27 | Ab9 & Ab23 | Ab17 Ab10 | Ab29 Ab11 | Ab23 Ab11 | Ab18 Ab12 | Ab14 Ab13 | Ab26 Ab13 & |
| Ab7 & Ab17 | Ab8 & Ab12 | Ab8 & Ab28 | Ab9 & Ab24 | Ab18 Ab10 | & Ab12 A | & Ab24 | & Ab19 | & Ab15 | & Ab27 |
| Ab7 & Ab18 | Ab8 & Ab13 | Ab8 & Ab29 | Ab9 & Ab25 | Ab10 & | Ab11 & | Ab11 & | Ab12 & | Ab13 & | Ab13 & |
| Ab7 & Ab19 | Ab8 & Ab14 | Ab9 & Ab10 | Ab9 & Ab26 | Ab19 Ab10 | Ab13 Ab11 | Ab25 Ab11 | Ab20 Ab12 | Ab16 Ab13 | Ab28 Ab13 & |
| Ab7 & Ab20 | Ab8 & Ab15 | Ab9 & Ab11 | Ab9 & Ab27 | Ab20 | Ab14 | Ab26 | Ab21 | Ab17 | Ab29 |
| Ab7 & Ab21 | Ab8 & Ab16 | Ab9 & Ab12 | Ab9 & Ab28 | Ab10 & | Ab11 & | Ab11 & | Ab12 & | Ab13 & | Ab14 & |
| Ab7 & Ab22 | Ab8 & Ab17 | Ab9 & Ab13 | Ab9 & Ab29 | Ab21 Ab10 | Ab15 Ab11 | Ab27 Ab11 | Ab22 Ab12 | Ab18 Ab13 | Ab15 Ab14 & |
| Ab7 & Ab23 | Ab8 & Ab18 | Ab9 & Ab14 | Ab10 & | Ab22 | Ab16 | Ab28 | Ab23 | Ab19 | Ab16 |
| Ab7 & Ab24 | Ab8 & Ab19 | Ab9 & Ab15 | Ab10 & | Ab10 & | Ab11 & | Ab11 & | Ab12 & | Ab13 & | Ab14 & |
| Ab7 & Ab25 | Ab8 & Ab20 | Ab9 & Ab16 | Ab12 Ab10 | Ab23 Ab10 | Ab17 Ab11 | Ab29 Ab11 | Ab24 Ab12 | Ab20 Ab13 | Ab17 Ab14 & |
| Ab7 & Ab26 | Ab8 & Ab21 | Ab9 & Ab17 | & Ab10 | Ab24 | Ab18 | Ab13 | Ab25 | Ab21 | Ab18 |
| Ab7 & Ab27 | Ab8 & Ab22 | Ab9 & Ab18 | Ab13 Ab10 | Ab10 & | Ab11 & | Ab12 & | Ab12 & | Ab13 & | Ab14 & |
| Ab7 & Ab28 | Ab8 & Ab23 | Ab9 & Ab19 | & Ab14 | Ab25 Ab10 | Ab19 Ab11 | Ab14 Ab12 | Ab26 Ab12 | Ab22 Ab13 | Ab19 Ab14 & |
| Ab7 & Ab29 | Ab8 & Ab24 | Ab9 & Ab20 | Ab10 & | Ab26 | Ab20 | Ab15 | Ab27 | Ab23 | Ab20 |
| Ab8 & Ab9 | Ab8 & Ab25 | Ab9 & Ab21 | Ab15 Ab10 | Ab10 & | Ab11 & | Ab12 & | Ab12 & | Ab13 & | Ab14 & |
| Ab14 & Ab23 | Ab15 & Ab21 | Ab16 & Ab20 | Ab16 Ab17 | Ab27 Ab10 | Ab21 Ab11 | Ab16 Ab12 | Ab28 Ab12 | Ab24 Ab13 | Ab21 Ab14 & |
| Ab14 & Ab24 | Ab15 & Ab22 | Ab16 & Ab21 | Ab17 & | Ab28 Ab18 | Ab22 Ab19 | Ab17 Ab20 | Ab29 Ab22 | Ab25 Ab23 | Ab22 Ab26 |
| Ab14 & Ab25 | Ab15 & Ab23 | Ab16 & Ab22 | Ab17 & | Ab21 Ab18 | Ab23 Ab19 | Ab26 Ab20 | Ab23 Ab22 | Ab29 Ab24 | Ab29 Ab27 & |
| Ab14 & Ab26 | Ab15 & Ab24 | Ab16 & Ab23 | Ab17 | Ab22 Ab18 | Ab24 Ab19 | Ab27 Ab20 | Ab24 Ab22 | Ab25 Ab24 | Ab28 Ab27 |
| Ab14 & Ab27 | Ab15 & Ab25 | Ab16 & Ab24 | Ab17 | Ab23 Ab18 | Ab25 Ab19 | Ab28 Ab20 | Ab25 Ab22 | Ab26 Ab24 | Ab29 Ab28 |
| Ab14 & Ab28 | Ab15 & Ab26 | Ab16 & Ab25 | Ab17 | Ab24 Ab18 | Ab26 Ab19 | Ab29 Ab21 | Ab26 Ab22 | Ab27 Ab24 | Ab29 Ab1 & Ab30 |
| Ab14 & Ab15 & | Ab16 & | Ab23 | Ab25 | Ab27 | Ab22 | Ab27 | Ab28 | Ab2 & |

-continued

| | | | | | | | | | |
|---|---|---|---|---|---|---|---|---|---|
| & | & | & | Ab25 | Ab18 | Ab19 | Ab21 | Ab22 | Ab24 | Ab30 |
| Ab29 | Ab27 | Ab26 | Ab17 | & | & | & | & | & | Ab3 & |
| Ab15 | Ab15 | Ab16 | & | Ab26 | Ab28 | Ab23 | Ab28 | Ab29 | Ab30 |
| & | & | & | Ab26 | Ab18 | Ab19 | Ab21 | Ab22 | Ab25 | Ab4 & |
| Ab16 | Ab28 | Ab27 | Ab17 | & | & | & | & | & | Ab30 |
| Ab15 | Ab15 | Ab16 | & | Ab27 | Ab29 | Ab24 | Ab29 | Ab26 | Ab5 & |
| & | & | & | Ab27 | Ab18 | Ab20 | Ab21 | Ab23 | Ab25 | Ab30 |
| Ab17 | Ab29 | Ab28 | Ab17 | & | & | & | & | & | Ab6 & |
| Ab15 | Ab16 | Ab16 | & | Ab28 | Ab21 | Ab25 | Ab24 | Ab27 | Ab30 |
| & | & | & | Ab28 | Ab18 | Ab20 | Ab21 | Ab23 | Ab25 | Ab7 & |
| Ab18 | Ab17 | Ab29 | Ab17 | & | & | & | & | & | Ab30 |
| Ab15 | Ab16 | Ab17 | & | Ab29 | Ab22 | Ab26 | Ab25 | Ab28 | Ab8 & |
| & | & | & | Ab29 | Ab19 | Ab20 | Ab21 | Ab23 | Ab25 | Ab30 |
| Ab19 | Ab18 | Ab18 | Ab18 | & | & | & | & | & | Ab9 & |
| Ab15 | Ab16 | Ab17 | & | Ab20 | Ab23 | Ab27 | Ab26 | Ab29 | Ab30 |
| & | & | & | Ab19 | Ab19 | Ab20 | Ab21 | Ab23 | Ab26 | Ab10 |
| Ab20 | Ab19 | Ab19 | Ab18 | & | & | & | & | & | & |
| Ab11 | Ab13 | Ab15 | & | Ab21 | Ab24 | Ab28 | Ab27 | Ab27 | Ab30 |
| & | & | & | Ab20 | Ab19 | Ab20 | Ab21 | Ab23 | Ab26 | Ab29 |
| Ab30 | Ab30 | Ab30 | Ab17 | & | & | & | & | & | & |
| Ab12 | Ab14 | Ab16 | & | Ab22 | Ab25 | Ab29 | Ab28 | Ab28 | Ab30 |
| & | & | & | Ab30 | Ab19 | Ab21 | Ab23 | Ab25 | Ab27 | |
| Ab30 | Ab30 | Ab30 | Ab18 | & | & | & | & | & | |
| | | | & | Ab30 | Ab30 | Ab30 | Ab30 | Ab30 | |
| | | | Ab30 | Ab20 | Ab22 | Ab24 | Ab26 | Ab28 | |
| | | | | & | & | & | & | & | |
| | | | | Ab30 | Ab30 | Ab30 | Ab30 | Ab30 | |

In an embodiment of the invention, the composition comprises two or more non-competing antigen-binding proteins. Cross-competition between anti-PfRH5 antibodies of the present invention is summarized below in Table 6-1.

The term "in association with" indicates that components, an anti-PfRH5 antigen-binding protein, e.g., antibody or antigen-binding fragment thereof of the present invention, along with another agent such as chloroquine, can be formulated into a single composition, e.g., for simultaneous delivery, or formulated separately into two or more compositions (e.g., a kit including each component). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route.

Testing and Diagnosis

Early diagnosis of malaria is helpful to obtaining a positive clinical outcome. The present invention provides methods for treating *Plasmodium falciparum* infection (e.g., malaria), in a subject, comprising diagnosing the infection in the subject and, if the subject is diagnosed as having the infection, administering a therapeutically effective amount of the anti-PfRH5 antigen-binding protein, e.g., antibody or antigen-binding fragment, to the subject. See e.g., Moody, Rapid Diagnostic Tests for Malaria Parasites, Clinical Microbiology Reviews 15(1): 66-78 (2002).

*Plasmodium falciparum* infection can be diagnosed microscopically (e.g., fluorescence microscopy). For example, *Plasmodium falciparum* can be identified by examining, under the microscope, a drop of a subject's blood, e.g., spread out as a "blood smear" on a microscope slide (e.g., thick blood film or thin blood film). Prior to examination, the specimen can be stained (e.g., with Giemsa stain). The present invention includes methods for treatment of *Plasmodium falciparum* infection (as discussed herein) wherein the infection is diagnosed microscopically.

In an embodiment of the invention, the presence of *Plasmodium falciparum* in a sample from the subject is detected by detecting *Plasmodium falciparum* lactate dehydrogenase. If LDH is detected in a test sample above that of a control sample of a known uninfected sample, then the test sample is determined to contain *Plasmodium falciparum*. See e.g., Miura, H. Zhou, A. Diouf, SE. Moretz, M P. Fay, L H. Miller, L B. Martin, M A. Pierce, R D. Ellis, G E D. Mullen, C A. Long. Anti-Apical-Membrane-Antigen-1 antibody is more effective than anti-42-kilodalton-Merozoite-Surface-Protein-1 antibody in inhibiting *Plasmodium falciparum* growth, as determined by the in vitro growth inhibition assay. Clin Vaccine Immunol. 16, 963-968 (2009). PMID: PMC2708396.

The presence of *Plasmodium falciparum* nucleic acids can also be detected, e.g., using polymerase chain reaction (PCR) to detect, for example, the small-subunit 18S rRNA and/or circumsporozoite (CS) genes.

*Plasmodium falciparum* infection can also be diagnosed by detection of the parasite's antigens in the body of a subject. For example, in an embodiment of the invention, the antigen is detected immunogenically, e.g., using a rapid diagnostic test. See e.g., Van der Palen et al. Test characteristics of two rapid antigen detection tests (SD FK50 and SD FK60) for the diagnosis of malaria in returned travelers, Malaria Journal 8:90 (2009); or U.S. Pat. No. 5,712,170.

The anti-PfRH5 antigen-binding proteins, e.g., antibodies or antigen-binding fragments thereof of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), may be used to detect and/or measure PfRH5 (e.g., a *Plasmodium falciparum* cell which includes the PfRH5 protein) in a sample (e.g., a bodily fluid such as blood). Exemplary assays for PfRH5 may include, e.g., contacting the sample with an anti-PfRH5 antigen-binding protein of the invention, wherein, for example, the anti-PfRH5 antigen-binding protein is labeled with a detectable label or reporter molecule. If the anti-PfRH5 antigen-binding protein complexed with PfRH5 is detected, then this indicates the presence of PfRH5 in the sample and/or the presence of *Plasmodium falciparum* in the sample and in the body of the subject.

For example, the present invention includes methods for detecting PfRH5 polypeptide or a cell including such a polypeptide (e.g., *Plasmodium falciparum*) using a lateral flow 'immuno-chromatographic' antigen-detection test. Such lateral flow tests rely on the capture of detectably labeled antigen-binding proteins (e.g., antibodies and antigen-binding fragments thereof) to produce a visible band on a strip of substrate. With *Plasmodium falciparum* malaria diagnostic tests, the labeled antigen-binding protein first binds to the parasite antigen, PfRH5, and the resultant complex is captured on the strip by a band of bound antigen-binding protein, forming a visible line (test line). A control line gives information on the integrity of the antibody-label conjugate, but does not confirm the ability to detect parasite antigen.

The present invention provides a lateral flow test strip for detecting the presence of PfRH5 (e.g., a *Plasmodium falciparum* cell) in a sample comprising a substrate (e.g., nitrocellulose) which includes the following regions arranged laterally across the substrate:
(i) a spot for introduction of a sample (sample zone);
(ii) a conjugate pad which includes a first anti-PfRH5 antigen-binding protein (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) which is detectably labeled, e.g., with a dye, but not immobilized to the substrate;
(iii) a test line containing a second anti-PfRH5 antigen-binding protein which is not detectably labeled and does not significantly compete with the first anti-PfRH5 antigen-binding protein for binding to PfRH5, but is immobilized to the substrate; and
(iv) a control line containing a secondary antigen-binding protein, immobilized to the substrate, which binds to the first anti-PfRH5 antigen-binding protein (e.g., an antibody or antigen-binding fragment or protein-A).

In an embodiment of the invention:
(i) once a liquid-containing sample is placed on the sample pad, the sample (and any PfRH5 polypeptide contained therein) diffuses, by capillary action, across the substrate, onto the conjugation pad, then into the test line and then into the control line;
(ii) PfRH5 polypeptide which reaches the conjugate pad forms a complex with the detectably labeled first anti-PfRH5 antigen-binding protein, and the complex further diffuses into the test line wherein a further complex is formed with the second anti-PfRH5 antigen-binding protein (forming a triple complex wherein PfRH5 is bound by said first and second antigen-binding proteins and immobilized within the test line);
(iii) any excess first anti-PfRH5 antigen-binding protein which does not immobilize at the test line continues to diffuse into the control line and binds to the secondary antigen-binding protein, thereby becoming immobilized in the control line; and/or
(iv) a positive test, indicating the presence of PfRH5 in the sample, is indicated by the presence of the detectable label in the test line; a negative test, indicating the lack of detectable levels of PfRH5 in the sample, is indicated by the absence of the detectable label in the test line; and detectable label in the control line indicates that the test system is operating properly.

In an embodiment of the invention, the detectable label is a dye (e.g., indigo blue), an enzyme, a ferritin, a fluorescent or colored microparticle/bead or nanoparticle/bead or a colloid metal (e.g., gold, selenium dye (e.g., in a liposome) or silver, e.g., a colloidal particle thereof). In an embodiment of the invention, the detectable label is visually detectable.

In an embodiment of the invention, the substrate is an insoluble material capable of supporting fluid flow, e.g., glass fiber filter paper; natural polymeric materials, cellulose-based materials, filter paper, chromatographic paper, nitrocellulose, cellulose acetate, poly(vinyl chloride), polyacrylamide or crosslinked dextran.

The present invention also provides a method for determining if a sample (e.g., bodily fluid such as, for example, blood) contains PfRH5 (e.g., a cell containing PfRH5 such as *Plasmodium falciparum*) comprising contacting the sample zone of a lateral flow device, as set forth herein, with the sample, waiting for capillary flow to carry the sample across the substrate to the control line, optionally waiting for a period of time, and observing the test and control lines, wherein the presence of the detectable label in the test line indicates that the sample contained PfRH5 and the presence of the detectable label in the control line indicates that the lateral flow test strip is functioning correctly. The absence of detectable label in the test line, with the presence of detectable label in the control line indicates the absence of PfRH5 from the sample. In an embodiment of the invention, the method further comprises treating the subject, from whom the sample was taken, with a therapeutically effective amount of anti-PfRH5 antigen-binding protein (e.g., antibody or antigen-binding fragment) if the test indicates the presence of PfRH5 in the sample and the flow test strip is functioning correctly.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies that Bind to PfRH5

Human antibodies to *P. falciparum* RH5 (PfRH5) were generated in a VELOCIMMUNE® mouse comprising DNA encoding human immunoglobulin heavy and kappa light chain variable regions. The mice were immunized with recombinant RH5 protein (PfRH5ΔNL). Some mice were immunized with recombinant PfRH5 protein (PfRH5ΔNL.6his) followed by a booster of *P. falciparum* merozoites isolated from strain 3D7. The antibody immune response was monitored by a PfRH5-specific immunoassay. When a desired immune response was achieved, splenocytes were harvested and antibodies isolated directly from antigen-positive mouse B cells without fusion to myeloma cells, as described in U.S. Pat. No. 7,582,298, herein specifically incorporated by reference in its entirety. Using this method, several fully human anti-PfRH5 antibodies (i.e., antibodies possessing human variable domains and human constant domains) were obtained; exemplary antibodies generated in this manner were designated as H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2.

The biological properties of the exemplary antibodies generated in accordance with the methods of this Example are described in detail in the Examples set forth below. Sequences of the antibody immunoglobulin chains are set forth below.

TABLE 1-1

Immunoglobulin chain sequences of the present invention*

| Antibody | | $V_H$ | | CDR-H1 | | CDR-H2 | | CDR-H3 | | $V_L$ | | CDR-L1 | | CDR-L2 | | CDR-L3 | |
|---|---|---|---|---|---|---|---|---|---|---|---|---|---|---|---|---|---|
| # | Name | DNA | PEP | DNA | PEP | DNA | PEP | DNA | PEP | DNA | PEP | DNA | PEP | DNA | PEP | DNA | PEP |
| 1 | H1H29089P | 1 | 2 | 3 | 4 | 5 | 6 | 7 | 8 | 9 | 10 | 11 1 | 12 | 13 | 14 | 15 | 16 |
| 2 | H1H29094P | 17 | 18 | 19 | 20 | 21 | 22 | 23 | 24 | 25 | 26 | 27 | 28 | 29 | 30 | 31 | 32 |
| 3 | H1H29100P | 33 | 34 | 35 | 36 | 37 | 38 | 39 | 40 | 41 | 42 | 43 | 44 | 45 | 46 | 47 | 48 |
| 4 | H1H29104P | 49 | 50 | 51 | 52 | 53 | 54 | 55 | 56 | 57 | 58 | 59 | 60 | 6 | 62 | 63 | 64 |
| 5 | H1H29106P | 65 | 66 | 67 | 68 | 69 | 70 | 71 | 72 | 73 | 74 | 75 | 76 | 77 | 78 | 79 | 80 |
| 6 | H1H29109P | 81 | 82 | 83 | 84 | 85 | 86 | 87 | 88 | 89 | 90 | 91 | 92 | 93 | 94 | 95 | 96 |
| 7 | H1H29125P | 97 | 98 | 99 | 100 | 101 | 102 | 103 | 104 | 105 | 106 | 107 | 108 | 109 | 110 | 111 | 112 |
| 8 | H1H29127P | 113 | 114 | 115 | 116 | 117 | 118 | 119 | 120 | 121 | 122 | 123 | 124 | 125 | 126 | 127 | 128 |
| 9 | H1H29131P | 129 | 130 | 131 | 132 | 133 | 134 | 135 | 136 | 137 | 138 | 139 | 140 | 141 | 142 | 143 | 144 |
| 10 | H1H29134P | 145 | 146 | 147 | 148 | 149 | 150 | 151 | 152 | 153 | 154 | 155 | 156 | 157 | 158 | 159 | 160 |
| 11 | H1H29138P | 161 | 162 | 163 | 164 | 165 | 166 | 167 | 168 | 169 | 170 | 171 | 172 | 173 | 174 | 175 | 176 |
| 12 | H1H29141P | 177 | 178 | 179 | 180 | 181 | 182 | 183 | 184 | 185 | 186 | 187 | 188 | 189 | 190 | 191 | 192 |
| 13 | H1H29143P | 193 | 194 | 195 | 196 | 197 | 198 | 199 | 200 | 201 | 202 | 203 | 204 | 205 | 206 | 207 | 208 |
| 14 | H1H29146P2 | 209 | 210 | 211 | 212 | 213 | 214 | 215 | 216 | 217 | 218 | 219 | 220 | 221 | 222 | 223 | 224 |
| 15 | H1H29147P2 | 225 | 226 | 227 | 228 | 229 | 230 | 231 | 232 | 217 | 218 | 219 | 220 | 221 | 222 | 223 | 224 |
| 16 | H1H29149P2 | 233 | 234 | 235 | 236 | 237 | 238 | 239 | 240 | 217 | 218 | 219 | 220 | 221 | 222 | 223 | 224 |
| 17 | H1H29151P2 | 241 | 242 | 243 | 244 | 245 | 246 | 247 | 248 | 217 | 218 | 219 | 220 | 221 | 222 | 223 | 224 |
| 18 | H1H29163P2 | 249 | 250 | 251 | 252 | 253 | 254 | 255 | 256 | 217 | 218 | 219 | 220 | 221 | 222 | 223 | 224 |
| 19 | H1H29166P2 | 257 | 258 | 259 | 260 | 261 | 262 | 263 | 264 | 217 | 218 | 219 | 220 | 221 | 222 | 223 | 224 |
| 20 | H1H29171P2 | 265 | 266 | 267 | 268 | 269 | 270 | 271 | 272 | 217 | 218 | 219 | 220 | 221 | 222 | 223 | 224 |
| 21 | H1H29179P2 | 273 | 274 | 275 | 276 | 277 | 278 | 279 | 280 | 217 | 218 | 219 | 220 | 221 | 222 | 223 | 224 |
| 22 | H1H29183P2 | 281 | 282 | 283 | 284 | 285 | 286 | 287 | 288 | 217 | 218 | 219 | 220 | 221 | 222 | 223 | 224 |
| 23 | H1H29187P2 | 289 | 290 | 291 | 292 | 293 | 294 | 295 | 296 | 217 | 218 | 219 | 220 | 221 | 222 | 223 | 224 |
| 24 | H1H29192P2 | 297 | 298 | 299 | 300 | 301 | 302 | 303 | 304 | 305 | 306 | 307 | 308 | 309 | 310 | 311 | 312 |
| 25 | H1H29196P2 | 313 | 314 | 315 | 316 | 317 | 318 | 319 | 320 | 305 | 306 | 307 | 308 | 309 | 310 | 311 | 312 |
| 26 | H1H29198P2 | 321 | 322 | 323 | 324 | 325 | 326 | 327 | 328 | 305 | 306 | 307 | 308 | 309 | 310 | 311 | 312 |
| 27 | H1H29207P2 | 329 | 330 | 331 | 332 | 333 | 334 | 335 | 336 | 305 | 306 | 307 | 308 | 309 | 310 | 311 | 312 |
| 28 | H1H29214P2 | 337 | 338 | 339 | 340 | 341 | 342 | 343 | 344 | 305 | 306 | 307 | 308 | 309 | 310 | 311 | 312 |
| 29 | H1H29215P2 | 345 | 346 | 347 | 348 | 349 | 350 | 351 | 352 | 305 | 306 | 307 | 308 | 309 | 310 | 311 | 312 |
| 30 | H1H29209P2 | 353 | 354 | 355 | 356 | 357 | 358 | 359 | 360 | 305 | 306 | 307 | 308 | 309 | 310 | 311 | 312 |

*Numbers corresponding to $V_H$, CDR-H1, CDR-H2, CDR-H3, $V_L$, CDR-L1, CDR-L2 and CDR-L3 refer to SEQ ID NOs set forth herein.
"PEP" refers to an amino acid sequence;
"DNA" refers to a nucleotide sequence.

The immunoglobulin sequences and their corresponding SEQ ID NOs which are summarized in Table 1-1 are set forth below. The sequences below are also in a Sequence Listing which is incorporated herein by reference.

SEQ ID NO: 1

GAGGTGCAGCTGGTGCAGTCTGGAGCAGAGGTGAAAAAGCCCGGGGAGTCTCTGAAGATCT

CCTGTAAGGGTTCTGGATA

CAGCTTTACCAGTTACTGGATCGTCTGGGTGCGCCAGATGCCCGGGAAAGGCCTGGAGTGG

ATGGGGATCATCTATCCTG

GTGACTCTGATACCAGATACAGCCCGTCCTTCCAAGGCCAGGTCACCATCTCAGCCGACAAG

TCCATCAGCACCGCCTAC

CTGCAGTGGAGCAGCCTGAAGGCCTCGGACACCGCCATGTATTACTGTGCGAGACAAGATAT

AACTGGAACTACGGGGTT

TGACTACTGGGGCCAGGGAACCCTGGTCACCGTCTCCTCA;

-continued

SEQ ID NO: 2
EVQLVQSGAEVKKPGESLKISCKGSGYSFTSYWIVWVRQMPGKGLEWMGIIYPGDSDTRYSPSF
QGQVTISADKSISTAY
LQWSSLKASDTAMYYCARQDITGTTGFDYWGQGTLVTVSS;

SEQ ID NO: 3
GGA TAC AGC TTT ACC AGT TAC TGG;

SEQ ID NO: 4
G Y S F T S Y W;

SEQ ID NO: 5
ATC TAT CCT GGT GAC TCT GAT ACC;

SEQ ID NO: 6
I Y P G D S D T;

SEQ ID NO: 7
GCG AGA CAA GAT ATA ACT GGA ACT ACG GGG TTT GAC TAC;

SEQ ID NO: 8
A R Q D I T G T T G F D Y;

SEQ ID NO: 9
GACATCCAGATGACCCAGTCTCCATCCTCCCTGTCTGCATCTGTAGGAGACAGAGTCACCAT
CACTTGCCGGGCAAGTCA
GAGCATTAGGAACTATTTGAATTGGTATCAGCAGAAACCAGGGAAAGCCCCTAAGCTCCTGAT
CTATGCTGCATCCAGTT
TGCAAAGTGGGGTCCCATCAAGGTTCAGTGGCAGTGGATCTGGGACAGATTTCACTCTCACC
ATCAGCAGTCTGCAACCT
GAAGATTTTGCAACTTATTTCTGTCAACAGAGTTACAGTACCCCATTCACTTTCGGCCCTGGG
ACCAAAGTGGATATCAA
ACGA;

SEQ ID NO: 10
DIQMTQSPSSLSASVGDRVTITCRASQSIRNYLNWYQQKPGKAPKLLIYAASSLQSGVPSRFSGS
GSGTDFTLTISSLQP
EDFATYFCQQSYSTPFTFGPGTKVDIKR;

SEQ ID NO: 11
CAG AGC ATT AGG AAC TAT;

SEQ ID NO: 12
Q S I R N Y;

SEQ ID NO: 13
GCT GCA TCC;

SEQ ID NO: 14
A A S;

SEQ ID NO: 15
CAA CAG AGT TAC AGT ACC CCA TTC ACT;

SEQ ID NO: 16
Q Q S Y S T P F T;

SEQ ID NO: 17
CAGGTGCAGCTGGTGGAGTCTGGGGGAGACGTGGTCCAGCCTGGGAGGTCCCTGCGACTCT
CCTGTTCAGGCACTGGATT
CACCTTCAGTAGCTATGCCATGCACTGGGTCCGCCAGGCTCCAGGCAAGGGACTGGAATGG
GTGGCACTTATATCATATG
ATGGAAGTAATAAATATTATGGAGACTCCGTGAAGGGCCGATTCACCGTCTCCAGAGACAATT
CCAAGAACACGCTGTCT
CTGCAAATGAACAGCCTGAAAACTGAGGACACGGCGATATATTACTGTGCGAAAGAGAGGCT
TTTTGGAGTGGTCTCTTA
TTACGGTATGGACGTCTGGGGCCAAGGGACCACGGTCACCGTCTCCTCA;

SEQ ID NO: 18
QVQLVESGGDVVQPGRSLRLSCSGTGFTFSSYAMHWVRQAPGKGLEWVALISYDGSNKYYGDS
VKGRFTVSRDNSKNTLS
LQMNSLKTEDTAIYYCAKERLFGVVSYYGMDVWGQGTTVTVSS;

SEQ ID NO: 19
GGA TTC ACC TTC AGT AGC TAT GCC;

SEQ ID NO: 20
G F T F S S Y A;

SEQ ID NO: 21

```
                                                         -continued
ATA TCA TAT GAT GGA AGT AAT AAA;

SEQ ID NO: 22
I S Y D G S N K;

SEQ ID NO: 23
GCG AAA GAG AGG CTT TTT GGA GTG GTC TCT TAT TAC GGT ATG GAC GTC;

SEQ ID NO: 24
A K E R L F G V V S Y Y G M D V;

SEQ ID NO: 25
GACATCCAGATGACCCAGTCTCCATCCTCCCTGTCTGCATCTGTAGGAGACAGAGTCACCAT
CACTTGCCAGGCGAGTCA
GGACATTAATAGGGATCTAAATTGGTATCAGCAGAAATCAGGGAAAGGCCCCAAACTCCTGAT
CTACGATGCATCCAATT
TGGAAACAGGGGTCCCATCAAGGTTCAGTGGAAATAGATTTGGGACAGATTTTACTTTCACCA
TCAGCAGACTGCAGCCT
GAAGATATTGCAACATATTTCTGTCAACAGTATAAAAATCTCCCGTACACTTTTGGCCAGGGGA
CCAAGCTGGAGATCAA
ACGA;

SEQ ID NO: 26
DIQMTQSPSSLSASVGDRVTITCQASQDINRDLNWYQQKSGKGPKLLIYDASNLETGVPSRFSGN
RFGTDFTFTISRLQP
EDIATYFCQQYKNLPYTFGQGTKLEIKR;

SEQ ID NO: 27
CAG GAC ATT AAT AGG GAT;

SEQ ID NO: 28
Q D I N R D;

SEQ ID NO: 29
GAT GCA TCC;

SEQ ID NO: 30
D A S;

SEQ ID NO: 31
CAA CAG TAT AAA AAT CTC CCG TAC ACT;

SEQ ID NO: 32
Q Q Y K N L P Y T;

SEQ ID NO: 33
CAGCTGCAGCTGCAGGAGTCGGGCCCAGGACTGGTGAAGCCTTCGGAGACCCTGTCCCTCA
CCTGCACTGTCTCTGGTGG
CTCCATCAGCAGTAGTAGTTACTACTGGGGCTGGATCCGCCAGCCCCCAGGGAAGGGCCTG
GAGTGGATTGGGATTATCT
ATTATAGTGGGAGCACCTACTACAACCCGTCCCTCAAGAGTCGAGTCACCATTTCCGTAGACA
CGTCCAAGAACCAGTTC
TCCCTGAAGCTGAGCTCTGTGACCGCCGCAGACACGGCTGTGTATTACTGTGCGAGACAGGA
CAGGGAGGCCCTCTTTGA
CTACTGGGGCCAGGGAACCCTGGTCACCGTCTCCTCA;

SEQ ID NO: 34
QLQLQESGPGLVKPSETLSLTCTVSGGSISSSSYYWGWIRQPPGKGLEWIGIIYYSGSTYYNPSLK
SRVTISVDTSKNQF
SLKLSSVTAADTAVYYCARQDREALFDYWGQGTLVTVSS;

SEQ ID NO: 35
GGT GGC TCC ATC AGC AGT AGT AGT TAC TAC;

SEQ ID NO: 36
G G S I S S S S Y Y;

SEQ ID NO: 37
ATC TAT TAT AGT GGG AGC ACC;

SEQ ID NO: 38
I Y Y S G S T;

SEQ ID NO: 39
GCG AGA CAG GAC AGG GAG GCC CTC TTT GAC TAC;

SEQ ID NO: 40
A R Q D R E A L F D Y;

SEQ ID NO: 41
GAAATTGTGCTGACTCAGTCTCCAGACTTTCAGTCTGTGACTCCAAAGGAGAAAGTCACCATC
```

-continued
```
ACCTGCCGGGCCAGTCA
GCGCATTGGTAGTAGCTTACACTGGTACCAGCAGAAACCAGATCAGTCTCCAAAGCTCCTCAT
CAAGTATGCTTCCCAGT
CCTTCTCAGGGGTCCCCTCGAGGTTCAGTGGCAGTGGATCTGGGACAGATTTCACCCTCACC
ATCAATAGCCTGGAAGCT
GAAGATGCTGCAACGTATTACTGTCATCAGAGTAGTACTTTACCCACCTTCGGCCAAGGGACA
CGACTGGAGATTAAACG
A;
```

SEQ ID NO: 42
```
EIVLTQSPDFQSVTPKEKVTITCRASQRIGSSLHWYQQKPDQSPKLLIKYASQSFSGVPSRFSGSG
SGTDFTLTINSLEA
EDAATYYCHQSSTLPTFGQGTRLEIKR;
```

SEQ ID NO: 43
```
CAG CGC ATT GGT AGT AGC;
```

SEQ ID NO: 44
```
Q R I G S S;
```

SEQ ID NO: 45
```
TAT GCT TCC;
```

SEQ ID NO: 46
```
Y A S;
```

SEQ ID NO: 47
```
CAT CAG AGT AGT ACT TTA CCC ACC;
```

SEQ ID NO: 48
```
H Q S S T L P T;
```

SEQ ID NO: 49
```
GAAGTGCAGCTGGTGGAGTCTGGGGGAGGCCTGGTACAGCCTGGCAGGTCCCTGAGACTCT
CCTGTGCAGCCTCTGGATT
CAGGTTTGACGATTATGCCATGCACTGGGTCCGACAAGCTCCAGGGAAGGGCCTGGAATGG
GTCTCAGGTATTAATTGGA
ATAGTGGTGGCAAAGGCTATGCGGACTCTGTGCAGGGCCGATTCACCATCTCCAGAGACAAC
GCCAAGAACTCCCTTTAT
CTGCAAATGAACAGTCTGAGAACTGAGGACACGGCCTTGTATTATTGTGCAAAAGATAGGGGT
ATAGCAGCTCGTCTTCT
CTCTCGTGATGCTTTTGATATGTGGGGCCAAGGGACAATGGTCACCGTCTCTTCA;
```

SEQ ID NO: 50
```
EVQLVESGGGLVQPGRSLRLSCAASGFRFDDYAMHWVRQAPGKGLEWVSGINWNSGGKGYAD
SVQGRFTISRDNAKNSLY
LQMNSLRTEDTALYYCAKDRGIAARLLSRDAFDMWGQGTMVTVSS;
```

SEQ ID NO: 51
```
GGA TTC AGG TTT GAC GAT TAT GCC;
```

SEQ ID NO: 52
```
G F R F D D Y A;
```

SEQ ID NO: 53
```
ATT AAT TGG AAT AGT GGT GGC AAA;
```

SEQ ID NO: 54
```
I N W N S G G K;
```

SEQ ID NO: 55
```
GCA AAA GAT AGG GGT ATA GCA GCT CGT CTT CTC TCT CGT GAT GCT TTT GAT ATG;
```

SEQ ID NO: 56
```
A K D R G I A A R L L S R D A F D M;
```

SEQ ID NO: 57
```
GACATCCAGTTGACCCAGTCTCCATCCTTCCTGTCTGCATCTGTAGGAGACAGAGTCACCATC
ACTTGCTGGGCCAGTCA
GGACGTTAGCAGTTATTTAGCCTGGTATCAGCAAAAACCAGGGAAATCCCCTAAGCTCCTAAT
CTTTGCTGCATCCACTT
TGCAAGGTGGGATCCCATCAAGGTTCAGCGGCAGTGGATCTGGGACAGAATTCACTCTCACA
ATCAGCAGCCTGCGGCCT
GAAGATTTTGCAACTTATTACTGTCAACACCTTAATACTTACCCGTACACTTTTGGCCAGGGGA
CCAAGCTGGAGATCAA
ACGA;
```

SEQ ID NO: 58
```
DIQLTQSPSFLSASVGDRVTITCWASQDVSSYLAWYQQKPGKSPKLLIFAASTLQGGIPSRFSGSG
SGTEFTLTISSLRP
EDFATYYCQHLNTYPYTFGQGTKLEIKR;
```

```
                                                          SEQ ID NO: 59
CAG GAC GTT AGC AGT TAT;

SEQ ID NO: 60
Q D V S S Y;

SEQ ID NO: 61
GCT GCA TCC;

SEQ ID NO: 62
A A S;

SEQ ID NO: 63
CAA CAC CTT AAT ACT TAC CCG TAC ACT;

SEQ ID NO: 64
Q H L N T Y P Y T;

SEQ ID NO: 65
CAGGTGCAGCTGGTGGAGTCTGGGGGAGGCGTGGTCCAGTCTGGGAGGTCCCTGAGACTCT
CCTGTGCAGCGTCTTCATT
CACCTTCAGTAGCTATGGCATGCACTGGGTCCGCCAGTCTCCAGGCAAGGGGCTGGAGTGG
GTGGCAGTTATAAGTTATG
ATGGAAGTAATAAATACTATGGAGACTTCGTGAGGGGCCGATTCACCATCTCCAGAGACAATT
CCAAGAACACGCTGTAT
CTGCAAATGAACAGCCTGAGAGCCGAGGACACGGCTATGTATTATTGTGCGAGAGAAGTTCG
TCGCTACTATTATTACGG
TATGGACGTCTGGGGCCAAGGGACCACGGTCACCGTCTCCTCA;

SEQ ID NO: 66
QVQLVESGGGVVQSGRSLRLSCAASSFTFSSYGMHWVRQSPGKGLEWVAVISYDGSNKYYGDF
VRGRFTISRDNSKNTLY
LQMNSLRAEDTAMYYCAREVRRYYYYGMDVWGQGTTVTVSS;

SEQ ID NO: 67
TCA TTC ACC TTC AGT AGC TAT GGC;

SEQ ID NO: 68
S F T F S S Y G;

SEQ ID NO: 69
ATA AGT TAT GAT GGA AGT AAT AAA;

SEQ ID NO: 70
I S Y D G S N K;

SEQ ID NO: 71
GCG AGA GAA GTT CGT CGC TAC TAT TAT TAC GGT ATG GAC GTC;

SEQ ID NO: 72
A R E V R R Y Y Y Y G M D V;

SEQ ID NO: 73
GACATCCAGATGACCCAGTCTCCATCCTCCCTGTCTGCATCTGTAGGAGACAGAGTCACCAT
CACTTGCCAGGCGAGTCA
GGACATTAGTAATTATTTAAATTGGTATCTGCAGAAACCAGGGAAAGCCCCTAAGCTCCTGAT
CTCCGATGCATCCAATT
TGGAAACAGGGGTCCCATCAAGGTTCAGTGGAAGTGGATCTGGGACAGATTTTACTTTCACC
ATCAGCAGCCTGCAGCCT
GAAGATATTGCAACATATTACTGTCAACAGTATAATAATCTCCCGCTCACTTTCGGCGGAGGG
ACCAAGGTGGAGATCAA
ACGA;

SEQ ID NO: 74
DIQMTQSPSSLSASVGDRVTITCQASQDISNYLNWYLQKPGKAPKLLISDASNLETGVPSRFSGSG
SGTDFTFTISSLQP
EDIATYYCQQYNNLPLTFGGGTKVEIKR;

SEQ ID NO: 75
CAG GAC ATT AGT AAT TAT;

SEQ ID NO: 76
Q D I S N Y;

SEQ ID NO: 77
GAT GCA TCC;

SEQ ID NO: 78
D A S;
```

```
                                                    SEQ ID NO: 79
CAA CAG TAT AAT AAT CTC CCG CTC ACT;

SEQ ID NO: 80
Q Q Y N N L P L T;

SEQ ID NO: 81
GAAGTGCAGCTGGTGGAGTCTGGGGGAGGCTTGGTACAGCCTGGCAGGTCCCTGAGACTCT
CCTGTGCAGTCTCTGGATT
CACCTTTGATGATTATGCCATGCACTGGGTCCGGCAAGCTCCAGGGAAGGGCCTGGAGTGG
GTCTCAGGTATTAGTTGGA
ATAGTGGTGACATAGACTATGCGGACTCTGTGAAGGGCCGATTCACCATTTCCAGAGACAAC
GCCAAGAACTCCCTGTAT
CTGCAAATGAACAGTCTGAGAGCTGAGGACACGGCCTTGTATTACTGTGCAAAAGATACCCTC
TCAGGGACTGGAACTAC
GTGGTACTATTTTGACTACTGGGGCCAGGGAACCCTGGTCACCGTCTCCTCA;

SEQ ID NO: 82
EVQLVESGGGLVQPGRSLRLSCAVSGFTFDDYAMHWVRQAPGKGLEWVSGISWNSGDIDYADS
VKGRFTISRDNAKNSLY
LQMNSLRAEDTALYYCAKDTLSGTGTTWYYFDYWGQGTLVTVSS;

SEQ ID NO: 83
GGA TTC ACC TTT GAT GAT TAT GCC;

SEQ ID NO: 84
G F T F D D Y A;

SEQ ID NO: 85
ATT AGT TGG AAT AGT GGT GAC ATA;

SEQ ID NO: 86
I S W N S G D I;

SEQ ID NO: 87
GCA AAA GAT ACC CTC TCA GGG ACT GGA ACT ACG TGG TAC TAT TTT GAC TAC;

SEQ ID NO: 88
A K D T L S G T G T T W Y Y F D Y;

SEQ ID NO: 89
GACATCCAGTTGACCCAGTCTCCATCCTTCCTGTCTGCATCTGTAGGAGACAGAGTCACCATC
ACTTGCTGGGCCAGTCA
GGGTATTAGCAGTTATTTAATCTGGTATCAGCAAAAACCAGGGAAAGCCCCTAAGCTCCTGAT
CTATGCTGCATCCACTT
TGCAAAGTGGGGTCCCATCAAGGTTCAGCGGCAGTGGATCTGGGACAGAATTCACTCTCACA
ATCAGCAGCCTGCAGCCT
GAAGATTTTGCAACTTATTACTGTCAACAGGTGAATAGTTACCCTCTCACTTTCGGCGGAGGG
ACCAAGGTGGAGATCAA
ACGA;

SEQ ID NO: 90
DIQLTQSPSFLSASVGDRVTITCWASQGISSYLIWYQQKPGKAPKLLIYAASTLQSGVPSRFSGSG
SGTEFTLTISSLQP
EDFATYYCQQVNSYPLTFGGGTKVEIKR;

SEQ ID NO: 91
CAG GGT ATT AGC AGT TAT;

SEQ ID NO: 92
Q G I S S Y;

SEQ ID NO: 93
GCT GCA TCC;

SEQ ID NO: 94
A A S;

SEQ ID NO: 95
CAA CAG GTG AAT AGT TAC CCT CTC ACT;

SEQ ID NO: 96
Q Q V N S Y P L T;

SEQ ID NO: 97
CAGGTGCAGCTGGTGGAGTCTGGGGGAGGCGTGGTCCAGCCTGGGAGGTCCCTGAGACTC
TCCTGTGCAGCCTCTGGATT
CACCTTCAGTAGTTATGGCATGCACTGGGTCCGCCAGGCTCCAGGCAAGGGACTGGAGTGG
ATGGCAGTTATATCATATG
ATGGAAGTAATAAATATTATGCAGACTCCGTGAAGGGCCGATTCACCATCTCCAGAGACAATT
CCAAGAACACGCTGTTT
```

-continued

CTGCAAATGAACAGCCTGAGACCTGAAGACACGGCTGTATATTACTGTGCGCAAGATGGCAG
CTCGGCGATTTACTATTT
CTACGGTATGGACGTCTGGGGCCAAGGGACCACGGTCACCGTCTCCTCA;

SEQ ID NO: 98
QVQLVESGGGVVQPGRSLRLSCAASGFTFSSYGMHWVRQAPGKGLEWMAVISYDGSNKYYAD
SVKGRFTISRDNSKNTLF
LQMNSLRPEDTAVYYCAQDGSSAIYYFYGMDVWGQGTTVTVSS;

SEQ ID NO: 99
GGA TTC ACC TTC AGT AGT TAT GGC;

SEQ ID NO: 100
G F T F S S Y G;

SEQ ID NO: 101
ATA TCA TAT GAT GGA AGT AAT AAA;

SEQ ID NO: 102
I S Y D G S N K;

SEQ ID NO: 103
GCG CAA GAT GGC AGC TCG GCG ATT TAC TAT TTC TAC GGT ATG GAC GTC;

SEQ ID NO: 104
A Q D G S S A I Y Y F Y G M D V;

SEQ ID NO: 105
GACATCCAGATGACCCAGTCTCCATCCTCACTGTCTGCATCTATAGGAGACAGAGTCACCATC
ACTTGTCGGGCGAGTCA
GGACATCAACAATTATTTAGCCTGGTTTCAGCAGAAACCAGGGAAAGCCCCTAAGTCCCTGAT
CTATGCTGCATCCAGTT
TGCAAAGTGGGGTCCCATCAAAGTTCAGCGGCAGTGGATCTGGGACAGATTTCACTCTCACC
ATCAGCAGCCTGCAGCCT
GAAGATTTTGCAACTTATTACTGCCTTCAGTATAATAGTTACCATCCCACTTTTGGCCAGGGGA
CCAAGCTGGAGATCAA
ACGA;

SEQ ID NO: 106
DIQMTQSPSSLSASIGDRVTITCRASQDINNYLAWFQQKPGKAPKSLIYAASSLQSGVPSKFSGSG
SGTDFTLTISSLQP
EDFATYYCLQNSYHPTFGQGTKLEIKR;

SEQ ID NO: 107
CAG GAC ATC AAC AAT TAT;

SEQ ID NO: 108
Q D I N N Y;

SEQ ID NO: 109
GCT GCA TCC;

SEQ ID NO: 110
A A S;

SEQ ID NO: 111
CTT CAG TAT AAT AGT TAC CAT CCC ACT;

SEQ ID NO: 112
L Q Y N S Y H P T;

SEQ ID NO: 113
CAGGTGCAGCTGGTGGAGTCTGGGGGAGGCGTGGTCCAGCCTGGGAGGTCCCTGAGACTC
TCCTGTGCAGCGTCTGGATT
CACCTTCAGTAGCTATGGCATGCACTGGGTCCGCCAGGCTCCAGGCAAGGGGCTGGAGTGG
GTGGCAGCTATATGGTATG
ATGGAAGTAATAAATATTATGCAGACTCCGTGAAGGGCCGATTCACCATCTCCAGAGACAATT
CCAAGAACACGCTGTAT
CTGCAAATGAACAGCCTGAGAGCCGAGGACACGGCTGTGTATTTCTGTGCGAGAGGGGAAC
ATTACTATGGTTCGGGGCC
GTTCGACCCCTGGGGCCAGGGAACCCTGGTCACCGTCTCCTCA;

SEQ ID NO: 114
QVQLVESGGGVVQPGRSLRLSCAASGFTFSSYGMHWVRQAPGKGLEWVAAIWYDGSNKYYAD
SVKGRFTISRDNSKNTLY
LQMNSLRAEDTAVYFCARGEHYYGSGPFDPWGQGTLVTVSS;

SEQ ID NO: 115
GGA TTC ACC TTC AGT AGC TAT GGC;

SEQ ID NO: 116

```
                                                               -continued
G F T F S S Y G;

SEQ ID NO: 117
ATA TGG TAT GAT GGA AGT AAT AAA;

SEQ ID NO: 118
I W Y D G S N K;

SEQ ID NO: 119
GCG AGA GGG GAA CAT TAC TAT GGT TCG GGG CCG TTC GAC CCC;

SEQ ID NO: 120
A R G E H Y Y G S G P F D P;

SEQ ID NO: 121
GACATCCAGATGACCCAGTCTCCATCCTCCCTGTCTGCATCTGTAGGAGACAGAGTCACCAT
CACTTGCCGGGCAAGTCA
GAGCATTAGCAACTATTTAAATTGGTATCAGCAGAAACCAGGGAAAGCCCCTAAGCTCCTGAT
CTTTGCTGCATCCAGTT
TACAAAGTGGGGTCCCATCAAGGTTCAGTGGCAGTGGATCTGGGACAGATTTCACTCTCACC
ATCAGCAGTCTGCAACCT
GAAGATTTTGCAACTTACTACTGTCAACAGAGTTACAGTTCCCCGCTCACTTTCGGCGGAGGG
ACCAAGGTGGAGATCAA
ACGA;

SEQ ID NO: 122
DIQMTQSPSSLSASVGDRVTITCRASQSISNYLNWYQQKPGKAPKLLIFAASSLQSGVPSRFSGSG
SGTDFTLTISSLQP
EDFATYYCQQSYSSPLTFGGGTKVEIKR;

SEQ ID NO: 123
CAG AGC ATT AGC AAC TAT;

SEQ ID NO: 124
Q S I S N Y;

SEQ ID NO: 125
GCT GCA TCC;

SEQ ID NO: 126
A A S;

SEQ ID NO: 127
CAA CAG AGT TAC AGT TCC CCG CTC ACT;

SEQ ID NO: 128
Q Q S Y S S P L T;

SEQ ID NO: 129
CAGGTGCAGCTGCAGGAGTCGGGGCCAGGACTGGTGAAGCCTTCACAGACCCTGTCCCTCA
CCTGCACTGTCTCAGGTGG
CTCCATCAGCAGTTTTGGTTACTACTGGAGCTGGATCCGCCAGCACCCAGGGAAGGGCCTGG
AGTGGATTGGGTACATCT
ATTACAGTGGGAGCATCGACTACAACCCGTCCCTCAAGAGTCGAATTACCATATCAGTCGACA
CGTCTAAGAACCAGTTC
TCCCTGAAGCTGAGCTCTGTGACTGCCGCGGACACGGCCGTGTATTACTGTGCGAGAGAAAG
GGACTACGGTGACTACTT
TGACTACTGGGGCCAGGGAACCCTGGTCACCGTCTCCTCA;

SEQ ID NO: 130
QVQLQESGPGLVKPSQTLSLTCTVSGGSISSFGYYWSWIRQHPGKGLEWIGYIYYSGSIDYNPSL
KSRITISVDTSKNQF
SLKLSSVTAADTAVYYCARERDYGDYFDYWGQGTLVTVSS;

SEQ ID NO: 131
GGT GGC TCC ATC AGC AGT TTT GGT TAC TAC;

SEQ ID NO: 132
G G S I S S F G Y Y;

SEQ ID NO: 133
ATC TAT TAC AGT GGG AGC ATC;

SEQ ID NO: 134
I Y Y S G S I;

SEQ ID NO: 135
GCG AGA GAA AGG GAC TAC GGT GAC TAC TTT GAC TAC;

SEQ ID NO: 136
A R E R D Y G D Y F D Y;
```

```
                                                      SEQ ID NO: 137
GAAATAGTGATGACGCAGTCTCCAGCCACCCTGTCTGTCTCTCCAGGGGAAAGAGCCACCCT
CTCCTGCAGGGCCAGTCA
GAGTGTTAGCAGCAACTTAGCCTGGTACCAGCAGAAACCTGGCCAGGCTCCCAGGCTCCTCA
TCTATGGTGCATCCACCA
GGGCCACTGGTGTCCCAGCCAGGTTCAGTGGCAGTGGGTCTGGGACAGAGTTCACTCTCAC
CATCAGCAGTTTGCAGTCT
GAGGATTTTGCAGTTTATTCCTGTCAGCAGTATAATAACTGGCCTCTCACTTTCGGCGGAGGG
ACCAAGGTGGAGATCAA
ACGA;

SEQ ID NO: 138
EIVMTQSPATLSVSPGERATLSCRASQSVSSNLAWYQQKPGQAPRLLIYGASTRATGVPARFSGS
GSGTEFTLTISSLQS
EDFAVYSCQQYNNWPLTFGGGTKVEIKR;

SEQ ID NO: 139
CAG AGT GTT AGC AGC AAC;

SEQ ID NO: 140
Q S V S S N;

SEQ ID NO: 141
GGT GCA TCC;

SEQ ID NO: 142
G A S;

SEQ ID NO: 143
CAG CAG TAT AAT AAC TGG CCT CTC ACT;

SEQ ID NO: 144
Q Q Y N N W P L T;

SEQ ID NO: 145
CAGGTGCAGCTGGTGGAGTCTGGGGGAGGCGTGGTCCAGCCTGGGAGGTCCCTGAGACTC
TCCTGTGCAGCGTCTGGATT
CACCTTCAGTAGCTATGGCATACACTGGGTCCGCCAGGCTCCAGGCAAGGGGCTGGAGTGG
GTGGCACTTATATGGTATG
ATGGAAGTAATAAATACTATGCAGACTCCGTGAAGGGCCGATTCACCATCTCCAGAGACAATT
CCAAGAACACGCTGTAT
CTGCAAATGAACAGCCTGAGAGCCGAGGACACGGCTGTGTATTACTGTGCGAGAGATCAGGA
TTACTATGGTTCGGGGAG
TTCCTACGGTATGGACGTCTGGGGCCAAGGGACCACGGTCACCGTCTCCTCA;

SEQ ID NO: 146
QVQLVESGGGVVQPGRSLRLSCAASGFTFSSYGIHWVRQAPGKGLEWVALIWYDGSNKYYADS
VKGRFTISRDNSKNTLY
LQMNSLRAEDTAVYYCARDQDYYGSGSSYGMDVWGQGTTVTVSS;

SEQ ID NO: 147
GGA TTC ACC TTC AGT AGC TAT GGC;

SEQ ID NO: 148
G F T F S S Y G;

SEQ ID NO: 149
ATA TGG TAT GAT GGA AGT AAT AAA;

SEQ ID NO: 150
I W Y D G S N K;

SEQ ID NO: 151
GCG AGA GAT CAG GAT TAC TAT GGT TCG GGG AGT TCC TAC GGT ATG GAC GTC;

SEQ ID NO: 152
A R D Q D Y Y G S G S S Y G M D V;

SEQ ID NO: 153
GACATCCAGATGACCCAGTCGCCAGCCTCCCTGTCTGCATCTGTAGGAGACAGAGTCACCAT
CACTTGCCGGGCAAGTCA
GAGCATTAGCAGCTATTTAAATTGGTATCAGCAGAAACCAGGGAAAGCCCCTAAGCGCCTGAT
CTATGCTGCATCCAGTT
TGCAAAGTGGGGTCCCATCAAGGTTCAGTGGCAGTGGATCTGGGACAGATTTCACTCTCACC
ATCAGCAGTCTGCAACCT
GAAGATTTTGCAACTTACTACTGTCAACAGAGTTACAGTACCCCTCTCACTTTTGGCCAGGGG
ACCAAGCTGGAGATCAA
ACGA;

SEQ ID NO: 154
```

-continued

DIQMTQSPASLSASVGDRVTITCRASQSISSYLNWYQQKPGKAPKRLIYAASSLQSGVPSRFSGS
GSGTDFTLTISSLQP
EDFATYYCQQSYSTPLTFGQGTKLEIKR;

SEQ ID NO: 155
CAG AGC ATT AGC AGC TAT;

SEQ ID NO: 156
Q S I S S Y;

SEQ ID NO: 157
GCT GCA TCC;

SEQ ID NO: 158
A A S;

SEQ ID NO: 159
CAA CAG AGT TAC AGT ACC CCT CTC ACT;

SEQ ID NO: 160
Q Q S Y S T P L T;

SEQ ID NO: 161
CAGGTGCAGCTGGTGGAGTCTGGGGGAGGCGTGGTCCAGCCTGGGAGGTCCCTGAGACTC
TCCTGTGCAGCGTCTGGATT
CACCTTCAGTACCTATGGCATGCACTGGGTCCGCCAGGCTCCAGGCAAGGGGCTGGAGTGG
GTGGCAGTTATATGGTATG
ATGGAACTAATAAATACTATGCAGACTCCGTGAAGGGCCGATTCACCATCTCCAGAGACAATT
CCAAGAACACGCTGTAT
CTGCAAATGATCAGCCTGAGAGCCGAGGACACGGCTGTGTATTACTGTGCGAGAGACCCCTC
AGGTGGGGACCACTACTA
TTACTACGGTATGGACGTCTGGGGCCAAGGGACCACGGTCACCGTCTCCTCA;

SEQ ID NO: 162
QVQLVESGGGVVQPGRSLRLSCAASGFTFSTYGMHWVRQAPGKGLEWVAVIWYDGTNKYYAD
SVKGRFTISRDNSKNTLY
LQMISLRAEDTAVYYCARDPSGGDHYYYYGMDVWGQGTTVTVSS;

SEQ ID NO: 163
GGA TTC ACC TTC AGT ACC TAT GGC;

SEQ ID NO: 164
G F T F S T Y G;

SEQ ID NO: 165
ATA TGG TAT GAT GGA ACT AAT AAA;

SEQ ID NO: 166
I W Y D G T N K;

SEQ ID NO: 167
GCG AGA GAC CCC TCA GGT GGG GAC CAC TAC TAT TAC TAC GGT ATG GAC GTC;

SEQ ID NO: 168
A R D P S G G D H Y Y Y Y G M D V;

SEQ ID NO: 169
GACATCCAGATGACCCAGTCTCCATCCTCCCTGTCTGCATCTGTAGGAGACAGAATCACCATC
ACTTGCCAGGCGAGTCA
GGACATTAGCAACTATTTAAATTGGTATCAGCAGAAGCCAGGGAAAGCCCCTAACCTCCTGAT
CTCCGATGCATCCGATT
TGGAAACAGGGGTCCCATCAAGGTTCAGTGGAAGTGGATCTGGGACAGATTTTACTTTCACC
ATCAGCAGCCTGCAGCCT
GAAGATTTTGCAACATATTACTGTCAACAGTATGATAATATACCGATCACCTTCGGCCAAGGG
ACACGACTGGAGATTAA
ACGA;

SEQ ID NO: 170
DIQMTQSPSSLSASVGDRITITCQASQDISNYLNWYQQKPGKAPNLLISDASDLETGVPSRFSGSG
SGTDFTFTISSLQP
EDFATYYCQQYDNIPITFGQGTRLEIKR;

SEQ ID NO: 171
CAG GAC ATT AGC AAC TAT;

SEQ ID NO: 172
Q D I S N Y;

SEQ ID NO: 173
GAT GCA TCC;

```
                                                      SEQ ID NO: 174
D A S;

SEQ ID NO: 175
CAA CAG TAT GAT AAT ATA CCG ATC ACC;

SEQ ID NO: 176
Q Q Y D N I P I T;

SEQ ID NO: 177
CAGGTGCAGCTGGTGGAGTCAGGGGGAGGCGTGGTCCAGCCTGGGAGGTCCCTGAGACTC
TCCTGTGCAGCCTCTGGATT
CACCTTCAGTAGCTATGGCATGCACTGGGTCCGCCAGGCTCCAGGCAAGGGGCTGGAGTGG
GTGACATTTATATCATTTG
ATGAAAGGAATAAATACTATGCAGACTCCGTTAAGGGCCGATTCACCATCTCCAGAGACAATT
CCAAGAACACGCTGTAT
CTGCAAATGAACAGCCTGAGAGCTGAGGACACGGCTATGTATTACTGTGCGAGCGAAGTCGG
GTACAGTTTTGGTCATGA
TGCTTTTGATATCTGGGGCCAAGGGACAATGGTCACCGTCTCTTCA;

SEQ ID NO: 178
QVQLVESGGGVVQPGRSLRLSCAASGFTFSSYGMHWVRQAPGKGLEWVTFISFDERNKYYADS
VKGRFTISRDNSKNTLY
LQMNSLRAEDTAMYYCASEVGYSFGHDAFDIWGQGTMVTVSS;

SEQ ID NO: 179
GGA TTC ACC TTC AGT AGC TAT GGC;

SEQ ID NO: 180
G F T F S S Y G;

SEQ ID NO: 181
ATA TCA TTT GAT GAA AGG AAT AAA;

SEQ ID NO: 182
I S F D E R N K;

SEQ ID NO: 183
GCG AGC GAA GTC GGG TAC AGT TTT GGT CAT GAT GCT TTT GAT ATC;

SEQ ID NO: 184
A S E V G Y S F G H D A F D I;

SEQ ID NO: 185
GACATCCAGATGACCCAGTCTCCATCCTCCCTGTCTGCATCTGTAGGAGACAGAGTCACCAT
CACTTGCCAGGCGAGTCA
GGACATTAGCAACTATTTAAATTGGTATCAGAAGAAACCAGGGAAAGCCCCTAAACTCCTGAT
CTACGATGCATCCAATT
TGGAAACAGGGGTCCCGTCAAGGTTCAGTGGAAGTGGATCTGGGACAGATTTTACTTTCACC
ATCAGCAGCCTGCAGCCT
GAAGATATTGCAACATATTACTGTCAACAGTATGATAATTTCCCGCTCACTTTCGGCGGAGGG
ACCAAGGTGGAGATCAA
ACGA;

SEQ ID NO: 186
DIQMTQSPSSLSASVGDRVTITCQASQDISNYLNWYQKKPGKAPKLLIYDASNLETGVPSRFSGSG
SGTDFTFTISSLQP
EDIATYYCQQYDNFPLTFGGGTKVEIKR;

SEQ ID NO: 187
CAG GAC ATT AGC AAC TAT;

SEQ ID NO: 188
Q D I S N Y;

SEQ ID NO: 189
GAT GCA TCC;

SEQ ID NO: 190
D A S;

SEQ ID NO: 191
CAA CAG TAT GAT AAT TTC CCG CTC ACT;

SEQ ID NO: 192
Q Q Y D N F P L T;

SEQ ID NO: 193
GAGGTGCAGCTGGTGGAGTCTGGGGGAGGCTTGGTACAGCCTGGGGGGTCCCTGAGACTCT
CCTGTGCAGCCTCTGGATT
CACCTTTAACAACTATGCCATGAGCTGGGTCCGCCAGGCTCCAGGGAGGGGGCTGGAGTGG
```

-continued

```
GTCTCAGCTATTAGTGGTA
GTGGTGATAGCACATACTACTCAGACTCCGTGAAGGGCCGGTTCACCATCTCCAGAGACAAT
TCCAAGAACACGCTGTAT
CTGCAAATGAACAGCCTGAGAGCCGAGGACACGGCCGTATATTACTGTGCGAAAGATCAGGG
CCTGTATTACTATGGTTC
GGGGAGTTTTGACTACTGGGGCCAGGGAACCCTGGTCACCGTCTCCTCA;
```

SEQ ID NO: 194
```
EVQLVESGGGLVQPGGSLRLSCAASGFTFNNYAMSWVRQAPGRGLEWVSAISGSGDSTYYSDS
VKGRFTISRDNSKNTLY
LQMNSLRAEDTAVYYCAKDQGLYYYGSGSFDYWGQGTLVTVSS;
```

SEQ ID NO: 195
```
GGA TTC ACC TTT AAC AAC TAT GCC;
```

SEQ ID NO: 196
```
G F T F N N Y A;
```

SEQ ID NO: 197
```
ATT AGT GGT AGT GGT GAT AGC ACA;
```

SEQ ID NO: 198
```
I S G S G D S T;
```

SEQ ID NO: 199
```
GCG AAA GAT CAG GGC CTG TAT TAC TAT GGT TCG GGG AGT TTT GAC TAC;
```

SEQ ID NO: 200
```
A K D Q G L Y Y Y G S G S F D Y;
```

SEQ ID NO: 201
```
GACATCCAGATGACCCAGTCTCCATCCTCCCTGTCTGCATCTGTAGGAGACAGAGTCACCAT
CACTTGCCGGGCAAGTCA
GAGCATTAGCAGCTATTTAAATTGGTATCAGCAGAAACCAGGGAAAGCCCCTAAGCTCCTGAT
CCAAGCTGCATCCAGTT
TGCAAAGTGGGGTCCCATCAAGGTTCAGTGGCAGTGGATCTGGGACAGATATCACTCTCACC
ATCAGCAGTCTGCAACCC
GAAGATTTTGCAACTTACTACTGTCAACAGAGTTACAGTACCCCATTCACTTTCGGCCCTGGG
ACCAAAGTGGATATCAA
ACGA;
```

SEQ ID NO: 202
```
DIQMTQSPSSLSASVGDRVTITCRASQSISSYLNWYQQKPGKAPKLLIQAASSLQSGVPSRFSGS
GSGTDITLTISSLQP
EDFATYYCQQSYSTPFTFGPGTKVDIKR;
```

SEQ ID NO: 203
```
CAG AGC ATT AGC AGC TAT;
```

SEQ ID NO: 204
```
Q S I S S Y;
```

SEQ ID NO: 205
```
GCT GCA TCC;
```

SEQ ID NO: 206
```
A A S;
```

SEQ ID NO: 207
```
CAA CAG AGT TAC AGT ACC CCA TTC ACT;
```

SEQ ID NO: 208
```
Q Q S Y S T P F T;
```

SEQ ID NO: 209
```
GAGGTGCAGCTGGTGGAGTCTGGGGGAGGCTTGGTCCAGCCTGGGGGGTCCCTGCAACTCT
CCTGTGCAGCCTCTGGGTT
TGCCTTCAGCGACTCTGCTATATACTGGGTCCGCCAGGCTTCCGGGAAAGGGCTGGAGTGG
GTTGGCCGCATTAGAAACA
AAGCTAATAGGTTCGCGACAGCATATGGTGCGTCGGTGAAAGGCAGGTTCAGCATACACAGA
GATGATTCAAAGAACACG
GCGTATCTACAAATGAACAGCCTGAAAACCGAGGACACGGCCGTGTATTACTGTGCCAGACA
TGGACACGATACTTTGAC
TGAGGGCTACGGTATGGACGTCTGGGGCCAAGGGACCACGGTCACCGTCTCCTCA;
```

SEQ ID NO: 210
```
EVQLVESGGGLVQPGGSLQLSCAASGFAFSDSAIYWVRQASGKGLEWVGRIRNKANRFATAYGA
SVKGRFSIHRDDSKNT
AYLQMNSLKTEDTAVYYCARHGHDTLTEGYGMDVWGQGTTVTVSS;
```

SEQ ID NO: 211

-continued

GGG TTT GCC TTC AGC GAC TCT GCT;

SEQ ID NO: 212
G F A F S D S A;

SEQ ID NO: 213
ATT AGA AAC AAA GCT AAT AGG TTC GCG ACA;

SEQ ID NO: 214
I R N K A N R F A T;

SEQ ID NO: 215
GCC AGA CAT GGA CAC GAT ACT TTG ACT GAG GGC TAC GGT ATG GAC GTC;

SEQ ID NO: 216
A R H G H D T L T E G Y G M D V;

Light chain #1-

SEQ ID NO: 217
GACATCCAGATGACCCAGTCTCCATCCTCCCTGTCTGCATCTGTAGGAGACAGAGTCACCAT
CACTTGCCGGGCAAGTCA
GAGCATTAGCAGCTATTTAAATTGGTATCAGCAGAAACCAGGGAAAGCCCCTAAGCTCCTGAT
CTATGCTGCATCCAGTT
TGCAAAGTGGGGTCCCGTCAAGGTTCAGTGGCAGTGGATCTGGGACAGATTTCACTCTCACC
ATCAGCAGTCTGCAACCT
GAAGATTTTGCAACTTACTACTGTCAACAGAGTTACAGTACCCCTCCGATCACCTTCGGCCAA
GGGACACGACTGGAGAT
TAAA;

Light chain #1-

SEQ ID NO: 218
DIQMTQSPSSLSASVGDRVTITCRASQSISSYLNWYQQKPGKAPKLLIYAASSLQSGVPSRFSGSG
SGTDFTLTISSLQP
EDFATYYCQQSYSTPPITFGQGTRLEIK;

SEQ ID NO: 219
CAG AGC ATT AGC AGC TAT;

SEQ ID NO: 220
Q S I S S Y;

SEQ ID NO: 221
GCT GCA TCC;

SEQ ID NO: 222
A A S;

SEQ ID NO: 223
CAA CAG AGT TAC AGT ACC CCT CCG ATC ACC;

SEQ ID NO: 224
Q Q S Y S T P P I T;

SEQ ID NO: 225
CAGGTGCAGCTGGTGCAGTCTGGGGCTGAGGTAAAGAACCCTGGGTCCTCGGTGAAGGTCT
CCTGCAAGGCTTCTGGAGG
CACCTTCAGCAGTTATACTATCAACTGGGTGCGACAGGCCCCTGGACAAGGGCTTGAGTGGA
TGGGAGGGATCATCCCTC
TCTATGGAACAGCAAACTACGCACAGAAGTTCCAGGCCAGAGTCACGATTTCCACGGACGAA
TCCACGAACACAGCCTAC
ATGGAACTGAGCAACCTGAGATTTGAAGACACGGCCGTGTATTTCTGTGCGAGTACACTGGA
ACTACGGGCTTTTGATGC
CTTTGATATCTGGGGCCAAGGGACAATGGTCACCGTCTCTTCA;

SEQ ID NO: 226
QVQLVQSGAEVKNPGSSVKVSCKASGGTFSSYTINWVRQAPGQGLEWMGGIIPLYGTANYAQKF
QARVTISTDESTNTAY
MELSNLRFEDTAVYFCASTLELRAFDAFDIWGQGTMVTVSS;

SEQ ID NO: 227
GGA GGC ACC TTC AGC AGT TAT ACT;

SEQ ID NO: 228
G G T F S S Y T;

SEQ ID NO: 229
ATC ATC CCT CTC TAT GGA ACA GCA;

SEQ ID NO: 230
I I P L Y G T A;

-continued

SEQ ID NO: 231
GCG AGT ACA CTG GAA CTA CGG GCT TTT GAT GCC TTT GAT ATC;

SEQ ID NO: 232
A S T L E L R A F D A F D I;

SEQ ID NO: 233
CAGGTGCAGCTGCAGGAGTCGGGCCCAGGACTGGTGAAGCCTTCACAGACCCTGTCCCTCA
CCTGCACTGTCTCTGGTGG
CTCCATCAGCAGTGGTGGTTACTACTGGAACTGGATCCGCCAGCACCCAGGGAAGGGCCTG
GAGTGGATTGGGTACATCT
ATTACAGTGGAAGCACCTACTACAACCCGTCCCTCAAGAGTCGAGTTACCATATCAGTAGACA
CGTCTAAGAACCAGTTC
TCCCTGAAGCTGGGCTCTGTGACTGCCGCGGACACGGCCGTGTATTACTGTGCGCGAGCTC
CTCCTTATAACTGGTTTGA
CTACTGGGGCCAGGGAACCCTGGTCACCGTCTCCTCA;

SEQ ID NO: 234
QVQLQESGPGLVKPSQTLSLTCTVSGGSISSGGYYWNWIRQHPGKGLEWIGYIYYSGSTYYNPSL
KSRVTISVDTSKNQF
SLKLGSVTAADTAVYYCARAPPYNWFDYWGQGTLVTVSS;

SEQ ID NO: 235
GGT GGC TCC ATC AGC AGT GGT GGT TAC TAC;

SEQ ID NO: 236
G G S I S S G G Y Y;

SEQ ID NO: 237
ATC TAT TAC AGT GGA AGC ACC;

SEQ ID NO: 238
I Y Y S G S T;

SEQ ID NO: 239
GCG CGA GCT CCT CCT TAT AAC TGG TTT GAC TAC;

SEQ ID NO: 240
A R A P P Y N W F D Y;

SEQ ID NO: 241
CAGGTGCAGCTGGTGGAGTCTGGGGGAGGCTTGGTCAAGCCTGGAGGGTCCCTGAGACTCT
CCTGTGCAGCCTCTGGATT
CACCTTCAGTGACTACTACATGAACTGGGTCCGCCAGGCTCCAGGGAAGGGGCTGGAATGG
GTTTCATACATTAGTAATA
GTGGTAATACCCAATACTACGCAGACTCTGTGAAGGGCCGGTTCACCATCTCCAGGGACAAT
GCCAAGAACTCCCTGTTT
CTGCAAATGAACAGCCTGCGAGCCGAGGACACGGCCGTTTATTACTGTACGAGAGAGGGACT
CGAATATAGCAGCTCGGA
GCCCTTTGACTACTGGGGCCAGGGAACCCTGGTCACCGTCTCCTCA;

SEQ ID NO: 242
QVQLVESGGGLVKPGGSLRLSCAASGFTFSDYYMNWVRQAPGKGLEWVSYISNSGNTQYYADS
VKGRFTISRDNAKNSLF
LQMNSLRAEDTAVYYCTREGLEYSSSEPFDYWGQGTLVTVSS;

SEQ ID NO: 243
GGA TTC ACC TTC AGT GAC TAC TAC;

SEQ ID NO: 244
G F T F S D Y Y;

SEQ ID NO: 245
ATT AGT AAT AGT GGT AAT ACC CAA;

SEQ ID NO: 246
I S N S G N T Q;

SEQ ID NO: 247
ACG AGA GAG GGA CTC GAA TAT AGC AGC TCG GAG CCC TTT GAC TAC;

SEQ ID NO: 248
T R E G L E Y S S S E P F D Y;

SEQ ID NO: 249
CAGGTGCAGCTGGTGCAGTCTGGGGCTGAAGTGAAGAAGCCTGGGGCCTCAGTGAAGGTCT
CCTGCAAGACTTCTGGATA
CACCTTCACCGCCTACTACATACACTGGGTGCGACAGGCCCCTGGACAAGGGCTTGAGTGGA
TGGGATGGATCAACCCTA
ACAATGGTGACACAAACTATGCACTGAGGTTTCAGGGCAGGGTCACCATGACCAGGGACATG
TCCATCAACACAGCCTAC

-continued

ATGGAGCTGCGCGGGCTGAGATCTGACGACACGGCCGTGTATTATTGTGCGAGAGATGATCT
AGCAGCAGCGGGTATCGG
CTGGTTCGACTCCTGGGGCCAGGGAACCCTGGTCACCGTCTCCTCA;

SEQ ID NO: 250

QVQLVQSGAEVKKPGASVKVSCKTSGYTFTAYYIHWVRQAPGQGLEWMGWINPNNGDTNYALR
FQGRVTMTRDMSINTAY
MELRGLRSDDTAVYYCARDDLAAAGIGWFDSWGQGTLVTVSS;

SEQ ID NO: 251

GGA TAC ACC TTC ACC GCC TAC TAC;

SEQ ID NO: 252

G Y T F T A Y Y;

SEQ ID NO: 253

ATC AAC CCT AAC AAT GGT GAC ACA;

SEQ ID NO: 254

I N P N N G D T;

SEQ ID NO: 255

GCG AGA GAT GAT CTA GCA GCA GCG GGT ATC GGC TGG TTC GAC TCC;

SEQ ID NO: 256

A R D D L A A A G I G W F D S;

SEQ ID NO: 257

GAAGTGCAGCTGGTGGAGTCTGGGGGAGGCTTGCTACAGCCTGGCAGGTCCCTGAGACTCT
CCTGTGTAGCCTCTGGATT
CACCTTTGATGATTATGCCATGCACTGGGTCCGGCAAGCTCCAGGGAAGGGCCTGGAGTGG
GTCTCAGGAATTAGTTGGA
ATAGTGAAAGTATAGGCTATGCGGACTCTGTGAGGGGCCGATTCACCATTTCCAGAGACAAC
GCCAAGAACTCCCTGTAT
CTCCAAATGAACAGTCTGAGAGCTGAGGACACGGCCTTGTATTACTGTGCAAAAGCCCCGTA
TAGTGGGACCTACTTCGA
ATACTTCCGCCACTGGGGCCAGGGCACCCTGGTCACCGTCTCCTCA;

SEQ ID NO: 258

EVQLVESGGGLLQPGRSLRLSCVASGFTFDDYAMHWVRQAPGKGLEWVSGISWNSESIGYADS
VRGRFTISRDNAKNSLY
LQMNSLRAEDTALYYCAKAPYSGTYFEYFRHWGQGTLVTVSS;

SEQ ID NO: 259

GGA TTC ACC TTT GAT GAT TAT GCC;

SEQ ID NO: 260

G F T F D D Y A;

SEQ ID NO: 261

ATT AGT TGG AAT AGT GAA AGT ATA;

SEQ ID NO: 262

I S W N S E S I;

SEQ ID NO: 263

GCA AAA GCC CCG TAT AGT GGG ACC TAC TTC GAA TAC TTC CGC CAC;

SEQ ID NO: 264

A K A P Y S G T Y F E Y F R H;

SEQ ID NO: 265

CAGGTGCAGCTGGTGGAGTCTGGGGGAGGCGTGGTCCAGCCTGGGAGGTCCCTGAGACTC
TCCTGTGCAGCCTCTGGATT
CACCTTCAGTAGCTATGGCATGCACTGGGTCCGCCAGGCTCCAGGCAAGGGGCTGGAGTGG
GTGGCAGTTATATCATATG
ATGGAAGTAATAAATACTATGCAGACTCCGTGAAGGGCCGATTCACCATCTCCAGAGACAATT
CCAAGAACACGCTGTAT
CTGCAAATGAACAGCCTGAGAGCTGAGGACACGGCTGTGTATTACTGTGCGAAAGATGACTG
GAACTACGACGCCTTTGA
TATCTGGGGCCAAGGGACAATGGTCACCGTCTCTTCA;

SEQ ID NO: 266

QVQLVESGGGVVQPGRSLRLSCAASGFTFSSYGMHWVRQAPGKGLEWVAVISYDGSNKYYADS
VKGRFTISRDNSKNTLY
LQMNSLRAEDTAVYYCAKDDWNYDAFDIWGQGTMVTVSS;

SEQ ID NO: 267

GGA TTC ACC TTC AGT AGC TAT GGC;

SEQ ID NO: 268

-continued

G F T F S S Y G;

SEQ ID NO: 269
ATA TCA TAT GAT GGA AGT AAT AAA;

SEQ ID NO: 270
I S Y D G S N K;

SEQ ID NO: 271
GCG AAA GAT GAC TGG AAC TAC GAC GCC TTT GAT ATC;

SEQ ID NO: 272
A K D D W N Y D A F D I;

SEQ ID NO: 273
CAGGTGCAGCTGCAGGAGTCGGGCCCAGGACTGGTGAAGCCTTCACAGACCCTGTCCCTCA
CCTGCACTGTCTCTGGTGG
CTCCATCAGCAGTAGTGGTTACTACTGGAGCTGGATCCGCCAGCACCCAGGGAGGGGCCTG
GAGTGGATTGGATACATCT
ATTACAGTGGGAGCACCTACTACAACCCGTCCCTCAAGAGTCGAGTTACCATATCAGTAGACA
CGTCTAAGAACCAGTTC
TCCCTGAAGCTGAACTCTGTGACTGCCGCGGACACGGCCGTGTATTACTGTGCGAGAGTGGA
CTATGGTTCGGGGAGTTC
GTTTGACTACTGGGGCCAGGGAACCCTGGTCACCGTCTCCTCA;

SEQ ID NO: 274
QVQLQESGPGLVKPSQTLSLTCTVSGGSISSSGYYWSWIRQHPGRGLEWIGYIYYSGSTYYNPSL
KSRVTISVDTSKNQF
SLKLNSVTAADTAVYYCARVDYGSGSSFDYWGQGTLVTVSS;

SEQ ID NO: 275
GGT GGC TCC ATC AGC AGT AGT GGT TAC TAC;

SEQ ID NO: 276
G G S I S S S G Y Y;

SEQ ID NO: 277
ATC TAT TAC AGT GGG AGC ACC;

SEQ ID NO: 278
I Y Y S G S T;

SEQ ID NO: 279
GCG AGA GTG GAC TAT GGT TCG GGG AGT TCG TTT GAC TAC;

SEQ ID NO: 280
A R V D Y G S G S S F D Y;

SEQ ID NO: 281
CAGGTTCAGCTGGTGCAGTCTGGACCTGAGGTGAAGAAGCCTGGGGCCTCAGTGAAGGTCT
CCTGCAAGGCTTCTGGTTA
CACCTTTACCAGCTATGGCATCAGCTGGGTGCGACAGGCCCCTGGACAAGGGCTTGAGTGG
CTGGGATGGATCAGCGGTT
TCAATGGTAGAACAGACTATACAGAGAAGCTCCAGGACAGAATCACCATGACCACAGACAGA
TCCTCGAGCACAGCCTAC
ATGGAACTGAGGAGCCTGAGATATGACGACACGGCCGTGTATTACTGTGCGAGAGATGGACT
GGAAAAACTTGGTGACTA
CTGGGGCCAGGGAACCCTGGTCACCGTCTCCTCA;

SEQ ID NO: 282
QVQLVQSGPEVKKPGASVKVSCKASGYTFTSYGISWVRQAPGQGLEWLGWISGFNGRTDYTEK
LQDRITMTTDRSSTAY
MELRSLRYDDTAVYYCARDGLEKLGDYWGQGTLVTVSS;

SEQ ID NO: 283
GGT TAC ACC TTT ACC AGC TAT GGC;

SEQ ID NO: 284
G Y T F T S Y G;

SEQ ID NO: 285
ATC AGC GGT TTC AAT GGT AGA ACA;

SEQ ID NO: 286
I S G F N G R T;

SEQ ID NO: 287
GCG AGA GAT GGA CTG GAA AAA CTT GGT GAC TAC;

SEQ ID NO: 288
A R D G L E K L G D Y;

SEQ ID NO: 289
CAGGTGCAGCTGGTGGAGTCTGGGGGAGGCGTGGTCCAGCCGGGGAGGTTCCTGAGACTC
TCCTGTGCAGCGTCTGGATT
CACCTTCAGTAACTCTGGCATGCACTGGGTCCGCCAGGCTCCAGGCAAGGGGCTGGAGTGG
GTGGCAGGAATATGGCATG
ATGGAAGTTATAAATATTATGTAGACTCCGTGAAGGGCCGATTCACCATCTCCAGAGACAATT
CTAAGAACACGCTGTTT
CTGCAAATGAACAGCCTGCGAGCCGAGGACACGGCTGTATATTATTGTGCGAGAGATGATTA
CTATGCTTCGGGGACCAG
CGTGGACGTATGGGGCCAAGGGACCACGGTCACCGTCTCCTCA;

SEQ ID NO: 290
QVQLVESGGGVVQPGRFLRLSCAASGFTFSNSGMHWVRQAPGKGLEWVAGIWHDGSYKYYVD
SVKGRFTISRDNSKNTLF
LQMNSLRAEDTAVYYCARDDYYASGTSVDVWGQGTTVTVSS;

SEQ ID NO: 291
GGA TTC ACC TTC AGT AAC TCT GGC;

SEQ ID NO: 292
G F T F S N S G;

SEQ ID NO: 293
ATA TGG CAT GAT GGA AGT TAT AAA;

SEQ ID NO: 294
I W H D G S Y K;

SEQ ID NO: 295
GCG AGA GAT GAT TAC TAT GCT TCG GGG ACC AGC GTG GAC GTA;

SEQ ID NO: 296
A R D D Y Y A S G T S V D V;

SEQ ID NO: 297
CAGGTGCAGCTGGTGCAGTCTGGGGCTGAGGTGAAGAAGCCTGGGGCCTCAGTGAGGGTCT
CCTGCATGGCCTCTGGATA
CACCTTCACCGGCTACTATATGCACTGGGTGCGACAGGCCCCTGGACAAGGGCTTGAGTGG
ATGGGATGGATCAACCCTA
ACAGTGGTGGCACAAAATATGCACAGAAGTTTCAGGGCAGGGTCACCATGACCAGGGACACG
TCCATCAGCACAGCCTAC
ATGGAGCTGAGCAGACTGAGATCTGACGACACGGCCGTATATTACTGTGCGAGAGAAGAAGT
CGACGATTTTTGGAGTGG
TTACCTTGACTACTGGGGCCAGGGAACCCTGGTCACCGTCTCCTCA;

SEQ ID NO: 298
QVQLVQSGAEVKKPGASVRVSCMASGYTFTGYYMHWVRQAPGQGLEWMGWINPNSGGTKYA
QKFQGRVTMTRDTSISTAY
MELSRLRSDDTAVYYCAREEVDDFWSGYLDYWGQGTLVTVSS;

SEQ ID NO: 299
GGA TAC ACC TTC ACC GGC TAC TAT;

SEQ ID NO: 300
G Y T F T G Y Y;

SEQ ID NO: 301
ATC AAC CCT AAC AGT GGT GGC ACA;

SEQ ID NO: 302
I N P N S G G T;

SEQ ID NO: 303
GCG AGA GAA GAA GTC GAC GAT TTT TGG AGT GGT TAC CTT GAC TAC;

SEQ ID NO: 304
A R E E V D D F W S G Y L D Y;

Light chain #2-
SEQ ID NO: 305
GAAATTGTGTTGACGCAGTCTCCAGGCACCCTGTCTTTGTCTCCAGGGGAAAGAGCCACCCT
CTCCTGCAGGGCCAGTCA
GAGTGTTAGCAGCAGCTACTTAGCCTGGTACCAGCAGAAACCTGGCCAGGCTCCCAGGCTCC
TCATCTATGGTGCATCCA
GCAGGGCCACTGGCATCCCAGACAGGTTCAGTGGCAGTGGGTCTGGGACAGACTTCACTCT
CACCATCAGCAGACTGGAG
CCTGAAGATTTTGCAGTGTATTACTGTCAGCAGTATGGTAGCTCACCTTGGACGTTCGGCCAA
GGGACCAAGGTGGAAAT
CAAA;

-continued

Light chain #2-

SEQ ID NO: 306
EIVLTQSPGTLSLSPGERATLSCRASQSVSSSYLAWYQQKPGQAPRLLIYGASSRATGIPDRFSGS
GSGTDFTLTISRLE
PEDFAVYYCQQYGSSPWTFGQGTKVEIK;

SEQ ID NO: 307
CAG AGT GTT AGC AGC AGC TAC;

SEQ ID NO: 308
Q S V S S S Y;

SEQ ID NO: 309
GGT GCA TCC;

SEQ ID NO: 310
G A S;

SEQ ID NO: 311
CAG CAG TAT GGT AGC TCA CCT TGG ACG;

SEQ ID NO: 312
Q Q Y G S S P W T;

SEQ ID NO: 313
GAGGTGCAGCTGGTGGAGTCTGGAGGAGACTTGGTCCAGCCGGGGGGGTCCCTGAGACTCT
CCTGTGCAGCCTCTGGGTT
CGCCGTCAATGGCGACTATTTTAGTTGGGTCCGCCAGGCTCCAGGGAAGGGGCTGGAGTGG
ATCTCAGTTATTTATAGCA
GTGGTAACACATACTACGCAGACTCCGTGAAGGGCCGATTCACCATCTCCAGACACAATTCC
AAGAACACGCTGTATCTT
CAAATGAGCAGCCTAAGACCTGAGGACACGGCCGTGTATTACTGTGCGAGAGACTTCCCTCC
AATGTCTGGTGCGGACTA
CTGGGGCCAGGGAACCCTGGTCACCGTCTCCTCA;

SEQ ID NO: 314
EVQLVESGGDLVQPGGSLRLSCAASGFAVNGDYFSWVRQAPGKGLEWISVIYSSGNTYYADSVK
GRFTISRHNSKNTLYL
QMSSLRPEDTAVYYCARDFPPMSGADYWGQGTLVTVSS;

SEQ ID NO: 315
GGG TTC GCC GTC AAT GGC GAC TAT;

SEQ ID NO: 316
G F A V N G D Y;

SEQ ID NO: 317
ATT TAT AGC AGT GGT AAC ACA;

SEQ ID NO: 318
I Y S S G N T;

SEQ ID NO: 319
GCG AGA GAC TTC CCT CCA ATG TCT GGT GCG GAC TAC;

SEQ ID NO: 320
A R D F P P M S G A D Y;

SEQ ID NO: 321
CAGGTCCAGCTGGTGCAGTCTGGGGCTGAGGTGAAGAAGCCTGGGGCCTCAGTGAAGGTCT
CCTGCAAGGTTTCCGGATA
CACCCTCACTGAATTGTCCATGCACTGGGTGCGACAGGCTCCTGGAAAAGGGCTTGAATGGA
TGGGAGGTTTTGATCCTG
AACATGGTAAAATAATCTACGCACAGAAATTCCAGGGCAGAGTCACCATGACCGAGGACACAT
CTACAGACACAGCCTAC
ATGGAACTGAGCAGCCTGAGATCTGAGGACACGGCCGTCTATTACTGTGCAACATTTTATAAC
TGGAACTCCTACTACTT
CGGTATGGACGTCTGGGGCCACGGGACCACGGTCACCGTCTCCTCA;

SEQ ID NO: 322
QVQLVQSGAEVKKPGASVKVSCKVSGYTLTELSMHWVRQAPGKGLEWMGGFDPEHGKIIYAQK
FQGRVTMTEDTSTDTAY
MELSSLRSEDTAVYYCATFYNWNSYYFGMDVWGHGTTVTVSS;

SEQ ID NO: 323
GGA TAC ACC CTC ACT GAA TTG TCC;

SEQ ID NO: 324
G Y T L T E L S;

SEQ ID NO: 325

```
                                                    -continued
TTT GAT CCT GAA CAT GGT AAA ATA;

SEQ ID NO: 326
F D P E H G K I;

SEQ ID NO: 327
GCA ACA TTT TAT AAC TGG AAC TCC TAC TAC TTC GGT ATG GAC GTC;

SEQ ID NO: 328
A T F Y N W N S Y Y F G M D V;

SEQ ID NO: 329
GAGGTGCAGCTGGTGGAGTCGGGGGGAGGCTTGGTACAGCCTGGGGGGTCCCTGAGACTC
TCCTGTGCAGCCTCTGGATT
CACCTTTAGCAGCTATGCCATGAACTGGGTCCGCCAGGCTCCAGGAAAGGGACTGGAGTGG
GTCTCAGCTGTTAGTGGAA
GTGCTGATATCACAAACTACGCAGACTCCGTGAAGGGCCGGTTCACCATCTCCAGAGACAAT
TCCAAACACACGCTGTAT
CTGCAAATGAACAGCCTGAGAGCCGAGGACACGGCCGTATATTACTGTGCGAAGGATAAAGT
GTATAACTGGAACTACGG
GATCTACTACGGTATGGACGTCTGGGGCCAAGGGACCACGGTCACCGTCTCCTCA;

SEQ ID NO: 330
EVQLVESGGGLVQPGGSLRLSCAASGFTFSSYAMNWVRQAPGKGLEWVSAVSGSADITNYADS
VKGRFTISRDNSKHTLY
LQMNSLRAEDTAVYYCAKDKVYNWNYGIYYGMDVWGQGTTVTVSS;

SEQ ID NO: 331
GGA TTC ACC TTT AGC AGC TAT GCC;

SEQ ID NO: 332
G F T F S S Y A;

SEQ ID NO: 333
GTT AGT GGA AGT GCT GAT ATC ACA;

SEQ ID NO: 334
V S G S A D I T;

SEQ ID NO: 335
GCG AAG GAT AAA GTG TAT AAC TGG AAC TAC GGG ATC TAC TAC GGT ATG GAC GTC;

SEQ ID NO: 336
A K D K V Y N W N Y G I Y Y G M D V;

SEQ ID NO: 337
CAGCTGCAGCTGCAGGAGTCGGGCCCAGGACTGGTGAAGCCTTCGGAGACCCTGTCCCTCA
CCTGCACTGTCTCTGGTGG
CTCCATCAGCAGTAGTAGTTACTACTGGGGCTGGATCCGCCAGCCCCCAGGGAAGGGACTA
GAGTGGATTGGGAGTATCT
ATTATAGTGGGAGCACCTACTACAATCCGTCCCTCAAGAGTCGAGTCACCATATCCGTAGACA
CGTCCAAGAACCAGTTC
TCCCTGAAGCTGAGCTCTGTGACCGCCGCAGACACGGCTGTGTATTACTGTGCGAGACAAGG
GAGGTGGGAGCGAGAAAA
CTTTGACTACTGGGGCCAGGGAACCCTGGTCACCGTCTCCTCA;

SEQ ID NO: 338
QLQLQESGPGLVKPSETLSLTCTVSGGSISSSSYYWGWIRQPPGKGLEWIGSIYYSGSTYYNPSL
KSRVTISVDTSKNQF
SLKLSSVTAADTAVYYCARQGRWERENFDYWGQGTLVTVSS;

SEQ ID NO: 339
GGT GGC TCC ATC AGC AGT AGT AGT TAC TAC;

SEQ ID NO: 340
G G S I S S S S Y Y;

SEQ ID NO: 341
ATC TAT TAT AGT GGG AGC ACC;

SEQ ID NO: 342
I Y Y S G S T;

SEQ ID NO: 343
GCG AGA CAA GGG AGG TGG GAG CGA GAA AAC TTT GAC TAC;

SEQ ID NO: 344
A R Q G R W E R E N F D Y;

SEQ ID NO: 345
CAGGTGCAGCTACAGCAGTGGGGCGCAGGACTATTGAAGCCTTCGGAGACCCTGTCCCTCA
```

```
CCTGCGCTGTCTCTGATGA
GTCCTTCAGTGATTACTACTGGACCTGGATCCGCCAGCCCCCAGGGAAGGGGCTGGAGTGG
ATTGGGGAAATTACTCATA
GTGGAAGTACCCACTACAACCCGTCCCTCAAGAGCCGAGTCACCCTGTCAGTTGACACGTCC
AAGAACCACTTCTCCCTG
AGCCTCAACTCTGTGACCGCCGCGGACACGGCTATTTATTACTGTGCGAGAGGCGGTGACTA
CGGTGGTTTACTTGACTA
CTGGGGCCAGGGAACCCTGGTCACCGTCTCCTCA;
```

SEQ ID NO: 346
QVQLQQWGAGLLKPSETLSLTCAVSDESFSDYYWTWIRQPPGKGLEWIGEITHSGSTHYNPSLK
SRVTLSVDTSKNHFSL
SLNSVTAADTAIYYCARGGDYGGLLDYWGQGTLVTVSS;

SEQ ID NO: 347
GAT GAG TCC TTC AGT GAT TAC TAC;

SEQ ID NO: 348
D E S F S D Y Y;

SEQ ID NO: 349
ATT ACT CAT AGT GGA AGT ACC;

SEQ ID NO: 350
I T H S G S T;

SEQ ID NO: 351
GCG AGA GGC GGT GAC TAC GGT GGT TTA CTT GAC TAC;

SEQ ID NO: 352
A R G G D Y G G L L D Y;

SEQ ID NO: 353
```
CAGCTGCAGCTGCAGGAGTCGGGCCCAGGACTGGTGAAGCCCTCGGAGACCCTGTCCCTCA
CCTGCACTGTCTCTGGTGG
CTCCATCAGCAGTAGGAGTCACTACTGGGGCTGGATCCGCCAGCCCCCAGGGAAGGGGCTG
GAGTGGATTGGGAGTATCT
ATTATATAGTGGGAGCACCTATTACAACCCGTCCCTCAAGAGTCGAGTCACCATATCCGTAGACA
CGTCCAAGAACCAGTTC
TCCCTGAAGCTGAGCTCTGTGACCGCCGCAGACACGGCTGTGTATTACTGTGCGAGACTTGG
CTGGTACGCAGAGGAGGC
TTTTGAAATCTGGGGTCAAGGGACAATGGTCACCGTCTCTTCA;
```

SEQ ID NO: 354
QLQLQESGPGLVKPSETLSLTCTVSGGSISSRSHYWGWIRQPPGKGLEWIGSIYYSGSTYYNPSL
KSRVTISVDTSKNQF
SLKLSSVTAADTAVYYCARLGWYAEEAFEIWGQGTMVTVSS;

SEQ ID NO: 355
GGT GGC TCC ATC AGC AGT AGG AGT CAC TAC;

SEQ ID NO: 356
G G S I S S R S H Y;

SEQ ID NO: 357
ATC TAT TAT AGT GGG AGC ACC;

SEQ ID NO: 358
I Y Y S G S T;

SEQ ID NO: 359
GCG AGA CTT GGC TGG TAC GCA GAG GAG GCT TTT GAA ATC;

SEQ ID NO: 360
A R L G W Y A E E A F E I

Example 2: Growth Inhibition Assay to Assess the Ability of Anti-PfRH5 Antibodies to Inhibit the In Vitro Invasion of Human Red Blood Cells and Growth of *P. falciparum* Parasites In this example, a set of four PfRH5-specific mAbs of the invention were tested alone and in combination in a standard growth inhibition assay with one strain of *Plasmodium falciparum* (Dd2).

Experimental Procedure

The *P. falciparum* strain, Dd2 (BEI Resources) was first synchronized with 5% D-sorbitol following standard protocols at 3-5% hematocrit and 1-2% parasitaemia 20-24 hours prior to the start of the assay. Infected human erythrocytes were prepared at a starting parasitaemia of 0.4-0.7% and 2% hematocrit. Infected erythrocytes were combined with PfRH5-specific or control antibodies, starting at a concentration of 666.67 nM with 1:5 serial dilution for each antibody or antibody combination. All antibodies used were human IgG1. The parasites were grown for 40-48 h until the schizont stage was reached (one complete life cycle). Parasite growth was stopped with three washes of cold PBS. Final parasitaemia was determined by measuring the parasite lactate dehydrogenase (LDH) activity (Miura, H. Zhou, A. Diouf, S E. Moretz, M P. Fay, L H. Miller, L B. Martin, M A. Pierce, R D. Ellis, G E D. Mullen, C A. Long. Anti-Apical-Membrane-Antigen-1 antibody is more effective than anti-42-kilodalton-Merozoite-Surface-Protein-1 antibody in inhibiting *Plasmodium falciparum* growth, as determined by the in vitro growth inhibition assay. Clin Vaccine Immunol. 16, 963-968 (2009). PMID: PMC2708396). Percent growth inhibition is expressed relative to uninfected erythrocytes.

Results Summary and Conclusions

PfRH5-specific antibodies were produced and tested in vitro in a growth inhibition assay in the laboratory-adapted strain as described above. Table 2-1 shows the maximum percent growth inhibition for a subset of PfRH5-specific antibodies and PfRH5-specific antibody combinations. The individual antibodies and antibody combinations displayed similar percent maximum growth inhibition, ranging from approximately 51-69%.

TABLE 2-1

Summary of maximum growth inhibition activity of antibodies against PfRH5 from *Plasmodium falciparum* strain Dd2.*

| mAb/combo mAbs | Maximum growth inhibition (%) Dd2 |
|---|---|
| H1H29127P + H1H29100P | 66.33 |
| H1H29127P + H1H29143P | 51.37 |
| H1H29127P + H1H29104P | 56.96 |
| H1H29100P + H1H29143P | 68.70 |
| H1H29100P + H1H29104P | 54.04 |
| H1H29143P + H1H29104P | 58.54 |
| H1H29100P | 65.73 |
| H1H29104P | 54.12 |
| H1H29127P | 56.87 |
| H1H29143P | 56.00 |
| human IgG1 negative control antibody specific for cat allergy antigen - Fel d 1 | −0.93 |

*Maximum growth inhibition of antibodies against PfRH5 relative to uninfected human red blood cells. The growth inhibition assay was performed on *P. falciparum* (mature trophozoite or early schizont) infected red blood cells at 0.4-0.7% parasitaemia. The antibodies were combined with the infected red blood cells. The parasites were grown for 40-48 hours (the timing is parasite strain-dependent) until the schizont stage was reached. Parasite growth was stopped with three washes of cold PBS. Parasite lactate dehydrogenase (LDH) activity was measured immediately after the washes. Percent growth inhibition was expressed relative to uninfected erythrocytes. The results of one representative assay of the growth inhibition assay are shown above.

Example 3: Growth Inhibition Assay to Assess the Ability of Anti-PfRH5 Antibodies to Inhibit the In Vitro Invasion of Human Red Blood Cells and Growth of *P. falciparum* Parasites in Combination with Chloroquine In this example, a subset of four PfRH5-specific mAbs of the invention were tested alone and in combination with chloroquine (CQ), a commonly-used antimalarial drug in a standard growth inhibition assay with two laboratory strains. One strain of the *Plasmodium falciparum* parasite, 3D7, is susceptible to chloroquine, while strain 7G8 is resistant to the drug.

Experimental Procedure

Each *P. falciparum* strain (BEI Resources) was first synchronized with 5% D-sorbitol following standard protocols at 3-5% hematocrit and 1-2% parasitaemia 20-24 hours prior to the start of the assay. Infected human erythrocytes were prepared at a starting parasitaemia of 0.4-0.7% and 2% hematocrit. Infected erythrocytes were combined with PfRH5-specific or control antibodies starting at a concentration of 666.67 nM with 1:5 serial dilution for each IgG1 antibody and chloroquine at one of two concentrations, 4.91 or 6.58 nM. The two concentrations were selected based on the $IC_{25}$, 4.91 nM, and $IC_{50}$, 6.58 nM, of chloroquine with the susceptible 3D7 strain. The parasites were grown for 40-48 h until the schizont stage was reached (one complete life cycle). Parasite growth was stopped with three washes of cold PBS. Final parasitaemia was determined by measuring the parasite lactate dehydrogenase (LDH) activity. Percent growth inhibition was expressed relative to uninfected erythrocytes.

Results Summary and Conclusions

Table 3-1 shows the maximum percent growth inhibition for each antibody alone and antibody/chloroquine combination. Combining chloroquine with PfRH5-specific antibodies further increased the percent maximum growth inhibition obtained with the antibodies alone in the 3D7 strain. Maximum growth inhibition with antibody alone was approximately 34 to 61%, while the addition of 4.81 nM CQ to the mAb had similar maximum growth inhibition (32 to 51%). The addition of 6.58 nM of CQ to the mAb increased the range of growth inhibition at least 20% to 59 to 75%. On the other hand, the individual antibodies and antibody/drug combinations displayed similar percent maximum growth inhibition with the 7G8 strain (mAb alone: 47-51%; mAb+ 4.81 nM CQ: 44-53%; mAb+6.58 nM CQ: 30-52%).

TABLE 3-1

Summary of maximum growth inhibition activity of antibodies against PfRH5 from various *Plasmodium falciparum* strains.*

| Chloroquine Phosphate | mAb | Max growth inhibition (%) | |
|---|---|---|---|
| | | 3D7 | 7G8 |
| N/A | H1H29089P | 61.06 | 51.10 |
| | H1H29100P | 58.02 | 48.85 |
| | H1H29147P2 | 34.93 | 47.34 |
| | H1H29187P2 | 47.58 | 49.30 |
| 4.81 nM | H1H29089P | 51.32 | 48.69 |
| | H1H29100P | 46.64 | 53.76 |
| | H1H29147P2 | 31.45 | 44.22 |
| | H1H29187P2 | 44.53 | 48.70 |
| 6.58 nM | H1H29089P | 75.59 | 52.78 |
| | H1H29100P | 71.21 | 50.67 |
| | H1H29147P2 | 59.11 | 29.96 |
| | H1H29187P2 | 71.20 | 38.95 |

*Maximum growth inhibition of antibodies against PfRH5 relative to uninfected human red blood cells. The growth inhibition assay was performed on *P. falciparum*- (mature trophozoite or early schizont) infected red blood cells at 0.4-0.7% parasitaemia. The antibodies were combined with the infected red blood cells. The parasites were grown for 40-48 hours (parasite strain dependent) until the schizont stage was reached. Parasite growth was stopped with three washes of cold PBS. Parasite lactate dehydrogenase activity was measured immediately after the washes. Percent growth inhibition was expressed relative to uninfected erythrocytes. The results of one representative assay of the growth inhibition assay are shown above.

Example 4: Growth Inhibition Assay to Assess the Ability of Anti-PfRH5 Antibodies to Inhibit the In Vitro Invasion of Human Red Blood Cells and Growth of *P. falciparum* Parasites In this example, a set of 30 PfRH5-specific mAbs of the invention were tested in a standard growth inhibition assay against a number of common laboratory strains (both susceptible and resistant to various antimalarial drugs) and multidrug resistant clinical lines.

Experimental Procedure

Each *P. falciparum* strain (BEI Resources) was first synchronized with 5% D-sorbitol following standard protocols at 3-5% hematocrit and 1-2% parasitaemia 20-24 hours prior to the start of the assay. Infected human erythrocytes were prepared at a starting parasitaemia of 0.4-0.7% and 2% hematocrit. Infected erythrocytes were combined with PfRH5-specific or control IgG1 antibodies starting at a concentration of 666.67 nM with 1:5 serial dilution for each antibody.

The parasites were grown for 40-48 h until the schizont stage was reached (one complete life cycle). Parasite growth was stopped with three washes of cold PBS. Final parasitaemia was determined by measuring the parasite lactate dehydrogenase (LDH) activity (Miura et al, Clin Vaccine Immunol. 16: 963-968 (2009). PMID: PMC2708396). Percent growth inhibition was expressed relative to uninfected erythrocytes.

Results Summary and Conclusions

Table 4-1 shows the maximum percent growth inhibition for each of the 30 PfRH5-specific mAbs tested at 666.67 nM. Application of several antibodies resulted in decreased growth in all tested laboratory-adapted and clinical *P. falciparum* strains.

Example 5: Biacore Binding Kinetics of Anti-PfRH5 Monoclonal Antibodies Binding to PfRH5ΔNL.his at 25° C. and 37° C.

The binding kinetics of the various anti-PfRH5 antibodies of the present invention were determined in this example.

Equilibrium dissociation constants ($K_D$) for different PfRH5 reagents binding to purified anti-PfRH5 monoclonal antibodies were determined using a real-time surface plasmon resonance based Biacore T200 biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM4 sensor chip surface was first derivatized by amine coupling with the goat anti-human Fcγ specific polyclonal antibody (Jackson ImmunoResearch Laboratories, Cat #109-005-098) or rabbit anti-mouse Fc specific polyclonal antibody (GE Healthcare Cat #BR100838) to capture anti-PfRH5 IgG1 monoclonal antibodies. Binding studies were performed on recombinant PfRH5 removing the amino terminus M1-Y139 and including residues K140-Q526 but lacking K247-L295 and T216A and T299A expressed with

TABLE 4-1

Summary of maximum growth inhibition activity of antibodies against PfRH5 from various *Plasmodium falciparum* strains.*

| mAb | Max growth inhibition (%) | | | | | | | | |
|---|---|---|---|---|---|---|---|---|---|
| | D10 | Dd2 | 7G8 | W2-mef | 3D7 | HB3 | FCR-1/FVO | Cam3.II | RF7 |
| H1H29089P | 82.32 | 71.29 | 70.09 | 66.39 | 67.59 | 59.15 | 65.98 | 56.16 | 28.95 |
| H1H29094P | 35.86 | 41.58 | 29.95 | 34.94 | 14.38 | 45.39 | 51.23 | 26.18 | 15.23 |
| H1H29100P | 81.73 | 64.60 | 66.40 | 67.29 | 61.80 | 62.61 | 66.89 | 52.44 | 17.02 |
| H1H29104P | 55.70 | 61.31 | 35.16 | 47.40 | 34.42 | 39.81 | 67.38 | 50.02 | 23.62 |
| H1H29106P | 74.86 | 53.97 | 55.49 | 48.93 | 57.97 | 48.36 | 54.28 | 51.68 | 27.41 |
| H1H29109P | 44.79 | 42.05 | 39.04 | 37.92 | 32.22 | 32.24 | 56.74 | 35.91 | 8.24 |
| H1H29125P | 75.39 | 51.39 | 46.96 | 64.57 | 51.14 | 52.09 | 67.62 | 42.69 | 20.99 |
| H1H29127P | 74.44 | 64.67 | 61.19 | 53.61 | 63.90 | 59.36 | 61.13 | 47.00 | 25.68 |
| H1H29131P | 63.00 | 68.75 | 50.30 | 63.16 | 50.61 | 59.45 | 71.77 | 50.18 | 26.66 |
| H1H29134P | 50.59 | 39.99 | 34.84 | 26.89 | 40.72 | 28.21 | 41.17 | 28.53 | 16.69 |
| H1H29138P | 57.06 | 74.44 | 57.36 | 66.44 | 58.45 | 51.38 | 84.07 | 48.69 | 51.37 |
| H1H29141P | 50.01 | 65.27 | 54.63 | 56.19 | 48.20 | 49.98 | 74.25 | 49.31 | 32.06 |
| H1H29143P | 79.41 | 62.70 | 61.87 | 58.27 | 60.27 | 60.87 | 67.19 | 53.25 | 28.21 |
| H1H29146P2 | 10.78 | 26.90 | 19.07 | 0.57 | 8.57 | 33.87 | 7.32 | 8.18 | 5.97 |
| H1H29147P2 | 81.44 | 65.31 | 65.20 | 64.71 | 60.27 | 64.85 | 70.32 | 51.93 | 31.44 |
| H1H29149P2 | 66.03 | 50.32 | 41.38 | 42.77 | 44.15 | 40.01 | 57.98 | 36.22 | 14.74 |
| H1H29151P2 | 38.66 | 57.97 | 47.52 | 53.90 | 35.49 | 31.74 | 53.70 | 26.34 | 18.26 |
| H1H29163P2 | 71.83 | 61.17 | 62.62 | 63.66 | 55.62 | 56.45 | 64.52 | 46.72 | 10.73 |
| H1H29166P2 | 70.94 | 60.02 | 54.60 | 61.87 | 53.11 | 54.93 | 69.69 | 55.90 | 19.41 |
| H1H29171P2 | 10.60 | 7.71 | 17.03 | 0.74 | 4.04 | 0.52 | 11.67 | 5.45 | −12.52 |
| H1H29179P2 | 62.50 | 13.49 | 34.11 | 22.88 | 24.24 | 40.86 | 49.01 | 33.41 | −2.99 |
| H1H29183P2 | 6.79 | 0.68 | 17.83 | −0.55 | 5.68 | 4.92 | 16.05 | 8.66 | −6.27 |
| H1H29187P2 | 79.61 | 66.02 | 71.80 | 67.28 | 70.71 | 63.91 | 72.16 | 49.22 | 32.73 |
| H1H29192P2 | 8.70 | −15.16 | 12.42 | 4.35 | −1.03 | 5.62 | 15.10 | −3.38 | −7.69 |
| H1H29196P2 | 14.33 | −1.65 | 23.44 | 17.00 | 6.72 | 26.76 | 21.94 | 6.09 | 3.78 |
| H1H29198P2 | 4.38 | 10.13 | 5.31 | −3.61 | −5.40 | 15.53 | 11.08 | 14.66 | 1.53 |
| H1H29207P2 | 73.90 | 61.30 | 58.68 | 65.21 | 61.84 | 49.30 | 69.23 | 45.30 | 31.06 |
| H1H29209P2 | 72.66 | 38.09 | 49.89 | 39.61 | 48.32 | 52.40 | 19.16 | 47.26 | 11.91 |
| H1H29214P2 | 76.52 | 47.21 | 56.74 | 52.72 | 52.09 | 59.09 | 13.05 | 46.67 | 11.18 |
| H1H29215P2 | 35.80 | 22.79 | 33.23 | 37.23 | 19.97 | 30.11 | 54.03 | 27.22 | 11.28 |
| Human IgG1 negative control antibody specific for cat allergy antigen-Fel d 1 | −1.42 | 11.02 | −11.68 | 6.66 | 13.18 | 27.50 | 4.04 | −0.41 | −6.62 |

*Maximum growth inhibition of antibodies against PfRH5 relative to uninfected human red blood cells. The growth inhibition assay was performed on *P. falciparum*-(mature trophozoite or early schizont) infected red blood cells at 0.4-0.7% parasitaemia. The antibodies were combined with the infected red blood cells. The parasites were grown for 40-48 hours (parasite strain dependent) until the schizont stage was reached. Parasite growth was stopped with three washes of cold PBS. Parasite lactate dehydrogenase(LDH) activity was measured immediately after the washes. Percent growth inhibition is expressed relative to uninfected erythrocytes. The results of one representative assay of the growth inhibition assay for each *P. falciparum* strain are shown above.

a C-terminal hexahistidine tag (PfRH5ΔNL.6his). Different concentrations of PfRH5ΔNL.6his (3.125-50 nM; 2-fold serial dilution or 0.48-60 nM; 5-fold serial dilution) were first prepared in HBS-ET running buffer and were injected over anti-human Fcγ or anti-mouse Fc captured anti-PfRH5 monoclonal antibody surface for four minutes at a flow rate of 50 µL/minute, while the dissociation of monoclonal antibody bound PfRH5 reagent was monitored for ten minutes in HBS-ET running buffer. The association rate ($k_a$) and dissociation rate ($k_d$) constants were determined by fitting the real-time binding sensorgrams to a 1:1 binding model with mass transport limitation using Scrubber 2.0c curve-fitting software. Binding dissociation equilibrium constant ($K_D$) and dissociative half-life (t/2) were calculated from the kinetic rates as:

$$K_D(M) = \frac{kd}{ka}, \text{ and } t^{1/2}(\min) = \frac{\ln(2)}{60*kd}$$

Kinetics parameters for PfRH5ΔNL.6his binding to different anti-PfRH5 monoclonal antibodies of the invention at 25° C. and 37° C. are shown in Tables 5-1 through 5-2, respectively.

At 25° C., all of the anti-PfRH5 monoclonal antibodies of the invention bound to PfRH5ΔNL.6his with $K_D$ values ranging from 4.72 pM to 1.67 nM, as shown in Table 5-1. At 37° C., all of the anti-PfRH5 monoclonal antibodies of the invention bound to PfRH5ΔNL.6his with $K_D$ values ranging from 1.10 pM to 1.10 nM, as shown in Table 5-2.

TABLE 5-1

Binding kinetics parameters of PfRH5ΔNL.6his binding to anti-PfRH5 monoclonal antibodies at 25° C.

| Antibody | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H1H29141P | 62.8 ± 4.0 | 29.9 | 2.75E+06 | 1.30E−05 | 4.72E−12 | 888 |
| H1H29209P2 | 152.6 ± 0.6 | 79.5 | 1.54E+06 | 1.37E−05 | 9.09E−12 | 843 |
| H1H29125P | 175.4 ± 1.3 | 88.3 | 8.10E+05 | 1.00E−05* | 1.23E−11 | 1155 |
| H1H29138P | 118.1 ± 0.4 | 61.2 | 1.98E+07 | 4.04E−04 | 2.04E−11 | 28.6 |
| H1H29106P | 109.4 ± 4.0 | 49.3 | 6.31E+06 | 9.93E−04 | 1.57E−10 | 11.6 |
| H1H29134P | 147.7 ± 0.6 | 68.3 | 7.98E+05 | 1.00E−05* | 1.25E−11 | 1155 |
| H1H29109P | 70.4 ± 4.4 | 36.7 | 2.17E+06 | 1.01E−03 | 4.68E−10 | 11.4 |
| H1H29100P | 163.2 ± 1.1 | 83.3 | 2.49E+06 | 1.96E−04 | 7.87E−11 | 59.1 |
| H1H29127P | 177.5 ± 0.3 | 88.1 | 1.91E+06 | 9.12E−04 | 4.76E−10 | 12.7 |
| H1H29089P | 180.4 ± 0.9 | 96 | 1.46E+06 | 3.99E−04 | 2.73E−10 | 29 |
| H1H29094P | 186.1 ± 0.9 | 87.2 | 1.07E+06 | 5.30E−04 | 4.98E−10 | 21.8 |
| H1H29179P2 | 171.7 ± 1.0 | 66.3 | 1.83E+06 | 4.88E−03 | 2.66E−09 | 2.4 |
| H1H29214P2 | 115.5 ± 2.9 | 59.9 | 1.71E+06 | 2.17E−04 | 1.27E−10 | 53.3 |
| H1H29131P | 103.8 ± 5.1 | 52.4 | 3.14E+06 | 2.23E−03 | 7.11E−10 | 5.2 |
| H1H29215P2 | 74.5 ± 0.4 | 34.6 | 1.56E+06 | 1.52E−03 | 9.74E−10 | 7.6 |
| H1H29147P2 | 91.5 ± 4.5 | 43.2 | 3.29E+06 | 1.67E−03 | 5.07E−10 | 6.9 |
| H1H29163P2 | 93.6 ± 0.2 | 38 | 3.02E+06 | 2.00E−03 | 6.63E−10 | 5.8 |
| H1H29187P2 | 108.1 ± 1.3 | 53.2 | 2.18E+06 | 2.19E−04 | 1.01E−10 | 52.8 |
| H1H29149P2 | 195.6 ± 1.6 | 82.9 | 1.51E+06 | 4.14E−04 | 2.74E−10 | 27.9 |
| H1H29207P2 | 204.0 ± 2.0 | 104.9 | 1.68E+06 | 1.72E−03 | 1.03E−09 | 6.7 |
| H1H29104P | 139.4 ± 2.6 | 58.4 | 1.24E+06 | 1.30E−03 | 1.05E−09 | 8.9 |
| H1H29196P2 | 138.3 ± 0.9 | 61 | 1.22E+06 | 2.21E−03 | 1.80E−09 | 5.2 |
| H1H29183P2 | 156.6 ± 1.0 | 23 | 1.59E+05 | 1.00E−05* | 6.28E−11 | 1155 |
| H1H29143P | 110.8 ± 0.3 | 53.4 | 3.41E+06 | 2.77E−03 | 8.13E−10 | 4.2 |
| H1H29166P2 | 102.5 ± 6.6 | 28 | 4.27E+06 | 3.56E−03 | 8.34E−10 | 3.2 |
| H1H29151P2 | 122.4 ± 0.2 | 26 | 1.48E+07 | 2.47E−02 | 1.67E−09 | 0.5 |
| H1H29192P2 | 148.3 ± 0.6 | −0.4 | NB$ | NB$ | NB$ | NB$ |
| H1H29198P2 | 121.7 ± 0.3 | −0.8 | NB$ | NB$ | NB$ | NB$ |
| H1H29146P2 | 143.2 ± 0.4 | −1.5 | NB$ | NB$ | NB$ | NB$ |
| H1H29171P2 | 144.2 ± 0.4 | 0.4 | NB$ | NB$ | NB$ | NB$ |
| IgG1 Isotype Control | 165.3 ± 0.9 | −1.3 | NB$ | NB$ | NB$ | NB$ |

*indicates that no dissociation of PfRH5ΔNL.6his was observed under the current experimental conditions and the $k_d$ value was manually fixed at 1.00E−05 while fitting the data.
$indicates that no binding was observed under the current experimental conditions.
NB means no binding

TABLE 5-2

Binding kinetics parameters of PfRH5ΔNL.6his binding to anti-PfRH5 monoclonal antibodies at 37° C.

| Antibody | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H1H29141P | 38.8 ± 1.3 | 18.8 | 9.11E+06 | 1.00E−05* | 1.10E−12 | 1155 |
| H1H29209P2 | 66.7 ± 0.8 | 28.6 | 2.11E+06 | 1.00E−05* | 4.74E−12 | 1155 |
| H1H29125P | 65.8 ± 2.6 | 19.9 | 1.58E+06 | 1.00E−05* | 6.34E−12 | 1155 |
| H1H29138P | 40.3 ± 0.2 | 18.7 | 4.26E+07 | 6.87E−04 | 1.61E−11 | 16.8 |

TABLE 5-2-continued

Binding kinetics parameters of PfRH5ΔNL.6his binding to anti-PfRH5 monoclonal antibodies at 37° C.

| Antibody | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H1H29106P | 58.6 ± 6.5 | 17.3 | 1.60E+07 | 6.36E−04 | 3.97E−11 | 18.2 |
| H1H29134P | 58.9 ± 0.6 | 19.8 | 2.71E+07 | 1.18E−03 | 4.37E−11 | 9.8 |
| H1H29109P | 40.5 ± 8.0 | 19.7 | 1.20E+07 | 5.51E−04 | 4.58E−11 | 21 |
| H1H29100P | 72.4 ± 1.1 | 33.2 | 4.03E+06 | 2.10E−04 | 5.21E−11 | 55 |
| H1H29127P | 67.3 ± 0.6 | 27.3 | 1.29E+07 | 7.02E−04 | 5.46E−11 | 16.4 |
| H1H29089P | 76.0 ± 1.9 | 32.7 | 4.04E+06 | 2.33E−04 | 5.77E−11 | 49.5 |
| H1H29094P | 72.1 ± 2.1 | 21.2 | 2.05E+06 | 1.19E−04 | 5.79E−11 | 97.2 |
| H1H29179P2 | 79.6 ± 1.1 | 15.3 | 2.14E+07 | 1.26E−03 | 5.88E−11 | 9.2 |
| H1H29214P2 | 59.0 ± 0.7 | 22.9 | 2.70E+06 | 1.63E−04 | 6.04E−11 | 70.9 |
| H1H29131P | 64.8 ± 0.4 | 26.6 | 1.31E+07 | 8.66E−04 | 6.61E−11 | 13.3 |
| H1H29215P2 | 41.9 ± 3.3 | 9.9 | 1.40E+07 | 1.21E−03 | 8.64E−11 | 9.5 |
| H1H29147P2 | 54.6 ± 1.5 | 24.9 | 1.24E+07 | 1.12E−03 | 9.01E−11 | 10.3 |
| H1H29163P2 | 32.7 ± 0.2 | 13 | 1.54E+07 | 1.68E−03 | 1.09E−10 | 6.9 |
| H1H29187P2 | 76.4 ± 8.6 | 29 | 3.19E+06 | 6.87E−04 | 2.16E−10 | 16.8 |
| H1H29149P2 | 117.5 ± 4.1 | 33.9 | 1.49E+06 | 6.47E−04 | 4.36E−10 | 17.9 |
| H1H29207P2 | 111.6 ± 3.9 | 40.8 | 2.61E+06 | 1.23E−03 | 4.72E−10 | 9.4 |
| H1H29104P | 110.3 ± 11.5 | 23 | 1.91E+06 | 9.38E−04 | 4.92E−10 | 12.3 |
| H1H29196P2 | 73.6 ± 1.6 | 14.1 | 2.50E+06 | 2.74E−03 | 1.10E−09 | 4.2 |
| H1H29183P2 | 78.4 ± 1.7 | 3.5 | IC# | IC# | IC# | IC# |
| H1H29143P | 41.5 ± 0.2 | 12.3 | IC# | IC# | IC# | IC# |
| H1H29166P2 | 59.0 ± 1.0 | 23.5 | IC# | IC# | IC# | IC# |
| H1H29151P2 | 45.0 ± 0.2 | 2.7 | NB$ | NB$ | NB$ | NB$ |
| H1H29192P2 | 60.3 ± 0.8 | −1.2 | NB$ | NB$ | NB$ | NB$ |
| H1H29198P2 | 46.4 ± 1.6 | −3.2 | NB$ | NB$ | NB$ | NB$ |
| H1H29146P2 | 52.6 ± 0.4 | −2.6 | NB$ | NB$ | NB$ | NB$ |
| H1H29171P2 | 52.0 ± 0.3 | −5.6 | NB$ | NB$ | NB$ | NB$ |
| IgG1 Isotype Control | 74.3 ± 1.0 | −1.2 | NB$ | NB$ | NB$ | NB$ |

*indicates that no dissociation of PfRH5ΔNL.6his was observed under the current experimental conditions and the $k_d$ value was manually fixed at 1.00E−05 while fitting the data.
$indicates that no binding was observed under the current experimental conditions.
indicates that binding was observed under the current experimental conditions, but kinetic values is unfit table.
IC means inconclusive
NB means no binding

Example 6: Octet Cross-Competition Between Different Anti-PfRH5 Monoclonal Antibodies Binding competition between a panel of anti-PfRH5 monoclonal antibodies was determined using a real time, label-free bio-layer interferometry assay on the Octet HTX biosensor platform (Pall ForteBio Corp.).

The experiment was performed at 25° C. in 10 mM HEPES, 150 mM NaCl, 3 mM EDTA, 0.05% v/v Surfactant Tween-20, and 1 mg/mL BSA, pH7.4 (HBS-EBT) buffer with the plate shaking at the speed of 1000 rpm. To assess whether two antibodies are able to compete with one another for binding to their respective epitopes on the recombinant PfRH5 removing the amino terminus M1-Y139 and including residues K140-Q526 but lacking K247-L295 and T216A and T299A expressed with a C-terminal hexahistidine tag (PfRH5ΔNL.6his; SEQ ID: 362), around 1.4-2.0 nm of PfRH5ΔNL.6his was first captured onto anti-Penta-His antibody coated Octet biosensor tips (Fortebio Inc, #18-5122) by submerging the biosensor tips for 60 seconds in wells containing 20 μg/mL solution of PfRH5ΔNL.6his. The antigen captured biosensor tips were then saturated with a first anti-PfRH5 monoclonal antibody (subsequently referred to as mAb-1) by dipping into wells containing 50 μg/mL solution of mAb-1 for 3 minutes. Antibodies used were IgG1. The biosensor tips were then subsequently dipped into wells containing 50 μg/mL solution of second anti-PfRH5 monoclonal antibody (subsequently referred to as mAb-2) for 3 minutes. The biosensor tips were washed in HBS-ETB buffer in between every step of the experiment. The real-time binding response was monitored during the entire course of the experiment and the binding response at the end of every step was recorded. The response of mAb-2 binding to PfRH5ΔNL.6his pre-complexed with mAb-1 was compared and competitive/non-competitive behavior of different anti-PfRH5 monoclonal antibodies was determined as shown in Table 6-1.

TABLE 6-1

Cross-competition between anti-PfRH5 monoclonal antibodies.

| mAb-1 | mAb-2 that competes with mAb-1 |
|---|---|
| H1H29127P | H1H29106P |
|  | H1H29134P |
| H1H29106P | H1H29127P |
|  | H1H29134P |
| H1H29134P | H1H29106P |
|  | H1H29127P |
| H1H29143P | H1H29187P2 |
| H1H29187P2 | H1H29143P |
|  | H1H29151P2 |
| H1H29183P2 | No mAb |
| H1H29104P | No mAb |
| H1H29207P2 | H1H29109P |
|  | H1H29147P2 |
|  | H1H29166P2 |
|  | H1H29171P2 |
|  | H1H29163P2 |

TABLE 6-1-continued

Cross-competition between anti-PfRH5 monoclonal antibodies.

| mAb-1 | mAb-2 that competes with mAb-1 |
|---|---|
| H1H29109P | H1H29207P2 |
|  | H1H29147P2 |
|  | H1H29166P2 |
|  | H1H29171P2 |
|  | H1H29163P2 |
| H1H29147P2 | H1H29207P2 |
|  | H1H29109P |
|  | H1H29166P2 |
|  | H1H29171P2 |
|  | H1H29163P2 |
|  | H1H29131P |
| H1H29166P2 | H1H29207P2 |
|  | H1H29109P |
|  | H1H29147P2 |
|  | H1H29171P2 |
|  | H1H29163P2 |
|  | H1H29131P |
| H1H29171P2 | H1H29207P2 |
|  | H1H29109P |
|  | H1H29147P2 |
|  | H1H29166P2 |
|  | H1H29163P2 |
|  | H1H29131P |
|  | H1H29094P |
| H1H29163P2 | H1H29207P2 |
|  | H1H29109P |
|  | H1H29147P2 |
|  | H1H29166P2 |
|  | H1H29171P2 |
|  | H1H29131P |
|  | H1H29094P |
|  | H1H29215P2 |
| H1H29131P | H1H29147P2 |
|  | H1H29166P2 |
|  | H1H29171P2 |
|  | H1H29163P2 |
|  | H1H29094P |
|  | H1H29215P2 |
| H1H29094P | H1H29171P2 |
|  | H1H29163P2 |
|  | H1H29131P |
|  | H1H29215P2 |
|  | H1H29151P2 |
|  | H1H29138P |
| H1H29215P2 | H1H29163P2 |
|  | H1H29131P |
|  | H1H29094P |
|  | H1H29151P2 |
|  | H1H29125P |
| H1H29151P2 | H1H29187P2 |
|  | H1H29094P |
|  | H1H29215P2 |
|  | H1H29198P2 |
| H1H29125P | H1H29215P2 |
| H1H29149P2 | H1H29100P |
|  | H1H29209P2 |
|  | H1H29179P2 |
|  | H1H29214P2 |
|  | H1H29089P |
| H1H29100P | H1H29149P2 |
|  | H1H29209P2 |
|  | H1H29179P2 |
|  | H1H29214P2 |
|  | H1H29089P |
| H1H29209P2 | H1H29149P2 |
|  | H1H29100P |
|  | H1H29179P2 |
|  | H1H29214P2 |
|  | H1H29089P |
| H1H29179P2 | H1H29149P2 |
|  | H1H29100P |
|  | H1H29209P2 |
|  | H1H29214P2 |
|  | H1H29089P |
| H1H29214P2 | H1H29149P2 |
|  | H1H29100P |
|  | H1H29209P2 |
|  | H1H29179P2 |
|  | H1H29089P |
| H1H29089P | H1H29149P2 |
|  | H1H29100P |
|  | H1H29209P2 |
|  | H1H29179P2 |
|  | H1H29214P2 |
| H1H29138P | H1H29094P |
| H1H29141P | No mAb |
| H1H29196P2 | No mAb |
| H1H29198P2 | H1H29151P2 |
| H1H29146P2 | No mAb |

Example 7: Multicycle Growth Inhibition Assay to Assess the Resultant Parasites after Anti-PfRH5 Antibody Pressure

*Plasmodium falciparum* RH5 specific antibodies inhibit invasion of human red blood cells assay over multiple replication cycles and do not induce mutations in the PfRH5 gene. Invasion of host erythrocytes is an essential step of the *Plasmodium falciparum* (*P. falciparum*) life cycle and of malaria pathology. Multiple antimalarial drugs target the asexual blood stages however, their efficacy is threatened by the appearance of drug resistant strains (Arrow et al., Saving Lives, Buying Time: Economics of Malaria Drugs in an Age of Resistance. National Acamies Press (US). 254-266 (2004); Blasco et al., Antimalarial drug resistance: linking *Plasmodium falciparum* parasite biology to the clinic. Nature Medicine. 23, 917-928 (2017)). Furthermore, antimalarial drugs display different pharmacokinetic properties. Some antimalarial drugs, such as artemisinin and quinine, are rapidly cleared within one parasite life cycle. On the other hand, hydrophobic and lipophilic antimalarial drugs are eliminated slowly, but they are characterized by different absorption rates depending on the amount of dietary fat consumed (Arrow et al., Saving Lives, Buying Time: Economics of Malaria Drugs in an Age of Resistance. National Acamies Press (US). 254-266 (2004)).

Targeting the reticulocyte-binding protein homolog 5 (RH5) protein with polyclonal (pAb) and monoclonal antibodies (mAb) efficiently blocks parasite invasion of several *P. falciparum* strains into human erythrocytes in vitro (Wright et al., Structure of malaria invasion protein RH5 with erythrocyte basigin and blocking antibodies. Nature. 515, 427-430 (2014); Galaway et al., P113 is a merozoite surface protein that binds the N-terminus of *Plasmodium falciparum* RH5. Nature Communications. 8, 14333 (2017)). Targeting the RH5 protein with a single antibody or an antibody cocktail may be necessary to generate opposing selection pressures on the same target. In addition, antibodies could compensate for the short half-life of common antimalarial drugs.

Lastly, the *Plasmodium* parasite has developed ways to escape the host immune response that tries to block the parasite development such as gene polymorphisms. This genetic diversity is often the result of immune pressure (Renia & Goh, Malaria Parasites: The Great Escape. Front Immunol. 7, 463 (2016). PMC5098170). Whole genome sequencing of more than 300 *P. falciparum* clinical isolates or laboratory strains identified only 15 non-synonymous PfRH5 SNPs within the possible mAb epitopes, demonstrating the conserved nature and the importance of the protein. Immune pressure on conserved regions of a protein may limit the ability of the parasite to develop escape mechanisms (Bustamante et al., A full-length recombinant *Plasmodium falciparum* PfRH5 protein induces inhibitory antibodies that are effective across common PfRH5 genetic variants, Vaccine, 31, 373-9 (2013)).

In this example, a set of four (4) RH5-specific mAbs, each with hIgG1, of the invention were tested alone in an escape mutant assay with one strain of *Plasmodium falciparum* (3D7).

Monoclonal antibodies used were H1H29089P, H1H29100P, H1H29147P2, H1H29187P2 and REGN1932.

Experimental Procedure (include description of relevant cell lines, proteins, reagents, and instrument type and model): The *P. falciparum* strain, 3D7 (BEI Resources) was grown following standard protocols at 4% hematocrit and 0.5% parasitaemia. Infected erythrocytes were combined with PfRH5-specific or control antibodies at a concentration corresponding to their respective $IC_{50}$ value on the *P. falciparum* strain described above. Antibody concentration was gradually increased every 7-14 days, up to a final concentration corresponding to 110× their respective $IC_{50}$ values. Growth medium containing the antibody was refreshed every 48 hours and fresh blood was added to the culture weekly.

Every week, parasite RNA was extracted by Trizol lysis of infected red blood cells and purified by Qiagen RNeasy kit. Reverse transcription was completed with the High-Capacity cDNA Reverse Transcription Kit (Applied Biosystems). Amplification of the RH5 gene was performed using PfRH5-specific primers. PCR products were analyzed on 1.5% agarose gel and cloned into TOPO TA cloning vector (Life Technologies). Sequencing of RH5 was achieved with M13 forward and reverse sequencing primers.

Results summary and conclusions. Several groups have reported that targeting the reticulocyte-binding protein homolog 5 (PfRH5) protein would efficiently block parasite invasion of human erythrocytes in vitro with *P. falciparum*. Gradually increasing the PfRH5-specific antibody pressure on the *P. falciparum* 3D7 parasites did not result in PfRH5 polymorphisms compared to the isotype control antibody pressure. Table 7-1 shows the percent PfRH5 sequence identity scores of each sample relative to all other sequenced samples after 45 days of gradual increases in antibody pressure ($1 \times EC_{50}$ to $110 \times EC_{50}$). All sequences are 100% identical throughout. FIG. 1 shows the sequence alignments of PfRH5 corresponding to each PfRH5-specific antibody after 45 days of gradual increases in antibody pressure ($1 \times EC_{50}$ to $110 \times EC_{50}$) showing no differences in sequences at the nucleotide level.

TABLE 7-1

Percent PfRH5 sequence identity scores of each sample relative to all other sequenced samples after 45 days of gradual increases in antibody pressure ($1 \times EC_{50}$ to $110 \times EC_{50}$).

| | Percent Identity Scores (PfRH5 sequence) | | | | | |
|---|---|---|---|---|---|---|
| | H1H29089P | H1H29100P | H1H29147P2 | H1H29187P2 | REGN1932 | Reference sequence (3D7) |
| H1H29089P | 100 | 100 | 100 | 100 | 100 | 100 |
| H1H29100P | 100 | 100 | 100 | 100 | 100 | 100 |
| H1H29147P2 | 100 | 100 | 100 | 100 | 100 | 100 |
| H1H29187P2 | 100 | 100 | 100 | 100 | 100 | 100 |
| REGN1932 | 100 | 100 | 100 | 100 | 100 | 100 |
| Reference sequence (3D7) | 100 | 100 | 100 | 100 | 100 | 100 |

Example 8: Growth Inhibition Assay to Assess the Ability of Anti-PfRH5 Antibodies to Inhibit the In Vitro Invasion of Human Red Blood Cells and Growth of *P. falciparum* Parasites in the Presence of Serum

*Plasmodium falciparum* RH5 specific antibodies inhibit invasion of human red blood cells in a pLDH based growth inhibition assay in the presence of serum.

One group suggested that complement activation on the merozoite surface enhances the parasite's ability to invade red blood cells (Biryukov et al., Complement and Antibody-mediated Enhancement of Red Blood Cell Invasion and Growth of Malaria Parasites. EBioMedicine. 9, 207-216 (2016)). However, other studies indicate that the presence of complement active serum results in reduced or comparable parasite growth compared to complement inactive serum (Boyle et al, Human antibodies fix complement to inhibit *Plasmodium falciparum* invasion of erythrocytes and are associated with protection against malaria. Immunity. 42, 580-90 (2015); Chulay et al., Inhibition of in vitro growth of *Plasmodium falciparum* by immune serum from monkeys. J Infect Dis. 144, 270-278). Also, in all cases of vaccination of merozoite antigens in humans (or any malaria antigens), there are no documented cases of antibody-dependent increases in parasitemia.

In this example, a set of four (4) RH5-specific mAbs (each with hIgG1 (designated with a H1H prefix) or hIgG4 (designated with a H4H prefix)) of the invention were tested alone and in combination with *Aotus* monkey normal serum (ANS), *Aotus* heat-inactivated serum (AHIS), human normal serum (HNS) or human heat-inactivated serum (HHIS) in a standard growth inhibition assay with one strain of *Plasmodium falciparum* (FCR-1/FVO).

Monoclonal antibodies used were H1H29089P, H1H29100P, H1H29147P2, H1H29187P2, H4H29089P, H4H29100P, H4H29147P2, H4H29187P2, REGN1932 (anti-Fel d1 (human IgG1)) and REGN1945 (anti-Fel d1 (human IgG4)).

Experimental Procedure (include description of relevant cell lines, proteins, reagents, and instrument type and model). The *P. falciparum* strain, FCR-1/FVO (BEI Resources) was first synchronized with 5% D-sortibol following standard protocols at 3-5% hematocrit and 1-2% parasitaemia 20-24 hours prior to the start of the assay. Infected human erythrocytes were prepared at a starting parasitaemia of 0.4-0.7% and 2% hematocrit. Infected erythrocytes were combined with RH5-specific or control antibodies, at a concentration of 6.67 M in the presence of 10% *Aotus* normal serum, *Aotus* heat-inactivated serum, human normal serum or human heat-inactivated serum. The parasites were grown for 40-48 hours until the schizont stage was reached (one complete life cycle). Parasite growth was stopped with three washes of cold PBS. Final parasitaemia was determined by measuring the parasite lactate dehydrogenase (LDH) activity (Miura et al., Anti-Apical-Membrane-Antigen-1 antibody is more effective than anti-42-kilodalton-Merozoite-Surface-Protein-1 antibody in inhibiting *Plasmodium falciparum* growth, as determined by the in vitro growth inhibition assay. Clin Vaccine Immunol. 16, 963-968 (2009)). Percent growth inhibition is expressed relative to uninfected erythrocytes.

Results summary and conclusions. Targeting the reticulocyte-binding protein homolog 5 (RH5) protein efficiently blocks parasite invasion of human erythrocytes in vitro with *P. falciparum*. Conflicting findings have been published about the role of complement in merozoite invasion of red blood cells. RH5-specific antibodies were produced and tested in presence of *Aotus* or human sera in vitro in a growth inhibition assay in a *P. falciparum* strain as described above. Table 8-1 shows the maximum percent growth inhibition for each RH5-specific antibody (both hIgG1 and hIgG4 formats) with active or inactive serum complement. The individual antibodies and active or inactive serum combinations displayed similar percent maximum growth inhibition, ranging from approximately 67-86%.

TABLE 8-1

Summary of maximum growth inhibition activity of anti-PfRH5 antibodies, in the presence of 10% *Aotus* or human serum.

| | Percent Maximum Growth Inhibition | | | | |
|---|---|---|---|---|---|
| mAb | mAb (6.67 µM) + ANS (10%) | mAb (6.67 µM) + AHIS (10%) | mAb (6.67 µM) + HNS (10%) | mAb (6.67 µM) + HHIS (10%) | mAb (6.67 µM) + No serum |
| H1H29089P | 75.7 | 84.3 | 85.0 | 85.2 | 85.3 |
| H1H29100P | 73.2 | 82.5 | 82.4 | 81.9 | 83.9 |
| H1H29147P2 | 80.3 | 86.2 | 85.6 | 83.4 | 84.1 |
| H1H29187P2 | 80.1 | 89.4 | 85.9 | 85.4 | 85.3 |
| H4H29089P | 75.7 | 82.4 | 85.3 | 86.2 | 84.8 |
| H4H29100P | 67.7 | 79.8 | 75.5 | 79.6 | 83.9 |
| H4H29147P2 | 67.0 | 76.8 | 73.0 | 75.5 | 82.4 |
| H4H29187P2 | 69.9 | 82.9 | 77.0 | 77.8 | 84.0 |
| REGN1932 | 0 | 0 | 0 | 0 | 0 |
| REGN1945 | 0 | 0 | 0 | 0 | 0 |

Maximum growth inhibition of antibodies against PfRH5 relative to uninfected human red blood cells. The growth inhibition assay was performed on *P. falciparum* (mature trophozoite or early schizont) infected red blood cells at 0.4-0.7% parasitaemia. The antibodies and sera were combined with the infected red blood cells. The parasites were grown for 40-48 hours (the timing is parasite strain-dependent) until the schizont stage was reached. Parasite growth was stopped with three washes of cold PBS. Parasite lactate dehydrogenase (LDH) activity was measured immediately after the washes. Percent growth inhibition is expressed relative to uninfected erythrocytes. The results of one representative assay of the growth inhibition assay is shown above. ANS: *Aotus* monkey normal serum, AHIS: *Aotus* heat-inactivated serum, HNS: Normal human serum, HHIS: Human heat-inactivated serum.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, to relate to each and every individual publication, database entry (e.g., Genbank sequences or GeneID entries), patent application, or patent even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

TABLE 9

Sequences Excluded from ST.26-Formatted Sequence Listing

| SEQ ID NO: | Sequence |
|---|---|
| 13 | gctgcatcc |
| 14 | AAS |
| 29 | gatgcatcc |
| 30 | DAS |
| 45 | tatgcttcc |
| 46 | YAS |
| 61 | gctgcatcc |
| 62 | AAS |
| 77 | gatgcatcc |
| 78 | DAS |
| 93 | gctgcatcc |
| 94 | AAS |
| 109 | gctgcatcc |
| 110 | AAS |
| 125 | gctgcatcc |
| 126 | AAS |
| 141 | ggtgcatcc |
| 142 | GAS |
| 157 | gctgcatcc |
| 158 | AAS |
| 173 | gatgcatcc |
| 174 | DAS |
| 189 | gatgcatcc |
| 190 | DAS |
| 205 | gctgcatcc |
| 206 | AAS |
| 221 | gctgcatcc |
| 222 | AAS |
| 309 | ggtgcatcc |
| 310 | GAS |

SEQUENCE LISTING

```
Sequence total quantity: 365
SEQ ID NO: 1                moltype = DNA   length = 360
FEATURE                     Location/Qualifiers
source                      1..360
                            mol_type = other DNA
                            organism = Homo sapiens
SEQUENCE: 1
gaggtgcagc tggtgcagtc tggagcagag gtgaaaaagc ccggggagtc tctgaagatc   60
tcctgtaagg gttctggata cagctttacc agttactgga tcgtctgggt gcgccagatg  120
cccgggaaag gcctggagtg gatggggatc atctatcctg gtgactctga taccagatac  180
agcccgtcct tccaaggcca ggtcaccatc tcagccgaca agtccatcag caccgcctac  240
ctgcagtgga gcagcctgaa ggcctcggac accgccatgt attactgtgc gagacaagat  300
ataactggaa ctacggggtt tgactactgg ggccagggaa ccctggtcac cgtctcctca  360

SEQ ID NO: 2                moltype = AA   length = 120
FEATURE                     Location/Qualifiers
source                      1..120
                            mol_type = protein
                            organism = Homo sapiens
SEQUENCE: 2
EVQLVQSGAE VKKPGESLKI SCKGSGYSFT SYWIVWVRQM PGKGLEWMGI IYPGDSDTRY   60
SPSFQGQVTI SADKSISTAY LQWSSLKASD TAMYYCARQD ITGTTGFDYW GQGTLVTVSS  120

SEQ ID NO: 3                moltype = DNA   length = 24
FEATURE                     Location/Qualifiers
source                      1..24
                            mol_type = other DNA
                            organism = Homo sapiens
SEQUENCE: 3
ggatacagct ttaccagtta ctgg                                          24

SEQ ID NO: 4                moltype = AA   length = 8
FEATURE                     Location/Qualifiers
source                      1..8
                            mol_type = protein
                            organism = Homo sapiens
SEQUENCE: 4
GYSFTSYW                                                             8

SEQ ID NO: 5                moltype = DNA   length = 24
FEATURE                     Location/Qualifiers
source                      1..24
                            mol_type = other DNA
                            organism = Homo sapiens
SEQUENCE: 5
atctatcctg gtgactctga tacc                                          24

SEQ ID NO: 6                moltype = AA   length = 8
FEATURE                     Location/Qualifiers
source                      1..8
                            mol_type = protein
                            organism = Homo sapiens
SEQUENCE: 6
IYPGDSDT                                                             8

SEQ ID NO: 7                moltype = DNA   length = 39
FEATURE                     Location/Qualifiers
source                      1..39
                            mol_type = other DNA
                            organism = Homo sapiens
SEQUENCE: 7
gcgagacaag atataactgg aactacgggg tttgactac                          39

SEQ ID NO: 8                moltype = AA   length = 13
FEATURE                     Location/Qualifiers
source                      1..13
                            mol_type = protein
                            organism = Homo sapiens
SEQUENCE: 8
ARQDITGTTG FDY                                                      13

SEQ ID NO: 9                moltype = DNA   length = 324
FEATURE                     Location/Qualifiers
source                      1..324
                            mol_type = other DNA
                            organism = Homo sapiens
SEQUENCE: 9
gacatccaga tgacccagtc tccatcctcc ctgtctgcat ctgtaggaga cagagtcacc   60
```

```
atcacttgcc gggcaagtca gagcattagg aactatttga attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttattt ctgtcaacag agttacagta ccccattcac tttcggcccct   300
gggaccaaag tggatatcaa acga                                           324

SEQ ID NO: 10           moltype = AA   length = 108
FEATURE                 Location/Qualifiers
source                  1..108
                        mol_type = protein
                        organism = Homo sapiens
SEQUENCE: 10
DIQMTQSPSS LSASVGDRVT ITCRASQSIR NYLNWYQQKP GKAPKLLIYA ASSLQSGVPS     60
RFSGSGSGTD FTLTISSLQP EDFATYFCQQ SYSTPFTFGP GTKVDIKR                 108

SEQ ID NO: 11           moltype = DNA   length = 18
FEATURE                 Location/Qualifiers
source                  1..18
                        mol_type = other DNA
                        organism = Homo sapiens
SEQUENCE: 11
cagagcatta ggaactat                                                   18

SEQ ID NO: 12           moltype = AA   length = 6
FEATURE                 Location/Qualifiers
source                  1..6
                        mol_type = protein
                        organism = Homo sapiens
SEQUENCE: 12
QSIRNY                                                                 6

SEQ ID NO: 13           moltype =    length =
SEQUENCE: 13
000

SEQ ID NO: 14           moltype =    length =
SEQUENCE: 14
000

SEQ ID NO: 15           moltype = DNA   length = 27
FEATURE                 Location/Qualifiers
source                  1..27
                        mol_type = other DNA
                        organism = Homo sapiens
SEQUENCE: 15
caacagagtt acagtacccc attcact                                         27

SEQ ID NO: 16           moltype = AA   length = 9
FEATURE                 Location/Qualifiers
source                  1..9
                        mol_type = protein
                        organism = Homo sapiens
SEQUENCE: 16
QQSYSTPFT                                                              9

SEQ ID NO: 17           moltype = DNA   length = 369
FEATURE                 Location/Qualifiers
source                  1..369
                        mol_type = other DNA
                        organism = Homo sapiens
SEQUENCE: 17
caggtgcagc tggtggagtc tgggggagac gtggtccagc ctgggaggtc cctgcgactc     60
tcctgttcag gcactggatt caccttcagt agctatgcca tgcactgggt ccgccaggct    120
ccaggcaagg gactggaatg ggtggcactt atatcatatg atggaagtaa taaatattat    180
ggagactccg tgaagggccg attcaccgtc tccagagaca attccaagaa cacgctgtct    240
ctgcaaatga acagcctgaa aactgaggac acggcgatat attactgtgc gaaagagagg    300
cttttttggag tggtctctta ttacggtatg gacgtctggg gccaagggac cacggtcacc    360
gtctcctca                                                            369

SEQ ID NO: 18           moltype = AA   length = 123
FEATURE                 Location/Qualifiers
source                  1..123
                        mol_type = protein
                        organism = Homo sapiens
SEQUENCE: 18
QVQLVESGGD VVQPGRSLRL SCSGTGFTFS SYAMHWVRQA PGKGLEWVAL ISYDGSNKYY     60
GDSVKGRFTV SRDNSKNTLS LQMNSLKTED TAIYYCAKER LFGVVSYYGM DVWGQGTTVT    120
VSS                                                                  123
```

```
SEQ ID NO: 19              moltype = DNA   length = 24
FEATURE                    Location/Qualifiers
source                     1..24
                           mol_type = other DNA
                           organism = Homo sapiens
SEQUENCE: 19
ggattcacct tcagtagcta tgcc                                                 24

SEQ ID NO: 20              moltype = AA    length = 8
FEATURE                    Location/Qualifiers
source                     1..8
                           mol_type = protein
                           organism = Homo sapiens
SEQUENCE: 20
GFTFSSYA                                                                    8

SEQ ID NO: 21              moltype = DNA   length = 24
FEATURE                    Location/Qualifiers
source                     1..24
                           mol_type = other DNA
                           organism = Homo sapiens
SEQUENCE: 21
atatcatatg atggaagtaa taaa                                                 24

SEQ ID NO: 22              moltype = AA    length = 8
FEATURE                    Location/Qualifiers
source                     1..8
                           mol_type = protein
                           organism = Homo sapiens
SEQUENCE: 22
ISYDGSNK                                                                    8

SEQ ID NO: 23              moltype = DNA   length = 48
FEATURE                    Location/Qualifiers
source                     1..48
                           mol_type = other DNA
                           organism = Homo sapiens
SEQUENCE: 23
gcgaaagaga ggcttttgg agtggtctct tattacggta tggacgtc                        48

SEQ ID NO: 24              moltype = AA    length = 16
FEATURE                    Location/Qualifiers
source                     1..16
                           mol_type = protein
                           organism = Homo sapiens
SEQUENCE: 24
AKERLFGVVS YYGMDV                                                          16

SEQ ID NO: 25              moltype = DNA   length = 324
FEATURE                    Location/Qualifiers
source                     1..324
                           mol_type = other DNA
                           organism = Homo sapiens
SEQUENCE: 25
gacatccaga tgacccagtc tccatcctcc ctgtctgcat ctgtaggaga cagagtcacc          60
atcacttgcc aggcgagtca ggacattaat agggatctaa attggtatca gcagaaatca         120
gggaaaggcc ccaaactcct gatctacgat gcatccaatt tggaaacagg ggtcccatca         180
aggttcagtg gaaatagatt tgggacagat tttactttca ccatcagcag actgcagcct         240
gaagatattg caacatattt ctgtcaacag tataaaaatc tcccgtacac ttttggccag         300
gggaccaagc tggagatcaa acga                                                324

SEQ ID NO: 26              moltype = AA    length = 108
FEATURE                    Location/Qualifiers
source                     1..108
                           mol_type = protein
                           organism = Homo sapiens
SEQUENCE: 26
DIQMTQSPSS LSASVGDRVT ITCQASQDIN RDLNWYQQKS GKGPKLLIYD ASNLETGVPS          60
RFSGNRFGTD FTFTISRLQP EDIATYFCQQ YKNLPYTFGQ GTKLEIKR                      108

SEQ ID NO: 27              moltype = DNA   length = 18
FEATURE                    Location/Qualifiers
source                     1..18
                           mol_type = other DNA
                           organism = Homo sapiens
SEQUENCE: 27
caggacatta atagggat                                                        18

SEQ ID NO: 28              moltype = AA    length = 6
```

```
FEATURE                 Location/Qualifiers
source                  1..6
                        mol_type = protein
                        organism = Homo sapiens
SEQUENCE: 28
QDINRD                                                                      6

SEQ ID NO: 29           moltype =    length =
SEQUENCE: 29
000

SEQ ID NO: 30           moltype =    length =
SEQUENCE: 30
000

SEQ ID NO: 31           moltype = DNA   length = 27
FEATURE                 Location/Qualifiers
source                  1..27
                        mol_type = other DNA
                        organism = Homo sapiens
SEQUENCE: 31
caacagtata aaaatctccc gtacact                                              27

SEQ ID NO: 32           moltype = AA   length = 9
FEATURE                 Location/Qualifiers
source                  1..9
                        mol_type = protein
                        organism = Homo sapiens
SEQUENCE: 32
QQYKNLPYT                                                                   9

SEQ ID NO: 33           moltype = DNA   length = 357
FEATURE                 Location/Qualifiers
source                  1..357
                        mol_type = other DNA
                        organism = Homo sapiens
SEQUENCE: 33
cagctgcagc tgcaggagtc gggcccagga ctggtgaagc cttcggagac cctgtccctc           60
acctgcactg tctctggtgg ctccatcagc agtagtagtt actactgggg ctggatccgc          120
cagcccccag ggaagggcct ggagtggatt gggattatct attatagtgg gagcacctac          180
tacaacccgt ccctcaagag tcgagtcacc atttccgtag acacgtccaa gaaccagttc          240
tccctgaagc tgagctctgt gaccgccgca gacacggctg tgtattactg tgcgagacag          300
gacagggagg ccctctttga ctactggggc cagggaaccc tggtcaccgt ctcctca             357

SEQ ID NO: 34           moltype = AA   length = 119
FEATURE                 Location/Qualifiers
source                  1..119
                        mol_type = protein
                        organism = Homo sapiens
SEQUENCE: 34
QLQLQESGPG LVKPSETLSL TCTVSGGSIS SSSYYWGWIR QPPGKGLEWI GIIYYSGSTY           60
YNPSLKSRVT ISVDTSKNQF SLKLSSVTAA DTAVYYCARQ DREALFDYWG QGTLVTVSS           119

SEQ ID NO: 35           moltype = DNA   length = 30
FEATURE                 Location/Qualifiers
source                  1..30
                        mol_type = other DNA
                        organism = Homo sapiens
SEQUENCE: 35
ggtggctcca tcagcagtag tagttactac                                           30

SEQ ID NO: 36           moltype = AA   length = 10
FEATURE                 Location/Qualifiers
source                  1..10
                        mol_type = protein
                        organism = Homo sapiens
SEQUENCE: 36
GGSISSSSYY                                                                 10

SEQ ID NO: 37           moltype = DNA   length = 21
FEATURE                 Location/Qualifiers
source                  1..21
                        mol_type = other DNA
                        organism = Homo sapiens
SEQUENCE: 37
atctattata gtgggagcac c                                                    21

SEQ ID NO: 38           moltype = AA   length = 7
FEATURE                 Location/Qualifiers
```

```
source                      1..7
                            mol_type = protein
                            organism = Homo sapiens
SEQUENCE: 38
IYYSGST                                                                          7

SEQ ID NO: 39               moltype = DNA  length = 33
FEATURE                     Location/Qualifiers
source                      1..33
                            mol_type = other DNA
                            organism = Homo sapiens
SEQUENCE: 39
gcgagacagg acagggaggc cctctttgac tac                                            33

SEQ ID NO: 40               moltype = AA  length = 11
FEATURE                     Location/Qualifiers
source                      1..11
                            mol_type = protein
                            organism = Homo sapiens
SEQUENCE: 40
ARQDREALFD Y                                                                    11

SEQ ID NO: 41               moltype = DNA  length = 321
FEATURE                     Location/Qualifiers
source                      1..321
                            mol_type = other DNA
                            organism = Homo sapiens
SEQUENCE: 41
gaaattgtgc tgactcagtc tccagacttt cagtctgtga ctccaaagga gaaagtcacc               60
atcacctgcc gggccagtca gcgcattggt agtagcttac actggtacca gcagaaacca             120
gatcagtctc caaagctcct catcaagtat gcttcccagt ccttctcagg ggtcccctcg             180
aggttcagtg gcagtggatc tgggacagat ttcaccctca ccatcaatag cctggaagct             240
gaagatgctg caacgtatta ctgtcatcag agtagtactt tacccacctt cggccaaggg             300
acacgactgg agattaaacg a                                                        321

SEQ ID NO: 42               moltype = AA  length = 107
FEATURE                     Location/Qualifiers
source                      1..107
                            mol_type = protein
                            organism = Homo sapiens
SEQUENCE: 42
EIVLTQSPDF QSVTPKEKVT ITCRASQRIG SSLHWYQQKP DQSPKLLIKY ASQSFSGVPS               60
RFSGSGSGTD FTLTINSLEA EDAATYYCHQ SSTLPTFGQG TRLEIKR                            107

SEQ ID NO: 43               moltype = DNA  length = 18
FEATURE                     Location/Qualifiers
source                      1..18
                            mol_type = other DNA
                            organism = Homo sapiens
SEQUENCE: 43
cagcgcattg gtagtagc                                                             18

SEQ ID NO: 44               moltype = AA  length = 6
FEATURE                     Location/Qualifiers
source                      1..6
                            mol_type = protein
                            organism = Homo sapiens
SEQUENCE: 44
QRIGSS                                                                           6

SEQ ID NO: 45               moltype =   length =
SEQUENCE: 45
000

SEQ ID NO: 46               moltype =   length =
SEQUENCE: 46
000

SEQ ID NO: 47               moltype = DNA  length = 24
FEATURE                     Location/Qualifiers
source                      1..24
                            mol_type = other DNA
                            organism = Homo sapiens
SEQUENCE: 47
catcagagta gtactttacc cacc                                                      24

SEQ ID NO: 48               moltype = AA  length = 8
FEATURE                     Location/Qualifiers
source                      1..8
```

```
                         mol_type = protein
                         organism = Homo sapiens
SEQUENCE: 48
HQSSTLPT                                                                    8

SEQ ID NO: 49            moltype = DNA  length = 375
FEATURE                  Location/Qualifiers
source                   1..375
                         mol_type = other DNA
                         organism = Homo sapiens
SEQUENCE: 49
gaagtgcagc tggtggagtc tgggggaggc ctggtacagc ctggcaggtc cctgagactc          60
tcctgtgcag cctctggatt caggtttgac gattatgcca tgcactgggt ccgacaagct         120
ccagggaagg gcctggaatg ggtctcaggt attaattgga atagtggtgg caaaggctat         180
gcggactctg tgcagggccg attcaccatc tccagagaca cgccaagaa ctcccttat           240
ctgcaaatga acagtctgag aactgaggac acggccttgt attattgtgc aaaagatagg         300
ggtatagcag ctcgtcttct ctctcgtgat gcttttgata tgtggggcca agggacaatg         360
gtcaccgtct cttca                                                          375

SEQ ID NO: 50            moltype = AA  length = 125
FEATURE                  Location/Qualifiers
source                   1..125
                         mol_type = protein
                         organism = Homo sapiens
SEQUENCE: 50
EVQLVESGGG LVQPGRSLRL SCAASGFRFD DYAMHWVRQA PGKGLEWVSG INWNSGGKGY          60
ADSVQGRFTI SRDNAKNSLY LQMNSLRTED TALYYCAKDR GIAARLLSRD AFDMWGQGTM         120
VTVSS                                                                    125

SEQ ID NO: 51            moltype = DNA  length = 24
FEATURE                  Location/Qualifiers
source                   1..24
                         mol_type = other DNA
                         organism = Homo sapiens
SEQUENCE: 51
ggattcaggt ttgacgatta tgcc                                                 24

SEQ ID NO: 52            moltype = AA  length = 8
FEATURE                  Location/Qualifiers
source                   1..8
                         mol_type = protein
                         organism = Homo sapiens
SEQUENCE: 52
GFRFDDYA                                                                    8

SEQ ID NO: 53            moltype = DNA  length = 24
FEATURE                  Location/Qualifiers
source                   1..24
                         mol_type = other DNA
                         organism = Homo sapiens
SEQUENCE: 53
attaattgga atagtggtgg caaa                                                 24

SEQ ID NO: 54            moltype = AA  length = 8
FEATURE                  Location/Qualifiers
source                   1..8
                         mol_type = protein
                         organism = Homo sapiens
SEQUENCE: 54
INWNSGGK                                                                    8

SEQ ID NO: 55            moltype = DNA  length = 54
FEATURE                  Location/Qualifiers
source                   1..54
                         mol_type = other DNA
                         organism = Homo sapiens
SEQUENCE: 55
gcaaaagata gggtatagc agctcgtctt ctctcgtg atgcttttga tatg                   54

SEQ ID NO: 56            moltype = AA  length = 18
FEATURE                  Location/Qualifiers
source                   1..18
                         mol_type = protein
                         organism = Homo sapiens
SEQUENCE: 56
AKDRGIAARL LSRDAFDM                                                        18

SEQ ID NO: 57            moltype = DNA  length = 324
FEATURE                  Location/Qualifiers
```

-continued

```
source                  1..324
                        mol_type = other DNA
                        organism = Homo sapiens
SEQUENCE: 57
gacatccagt tgacccagtc tccatccttc ctgtctgcat ctgtaggaga cagagtcacc    60
atcacttgct gggccagtca ggacgttagc agttatttag cctggtatca gcaaaaacca   120
gggaaatccc ctaagctcct aatctttgct gcatccactt tgcaaggtgg gatcccatca   180
aggttcagcg gcagtggatc tgggacagaa ttcactctca caatcagcag cctgcggcct   240
gaagattttg caacttatta ctgtcaacac cttaatactt acccgtacac ttttggccag   300
gggaccaagc tggagatcaa acga                                          324

SEQ ID NO: 58           moltype = AA  length = 108
FEATURE                 Location/Qualifiers
source                  1..108
                        mol_type = protein
                        organism = Homo sapiens
SEQUENCE: 58
DIQLTQSPSF LSASVGDRVT ITCWASQDVS SYLAWYQQKP GKSPKLLIFA ASTLQGGIPS    60
RFSGSGSGTE FTLTISSLRP EDFATYYCQH LNTYPYTFGQ GTKLEIKR                108

SEQ ID NO: 59           moltype = DNA  length = 18
FEATURE                 Location/Qualifiers
source                  1..18
                        mol_type = other DNA
                        organism = Homo sapiens
SEQUENCE: 59
caggacgtta gcagttat                                                  18

SEQ ID NO: 60           moltype = AA  length = 6
FEATURE                 Location/Qualifiers
source                  1..6
                        mol_type = protein
                        organism = Homo sapiens
SEQUENCE: 60
QDVSSY                                                                6

SEQ ID NO: 61           moltype =   length =
SEQUENCE: 61
000

SEQ ID NO: 62           moltype =   length =
SEQUENCE: 62
000

SEQ ID NO: 63           moltype = DNA  length = 27
FEATURE                 Location/Qualifiers
source                  1..27
                        mol_type = other DNA
                        organism = Homo sapiens
SEQUENCE: 63
caacacctta atacttaccc gtacact                                        27

SEQ ID NO: 64           moltype = AA  length = 9
FEATURE                 Location/Qualifiers
source                  1..9
                        mol_type = protein
                        organism = Homo sapiens
SEQUENCE: 64
QHLNTYPYT                                                             9

SEQ ID NO: 65           moltype = DNA  length = 363
FEATURE                 Location/Qualifiers
source                  1..363
                        mol_type = other DNA
                        organism = Homo sapiens
SEQUENCE: 65
caggtgcagc tggtggagtc tgggggaggc gtggtccagt ctggaggtc cctgagactc    60
tcctgtgcag cgtcttcatt caccttcagt agctatggca tgcactgggt ccgccagtct   120
ccaggcaagg ggctggagtg ggtggcagtt ataagtaa taaatactat   180
ggagacttcg tgaggggccg attcaccatc tccagagaca attccaagaa cacgctgtat   240
ctgcaaatga acagcctgag agccgaggac acggctatgt attattgtgc gagagaagtt   300
cgtcgctact attattacgg tatggacgtc tggggccaag gaccacggt caccgtctcc   360
tca                                                                 363

SEQ ID NO: 66           moltype = AA  length = 121
FEATURE                 Location/Qualifiers
source                  1..121
                        mol_type = protein
                        organism = Homo sapiens
```

```
SEQUENCE: 66
QVQLVESGGG VVQSGRSLRL SCAASSFTFS SYGMHWVRQS PGKGLEWVAV ISYDGSNKYY    60
GDFVRGRFTI SRDNSKNTLY LQMNSLRAED TAMYYCAREV RRYYYYGMDV WGQGTTVTVS   120
S                                                                  121

SEQ ID NO: 67           moltype = DNA  length = 24
FEATURE                 Location/Qualifiers
source                  1..24
                        mol_type = other DNA
                        organism = Homo sapiens
SEQUENCE: 67
tcattcacct tcagtagcta tggc                                          24

SEQ ID NO: 68           moltype = AA  length = 8
FEATURE                 Location/Qualifiers
source                  1..8
                        mol_type = protein
                        organism = Homo sapiens
SEQUENCE: 68
SFTFSSYG                                                            8

SEQ ID NO: 69           moltype = DNA  length = 24
FEATURE                 Location/Qualifiers
source                  1..24
                        mol_type = other DNA
                        organism = Homo sapiens
SEQUENCE: 69
ataagttatg atggaagtaa taaa                                          24

SEQ ID NO: 70           moltype = AA  length = 8
FEATURE                 Location/Qualifiers
source                  1..8
                        mol_type = protein
                        organism = Homo sapiens
SEQUENCE: 70
ISYDGSNK                                                            8

SEQ ID NO: 71           moltype = DNA  length = 42
FEATURE                 Location/Qualifiers
source                  1..42
                        mol_type = other DNA
                        organism = Homo sapiens
SEQUENCE: 71
gcgagagaag ttcgtcgcta ctattattac ggtatggacg tc                      42

SEQ ID NO: 72           moltype = AA  length = 14
FEATURE                 Location/Qualifiers
source                  1..14
                        mol_type = protein
                        organism = Homo sapiens
SEQUENCE: 72
AREVRRYYYY GMDV                                                     14

SEQ ID NO: 73           moltype = DNA  length = 324
FEATURE                 Location/Qualifiers
source                  1..324
                        mol_type = other DNA
                        organism = Homo sapiens
SEQUENCE: 73
gacatccaga tgacccagtc tccatcctcc ctgtctgcat ctgtaggaga cagagtcacc    60
atcacttgcc aggcgagtca ggacattagt aattatttaa attggtatct gcagaaacca   120
gggaaagccc ctaagctcct gatctccgat gcatccaatt tggaaacagg ggtcccatca   180
aggttcagtg aagtggatc tgggacagat tttactttca ccatcagcag cctgcagcct    240
gaagatattg caacatatta ctgtcaacag tataataatc tcccgctcac tttcggcgga   300
gggaccaagg tggagatcaa acga                                          324

SEQ ID NO: 74           moltype = AA  length = 108
FEATURE                 Location/Qualifiers
source                  1..108
                        mol_type = protein
                        organism = Homo sapiens
SEQUENCE: 74
DIQMTQSPSS LSASVGDRVT ITCQASQDIS NYLNWYLQKP GKAPKLLISD ASNLETGVPS    60
RFSGSGSGTD FTFTISSLQP EDIATYYCQQ YNNLPLTFGG GTKVEIKR                108

SEQ ID NO: 75           moltype = DNA  length = 18
FEATURE                 Location/Qualifiers
source                  1..18
                        mol_type = other DNA
```

```
                        organism = Homo sapiens
SEQUENCE: 75
caggacatta gtaattat                                                   18

SEQ ID NO: 76           moltype = AA  length = 6
FEATURE                 Location/Qualifiers
source                  1..6
                        mol_type = protein
                        organism = Homo sapiens
SEQUENCE: 76
QDISNY                                                                 6

SEQ ID NO: 77           moltype =    length =
SEQUENCE: 77
000

SEQ ID NO: 78           moltype =    length =
SEQUENCE: 78
000

SEQ ID NO: 79           moltype = DNA  length = 27
FEATURE                 Location/Qualifiers
source                  1..27
                        mol_type = other DNA
                        organism = Homo sapiens
SEQUENCE: 79
caacagtata ataatctccc gctcact                                         27

SEQ ID NO: 80           moltype = AA  length = 9
FEATURE                 Location/Qualifiers
source                  1..9
                        mol_type = protein
                        organism = Homo sapiens
SEQUENCE: 80
QQYNNLPLT                                                              9

SEQ ID NO: 81           moltype = DNA  length = 372
FEATURE                 Location/Qualifiers
source                  1..372
                        mol_type = other DNA
                        organism = Homo sapiens
SEQUENCE: 81
gaagtgcagc tggtggagtc tgggggaggc ttggtacagc ctggcaggtc cctgagactc     60
tcctgtgcag tctctggatt cacctttgat gattatgcca tgcactgggt ccggcaagct    120
ccagggaagg gcctggagtg ggtctcaggt attagttgga atagtggtga catagactat    180
gcggactctg tgaagggccg attcaccatt tccagagaca cgccaagaa ctccctgtat     240
ctgcaaatga acagtctgag agctgaggac acggccttgt attactgtgc aaaagatacc    300
ctctcaggga ctggaactac gtggtactat tttgactact ggggccaggg aaccctggtc    360
accgtctcct ca                                                        372

SEQ ID NO: 82           moltype = AA  length = 124
FEATURE                 Location/Qualifiers
source                  1..124
                        mol_type = protein
                        organism = Homo sapiens
SEQUENCE: 82
EVQLVESGGG LVQPGRSLRL SCAVSGFTFD DYAMHWVRQA PGKGLEWVSG ISWNSGDIDY     60
ADSVKGRFTI SRDNAKNSLY LQMNSLRAED TALYYCAKDT LSGTGTTWYY FDYWGQGTLV    120
TVSS                                                                 124

SEQ ID NO: 83           moltype = DNA  length = 24
FEATURE                 Location/Qualifiers
source                  1..24
                        mol_type = other DNA
                        organism = Homo sapiens
SEQUENCE: 83
ggattcacct ttgatgatta tgcc                                            24

SEQ ID NO: 84           moltype = AA  length = 8
FEATURE                 Location/Qualifiers
source                  1..8
                        mol_type = protein
                        organism = Homo sapiens
SEQUENCE: 84
GFTFDDYA                                                               8

SEQ ID NO: 85           moltype = DNA  length = 24
FEATURE                 Location/Qualifiers
source                  1..24
```

-continued

```
                        mol_type = other DNA
                        organism = Homo sapiens
SEQUENCE: 85
attagttgga atagtggtga cata                                              24

SEQ ID NO: 86           moltype = AA   length = 8
FEATURE                 Location/Qualifiers
source                  1..8
                        mol_type = protein
                        organism = Homo sapiens
SEQUENCE: 86
ISWNSGDI                                                                8

SEQ ID NO: 87           moltype = DNA  length = 51
FEATURE                 Location/Qualifiers
source                  1..51
                        mol_type = other DNA
                        organism = Homo sapiens
SEQUENCE: 87
gcaaaagata ccctctcagg gactggaact acgtggtact attttgacta c                51

SEQ ID NO: 88           moltype = AA   length = 17
FEATURE                 Location/Qualifiers
source                  1..17
                        mol_type = protein
                        organism = Homo sapiens
SEQUENCE: 88
AKDTLSGTGT TWYYFDY                                                      17

SEQ ID NO: 89           moltype = DNA  length = 324
FEATURE                 Location/Qualifiers
source                  1..324
                        mol_type = other DNA
                        organism = Homo sapiens
SEQUENCE: 89
gacatccagt tgacccagtc tccatccttc ctgtctgcat ctgtaggaga cagagtcacc       60
atcacttgct gggccagtca gggtattagc agttatttaa tctggtatca gcaaaaacca      120
gggaaagccc ctaagctcct gatctatgct gcatccactt tgcaaagtgg ggtcccatca      180
aggttcagcg gcagtggatc tgggacagaa ttcactctca caatcagcag cctgcagcct      240
gaagattttg caacttatta ctgtcaacag gtgaatagtt accctctcac tttcggcgga      300
gggaccaagg tggagatcaa acga                                             324

SEQ ID NO: 90           moltype = AA   length = 108
FEATURE                 Location/Qualifiers
source                  1..108
                        mol_type = protein
                        organism = Homo sapiens
SEQUENCE: 90
DIQLTQSPSF LSASVGDRVT ITCWASQGIS SYLIWYQQKP GKAPKLLIYA ASTLQSGVPS       60
RFSGSGSGTE FTLTISSLQP EDFATYYCQQ VNSYPLTFGG GTKVEIKR                   108

SEQ ID NO: 91           moltype = DNA  length = 18
FEATURE                 Location/Qualifiers
source                  1..18
                        mol_type = other DNA
                        organism = Homo sapiens
SEQUENCE: 91
cagggtatta gcagttat                                                     18

SEQ ID NO: 92           moltype = AA   length = 6
FEATURE                 Location/Qualifiers
source                  1..6
                        mol_type = protein
                        organism = Homo sapiens
SEQUENCE: 92
QGISSY                                                                  6

SEQ ID NO: 93           moltype =      length =
SEQUENCE: 93
000

SEQ ID NO: 94           moltype =      length =
SEQUENCE: 94
000

SEQ ID NO: 95           moltype = DNA  length = 27
FEATURE                 Location/Qualifiers
source                  1..27
                        mol_type = other DNA
```

```
                          organism = Homo sapiens
SEQUENCE: 95
caacaggtga atagttaccc tctcact                                        27

SEQ ID NO: 96           moltype = AA  length = 9
FEATURE                 Location/Qualifiers
source                  1..9
                        mol_type = protein
                        organism = Homo sapiens
SEQUENCE: 96
QQVNSYPLT                                                            9

SEQ ID NO: 97           moltype = DNA  length = 369
FEATURE                 Location/Qualifiers
source                  1..369
                        mol_type = other DNA
                        organism = Homo sapiens
SEQUENCE: 97
caggtgcagc tggtggagtc tgggggaggc gtggtccagc ctggggaggtc cctgagactc   60
tcctgtgcag cctctggatt caccttcagt agttatggca tgcactgggt ccgccaggct  120
ccaggcaagg gactggagtg gatggcagtt atatcatatg atggaagtaa taaatattat  180
gcagactccg tgaagggccg attcaccatc tccagagaca attccaagaa cacgctgttt  240
ctgcaaatga acagcctgag acctgaagac acggctgtat attactgtgc gcaagatggc  300
agctcggcga tttactattt ctacggtatg gacgtctggg gccaagggac cacggtcacc  360
gtctcctca                                                          369

SEQ ID NO: 98           moltype = AA  length = 123
FEATURE                 Location/Qualifiers
source                  1..123
                        mol_type = protein
                        organism = Homo sapiens
SEQUENCE: 98
QVQLVESGGG VVQPGRSLRL SCAASGFTFS SYGMHWVRQA PGKGLEWMAV ISYDGSNKYY    60
ADSVKGRFTI SRDNSKNTLF LQMNSLRPED TAVYYCAQDG SSAIYYFYGM DVWGQGTTVT   120
VSS                                                                123

SEQ ID NO: 99           moltype = DNA  length = 24
FEATURE                 Location/Qualifiers
source                  1..24
                        mol_type = other DNA
                        organism = Homo sapiens
SEQUENCE: 99
ggattcacct tcagtagtta tggc                                           24

SEQ ID NO: 100          moltype = AA  length = 8
FEATURE                 Location/Qualifiers
source                  1..8
                        mol_type = protein
                        organism = Homo sapiens
SEQUENCE: 100
GFTFSSYG                                                             8

SEQ ID NO: 101          moltype = DNA  length = 24
FEATURE                 Location/Qualifiers
source                  1..24
                        mol_type = other DNA
                        organism = Homo sapiens
SEQUENCE: 101
atatcatatg atggaagtaa taaa                                           24

SEQ ID NO: 102          moltype = AA  length = 8
FEATURE                 Location/Qualifiers
source                  1..8
                        mol_type = protein
                        organism = Homo sapiens
SEQUENCE: 102
ISYDGSNK                                                             8

SEQ ID NO: 103          moltype = DNA  length = 48
FEATURE                 Location/Qualifiers
source                  1..48
                        mol_type = other DNA
                        organism = Homo sapiens
SEQUENCE: 103
gcgcaagatg gcagctcggc gatttactat ttctacggta tggacgtc                 48

SEQ ID NO: 104          moltype = AA  length = 16
FEATURE                 Location/Qualifiers
source                  1..16
```

```
                        mol_type = protein
                        organism = Homo sapiens
SEQUENCE: 104
AQDGSSAIYY FYGMDV                                                   16

SEQ ID NO: 105          moltype = DNA   length = 324
FEATURE                 Location/Qualifiers
source                  1..324
                        mol_type = other DNA
                        organism = Homo sapiens
SEQUENCE: 105
gacatccaga tgacccagtc tccatcctca ctgtctgcat ctataggaga cagagtcacc    60
atcacttgtc gggcgagtca ggacatcaac aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccttcag tataatagtt accatcccac ttttggccag   300
gggaccaagc tggagatcaa acga                                          324

SEQ ID NO: 106          moltype = AA    length = 108
FEATURE                 Location/Qualifiers
source                  1..108
                        mol_type = protein
                        organism = Homo sapiens
SEQUENCE: 106
DIQMTQSPSS LSASIGDRVT ITCRASQDIN NYLAWFQQKP GKAPKSLIYA ASSLQSGVPS    60
KFSGSGSGTD FTLTISSLQP EDFATYYCLQ YNSYHPTFGQ GTKLEIKR                108

SEQ ID NO: 107          moltype = DNA   length = 18
FEATURE                 Location/Qualifiers
source                  1..18
                        mol_type = other DNA
                        organism = Homo sapiens
SEQUENCE: 107
caggacatca acaattat                                                 18

SEQ ID NO: 108          moltype = AA    length = 6
FEATURE                 Location/Qualifiers
source                  1..6
                        mol_type = protein
                        organism = Homo sapiens
SEQUENCE: 108
QDINNY                                                              6

SEQ ID NO: 109          moltype =    length =
SEQUENCE: 109
000

SEQ ID NO: 110          moltype =    length =
SEQUENCE: 110
000

SEQ ID NO: 111          moltype = DNA   length = 27
FEATURE                 Location/Qualifiers
source                  1..27
                        mol_type = other DNA
                        organism = Homo sapiens
SEQUENCE: 111
cttcagtata atagttacca tcccact                                       27

SEQ ID NO: 112          moltype = AA    length = 9
FEATURE                 Location/Qualifiers
source                  1..9
                        mol_type = protein
                        organism = Homo sapiens
SEQUENCE: 112
LQYNSYHPT                                                           9

SEQ ID NO: 113          moltype = DNA   length = 363
FEATURE                 Location/Qualifiers
source                  1..363
                        mol_type = other DNA
                        organism = Homo sapiens
SEQUENCE: 113
caggtgcagc tggtggagtc tgggggaggc gtggtccagc ctggggaggtc cctgagactc    60
tcctgtgcag cgtctggatt caccttcagt agctatggca tgcactgggt ccgccaggct   120
ccaggcaagg ggctggagtg ggtggcagct atatggtatg atggaagtaa taaatattat   180
gcagactccg tgaagggccg attcaccatc tccagagaca attccaagaa cacgctgtat   240
ctgcaaatga acagcctgag agccgaggac acggctgtgt atttctgtgc gagagggaa    300
cattactatg gttcggggcc gttcgacccc tggggccagg gaaccctggt caccgtctcc   360
```

```
tca                                                                  363

SEQ ID NO: 114          moltype = AA  length = 121
FEATURE                 Location/Qualifiers
source                  1..121
                        mol_type = protein
                        organism = Homo sapiens
SEQUENCE: 114
QVQLVESGGG VVQPGRSLRL SCAASGFTFS SYGMHWVRQA PGKGLEWVAA IWYDGSNKYY     60
ADSVKGRFTI SRDNSKNTLY LQMNSLRAED TAVYFCARGE HYYGSGPFDP WGQGTLVTVS    120
S                                                                   121

SEQ ID NO: 115          moltype = DNA  length = 24
FEATURE                 Location/Qualifiers
source                  1..24
                        mol_type = other DNA
                        organism = Homo sapiens
SEQUENCE: 115
ggattcacct tcagtagcta tggc                                           24

SEQ ID NO: 116          moltype = AA  length = 8
FEATURE                 Location/Qualifiers
source                  1..8
                        mol_type = protein
                        organism = Homo sapiens
SEQUENCE: 116
GFTFSSYG                                                             8

SEQ ID NO: 117          moltype = DNA  length = 24
FEATURE                 Location/Qualifiers
source                  1..24
                        mol_type = other DNA
                        organism = Homo sapiens
SEQUENCE: 117
atatggtatg atggaagtaa taaa                                           24

SEQ ID NO: 118          moltype = AA  length = 8
FEATURE                 Location/Qualifiers
source                  1..8
                        mol_type = protein
                        organism = Homo sapiens
SEQUENCE: 118
IWYDGSNK                                                             8

SEQ ID NO: 119          moltype = DNA  length = 42
FEATURE                 Location/Qualifiers
source                  1..42
                        mol_type = other DNA
                        organism = Homo sapiens
SEQUENCE: 119
gcgagagggg aacattacta tggttcgggg ccgttcgacc cc                        42

SEQ ID NO: 120          moltype = AA  length = 14
FEATURE                 Location/Qualifiers
source                  1..14
                        mol_type = protein
                        organism = Homo sapiens
SEQUENCE: 120
ARGEHYYGSG PFDP                                                      14

SEQ ID NO: 121          moltype = DNA  length = 324
FEATURE                 Location/Qualifiers
source                  1..324
                        mol_type = other DNA
                        organism = Homo sapiens
SEQUENCE: 121
gacatccaga tgacccagtc tccatcctcc ctgtctgcat ctgtaggaga cagagtcacc     60
atcacttgcc gggcaagtca gagcattagc aactatttaa attggtatca gcagaaacca    120
gggaaagccc ctaagctcct gatctttgct gcatccagtt tacaaagtgg ggtcccatca    180
aggttcagtg gcagtggatc tgggacagat ttcactctca ccatcagcag tctgcaacct    240
gaagattttg caacttacta ctgtcaacag agttacagtt ccccgctcac tttcggcgga    300
gggaccaagg tggagatcaa acga                                           324

SEQ ID NO: 122          moltype = AA  length = 108
FEATURE                 Location/Qualifiers
source                  1..108
                        mol_type = protein
                        organism = Homo sapiens
SEQUENCE: 122
```

```
DIQMTQSPSS LSASVGDRVT ITCRASQSIS NYLNWYQQKP GKAPKLLIFA ASSLQSGVPS    60
RFSGSGSGTD FTLTISSLQP EDFATYYCQQ SYSSPLTFGG GTKVEIKR                108

SEQ ID NO: 123          moltype = DNA  length = 18
FEATURE                 Location/Qualifiers
source                  1..18
                        mol_type = other DNA
                        organism = Homo sapiens
SEQUENCE: 123
cagagcatta gcaactat                                                  18

SEQ ID NO: 124          moltype = AA  length = 6
FEATURE                 Location/Qualifiers
source                  1..6
                        mol_type = protein
                        organism = Homo sapiens
SEQUENCE: 124
QSISNY                                                               6

SEQ ID NO: 125          moltype =   length =
SEQUENCE: 125
000

SEQ ID NO: 126          moltype =   length =
SEQUENCE: 126
000

SEQ ID NO: 127          moltype = DNA  length = 27
FEATURE                 Location/Qualifiers
source                  1..27
                        mol_type = other DNA
                        organism = Homo sapiens
SEQUENCE: 127
caacagagtt acagttcccc gctcact                                        27

SEQ ID NO: 128          moltype = AA  length = 9
FEATURE                 Location/Qualifiers
source                  1..9
                        mol_type = protein
                        organism = Homo sapiens
SEQUENCE: 128
QQSYSSPLT                                                            9

SEQ ID NO: 129          moltype = DNA  length = 360
FEATURE                 Location/Qualifiers
source                  1..360
                        mol_type = other DNA
                        organism = Homo sapiens
SEQUENCE: 129
caggtgcagc tgcaggagtc ggggccagga ctggtgaagc cttcacagac cctgtccctc    60
acctgcactg tctcaggtgg ctccatcagc agttttggtt actactggag ctggatccgc   120
cagcacccag ggaagggcct ggagtggatt gggtacatct attacagtgg gagcatcgac   180
tacaacccgt ccctcaagag tcgaattacc atatcagtcg acacgtctaa gaaccagttc   240
tccctgaagc tgagctctgt gactgccgcg gacacggccg tgtattactg tgcgagaaa    300
agggactacg gtgactactt tgactactgg ggccagggaa ccctggtcac cgtctcctca   360

SEQ ID NO: 130          moltype = AA  length = 120
FEATURE                 Location/Qualifiers
source                  1..120
                        mol_type = protein
                        organism = Homo sapiens
SEQUENCE: 130
QVQLQESGPG LVKPSQTLSL TCTVSGGSIS SFGYYWSWIR QHPGKGLEWI GYIYYSGSID    60
YNPSLKSRIT ISVDTSKNQF SLKLSSVTAA DTAVYYCARE RDYGDYFDYW GQGTLVTVSS   120

SEQ ID NO: 131          moltype = DNA  length = 30
FEATURE                 Location/Qualifiers
source                  1..30
                        mol_type = other DNA
                        organism = Homo sapiens
SEQUENCE: 131
ggtggctcca tcagcagttt tggttactac                                     30

SEQ ID NO: 132          moltype = AA  length = 10
FEATURE                 Location/Qualifiers
source                  1..10
                        mol_type = protein
                        organism = Homo sapiens
SEQUENCE: 132
```

GGSISSFGYY                                                                    10

SEQ ID NO: 133          moltype = DNA   length = 21
FEATURE                 Location/Qualifiers
source                  1..21
                        mol_type = other DNA
                        organism = Homo sapiens
SEQUENCE: 133
atctattaca gtgggagcat c                                                       21

SEQ ID NO: 134          moltype = AA    length = 7
FEATURE                 Location/Qualifiers
source                  1..7
                        mol_type = protein
                        organism = Homo sapiens
SEQUENCE: 134
IYYSGSI                                                                       7

SEQ ID NO: 135          moltype = DNA   length = 36
FEATURE                 Location/Qualifiers
source                  1..36
                        mol_type = other DNA
                        organism = Homo sapiens
SEQUENCE: 135
gcgagagaaa gggactacgg tgactacttt gactac                                       36

SEQ ID NO: 136          moltype = AA    length = 12
FEATURE                 Location/Qualifiers
source                  1..12
                        mol_type = protein
                        organism = Homo sapiens
SEQUENCE: 136
ARERDYGDYF DY                                                                 12

SEQ ID NO: 137          moltype = DNA   length = 324
FEATURE                 Location/Qualifiers
source                  1..324
                        mol_type = other DNA
                        organism = Homo sapiens
SEQUENCE: 137
gaaatagtga tgacgcagtc tccagccacc ctgtctgtct ctccagggga aagagccacc             60
ctctcctgca gggccagtca gagtgttagc agcaacttag cctggtacca gcagaaacct            120
ggccaggctc ccaggctcct catctatggt gcatccacca gggccactgg tgtcccagcc            180
aggttcagtg gcagtgggtc tgggacagag ttcactctca ccatcagcag tttgcagtct            240
gaggattttg cagtttattc ctgtcagcag tataataact ggcctctcac tttcggcgga            300
gggaccaagg tggagatcaa acga                                                  324

SEQ ID NO: 138          moltype = AA    length = 108
FEATURE                 Location/Qualifiers
source                  1..108
                        mol_type = protein
                        organism = Homo sapiens
SEQUENCE: 138
EIVMTQSPAT LSVSPGERAT LSCRASQSVS SNLAWYQQKP GQAPRLLIYG ASTRATGVPA             60
RFSGSGSGTE FTLTISSLQS EDFAVYSCQQ YNNWPLTFGG GTKVEIKR                        108

SEQ ID NO: 139          moltype = DNA   length = 18
FEATURE                 Location/Qualifiers
source                  1..18
                        mol_type = other DNA
                        organism = Homo sapiens
SEQUENCE: 139
cagagtgtta gcagcaac                                                           18

SEQ ID NO: 140          moltype = AA    length = 6
FEATURE                 Location/Qualifiers
source                  1..6
                        mol_type = protein
                        organism = Homo sapiens
SEQUENCE: 140
QSVSSN                                                                        6

SEQ ID NO: 141          moltype =      length =
SEQUENCE: 141
000

SEQ ID NO: 142          moltype =      length =
SEQUENCE: 142
000

```
SEQ ID NO: 143          moltype = DNA  length = 27
FEATURE                 Location/Qualifiers
source                  1..27
                        mol_type = other DNA
                        organism = Homo sapiens
SEQUENCE: 143
cagcagtata ataactggcc tctcact                                          27

SEQ ID NO: 144          moltype = AA  length = 9
FEATURE                 Location/Qualifiers
source                  1..9
                        mol_type = protein
                        organism = Homo sapiens
SEQUENCE: 144
QQYNNWPLT                                                               9

SEQ ID NO: 145          moltype = DNA  length = 372
FEATURE                 Location/Qualifiers
source                  1..372
                        mol_type = other DNA
                        organism = Homo sapiens
SEQUENCE: 145
caggtgcagc tggtggagtc tgggggaggc gtggtccagc ctggggggtc cctgagactc       60
tcctgtgcag cgtctggatt caccttcagt agctatggca tacactgggt ccgccaggct      120
ccaggcaagg ggctggagtg ggtggcactt atatggtatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagatcag      300
gattactatg gttcggggag ttcctacggt atggacgtct ggggccaagg gaccacggtc      360
accgtctcct ca                                                         372

SEQ ID NO: 146          moltype = AA  length = 124
FEATURE                 Location/Qualifiers
source                  1..124
                        mol_type = protein
                        organism = Homo sapiens
SEQUENCE: 146
QVQLVESGGG VVQPGRSLRL SCAASGFTFS SYGIHWVRQA PGKGLEWVAL IWYDGSNKYY       60
ADSVKGRFTI SRDNSKNTLY LQMNSLRAED TAVYYCARDQ DYYGSGSSYG MDVWGQGTTV      120
TVSS                                                                  124

SEQ ID NO: 147          moltype = DNA  length = 24
FEATURE                 Location/Qualifiers
source                  1..24
                        mol_type = other DNA
                        organism = Homo sapiens
SEQUENCE: 147
ggattcacct tcagtagcta tggc                                             24

SEQ ID NO: 148          moltype = AA  length = 8
FEATURE                 Location/Qualifiers
source                  1..8
                        mol_type = protein
                        organism = Homo sapiens
SEQUENCE: 148
GFTFSSYG                                                                8

SEQ ID NO: 149          moltype = DNA  length = 24
FEATURE                 Location/Qualifiers
source                  1..24
                        mol_type = other DNA
                        organism = Homo sapiens
SEQUENCE: 149
atatggtatg atggaagtaa taaa                                             24

SEQ ID NO: 150          moltype = AA  length = 8
FEATURE                 Location/Qualifiers
source                  1..8
                        mol_type = protein
                        organism = Homo sapiens
SEQUENCE: 150
IWYDGSNK                                                                8

SEQ ID NO: 151          moltype = DNA  length = 51
FEATURE                 Location/Qualifiers
source                  1..51
                        mol_type = other DNA
                        organism = Homo sapiens
SEQUENCE: 151
```

```
gcgagagatc aggattacta tggttcgggg agttcctacg gtatggacgt c            51

SEQ ID NO: 152         moltype = AA   length = 17
FEATURE                Location/Qualifiers
source                 1..17
                       mol_type = protein
                       organism = Homo sapiens
SEQUENCE: 152
ARDQDYYGSG SSYGMDV                                                  17

SEQ ID NO: 153         moltype = DNA  length = 324
FEATURE                Location/Qualifiers
source                 1..324
                       mol_type = other DNA
                       organism = Homo sapiens
SEQUENCE: 153
gacatccaga tgacccagtc gccagcctcc ctgtctgcat ctgtaggaga cagagtcacc    60
atcacttgcc gggcaagtca gagcattagc agctatttaa attggtatca gcagaaacca   120
gggaaagccc ctaagcgcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctctcac ttttggccag   300
gggaccaagc tggagatcaa acga                                         324

SEQ ID NO: 154         moltype = AA   length = 108
FEATURE                Location/Qualifiers
source                 1..108
                       mol_type = protein
                       organism = Homo sapiens
SEQUENCE: 154
DIQMTQSPAS LSASVGDRVT ITCRASQSIS SYLNWYQQKP GKAPKRLIYA ASSLQSGVPS    60
RFSGSGSGTD FTLTISSLQP EDFATYYCQQ SYSTPLTFGQ GTKLEIKR                108

SEQ ID NO: 155         moltype = DNA  length = 18
FEATURE                Location/Qualifiers
source                 1..18
                       mol_type = other DNA
                       organism = Homo sapiens
SEQUENCE: 155
cagagcatta gcagctat                                                 18

SEQ ID NO: 156         moltype = AA   length = 6
FEATURE                Location/Qualifiers
source                 1..6
                       mol_type = protein
                       organism = Homo sapiens
SEQUENCE: 156
QSISSY                                                              6

SEQ ID NO: 157         moltype =   length =
SEQUENCE: 157
000

SEQ ID NO: 158         moltype =   length =
SEQUENCE: 158
000

SEQ ID NO: 159         moltype = DNA  length = 27
FEATURE                Location/Qualifiers
source                 1..27
                       mol_type = other DNA
                       organism = Homo sapiens
SEQUENCE: 159
caacagagtt acagtacccc tctcact                                       27

SEQ ID NO: 160         moltype = AA   length = 9
FEATURE                Location/Qualifiers
source                 1..9
                       mol_type = protein
                       organism = Homo sapiens
SEQUENCE: 160
QQSYSTPLT                                                           9

SEQ ID NO: 161         moltype = DNA  length = 372
FEATURE                Location/Qualifiers
source                 1..372
                       mol_type = other DNA
                       organism = Homo sapiens
SEQUENCE: 161
caggtgcagc tggtggagtc tgggggaggc gtggtccagc ctgggaggtc cctgagactc    60
```

```
tcctgtgcag cgtctggatt caccttcagt acctatggca tgcactgggt ccgccaggct   120
ccaggcaagg ggctggagtg ggtggcagtt atatggtatg atggaactaa taaatactat   180
gcagactccg tgaagggccg attcaccatc tccagagaca attccaagaa cacgctgtat   240
ctgcaaatga tcagcctgag agccgaggac acggctgtgt attactgtgc gagagacccc   300
tcaggtgggg accactacta ttactacggt atggacgtct ggggccaagg gaccacggtc   360
accgtctcct ca                                                        372

SEQ ID NO: 162          moltype = AA   length = 124
FEATURE                 Location/Qualifiers
source                  1..124
                        mol_type = protein
                        organism = Homo sapiens
SEQUENCE: 162
QVQLVESGGG VVQPGRSLRL SCAASGFTFS TYGMHWVRQA PGKGLEWVAV IWYDGTNKYY   60
ADSVKGRFTI SRDNSKNTLY LQMISLRAED TAVYYCARDP SGGDHYYYYG MDVWGQGTTV   120
TVSS                                                                 124

SEQ ID NO: 163          moltype = DNA   length = 24
FEATURE                 Location/Qualifiers
source                  1..24
                        mol_type = other DNA
                        organism = Homo sapiens
SEQUENCE: 163
ggattcacct tcagtaccta tggc                                           24

SEQ ID NO: 164          moltype = AA   length = 8
FEATURE                 Location/Qualifiers
source                  1..8
                        mol_type = protein
                        organism = Homo sapiens
SEQUENCE: 164
GFTFSTYG                                                             8

SEQ ID NO: 165          moltype = DNA   length = 24
FEATURE                 Location/Qualifiers
source                  1..24
                        mol_type = other DNA
                        organism = Homo sapiens
SEQUENCE: 165
atatggtatg atggaactaa taaa                                           24

SEQ ID NO: 166          moltype = AA   length = 8
FEATURE                 Location/Qualifiers
source                  1..8
                        mol_type = protein
                        organism = Homo sapiens
SEQUENCE: 166
IWYDGTNK                                                             8

SEQ ID NO: 167          moltype = DNA   length = 51
FEATURE                 Location/Qualifiers
source                  1..51
                        mol_type = other DNA
                        organism = Homo sapiens
SEQUENCE: 167
gcgagagacc cctcaggtgg ggaccactac tattactacg gtatggacgt c              51

SEQ ID NO: 168          moltype = AA   length = 17
FEATURE                 Location/Qualifiers
source                  1..17
                        mol_type = protein
                        organism = Homo sapiens
SEQUENCE: 168
ARDPSGGDHY YYYGMDV                                                   17

SEQ ID NO: 169          moltype = DNA   length = 324
FEATURE                 Location/Qualifiers
source                  1..324
                        mol_type = other DNA
                        organism = Homo sapiens
SEQUENCE: 169
gacatccaga tgacccagtc tccatcctcc ctgtctgcat ctgtaggaga cagaatcacc   60
atcacttgcc aggcgagtca ggacattagc aactatttaa attggtatca gcagaagcca   120
gggaaagccc ctaacctcct gatctctgat gcatccgatt tggaaacagg ggtcccatca   180
aggttcagtg gaagtggatc tgggacagat tttactttca ccatcagcag cctgcagcct   240
gaagattttg caacatatta ctgtcaacag tatgataata taccgatcac cttcggccaa   300
gggacacgac tggagattaa acga                                           324

SEQ ID NO: 170          moltype = AA   length = 108
```

```
FEATURE                 Location/Qualifiers
source                  1..108
                        mol_type = protein
                        organism = Homo sapiens
SEQUENCE: 170
DIQMTQSPSS LSASVGDRIT ITCQASQDIS NYLNWYQQKP GKAPNLLISD ASDLETGVPS    60
RFSGSGSGTD FTFTISSLQP EDFATYYCQQ YDNIPITFGQ GTRLEIKR                108

SEQ ID NO: 171          moltype = DNA  length = 18
FEATURE                 Location/Qualifiers
source                  1..18
                        mol_type = other DNA
                        organism = Homo sapiens
SEQUENCE: 171
caggacatta gcaactat                                                  18

SEQ ID NO: 172          moltype = AA  length = 6
FEATURE                 Location/Qualifiers
source                  1..6
                        mol_type = protein
                        organism = Homo sapiens
SEQUENCE: 172
QDISNY                                                                6

SEQ ID NO: 173          moltype =   length =
SEQUENCE: 173
000

SEQ ID NO: 174          moltype =   length =
SEQUENCE: 174
000

SEQ ID NO: 175          moltype = DNA  length = 27
FEATURE                 Location/Qualifiers
source                  1..27
                        mol_type = other DNA
                        organism = Homo sapiens
SEQUENCE: 175
caacagtatg ataatatacc gatcacc                                        27

SEQ ID NO: 176          moltype = AA  length = 9
FEATURE                 Location/Qualifiers
source                  1..9
                        mol_type = protein
                        organism = Homo sapiens
SEQUENCE: 176
QQYDNIPIT                                                             9

SEQ ID NO: 177          moltype = DNA  length = 366
FEATURE                 Location/Qualifiers
source                  1..366
                        mol_type = other DNA
                        organism = Homo sapiens
SEQUENCE: 177
caggtgcagc tggtggagtc agggggaggc gtggtccagc ctggggaggtc cctgagactc   60
tcctgtgcag cctctggatt caccttcagt agctatggca tgcactgggt ccgccaggct  120
ccaggcaagg ggctggagtg ggtgacattt atatcatttg atgaaaggaa taaatactat  180
gcagactccg ttaagggccg attcaccatc tccagagaca attccaagaa cacgctgtat  240
ctgcaaatga acagcctgag agctgaggac acggctatgt attactgtgc gagcgaagtc  300
gggtacagtt ttggtcatga tgcttttgat atctggggcc aagggacaat ggtcaccgtc  360
tcttca                                                              366

SEQ ID NO: 178          moltype = AA  length = 122
FEATURE                 Location/Qualifiers
source                  1..122
                        mol_type = protein
                        organism = Homo sapiens
SEQUENCE: 178
QVQLVESGGG VVQPGRSLRL SCAASGFTFS SYGMHWVRQA PGKGLEWVTF ISFDERNKYY    60
ADSVKGRFTI SRDNSKNTLY LQMNSLRAED TAMYYCASEV GYSFGHDAFD IWGQGTMVTV   120
SS                                                                  122

SEQ ID NO: 179          moltype = DNA  length = 24
FEATURE                 Location/Qualifiers
source                  1..24
                        mol_type = other DNA
                        organism = Homo sapiens
SEQUENCE: 179
ggattcacct tcagtagcta tggc                                           24
```

```
SEQ ID NO: 180            moltype = AA   length = 8
FEATURE                   Location/Qualifiers
source                    1..8
                          mol_type = protein
                          organism = Homo sapiens
SEQUENCE: 180
GFTFSSYG                                                                  8

SEQ ID NO: 181            moltype = DNA  length = 24
FEATURE                   Location/Qualifiers
source                    1..24
                          mol_type = other DNA
                          organism = Homo sapiens
SEQUENCE: 181
atatcatttg atgaaaggaa taaa                                               24

SEQ ID NO: 182            moltype = AA   length = 8
FEATURE                   Location/Qualifiers
source                    1..8
                          mol_type = protein
                          organism = Homo sapiens
SEQUENCE: 182
ISFDERNK                                                                  8

SEQ ID NO: 183            moltype = DNA  length = 45
FEATURE                   Location/Qualifiers
source                    1..45
                          mol_type = other DNA
                          organism = Homo sapiens
SEQUENCE: 183
gcgagcgaag tcgggtacag ttttggtcat gatgcttttg atatc                        45

SEQ ID NO: 184            moltype = AA   length = 15
FEATURE                   Location/Qualifiers
source                    1..15
                          mol_type = protein
                          organism = Homo sapiens
SEQUENCE: 184
ASEVGYSFGH DAFDI                                                         15

SEQ ID NO: 185            moltype = DNA  length = 324
FEATURE                   Location/Qualifiers
source                    1..324
                          mol_type = other DNA
                          organism = Homo sapiens
SEQUENCE: 185
gacatccaga tgacccagtc tccatcctcc ctgtctgcat ctgtaggaga cagagtcacc        60
atcacttgcc aggcgagtca ggacattagc aactatttaa attggtatca gaagaaacca      120
gggaaagccc ctaaactcct gatctacgat gcatccaatt tggaaacagg ggtcccgtca      180
aggttcagtg gaagtggatc tgggacagat tttactttca ccatcagcag cctgcagcct      240
gaagatattg caacatatta ctgtcaacag tatgataatt tcccgctcac tttcggcgga      300
gggaccaagg tggagatcaa acga                                              324

SEQ ID NO: 186            moltype = AA   length = 108
FEATURE                   Location/Qualifiers
source                    1..108
                          mol_type = protein
                          organism = Homo sapiens
SEQUENCE: 186
DIQMTQSPSS LSASVGDRVT ITCQASQDIS NYLNWYQKKP GKAPKLLIYD ASNLETGVPS        60
RFSGSGSGTD FTFTISSLQP EDIATYYCQQ YDNFPLTFGG GTKVEIKR                    108

SEQ ID NO: 187            moltype = DNA  length = 18
FEATURE                   Location/Qualifiers
source                    1..18
                          mol_type = other DNA
                          organism = Homo sapiens
SEQUENCE: 187
caggacatta gcaactat                                                      18

SEQ ID NO: 188            moltype = AA   length = 6
FEATURE                   Location/Qualifiers
source                    1..6
                          mol_type = protein
                          organism = Homo sapiens
SEQUENCE: 188
QDISNY                                                                    6
```

```
SEQ ID NO: 189          moltype =   length =
SEQUENCE: 189
000

SEQ ID NO: 190          moltype =   length =
SEQUENCE: 190
000

SEQ ID NO: 191          moltype = DNA  length = 27
FEATURE                 Location/Qualifiers
source                  1..27
                        mol_type = other DNA
                        organism = Homo sapiens
SEQUENCE: 191
caacagtatg ataatttccc gctcact                                          27

SEQ ID NO: 192          moltype = AA   length = 9
FEATURE                 Location/Qualifiers
source                  1..9
                        mol_type = protein
                        organism = Homo sapiens
SEQUENCE: 192
QQYDNFPLT                                                              9

SEQ ID NO: 193          moltype = DNA  length = 369
FEATURE                 Location/Qualifiers
source                  1..369
                        mol_type = other DNA
                        organism = Homo sapiens
SEQUENCE: 193
gaggtgcagc tggtggagtc tgggggaggc ttggtacagc ctggggggtc cctgagactc       60
tcctgtgcag cctctggatt cacctttaac aactatgcca tgagctgggt ccgccaggct      120
ccagggaggg gctggagtg gtctcagct attagtggta gtggtgatag cacatactac        180
tcagactccg tgaagggccg gttcaccatc tccagagaca attccaagaa cacgctgtat      240
ctgcaaatga acagcctgag agccgaggac acggccgtat attactgtgc gaaagatcag      300
ggcctgtatt actatggttc ggggagtttt gactactggg gccagggaac cctggtcacc      360
gtctcctca                                                             369

SEQ ID NO: 194          moltype = AA   length = 123
FEATURE                 Location/Qualifiers
source                  1..123
                        mol_type = protein
                        organism = Homo sapiens
SEQUENCE: 194
EVQLVESGGG LVQPGGSLRL SCAASGFTFN NYAMSWVRQA PGRGLEWVSA ISGSGDSTYY       60
SDSVKGRFTI SRDNSKNTLY LQMNSLRAED TAVYYCAKDQ GLYYYGSGSF DYWGQGTLVT      120
VSS                                                                   123

SEQ ID NO: 195          moltype = DNA  length = 24
FEATURE                 Location/Qualifiers
source                  1..24
                        mol_type = other DNA
                        organism = Homo sapiens
SEQUENCE: 195
ggattcacct ttaacaacta tgcc                                             24

SEQ ID NO: 196          moltype = AA   length = 8
FEATURE                 Location/Qualifiers
source                  1..8
                        mol_type = protein
                        organism = Homo sapiens
SEQUENCE: 196
GFTFNNYA                                                               8

SEQ ID NO: 197          moltype = DNA  length = 24
FEATURE                 Location/Qualifiers
source                  1..24
                        mol_type = other DNA
                        organism = Homo sapiens
SEQUENCE: 197
attagtggta gtggtgatag caca                                             24

SEQ ID NO: 198          moltype = AA   length = 8
FEATURE                 Location/Qualifiers
source                  1..8
                        mol_type = protein
                        organism = Homo sapiens
SEQUENCE: 198
ISGSGDST                                                               8
```

```
SEQ ID NO: 199          moltype = DNA  length = 48
FEATURE                 Location/Qualifiers
source                  1..48
                        mol_type = other DNA
                        organism = Homo sapiens
SEQUENCE: 199
gcgaaagatc agggcctgta ttactatggt tcggggagtt ttgactac              48

SEQ ID NO: 200          moltype = AA  length = 16
FEATURE                 Location/Qualifiers
source                  1..16
                        mol_type = protein
                        organism = Homo sapiens
SEQUENCE: 200
AKDQGLYYYG SGSFDY                                                 16

SEQ ID NO: 201          moltype = DNA  length = 324
FEATURE                 Location/Qualifiers
source                  1..324
                        mol_type = other DNA
                        organism = Homo sapiens
SEQUENCE: 201
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatccaagct gcatccagtt tgcaaagtgg ggtcccatca 180
aggttcagtg gcagtggatc tgggacagat atcactctca ccatcagcag tctgcaaccc 240
gaagattttg caacttacta ctgtcaacag agttacagta ccccattcac tttcggccct 300
gggaccaaag tggatatcaa acga                                       324

SEQ ID NO: 202          moltype = AA  length = 108
FEATURE                 Location/Qualifiers
source                  1..108
                        mol_type = protein
                        organism = Homo sapiens
SEQUENCE: 202
DIQMTQSPSS LSASVGDRVT ITCRASQSIS SYLNWYQQKP GKAPKLLIQA ASSLQSGVPS 60
RFSGSGSGTD ITLTISSLQP EDFATYYCQQ SYSTPFTFGP GTKVDIKR             108

SEQ ID NO: 203          moltype = DNA  length = 18
FEATURE                 Location/Qualifiers
source                  1..18
                        mol_type = other DNA
                        organism = Homo sapiens
SEQUENCE: 203
cagagcatta gcagctat                                               18

SEQ ID NO: 204          moltype = AA  length = 6
FEATURE                 Location/Qualifiers
source                  1..6
                        mol_type = protein
                        organism = Homo sapiens
SEQUENCE: 204
QSISSY                                                             6

SEQ ID NO: 205          moltype =  length =
SEQUENCE: 205
000

SEQ ID NO: 206          moltype =  length =
SEQUENCE: 206
000

SEQ ID NO: 207          moltype = DNA  length = 27
FEATURE                 Location/Qualifiers
source                  1..27
                        mol_type = other DNA
                        organism = Homo sapiens
SEQUENCE: 207
caacagagtt acagtacccc attcact                                     27

SEQ ID NO: 208          moltype = AA  length = 9
FEATURE                 Location/Qualifiers
source                  1..9
                        mol_type = protein
                        organism = Homo sapiens
SEQUENCE: 208
QQSYSTPFT                                                          9
```

```
SEQ ID NO: 209            moltype = DNA   length = 375
FEATURE                   Location/Qualifiers
source                    1..375
                          mol_type = other DNA
                          organism = Homo sapiens
SEQUENCE: 209
gaggtgcagc tggtggagtc tgggggaggc ttggtccagc ctgggggtc cctgcaactc        60
tcctgtgcag cctctgggtt tgccttcagc gactctgcta tatactgggt ccgccaggct     120
tccgggaaag ggctggagtg ggttggccgc attagaaaca aagctaatag gttcgcgaca     180
gcatatgtg  cgtcggtgaa aggcaggttc agcatacaca gagatgattc aaagaacacg     240
gcgtatctac aaatgaacag cctgaaaacc gaggacacgg ccgtgtatta ctgtgccaga     300
catggacacg atactttgac tgagggctac ggtatggacg tctgggcca  agggaccacg     360
gtcaccgtct cctca                                                     375

SEQ ID NO: 210            moltype = AA   length = 125
FEATURE                   Location/Qualifiers
source                    1..125
                          mol_type = protein
                          organism = Homo sapiens
SEQUENCE: 210
EVQLVESGGG LVQPGGSLQL SCAASGFAFS DSAIYWVRQA SGKGLEWVGR IRNKANRFAT       60
AYGASVKGRF SIHRDDSKNT AYLQMNSLKT EDTAVYYCAR HGHDTLTEGY GMDVWGQTT     120
VTVSS                                                                125

SEQ ID NO: 211            moltype = DNA   length = 24
FEATURE                   Location/Qualifiers
source                    1..24
                          mol_type = other DNA
                          organism = Homo sapiens
SEQUENCE: 211
gggtttgcct tcagcgactc tgct                                            24

SEQ ID NO: 212            moltype = AA   length = 8
FEATURE                   Location/Qualifiers
source                    1..8
                          mol_type = protein
                          organism = Homo sapiens
SEQUENCE: 212
GFAFSDSA                                                              8

SEQ ID NO: 213            moltype = DNA   length = 30
FEATURE                   Location/Qualifiers
source                    1..30
                          mol_type = other DNA
                          organism = Homo sapiens
SEQUENCE: 213
attagaaaca aagctaatag gttcgcgaca                                      30

SEQ ID NO: 214            moltype = AA   length = 10
FEATURE                   Location/Qualifiers
source                    1..10
                          mol_type = protein
                          organism = Homo sapiens
SEQUENCE: 214
IRNKANRFAT                                                            10

SEQ ID NO: 215            moltype = DNA   length = 48
FEATURE                   Location/Qualifiers
source                    1..48
                          mol_type = other DNA
                          organism = Homo sapiens
SEQUENCE: 215
gccagacatg gacacgatac tttgactgag ggctacggta tggacgtc                  48

SEQ ID NO: 216            moltype = AA   length = 16
FEATURE                   Location/Qualifiers
source                    1..16
                          mol_type = protein
                          organism = Homo sapiens
SEQUENCE: 216
ARHGHDTLTE GYGMDV                                                     16

SEQ ID NO: 217            moltype = DNA   length = 324
FEATURE                   Location/Qualifiers
source                    1..324
                          mol_type = other DNA
                          organism = Homo sapiens
SEQUENCE: 217
gacatccaga tgacccagtc tccatcctcc ctgtctgcat ctgtaggaga cagagtcacc      60
```

```
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

SEQ ID NO: 218          moltype = AA   length = 108
FEATURE                 Location/Qualifiers
source                  1..108
                        mol_type = protein
                        organism = Homo sapiens
SEQUENCE: 218
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                 108

SEQ ID NO: 219          moltype = DNA   length = 18
FEATURE                 Location/Qualifiers
source                  1..18
                        mol_type = other DNA
                        organism = Homo sapiens
SEQUENCE: 219
cagagcatta gcagctat                                                  18

SEQ ID NO: 220          moltype = AA   length = 6
FEATURE                 Location/Qualifiers
source                  1..6
                        mol_type = protein
                        organism = Homo sapiens
SEQUENCE: 220
QSISSY                                                               6

SEQ ID NO: 221          moltype =    length =
SEQUENCE: 221
000

SEQ ID NO: 222          moltype =    length =
SEQUENCE: 222
000

SEQ ID NO: 223          moltype = DNA   length = 30
FEATURE                 Location/Qualifiers
source                  1..30
                        mol_type = other DNA
                        organism = Homo sapiens
SEQUENCE: 223
caacagagtt acagtaccccc tccgatcacc                                    30

SEQ ID NO: 224          moltype = AA   length = 10
FEATURE                 Location/Qualifiers
source                  1..10
                        mol_type = protein
                        organism = Homo sapiens
SEQUENCE: 224
QQSYSTPPIT                                                           10

SEQ ID NO: 225          moltype = DNA   length = 363
FEATURE                 Location/Qualifiers
source                  1..363
                        mol_type = other DNA
                        organism = Homo sapiens
SEQUENCE: 225
caggtgcagc tggtgcagtc tggggctgag gtaaagaacc ctgggtcctc ggtgaaggtc    60
tcctgcaagg cttctggagg caccttcagc agttatacta tcaactgggt gcgacaggcc    120
cctggacaag ggcttgagtg gatgggaggg atcatccctc tctatggaac agcaaactac    180
gcacagaagt tccaggccag agtcacgatt tccacggacg aatccacgaa cacagcctac    240
atggaactga gcaacctgag atttgaagac acggccgtgt atttctgtgc gagtacactg    300
gaactacggg ctttttgatgc ctttgatatc tggggccaag gacaatggtc accgtctct    360
tca                                                                  363

SEQ ID NO: 226          moltype = AA   length = 121
FEATURE                 Location/Qualifiers
source                  1..121
                        mol_type = protein
                        organism = Homo sapiens
SEQUENCE: 226
QVQLVQSGAE VKNPGSSVKV SCKASGGTFS SYTINWVRQA PGQGLEWMGG IIPLYGTANY    60
AQKFQARVTI STDESTNTAY MELSNLRFED TAVYFCASTL ELRAFDAFDI WGQGTMVTVS    120
S                                                                    121
```

-continued

```
SEQ ID NO: 227            moltype = DNA  length = 24
FEATURE                   Location/Qualifiers
source                    1..24
                          mol_type = other DNA
                          organism = Homo sapiens
SEQUENCE: 227
ggaggcacct tcagcagtta tact                                                24

SEQ ID NO: 228            moltype = AA  length = 8
FEATURE                   Location/Qualifiers
source                    1..8
                          mol_type = protein
                          organism = Homo sapiens
SEQUENCE: 228
GGTFSSYT                                                                  8

SEQ ID NO: 229            moltype = DNA  length = 24
FEATURE                   Location/Qualifiers
source                    1..24
                          mol_type = other DNA
                          organism = Homo sapiens
SEQUENCE: 229
atcatccctc tctatggaac agca                                                24

SEQ ID NO: 230            moltype = AA  length = 8
FEATURE                   Location/Qualifiers
source                    1..8
                          mol_type = protein
                          organism = Homo sapiens
SEQUENCE: 230
IIPLYGTA                                                                  8

SEQ ID NO: 231            moltype = DNA  length = 42
FEATURE                   Location/Qualifiers
source                    1..42
                          mol_type = other DNA
                          organism = Homo sapiens
SEQUENCE: 231
gcgagtacac tggaactacg ggcttttgat gcctttgata tc                            42

SEQ ID NO: 232            moltype = AA  length = 14
FEATURE                   Location/Qualifiers
source                    1..14
                          mol_type = protein
                          organism = Homo sapiens
SEQUENCE: 232
ASTLELRAFD AFDI                                                           14

SEQ ID NO: 233            moltype = DNA  length = 357
FEATURE                   Location/Qualifiers
source                    1..357
                          mol_type = other DNA
                          organism = Homo sapiens
SEQUENCE: 233
caggtgcagc tgcaggagtc gggcccagga ctggtgaagc cttcacagac cctgtccctc         60
acctgcactg tctctggtgg ctccatcagc agtggtggtt actactggaa ctggatccgc        120
cagcacccag gaagggcct ggagtggatt gggtacatct attacagtgg aagcacctac         180
tacaacccgt ccctcaagag tcgagttacc atatcagtag acacgtctaa gaaccagttc        240
tccctgaagc tgggctctgt gactgccgcg gacacggccg tgtattactg tgcgcgagct        300
cctccttata actggtttga ctactggggc cagggaaccc tggtcaccgt ctcctca           357

SEQ ID NO: 234            moltype = AA  length = 119
FEATURE                   Location/Qualifiers
source                    1..119
                          mol_type = protein
                          organism = Homo sapiens
SEQUENCE: 234
QVQLQESGPG LVKPSQTLSL TCTVSGGSIS SGGYYWNWIR QHPGKGLEWI GYIYYSGSTY          60
YNPSLKSRVT ISVDTSKNQF SLKLGSVTAA DTAVYYCARA PPYNWFDYWG QGTLVTVSS         119

SEQ ID NO: 235            moltype = DNA  length = 30
FEATURE                   Location/Qualifiers
source                    1..30
                          mol_type = other DNA
                          organism = Homo sapiens
SEQUENCE: 235
ggtggctcca tcagcagtgg tggttactac                                          30

SEQ ID NO: 236            moltype = AA  length = 10
```

```
FEATURE              Location/Qualifiers
source               1..10
                     mol_type = protein
                     organism = Homo sapiens
SEQUENCE: 236
GGSISSGGYY                                                              10

SEQ ID NO: 237       moltype = DNA   length = 21
FEATURE              Location/Qualifiers
source               1..21
                     mol_type = other DNA
                     organism = Homo sapiens
SEQUENCE: 237
atctattaca gtggaagcac c                                                 21

SEQ ID NO: 238       moltype = AA    length = 7
FEATURE              Location/Qualifiers
source               1..7
                     mol_type = protein
                     organism = Homo sapiens
SEQUENCE: 238
IYYSGST                                                                 7

SEQ ID NO: 239       moltype = DNA   length = 33
FEATURE              Location/Qualifiers
source               1..33
                     mol_type = other DNA
                     organism = Homo sapiens
SEQUENCE: 239
gcgcgagctc ctccttataa ctggtttgac tac                                    33

SEQ ID NO: 240       moltype = AA    length = 11
FEATURE              Location/Qualifiers
source               1..11
                     mol_type = protein
                     organism = Homo sapiens
SEQUENCE: 240
ARAPPYNWFD Y                                                            11

SEQ ID NO: 241       moltype = DNA   length = 366
FEATURE              Location/Qualifiers
source               1..366
                     mol_type = other DNA
                     organism = Homo sapiens
SEQUENCE: 241
caggtgcagc tggtggagtc tgggggaggc ttggtcaagc ctggagggtc cctgagactc       60
tcctgtgcag cctctggatt cacccttcagt gactactaca tgaactgggt ccgccaggct     120
ccagggaagg ggctggaatg ggtttcatac attagtaata gtggtaatac ccaatactac     180
gcagactctg tgaagggccg gttcaccatc tccagggaca atgccaagaa ctccctgttt     240
ctgcaaatga acagcctgcg agccgaggac acggccgttt attactgtac gagagaggga     300
ctcgaatata gcagctcgga gccctttgac tactggggcc agggaaccct ggtcaccgtc     360
tcctca                                                                 366

SEQ ID NO: 242       moltype = AA    length = 122
FEATURE              Location/Qualifiers
source               1..122
                     mol_type = protein
                     organism = Homo sapiens
SEQUENCE: 242
QVQLVESGGG LVKPGGSLRL SCAASGFTFS DYYMNWVRQA PGKGLEWVSY ISNSGNTQYY       60
ADSVKGRFTI SRDNAKNSLF LQMNSLRAED TAVYYCTREG LEYSSSEPFD YWGQGTLVTV      120
SS                                                                    122

SEQ ID NO: 243       moltype = DNA   length = 24
FEATURE              Location/Qualifiers
source               1..24
                     mol_type = other DNA
                     organism = Homo sapiens
SEQUENCE: 243
ggattcacct tcagtgacta ctac                                              24

SEQ ID NO: 244       moltype = AA    length = 8
FEATURE              Location/Qualifiers
source               1..8
                     mol_type = protein
                     organism = Homo sapiens
SEQUENCE: 244
GFTFSDYY                                                                8
```

```
SEQ ID NO: 245          moltype = DNA  length = 24
FEATURE                 Location/Qualifiers
source                  1..24
                        mol_type = other DNA
                        organism = Homo sapiens
SEQUENCE: 245
attagtaata gtggtaatac ccaa                                          24

SEQ ID NO: 246          moltype = AA  length = 8
FEATURE                 Location/Qualifiers
source                  1..8
                        mol_type = protein
                        organism = Homo sapiens
SEQUENCE: 246
ISNSGNTQ                                                            8

SEQ ID NO: 247          moltype = DNA  length = 45
FEATURE                 Location/Qualifiers
source                  1..45
                        mol_type = other DNA
                        organism = Homo sapiens
SEQUENCE: 247
acgagagagg gactcgaata tagcagctcg gagccctttg actac                   45

SEQ ID NO: 248          moltype = AA  length = 15
FEATURE                 Location/Qualifiers
source                  1..15
                        mol_type = protein
                        organism = Homo sapiens
SEQUENCE: 248
TREGLEYSSS EPFDY                                                    15

SEQ ID NO: 249          moltype = DNA  length = 366
FEATURE                 Location/Qualifiers
source                  1..366
                        mol_type = other DNA
                        organism = Homo sapiens
SEQUENCE: 249
caggtgcagc tggtgcagtc tgggggctgaa gtgaagaagc ctggggcctc agtgaaggtc   60
tcctgcaaga cttctggata caccttcacc gcctactaca tacactgggt gcgacaggcc  120
cctggacaag gcttgagtg gatgggatgg atcaaccta acaatggtga cacaaactat  180
gcactgaggt ttcagggcag ggtcaccatg accaggggaca tgtccatcaa cacagcctac  240
atggagctgc gcgggctgag atctgacgac acggccgtgt attattgtgc gagagatgat  300
ctagcagcag cgggtatcgg ctggttcgac tcctgggccc agggaaccct ggtcaccgtc  360
tcctca                                                             366

SEQ ID NO: 250          moltype = AA  length = 122
FEATURE                 Location/Qualifiers
source                  1..122
                        mol_type = protein
                        organism = Homo sapiens
SEQUENCE: 250
QVQLVQSGAE VKKPGASVKV SCKTSGYTFT AYYIHWVRQA PGQGLEWMGW INPNNGDTNY   60
ALRFQGRVTM TRDMSINTAY MELRGLRSDD TAVYYCARDD LAAAGIGWFD SWGQGTLVTV  120
SS                                                                 122

SEQ ID NO: 251          moltype = DNA  length = 24
FEATURE                 Location/Qualifiers
source                  1..24
                        mol_type = other DNA
                        organism = Homo sapiens
SEQUENCE: 251
ggatacacct tcaccgccta ctac                                          24

SEQ ID NO: 252          moltype = AA  length = 8
FEATURE                 Location/Qualifiers
source                  1..8
                        mol_type = protein
                        organism = Homo sapiens
SEQUENCE: 252
GYTFTAYY                                                            8

SEQ ID NO: 253          moltype = DNA  length = 24
FEATURE                 Location/Qualifiers
source                  1..24
                        mol_type = other DNA
                        organism = Homo sapiens
SEQUENCE: 253
atcaacccta acaatggtga caca                                          24
```

```
SEQ ID NO: 254          moltype = AA   length = 8
FEATURE                 Location/Qualifiers
source                  1..8
                        mol_type = protein
                        organism = Homo sapiens
SEQUENCE: 254
INPNNGDT                                                                8

SEQ ID NO: 255          moltype = DNA  length = 45
FEATURE                 Location/Qualifiers
source                  1..45
                        mol_type = other DNA
                        organism = Homo sapiens
SEQUENCE: 255
gcgagagatg atctagcagc agcgggtatc ggctggttcg actcc                       45

SEQ ID NO: 256          moltype = AA   length = 15
FEATURE                 Location/Qualifiers
source                  1..15
                        mol_type = protein
                        organism = Homo sapiens
SEQUENCE: 256
ARDDLAAAGI GWFDS                                                        15

SEQ ID NO: 257          moltype = DNA  length = 366
FEATURE                 Location/Qualifiers
source                  1..366
                        mol_type = other DNA
                        organism = Homo sapiens
SEQUENCE: 257
gaagtgcagc tggtggagtc tgggggaggc ttgctacagc ctggcaggtc cctgagactc       60
tcctgtgtag cctctggatt cacctttgat gattatgcca tgcactgggt ccggcaagct      120
ccagggaagg gcctggagtg ggtctcagga attagttgga atagtgaaag tataggctat      180
gcggactctg tgaggggccg attcaccatt tccagagaca acgccaagaa ctccctgtat      240
ctccaaatga acagtctgag agctgaggac acggccttgt attactgtgc aaaagccccg      300
tatagtggga cctacttcga atacttccgc cactggggcc agggcaccct ggtcaccgtc      360
tcctca                                                                 366

SEQ ID NO: 258          moltype = AA   length = 122
FEATURE                 Location/Qualifiers
source                  1..122
                        mol_type = protein
                        organism = Homo sapiens
SEQUENCE: 258
EVQLVESGGG LLQPGRSLRL SCVASGFTFD DYAMHWVRQA PGKGLEWVSG ISWNSESIGY       60
ADSVRGRFTI SRDNAKNSLY LQMNSLRAED TALYYCAKAP YSGTYFEYFR HWGQGTLVTV      120
SS                                                                     122

SEQ ID NO: 259          moltype = DNA  length = 24
FEATURE                 Location/Qualifiers
source                  1..24
                        mol_type = other DNA
                        organism = Homo sapiens
SEQUENCE: 259
ggattcacct ttgatgatta tgcc                                              24

SEQ ID NO: 260          moltype = AA   length = 8
FEATURE                 Location/Qualifiers
source                  1..8
                        mol_type = protein
                        organism = Homo sapiens
SEQUENCE: 260
GFTFDDYA                                                                8

SEQ ID NO: 261          moltype = DNA  length = 24
FEATURE                 Location/Qualifiers
source                  1..24
                        mol_type = other DNA
                        organism = Homo sapiens
SEQUENCE: 261
attagttgga atagtgaaag tata                                              24

SEQ ID NO: 262          moltype = AA   length = 8
FEATURE                 Location/Qualifiers
source                  1..8
                        mol_type = protein
                        organism = Homo sapiens
SEQUENCE: 262
```

ISWNSESI                                                                    8

SEQ ID NO: 263          moltype = DNA   length = 45
FEATURE                 Location/Qualifiers
source                  1..45
                        mol_type = other DNA
                        organism = Homo sapiens
SEQUENCE: 263
gcaaaagccc cgtatagtgg gacctacttc gaatacttcc gccac                           45

SEQ ID NO: 264          moltype = AA    length = 15
FEATURE                 Location/Qualifiers
source                  1..15
                        mol_type = protein
                        organism = Homo sapiens
SEQUENCE: 264
AKAPYSGTYF EYFRH                                                            15

SEQ ID NO: 265          moltype = DNA   length = 357
FEATURE                 Location/Qualifiers
source                  1..357
                        mol_type = other DNA
                        organism = Homo sapiens
SEQUENCE: 265
caggtgcagc tggtggagtc tgggggaggc gtggtccagc ctggagggtc cctgagactc           60
tcctgtgcag cctctggatt cacctttcag agctatggca tgcactgggt ccgccaggct          120
ccaggcaagg ggctggagtg ggtggcagtt atatcatatg atggaagtaa taatactat           180
gcagactccg tgaagggccg attcaccatc tccagagaca attccaagaa cacgctgtat          240
ctgcaaatga acagcctgag agctgaggac acggctgtgt attactgtgc gaaagatgac          300
tggaactacg acgcctttga tatctggggc caagggacaa tggtcaccgt ctcttca            357

SEQ ID NO: 266          moltype = AA    length = 119
FEATURE                 Location/Qualifiers
source                  1..119
                        mol_type = protein
                        organism = Homo sapiens
SEQUENCE: 266
QVQLVESGGG VVQPGRSLRL SCAASGFTFS SYGMHWVRQA PGKGLEWVAV ISYDGSNKYY           60
ADSVKGRFTI SRDNSKNTLY LQMNSLRAED TAVYYCAKDD WNYDAFDIWG QGTMVTVSS           119

SEQ ID NO: 267          moltype = DNA   length = 24
FEATURE                 Location/Qualifiers
source                  1..24
                        mol_type = other DNA
                        organism = Homo sapiens
SEQUENCE: 267
ggattcacct tcagtagcta tggc                                                  24

SEQ ID NO: 268          moltype = AA    length = 8
FEATURE                 Location/Qualifiers
source                  1..8
                        mol_type = protein
                        organism = Homo sapiens
SEQUENCE: 268
GFTFSSYG                                                                    8

SEQ ID NO: 269          moltype = DNA   length = 24
FEATURE                 Location/Qualifiers
source                  1..24
                        mol_type = other DNA
                        organism = Homo sapiens
SEQUENCE: 269
atatcatatg atggaagtaa taaa                                                  24

SEQ ID NO: 270          moltype = AA    length = 8
FEATURE                 Location/Qualifiers
source                  1..8
                        mol_type = protein
                        organism = Homo sapiens
SEQUENCE: 270
ISYDGSNK                                                                    8

SEQ ID NO: 271          moltype = DNA   length = 36
FEATURE                 Location/Qualifiers
source                  1..36
                        mol_type = other DNA
                        organism = Homo sapiens
SEQUENCE: 271
gcgaaagatg actggaacta cgacgccttt gatatc                                     36

```
SEQ ID NO: 272           moltype = AA  length = 12
FEATURE                  Location/Qualifiers
source                   1..12
                         mol_type = protein
                         organism = Homo sapiens
SEQUENCE: 272
AKDDWNYDAF DI                                                              12

SEQ ID NO: 273           moltype = DNA  length = 363
FEATURE                  Location/Qualifiers
source                   1..363
                         mol_type = other DNA
                         organism = Homo sapiens
SEQUENCE: 273
caggtgcagc tgcaggagtc gggcccagga ctggtgaagc cttcacagac cctgtccctc           60
acctgcactg tctctggtgg ctccatcagc agtagtggtt actactggag ctggatccgc          120
cagcacccag ggaggggcct ggagtggatt ggatacatct attacagtgg gagcacctac          180
tacaacccgt ccctcaagag tcgagttacc atatcagtag acacgtctaa gaaccagttc          240
tccctgaagc tgaactctgt gactgccgcg gacacggccg tgtattactg tgcgagagtg          300
gactatggtt cggggagttc gtttgactac tggggccagg gaaccctggt caccgtctcc          360
tca                                                                       363

SEQ ID NO: 274           moltype = AA  length = 121
FEATURE                  Location/Qualifiers
source                   1..121
                         mol_type = protein
                         organism = Homo sapiens
SEQUENCE: 274
QVQLQESGPG LVKPSQTLSL TCTVSGGSIS SSGYYWSWIR QHPGRGLEWI GYIYYSGSTY           60
YNPSLKSRVT ISVDTSKNQF SLKLNSVTAA DTAVYYCARV DYGSGSSFDY WGQGTLVTVS          120
S                                                                         121

SEQ ID NO: 275           moltype = DNA  length = 30
FEATURE                  Location/Qualifiers
source                   1..30
                         mol_type = other DNA
                         organism = Homo sapiens
SEQUENCE: 275
ggtggctcca tcagcagtag tggttactac                                           30

SEQ ID NO: 276           moltype = AA  length = 10
FEATURE                  Location/Qualifiers
source                   1..10
                         mol_type = protein
                         organism = Homo sapiens
SEQUENCE: 276
GGSISSSGYY                                                                 10

SEQ ID NO: 277           moltype = DNA  length = 21
FEATURE                  Location/Qualifiers
source                   1..21
                         mol_type = other DNA
                         organism = Homo sapiens
SEQUENCE: 277
atctattaca gtgggagcac c                                                    21

SEQ ID NO: 278           moltype = AA  length = 7
FEATURE                  Location/Qualifiers
source                   1..7
                         mol_type = protein
                         organism = Homo sapiens
SEQUENCE: 278
IYYSGST                                                                    7

SEQ ID NO: 279           moltype = DNA  length = 39
FEATURE                  Location/Qualifiers
source                   1..39
                         mol_type = other DNA
                         organism = Homo sapiens
SEQUENCE: 279
gcgagagtgg actatggttc ggggagttcg tttgactac                                 39

SEQ ID NO: 280           moltype = AA  length = 13
FEATURE                  Location/Qualifiers
source                   1..13
                         mol_type = protein
                         organism = Homo sapiens
SEQUENCE: 280
```

ARVDYGSGSS FDY                                                      13

SEQ ID NO: 281          moltype = DNA  length = 354
FEATURE                 Location/Qualifiers
source                  1..354
                        mol_type = other DNA
                        organism = Homo sapiens
SEQUENCE: 281
caggttcagc tggtgcagtc tggacctgag gtgaagaagc ctggggcctc agtgaaggtc   60
tcctgcaagg cttctggtta cacctttacc agctatggca tcagctgggt gcgacaggcc  120
cctggacaag gcttgagtg gctgggatgg atcagcggtt tcaatggtag aacagactat   180
acagagaagc tccaggacag aatcaccatg accacagaca gatcctcgag cacagcctac  240
atggaactga ggagcctgag atatgacgac acggccgtgt attactgtgc gagagatgga  300
ctggaaaaac ttggtgacta ctggggccag ggaaccctgg tcaccgtctc ctca        354

SEQ ID NO: 282          moltype = AA  length = 118
FEATURE                 Location/Qualifiers
source                  1..118
                        mol_type = protein
                        organism = Homo sapiens
SEQUENCE: 282
QVQLVQSGPE VKKPGASVKV SCKASGYTFT SYGISWVRQA PGQGLEWLGW ISGFNGRTDY   60
TEKLQDRITM TTDRSSTAY MELRSLRYDD TAVYYCARDG LEKLGDYWGQ GTLVTVSS    118

SEQ ID NO: 283          moltype = DNA  length = 24
FEATURE                 Location/Qualifiers
source                  1..24
                        mol_type = other DNA
                        organism = Homo sapiens
SEQUENCE: 283
ggttacacct ttaccagcta tggc                                          24

SEQ ID NO: 284          moltype = AA  length = 8
FEATURE                 Location/Qualifiers
source                  1..8
                        mol_type = protein
                        organism = Homo sapiens
SEQUENCE: 284
GYTFTSYG                                                             8

SEQ ID NO: 285          moltype = DNA  length = 24
FEATURE                 Location/Qualifiers
source                  1..24
                        mol_type = other DNA
                        organism = Homo sapiens
SEQUENCE: 285
atcagcggtt tcaatggtag aaca                                          24

SEQ ID NO: 286          moltype = AA  length = 8
FEATURE                 Location/Qualifiers
source                  1..8
                        mol_type = protein
                        organism = Homo sapiens
SEQUENCE: 286
ISGFNGRT                                                             8

SEQ ID NO: 287          moltype = DNA  length = 33
FEATURE                 Location/Qualifiers
source                  1..33
                        mol_type = other DNA
                        organism = Homo sapiens
SEQUENCE: 287
gcgagagatg gactggaaaa acttggtgac tac                                33

SEQ ID NO: 288          moltype = AA  length = 11
FEATURE                 Location/Qualifiers
source                  1..11
                        mol_type = protein
                        organism = Homo sapiens
SEQUENCE: 288
ARDGLEKLGD Y                                                        11

SEQ ID NO: 289          moltype = DNA  length = 363
FEATURE                 Location/Qualifiers
source                  1..363
                        mol_type = other DNA
                        organism = Homo sapiens
SEQUENCE: 289
caggtgcagc tggtggagtc tgggggaggc gtggtccagc cggggaggtt cctgagactc   60

```
tcctgtgcag cgtctggatt caccttcagt aactctggca tgcactgggt ccgccaggct    120
ccaggcaagg ggctggagtg ggtggcagga atatggcatg atggaagtta taaatattat    180
gtagactccg tgaagggccg attcaccatc tccagagaca attctaagaa cacgctgttt    240
ctgcaaatga acagcctgcg agccgaggac acggctgtat attattgtgc gagagatgat    300
tactatgctt cggggaccag cgtggacgta tggggccaag gaccacggt caccgtctcc    360
tca                                                                   363

SEQ ID NO: 291          moltype = AA  length = 121
FEATURE                 Location/Qualifiers
source                  1..121
                        mol_type = protein
                        organism = Homo sapiens
SEQUENCE: 290
QVQLVESGGG VVQPGRFLRL SCAASGFTFS NSGMHWVRQA PGKGLEWVAG IWHDGSYKYY      60
VDSVKGRFTI SRDNSKNTLF LQMNSLRAED TAVYYCARDD YYASGTSVDV WGQGTTVTVS    120
S                                                                    121

SEQ ID NO: 291          moltype = DNA  length = 24
FEATURE                 Location/Qualifiers
source                  1..24
                        mol_type = other DNA
                        organism = Homo sapiens
SEQUENCE: 291
ggattcacct tcagtaactc tggc                                             24

SEQ ID NO: 292          moltype = AA  length = 8
FEATURE                 Location/Qualifiers
source                  1..8
                        mol_type = protein
                        organism = Homo sapiens
SEQUENCE: 292
GFTFSNSG                                                                8

SEQ ID NO: 293          moltype = DNA  length = 24
FEATURE                 Location/Qualifiers
source                  1..24
                        mol_type = other DNA
                        organism = Homo sapiens
SEQUENCE: 293
atatggcatg atggaagtta taaa                                             24

SEQ ID NO: 294          moltype = AA  length = 8
FEATURE                 Location/Qualifiers
source                  1..8
                        mol_type = protein
                        organism = Homo sapiens
SEQUENCE: 294
IWHDGSYK                                                                8

SEQ ID NO: 295          moltype = DNA  length = 42
FEATURE                 Location/Qualifiers
source                  1..42
                        mol_type = other DNA
                        organism = Homo sapiens
SEQUENCE: 295
gcgagagatg attactatgc ttcggggacc agcgtggacg ta                         42

SEQ ID NO: 296          moltype = AA  length = 14
FEATURE                 Location/Qualifiers
source                  1..14
                        mol_type = protein
                        organism = Homo sapiens
SEQUENCE: 296
ARDDYYASGT SVDV                                                        14

SEQ ID NO: 297          moltype = DNA  length = 366
FEATURE                 Location/Qualifiers
source                  1..366
                        mol_type = other DNA
                        organism = Homo sapiens
SEQUENCE: 297
caggtgcagc tggtgcagtc tggggctgag gtgaagaagc ctggggcctc agtgagggtc     60
tcctgcatgg cctctggata caccttcacc ggctactata tgcactgggt gcgacaggcc    120
cctggacaag ggcttgagtg gatgggatgg atcaaccccta acagtggtgg cacaaaatat    180
gcacagaagt tcagggcag ggtcaccatg accagggaca cgtccatcag cacagcctac      240
atggagctga gcagactgag atctgacgac acggccgtat attattgtgc gagagaagaa    300
gtcgacgatt tttggagtgg ttaccttgac tactggggcc agggaaccct ggtcaccgtc    360
tcctca                                                                366
```

```
SEQ ID NO: 298            moltype = AA  length = 122
FEATURE                   Location/Qualifiers
source                    1..122
                          mol_type = protein
                          organism = Homo sapiens
SEQUENCE: 298
QVQLVQSGAE VKKPGASVRV SCMASGYTFT GYYMHWVRQA PGQGLEWMGW INPNSGGTKY   60
AQKFQGRVTM TRDTSISTAY MELSRLRSDD TAVYYCAREE VDDFWSGYLD YWGQGTLVTV  120
SS                                                                 122

SEQ ID NO: 299            moltype = DNA  length = 24
FEATURE                   Location/Qualifiers
source                    1..24
                          mol_type = other DNA
                          organism = Homo sapiens
SEQUENCE: 299
ggatacacct tcaccggcta ctat                                          24

SEQ ID NO: 300            moltype = AA  length = 8
FEATURE                   Location/Qualifiers
source                    1..8
                          mol_type = protein
                          organism = Homo sapiens
SEQUENCE: 300
GYTFTGYY                                                             8

SEQ ID NO: 301            moltype = DNA  length = 24
FEATURE                   Location/Qualifiers
source                    1..24
                          mol_type = other DNA
                          organism = Homo sapiens
SEQUENCE: 301
atcaacccta acagtggtgg caca                                          24

SEQ ID NO: 302            moltype = AA  length = 8
FEATURE                   Location/Qualifiers
source                    1..8
                          mol_type = protein
                          organism = Homo sapiens
SEQUENCE: 302
INPNSGGT                                                             8

SEQ ID NO: 303            moltype = DNA  length = 45
FEATURE                   Location/Qualifiers
source                    1..45
                          mol_type = other DNA
                          organism = Homo sapiens
SEQUENCE: 303
gcgagagaag aagtcgacga tttttggagt ggttaccttg actac                   45

SEQ ID NO: 304            moltype = AA  length = 15
FEATURE                   Location/Qualifiers
source                    1..15
                          mol_type = protein
                          organism = Homo sapiens
SEQUENCE: 304
AREEVDDFWS GYLDY                                                    15

SEQ ID NO: 305            moltype = DNA  length = 324
FEATURE                   Location/Qualifiers
source                    1..324
                          mol_type = other DNA
                          organism = Homo sapiens
SEQUENCE: 305
gaaattgtgt tgacgcagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcacttg gacgttcggc  300
caagggacca aggtggaaat caaa                                         324

SEQ ID NO: 306            moltype = AA  length = 108
FEATURE                   Location/Qualifiers
source                    1..108
                          mol_type = protein
                          organism = Homo sapiens
SEQUENCE: 306
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPWTFG QGTKVEIK               108
```

```
SEQ ID NO: 307          moltype = DNA  length = 21
FEATURE                 Location/Qualifiers
source                  1..21
                        mol_type = other DNA
                        organism = Homo sapiens
SEQUENCE: 307
cagagtgtta gcagcagcta c                                              21

SEQ ID NO: 308          moltype = AA  length = 7
FEATURE                 Location/Qualifiers
source                  1..7
                        mol_type = protein
                        organism = Homo sapiens
SEQUENCE: 308
QSVSSSY                                                               7

SEQ ID NO: 309          moltype =     length =
SEQUENCE: 309
000

SEQ ID NO: 310          moltype =     length =
SEQUENCE: 310
000

SEQ ID NO: 311          moltype = DNA  length = 27
FEATURE                 Location/Qualifiers
source                  1..27
                        mol_type = other DNA
                        organism = Homo sapiens
SEQUENCE: 311
cagcagtatg gtagctcacc ttggacg                                        27

SEQ ID NO: 312          moltype = AA  length = 9
FEATURE                 Location/Qualifiers
source                  1..9
                        mol_type = protein
                        organism = Homo sapiens
SEQUENCE: 312
QQYGSSPWT                                                             9

SEQ ID NO: 313          moltype = DNA  length = 354
FEATURE                 Location/Qualifiers
source                  1..354
                        mol_type = other DNA
                        organism = Homo sapiens
SEQUENCE: 313
gaggtgcagc tggtggagtc tggaggagac ttggtccagc cggggggtc cctgagactc     60
tcctgtgcag cctctgggtt cgccgtcaat ggcgactatt ttagttgggt ccgccaggct   120
ccagggaagg ggctggagtg gatctcagtt atttatagca gtggtaacac atactacgca   180
gactccgtga agggccgatt caccatctcc agacacaatt ccaagaacac gctgtatctt   240
caaatgagca gcctaagacc tgaggacacg gccgtgtatt actgtgcgag agacttccct   300
ccaatgtctg gtgcggacta ctggggccag ggaaccctgg tcaccgtctc ctca         354

SEQ ID NO: 314          moltype = AA  length = 118
FEATURE                 Location/Qualifiers
source                  1..118
                        mol_type = protein
                        organism = Homo sapiens
SEQUENCE: 314
EVQLVESGGD LVQPGGSLRL SCAASGFAVN GDYFSWVRQA PGKGLEWISV IYSSGNTYYA    60
DSVKGRFTIS RHNSKNTLYL QMSSLRPEDT AVYYCARDFP PMSGADYWGQ GTLVTVSS    118

SEQ ID NO: 315          moltype = DNA  length = 24
FEATURE                 Location/Qualifiers
source                  1..24
                        mol_type = other DNA
                        organism = Homo sapiens
SEQUENCE: 315
gggttcgccg tcaatggcga ctat                                           24

SEQ ID NO: 316          moltype = AA  length = 8
FEATURE                 Location/Qualifiers
source                  1..8
                        mol_type = protein
                        organism = Homo sapiens
SEQUENCE: 316
GFAVNGDY                                                              8
```

```
SEQ ID NO: 317            moltype = DNA  length = 21
FEATURE                   Location/Qualifiers
source                    1..21
                          mol_type = other DNA
                          organism = Homo sapiens
SEQUENCE: 317
atttatagca gtggtaacac a                                                   21

SEQ ID NO: 318            moltype = AA  length = 7
FEATURE                   Location/Qualifiers
source                    1..7
                          mol_type = protein
                          organism = Homo sapiens
SEQUENCE: 318
IYSSGNT                                                                    7

SEQ ID NO: 319            moltype = DNA  length = 36
FEATURE                   Location/Qualifiers
source                    1..36
                          mol_type = other DNA
                          organism = Homo sapiens
SEQUENCE: 319
gcgagagact tccctccaat gtctggtgcg gactac                                   36

SEQ ID NO: 320            moltype = AA  length = 12
FEATURE                   Location/Qualifiers
source                    1..12
                          mol_type = protein
                          organism = Homo sapiens
SEQUENCE: 320
ARDFPPMSGA DY                                                             12

SEQ ID NO: 321            moltype = DNA  length = 366
FEATURE                   Location/Qualifiers
source                    1..366
                          mol_type = other DNA
                          organism = Homo sapiens
SEQUENCE: 321
caggtccagc tggtgcagtc tggggctgag gtgaagaagc ctggggcctc agtgaaggtc         60
tcctgcaagg tttccggata caccctcact gaattgtcca tgcactgggt gcgacaggct        120
cctgaaaaag gcttgaatg gatgggaggt tttgatcctg aacatggtaa aataatctac         180
gcacagaaat tccagggcag agtcaccatg accgaggaca catctacaga cacagcctac        240
atggaactga gcagcctgag atctgaggac acggccgtct attactgtgc aacatttat         300
aactggaact cctactactt cggtatggac gtctggggcc acgggaccac ggtcaccgtc        360
tcctca                                                                  366

SEQ ID NO: 322            moltype = AA  length = 122
FEATURE                   Location/Qualifiers
source                    1..122
                          mol_type = protein
                          organism = Homo sapiens
SEQUENCE: 322
QVQLVQSGAE VKKPGASVKV SCKVSGYTLT ELSMHWVRQA PGKGLEWMGG FDPEHGKIIY         60
AQKFQGRVTM TEDTSTDTAY MELSSLRSED TAVYYCATFY NWNSYYFGMD VWGHGTTVTV        120
SS                                                                      122

SEQ ID NO: 323            moltype = DNA  length = 24
FEATURE                   Location/Qualifiers
source                    1..24
                          mol_type = other DNA
                          organism = Homo sapiens
SEQUENCE: 323
ggatacaccc tcactgaatt gtcc                                                24

SEQ ID NO: 324            moltype = AA  length = 8
FEATURE                   Location/Qualifiers
source                    1..8
                          mol_type = protein
                          organism = Homo sapiens
SEQUENCE: 324
GYTLTELS                                                                   8

SEQ ID NO: 325            moltype = DNA  length = 24
FEATURE                   Location/Qualifiers
source                    1..24
                          mol_type = other DNA
                          organism = Homo sapiens
SEQUENCE: 325
tttgatcctg aacatggtaa aata                                                24
```

```
SEQ ID NO: 326          moltype = AA   length = 8
FEATURE                 Location/Qualifiers
source                  1..8
                        mol_type = protein
                        organism = Homo sapiens
SEQUENCE: 326
FDPEHGKI                                                                    8

SEQ ID NO: 327          moltype = DNA  length = 45
FEATURE                 Location/Qualifiers
source                  1..45
                        mol_type = other DNA
                        organism = Homo sapiens
SEQUENCE: 327
gcaacatttt ataactggaa ctcctactac ttcggtatgg acgtc                          45

SEQ ID NO: 328          moltype = AA   length = 15
FEATURE                 Location/Qualifiers
source                  1..15
                        mol_type = protein
                        organism = Homo sapiens
SEQUENCE: 328
ATFYNWNSYY FGMDV                                                           15

SEQ ID NO: 329          moltype = DNA  length = 375
FEATURE                 Location/Qualifiers
source                  1..375
                        mol_type = other DNA
                        organism = Homo sapiens
SEQUENCE: 329
gaggtgcagc tggtggagtc ggggggaggc ttggtacagc ctgggggtc cctgagactc           60
tcctgtgcag cctctggatt caccttagc agctatgcca tgaactgggt ccgccaggct          120
ccaggaaagg gactggagtg ggtctcagct gttagtggaa gtgctgatat cacaaactac         180
gcagactccg tgaaggccg gttcaccatc tccagagaca attccaaaca cacgctgtat          240
ctgcaaatga acagcctgag agccgaggac acggccgtat attactgtgc aaggataaa          300
gtgtataact ggaactacgg gatctactac ggtatggacg tctggggcca agggaccacg         360
gtcaccgtct cctca                                                          375

SEQ ID NO: 330          moltype = AA   length = 125
FEATURE                 Location/Qualifiers
source                  1..125
                        mol_type = protein
                        organism = Homo sapiens
SEQUENCE: 330
EVQLVESGGG LVQPGGSLRL SCAASGFTFS SYAMNWVRQA PGKGLEWVSA VSGSADITNY          60
ADSVKGRFTI SRDNSKHTLY LQMNSLRAED TAVYYCAKDK VYNWNYGIYY GMDVWGQGTT         120
VTVSS                                                                    125

SEQ ID NO: 331          moltype = DNA  length = 24
FEATURE                 Location/Qualifiers
source                  1..24
                        mol_type = other DNA
                        organism = Homo sapiens
SEQUENCE: 331
ggattcacct ttagcagcta tgcc                                                24

SEQ ID NO: 332          moltype = AA   length = 8
FEATURE                 Location/Qualifiers
source                  1..8
                        mol_type = protein
                        organism = Homo sapiens
SEQUENCE: 332
GFTFSSYA                                                                   8

SEQ ID NO: 333          moltype = DNA  length = 24
FEATURE                 Location/Qualifiers
source                  1..24
                        mol_type = other DNA
                        organism = Homo sapiens
SEQUENCE: 333
gttagtggaa gtgctgatat caca                                                24

SEQ ID NO: 334          moltype = AA   length = 8
FEATURE                 Location/Qualifiers
source                  1..8
                        mol_type = protein
                        organism = Homo sapiens
SEQUENCE: 334
```

```
VSGSADIT                                                             8

SEQ ID NO: 335         moltype = DNA  length = 54
FEATURE                Location/Qualifiers
source                 1..54
                       mol_type = other DNA
                       organism = Homo sapiens
SEQUENCE: 335
gcgaaggata aagtgtataa ctggaactac gggatctact acggtatgga cgtc         54

SEQ ID NO: 336         moltype = AA  length = 18
FEATURE                Location/Qualifiers
source                 1..18
                       mol_type = protein
                       organism = Homo sapiens
SEQUENCE: 336
AKDKVYNWNY GIYYGMDV                                                  18

SEQ ID NO: 337         moltype = DNA  length = 363
FEATURE                Location/Qualifiers
source                 1..363
                       mol_type = other DNA
                       organism = Homo sapiens
SEQUENCE: 337
cagctgcagc tgcaggagtc gggcccagga ctggtgaagc cttcggagac cctgtccctc   60
acctgcactg tctctggtgg ctccatcagc agtagtagtt actactgggg ctggatccgc   120
cagcccccag ggaagggact agagtggatt gggagtatct attatagtgg gagcacctac   180
tacaatccgt ccctcaagag tcgagtcacc atatccgtag acacgtccaa gaaccagttc   240
tccctgaagc tgagctctgt gaccgccgca gacacggctg tgtattactg tgcgagacaa   300
gggaggtggg agcgagaaaa ctttgactac tggggccagg gaaccctggt caccgtctcc   360
tca                                                                  363

SEQ ID NO: 338         moltype = AA  length = 121
FEATURE                Location/Qualifiers
source                 1..121
                       mol_type = protein
                       organism = Homo sapiens
SEQUENCE: 338
QLQLQESGPG LVKPSETLSL TCTVSGGSIS SSSYYWGWIR QPPGKGLEWI GSIYYSGSTY   60
YNPSLKSRVT ISVDTSKNQF SLKLSSVTAA DTAVYYCARQ GRWERENFDY WGQGTLVTVS  120
S                                                                   121

SEQ ID NO: 339         moltype = DNA  length = 30
FEATURE                Location/Qualifiers
source                 1..30
                       mol_type = other DNA
                       organism = Homo sapiens
SEQUENCE: 339
ggtggctcca tcagcagtag tagttactac                                     30

SEQ ID NO: 340         moltype = AA  length = 10
FEATURE                Location/Qualifiers
source                 1..10
                       mol_type = protein
                       organism = Homo sapiens
SEQUENCE: 340
GGSISSSSYY                                                           10

SEQ ID NO: 341         moltype = DNA  length = 21
FEATURE                Location/Qualifiers
source                 1..21
                       mol_type = other DNA
                       organism = Homo sapiens
SEQUENCE: 341
atctattata gtgggagcac c                                              21

SEQ ID NO: 342         moltype = AA  length = 7
FEATURE                Location/Qualifiers
source                 1..7
                       mol_type = protein
                       organism = Homo sapiens
SEQUENCE: 342
IYYSGST                                                              7

SEQ ID NO: 343         moltype = DNA  length = 39
FEATURE                Location/Qualifiers
source                 1..39
                       mol_type = other DNA
                       organism = Homo sapiens
```

```
SEQUENCE: 343
gcgagacaag ggaggtggga gcgagaaaac tttgactac                            39

SEQ ID NO: 344           moltype = AA   length = 13
FEATURE                  Location/Qualifiers
source                   1..13
                         mol_type = protein
                         organism = Homo sapiens
SEQUENCE: 344
ARQGRWEREN FDY                                                        13

SEQ ID NO: 345           moltype = DNA  length = 354
FEATURE                  Location/Qualifiers
source                   1..354
                         mol_type = other DNA
                         organism = Homo sapiens
SEQUENCE: 345
caggtgcagc tacagcagtg gggcgcagga ctattgaagc cttcggagac cctgtccctc     60
acctgcgctg tctctgatga gtccttcagt gattactact ggacctggat ccgccagccc    120
ccagggaagg ggctggagtg gattggggaa attactcata gtggaagtac ccactacaac    180
ccgtccctca agagccgagt cacccctgtca gttgacacgt ccaagaacca cttctccctg    240
agcctcaact ctgtgaccgc cgcggacacg gctatttatt actgtgcgag aggcggtgac    300
tacggtggtt tacttgacta ctggggccag ggaaccctgg tcaccgtctc ctca          354

SEQ ID NO: 346           moltype = AA   length = 118
FEATURE                  Location/Qualifiers
source                   1..118
                         mol_type = protein
                         organism = Homo sapiens
SEQUENCE: 346
QVQLQQWGAG LLKPSETLSL TCAVSDESFS DYYWTWIRQP PGKGLEWIGE ITHSGSTHYN     60
PSLKSRVTLS VDTSKNHFSL SLNSVTAADT AIYYCARGGD YGGLLDYWGQ GTLVTVSS     118

SEQ ID NO: 347           moltype = DNA  length = 24
FEATURE                  Location/Qualifiers
source                   1..24
                         mol_type = other DNA
                         organism = Homo sapiens
SEQUENCE: 347
gatgagtcct tcagtgatta ctac                                            24

SEQ ID NO: 348           moltype = AA   length = 8
FEATURE                  Location/Qualifiers
source                   1..8
                         mol_type = protein
                         organism = Homo sapiens
SEQUENCE: 348
DESFSDYY                                                               8

SEQ ID NO: 349           moltype = DNA  length = 21
FEATURE                  Location/Qualifiers
source                   1..21
                         mol_type = other DNA
                         organism = Homo sapiens
SEQUENCE: 349
attactcata gtggaagtac c                                               21

SEQ ID NO: 350           moltype = AA   length = 7
FEATURE                  Location/Qualifiers
source                   1..7
                         mol_type = protein
                         organism = Homo sapiens
SEQUENCE: 350
ITHSGST                                                                7

SEQ ID NO: 351           moltype = DNA  length = 36
FEATURE                  Location/Qualifiers
source                   1..36
                         mol_type = other DNA
                         organism = Homo sapiens
SEQUENCE: 351
gcgagaggcg gtgactacgg tggtttactt gactac                               36

SEQ ID NO: 352           moltype = AA   length = 12
FEATURE                  Location/Qualifiers
source                   1..12
                         mol_type = protein
                         organism = Homo sapiens
SEQUENCE: 352
```

ARGGDYGGLL DY 12

```
SEQ ID NO: 353         moltype = DNA   length = 363
FEATURE                Location/Qualifiers
source                 1..363
                       mol_type = other DNA
                       organism = Homo sapiens
SEQUENCE: 353
cagctgcagc tgcaggagtc gggcccagga ctggtgaagc cctcggagac cctgtccctc   60
acctgcactg tctctggtgg ctccatcagc agtaggagtc actactgggg ctggatccgc  120
cagcccccag ggaaggggct ggagtggatt gggagtatct attatagtgg gagcacctat  180
tacaacccgt ccctcaagag tcgagtcacc atatccgtag acacgtccaa gaaccagttc  240
tccctgaagc tgagctctgt gaccgccgca gacacggctg tgtattactg tgcgagactt  300
ggctggtacg cagaggaggc ttttgaaatc tggggtcaag gacaatggt caccgtctct  360
tca                                                                363

SEQ ID NO: 354         moltype = AA   length = 121
FEATURE                Location/Qualifiers
source                 1..121
                       mol_type = protein
                       organism = Homo sapiens
SEQUENCE: 354
QLQLQESGPG LVKPSETLSL TCTVSGGSIS SRSHYWGWIR QPPGKGLEWI GSIYYSGSTY   60
YNPSLKSRVT ISVDTSKNQF SLKLSSVTAA DTAVYYCARL GWYAEEAFEI WGQGTMVTVS  120
S                                                                  121

SEQ ID NO: 355         moltype = DNA   length = 30
FEATURE                Location/Qualifiers
source                 1..30
                       mol_type = other DNA
                       organism = Homo sapiens
SEQUENCE: 355
ggtggctcca tcagcagtag gagtcactac                                    30

SEQ ID NO: 356         moltype = AA   length = 10
FEATURE                Location/Qualifiers
source                 1..10
                       mol_type = protein
                       organism = Homo sapiens
SEQUENCE: 356
GGSISSRSHY                                                          10

SEQ ID NO: 357         moltype = DNA   length = 21
FEATURE                Location/Qualifiers
source                 1..21
                       mol_type = other DNA
                       organism = Homo sapiens
SEQUENCE: 357
atctattata gtgggagcac c                                             21

SEQ ID NO: 358         moltype = AA   length = 7
FEATURE                Location/Qualifiers
source                 1..7
                       mol_type = protein
                       organism = Homo sapiens
SEQUENCE: 358
IYYSGST                                                              7

SEQ ID NO: 359         moltype = DNA   length = 39
FEATURE                Location/Qualifiers
source                 1..39
                       mol_type = other DNA
                       organism = Homo sapiens
SEQUENCE: 359
gcgagacttg gctggtacgc agaggaggct tttgaaatc                          39

SEQ ID NO: 360         moltype = AA   length = 13
FEATURE                Location/Qualifiers
source                 1..13
                       mol_type = protein
                       organism = Homo sapiens
SEQUENCE: 360
ARLGWYAEEA FEI                                                      13

SEQ ID NO: 361         moltype = AA   length = 526
FEATURE                Location/Qualifiers
source                 1..526
                       mol_type = protein
                       organism = Plasmodium falciparum
```

```
SEQUENCE: 361
MIRIKKKLIL TIIYIHLFIL NRLSFENAIK KTKNQENNLT LLPIKSTEEE KDDIKNGKDI    60
KKEIDNDKEN IKTNNAKDHS TYIKSYLNTN VNDGLKYLFI PSHNSFIKKY SVFNQINDGM   120
LLNEKNDVKN NEDYKNVDYK NVNFLQYHFK ELSNYNIANS IDILQEKEGH LDFVIIPHYT   180
FLDYYKHLSY NSIYHKSSTY GKCIAVDAFI KKINETYDKV KSKCNDIKND LIATIKKLEH   240
PYDINNKNDD SYRYDISEEI DDKSEETDDE TEEVEDSIQD TDSNHTPSNK KKNDLMNRTF   300
KKMMDEYNTK KKKLIKCIKN HENDFNKICM DMKNYGTNLF EQLSCYNNNF CNTNGIRYHY   360
DEYIHKLILS VKSKNLNKDL SDMTNILQQS ELLLTNLNKK MGSYIYIDTI KFIHKEMKHI   420
FNRIEYHTKI INDKTKIIQD KIKLNIWRTF QKDELLKRIL DMSNEYSLFI TSDHLRQMLY   480
NTFYSKEKHL NNIFHHLIYV LQMKFNDVPI KMEYFQTYKK NKPLTQ                  526

SEQ ID NO: 362          moltype = AA  length = 344
FEATURE                 Location/Qualifiers
source                  1..344
                        mol_type = protein
                        organism = Plasmodium falciparum
SEQUENCE: 362
KNVNFLQYHF KELSNYNIAN SIDILQEKEG HLDFVIIPHY TFLDYYKHLS YNSIYHKSST    60
YGKYIAVDAF IKKINEAYDK VKSKCNDIKN DLIATIKKLE HPYDINNMNR AFKKMMDEYN   120
TKKKKLIKCI KNHENDFNKI CMDMKNYGTN LFEQLSCYNN NFCNTNGIRY HYDEYIHKLI   180
LSVKSKNLNK DLSDMTNILQ QSELLLTNLN KKMGSYIYID TIKFIHKEMK HIFNRIEYHT   240
KIINDKTKII QDKIKLNIWR TFQKDELLKR ILDMSNEYSL FITSDHLRQM LYNTFYSKEK   300
HLNNIFHHLI YVLQMKFNDV PIKMEYFQTY KKNKPLTQHH HHHH                    344

SEQ ID NO: 363          moltype = AA  length = 7
FEATURE                 Location/Qualifiers
REGION                  1..7
                        note = Linker sequence
source                  1..7
                        mol_type = protein
                        organism = synthetic construct
SEQUENCE: 363
DIEGRMD                                                               7

SEQ ID NO: 364          moltype = AA  length = 5
FEATURE                 Location/Qualifiers
REGION                  1..5
                        note = Linker sequence
source                  1..5
                        mol_type = protein
                        organism = synthetic construct
SEQUENCE: 364
GGGGS                                                                 5

SEQ ID NO: 365          moltype = AA  length = 6
FEATURE                 Location/Qualifiers
REGION                  1..6
                        note = HisX6 tag
source                  1..6
                        mol_type = protein
                        organism = synthetic construct
SEQUENCE: 365
HHHHHH                                                                6
```

I claim:

1. An antigen-binding protein that specifically binds to Plasmodium Falciparum reticulocyte binding protein homologue 5 (PfRH5) polypeptide, wherein the antigen binding protein comprises a heavy chain variable region (HCVR) comprising complementarity determining regions (CDRs) HCDR1, HCDR2 and HCDR3 comprising the amino acid sequences of SEQ ID NOs: 292, 294 and 296, respectively, and a light chain variable region (LCVR) comprising CDRs LCDR1, LCDR2 and LCDR3 comprising the amino acid sequences of SEQ ID NOs: 220, 222 and 224, respectively.

2. The antigen-binding protein of claim 1, which is an antibody or antigen-binding fragment thereof.

3. The antigen-binding protein of claim 1, which is multispecific.

4. The antigen-binding protein of claim 1, which comprises one or more of the following properties:

(a) Inhibits growth of Plasmodium falciparum: in human red blood cells;

(b) Inhibits growth of Plasmodium falciparum: strain D10, Dd2, 7G8, W2-mef, 3D7, HB3, FCR-1/FVO, Cam3.II or RF7 in human red blood cells;

(c) Binds to PfRH5 polypeptide or an antigenic fragment thereof with a $K_D$ of about 4.72 pM to about 1.67 nM at 25° C. and/or of about 1.10 pM to about 1.10 nM at 37° C. when measured by surface plasmon resonance;

(d) Blocks binding of PfRH5 polypeptide to basigin polypeptide;

(e) Binds to PfRH5 lacking the amino-terminal residues M1-Y139 and including residues K140-Q526 but lacking K247-L295 and having the mutations T216A and T299A;

(f) Causes maximal growth inhibition of Plasmodium falciparum: in heat inactivated human or Aotus monkey serum that is about 1-10% higher than that of non-heat-inactivated human or Aotus monkey serum, respectively; and/or (g) When exposed to said antigen-binding protein, does not induce mutation of PfRH5 in Plasmodium falciparum.

5. A complex comprising an antigen-binding protein of claim 1 bound to a *Plasmodium falciparum* reticulocyte binding protein homologue 5 (PfRH5) polypeptide.

6. A composition or kit comprising the antigen-binding protein of claim 1.

7. The composition or kit of claim 6 in association with a further therapeutic agent which is an anti-parasitic drug or a vaccine.

8. The composition or kit of claim 7, wherein the further therapeutic agent is selected from the group consisting of: chloroquine, atovaquone, proguanil, artemether, lumefantrine, mefloquine, quinine, quinidine, doxycycline, clindamycin, a vaccine, an anti-malarial vaccine and RTS,S/AS01.

9. A pharmaceutical composition comprising the antigen-binding protein of claim 1 and pharmaceutically acceptable carrier.

10. A vessel or injection device comprising the antigen-binding protein of claim 1.

11. The antigen-binding protein of claim 1, wherein the HCVR comprises the amino acid sequence of SEQ ID NO: 290 and the LCVR comprises the amino acid sequence of SEQ ID NO: 218.

\* \* \* \* \*